US010239873B2

United States Patent
Choi et al.

(10) Patent No.: US 10,239,873 B2
(45) Date of Patent: Mar. 26, 2019

(54) 7-AZAINDOLE OR 4,7-DIAZAINDOLE DERIVATIVES AS IKKε EPSILON AND TBK1 INHIBITOR AND PHARMACEUTICAL COMPOSITION COMPRISING SAME

(71) Applicant: GREEN CROSS CORPORATION, Yongin-si, Gyeonggi-do (KR)

(72) Inventors: Soongyu Choi, Yongin-si (KR); Kwang-Seop Song, Yongin-si (KR); Hee Jeong Seo, Yongin-si (KR); Sang-ho Ma, Yongin-si (KR); Eun-Jung Park, Yongin-si (KR); Younggyu Kong, Yongin-si (KR); So Ok Park, Yongin-si (KR); Kisoo Park, Yongin-si (KR); Ickhwan Son, Yongin-si (KR); Min Ju Kim, Yongin-si (KR); Man-Young Cha, Yongin-si (KR); Mi-Soon Kim, Yongin-si (KR); Sang Mi Kang, Yongin-si (KR); Dong Hyuk Jang, Yongin-si (KR); Jangwon Hong, Yongin-si (KR)

(73) Assignee: GREEN CROSS CORPORATION, Yongin-si (KR)

( * ) Notice: Subject to any disclaimer, the term of this patent is extended or adjusted under 35 U.S.C. 154(b) by 0 days.

(21) Appl. No.: 15/080,068

(22) Filed: Mar. 24, 2016

(65) Prior Publication Data
US 2016/0297815 A1 Oct. 13, 2016

(30) Foreign Application Priority Data
Apr. 3, 2015 (KR) .................. 10-2015-0047693

(51) Int. Cl.
C07D 471/04 (2006.01)
C07D 519/00 (2006.01)
C07D 487/04 (2006.01)

(52) U.S. Cl.
CPC ......... *C07D 471/04* (2013.01); *C07D 487/04* (2013.01); *C07D 519/00* (2013.01)

(58) Field of Classification Search
CPC ... C07D 471/04; C07D 487/04; C07D 519/00
See application file for complete search history.

(56) References Cited

U.S. PATENT DOCUMENTS 7,622,480 B2 * 11/2009 Fonquerna Pou ... C07D 471/04 514/300
7,906,648 B2 * 3/2011 Arnold ................ C07D 471/04 546/113

OTHER PUBLICATIONS

Huzar et al., Acta Poloniae Pharmaceutica-Drug Research, vol. 70 No. 1 pp. 41-49, 2013.*
Voskoglou-Nomikos et al., Clinical Cancer Research, vol. 9, 4227-4239.*
Ptcl.chem.ox.ac.uk/MSDS structure activity relationship; Jaworska, 1-8, 2004.*
Cancer and Metastasis Reviews (1998), 17(1), 91-106.*
Science (1999), vol. 286, 531-537.*
Valeur et al., Bioorganic & Medicinal Chemistry Letters 22 (2012) 5909-5914.*
Korean Intellectual Property Office, Communication dated May 11, 2016, issued in corresponding Korean Application No. 10-2015-0047693.
Soyoung Lee et al., "Development and Biological Evaluation of Potent and Selective c-KIT$^{D816V}$ Inhibitors", Journal of Medicinal Chemistry, 2014, vol. 57, pp. 6428-6443.
Venkateshwar Rao Gummadi et al., "Discovery of 7-azaindole based anaplastic lymphoma kinase (ALK) inhibitors: Wild type and mutant (L1196M) active compounds with unique binding mode", Bioorganics & Medicinal Chemistry Letters, 2013, vol. 23, pp. 4911-4918.
Seunghee Hong et al., "Discovery of new azaindole-based PI3Kα inhibitors: Apoptotic and antiangiogenic effect on cancer cells", Bioorganic & Medicinal Chemistry Letters, 2010, vol. 20, pp. 7212-7215.

* cited by examiner

Primary Examiner — Rebecca L Anderson
(74) Attorney, Agent, or Firm — Sughrue Mion, PLLC

(57) ABSTRACT

Provided are 7-azaindole or 4,7-diazaindole derivatives as an IKKε (I-kappa-B kinase epsilon) and TBK1 (TANK-binding kinase 1) inhibitor. The 7-azaindole or 4,7-diazaindole derivative effectively inhibits IKKε and TBK1, and thus is useful not only as an anticancer agent for the treatment of various cancers including colorectal cancer, breast cancer, CNS cancer, colon cancer, non-small cell lung cancer, kidney cancer, prostate cancer, ovarian cancer, uterus cancer, stomach cancer, liver cancer, skin cancer, lung cancer, brain cancer, bladder cancer, esophageal cancer, pancreatic cancer, thyroid cancer, head and neck cancer, squamous cell carcinoma, osteosarcoma, B-cell or T-cell lymphoma, acute or chronic leukemia and multiple myeloma, but as a therapeutic agent for chronic inflammation.

6 Claims, No Drawings

7-AZAINDOLE OR 4,7-DIAZAINDOLE DERIVATIVES AS IKKε EPSILON AND TBK1 INHIBITOR AND PHARMACEUTICAL COMPOSITION COMPRISING SAME

CROSS REFERENCE TO RELATED APPLICATIONS

This application claims priority based on Korean Patent Application No. 10-2015-0047693 filed Apr. 3, 2015, the contents of all of which are incorporated herein by reference in their entirety.

FIELD OF THE INVENTION

The present invention relates to novel 7-azaindole or 4,7-diazaindole derivatives as IKKε (I-kappa-B kinase epsilon) and TBK1 (TANK-binding kinase 1) inhibitors and a pharmaceutical composition comprising same for the prevention or treatment of cancer.

BACKGROUND OF THE INVENTION

Cancer, a genetic disorder caused by mutations of genes such as oncogene and tumor suppressor gene, is a serious life-threatening disease which is considered as top $1^{st}$ or $2^{nd}$ ranked leading cause of death in humans. Although various techniques have been developed for the treatment of cancer including surgical treatment, radiation therapy, immunotherapy, etc., problems related with inhibition and recurrence of malignant tumor still remain unresolved.

Protein kinase is a family of enzymes which plays an important role in signal transduction for various cellular activities including cellular proliferation, carcinogenesis, apoptosis, and cytodifferentiation, and it has been known that inhibitors thereof are useful in the treatment and prevention of proliferative diseases such as cancer (see Plowman, G. D, et al., *Drug Discovery Today*, 334-339 (1994)). In this regard, attempts have been made to treat proliferative diseases such as cancer by inhibiting protein kinase which is closely related with various signal transductions and disease mechanisms in cells.

IKKε and TBK1 are homologous Ser/Thr kinases which play an essential role in the innate immune responses derived by induction of Type I interferon and other cytokines, and are activated by viral and bacterial infection. The immune responses triggered by viral and bacterial infection include binding between Toll-like receptor and an antigen, e.g., lipopolysaccharide (LPS) or viral double-stranded RNA (dsRNA), followed by the activation of IKKε and/or TBK1 pathway. The activation of TBK1 and/or IKKε leads to phosphorylation of IFN regulatory factor 3 (IRF3) and/or IFN regulatory factor 7 (IRF7), which triggers dimerization and nuclear translocalization of interferon regulatory transcription factors, inducing signaling cascade that ultimately leads to the production of interferon (see Y.-H. Ou et al., *Molecular Cell* 41, 458-470, 2011 and D. A. Barbie et al., *Nature*, 1-5, 2009).

Recently, a study revealed that IKKε and TBK1 are over-activated in patients with colon cancer, breast cancer, brain tumor, gastric cancer, hepatic cancer, ovarian cancer, and the like (see J. S. Boehm et al., *Cell* 129, 1065-1079, 2007). Medications exhibiting inhibitory actions on IKKε and TBK1 block signal transduction pathways of IKKε and TBK1 by inhibiting phosphorylation of IRF3 and/or IRF7, which leads to the inhibition of angiogenesis, proliferation and survival of cancer, etc. Thus, it is expected that such medications can be effectively used as a therapeutic agent for treating cancer (see WO2010-100431 and WO2009-030890).

Additionally, it is known that IKKε and TBK1 play an important role not only in basic processes of memory and learning via cellular signaling pathways, but also in the regulation of learning ability and judgment (see Takaoka et al., *Drug Delivery Rev* 60, 847-857, 2008). It is also expected that IKKε and TBK1 inhibitors can be useful in the treatment and prevention of a wide range of diseases including inflammatory diseases as well as cancer.

Conventionally, a number of IKKε and TBK1 inhibitors have been developed, but such inhibitors have not yet been commercialized due to their poor effectiveness and deviations in therapeutic effects depending on the type of cancer. Thus, there is an increasing need for developing various compounds which are more effective in the treatment of cancer.

SUMMARY OF THE INVENTION

Therefore, it is an object of the present invention to provide 7-azaindole or 4,7-diazaindole derivatives as IKKε and TBK1 inhibitors.

Also, it is another object of the present invention to provide a pharmaceutical composition comprising the compound for the prevention or treatment of cancer.

In accordance with one object, the present invention provides a compound selected from the group consisting of a 7-azaindole or 4,7-diazaindole derivative of compound (I) below and a pharmaceutically acceptable salt, a hydrate, and a solvate thereof:

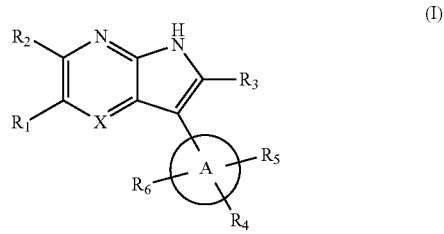

wherein,

X is C or N, ring A is $C_{6-14}$ aromatic ring, or saturated or unsaturated 5- to 7-membered heterocycle containing at least one N;

$R_1$ is H, halogen, substituted or unsubstituted $C_{5-14}$ aryl, substituted or unsubstituted 5- to 13-membered heteroaryl, or —NHY (wherein, Y is substituted or unsubstituted $C_{5-14}$ aryl; and said aryl or heteroaryl is optionally substituted with one or more substituents selected from the group consisting of 5- to 10-membered heterocycloalkyl-$C_{1-7}$ alkyl, $C_{1-7}$ alkoxy, halogen, $C_{1-7}$ alkyl, $C_{1-7}$ alkylamido, $C_{1-7}$ alkyl-5- to 10-membered heterocycloalkyl-$C_{1-7}$ alkyl, $C_{3-10}$ cycloalkyl-5- to 10-membered heterocycloalkyl-$C_{1-7}$ alkyl, 5- to 10-membered heterocycloalkyl-$C_{1-7}$ alkyl, $C_{1-7}$ alkyl-5- to 10-membered heterocycloalkyl-carbonyl, 5- to 10-membered heterocycloalkyl-amino, 5- to 10-membered heterocycloalkyl-oxy, $C_{1-7}$ alkyl-sulfonyl, $C_{3-10}$ cycloalkyl-sulfonyl, sulfamoyl, $C_{1-7}$ alkyl-sulfamoyl, 5- to 10-membered heteroaryl-sulfonyl, amino, oxo, 5- to 13-membered heteroaryl-$C_{1-7}$ alkyl-carbamoyl, 5- to 10-membered heterocycloalkyl-$C_{1-7}$ alkoxy, 5- to 10-membered heterocycloalkyl-carbonyl, $C_{1-7}$ alkoxy-carbonyl-5- to 10-membered heterocycloalkyl-$C_{1-7}$ alkyl, 5- to 10-membered heterocycloalkyl, $C_{1-7}$ alkyl-carbonyl, $C_{1-7}$ alkoxy-carbonyl, cyano, $C_{1-7}$ alkyl-5- to 13-membered heteroaryl, di $C_{1-7}$ alkyl-sulfonyl, $C_{1-7}$ alkyl-amino-sulfonyl, and $C_{1-7}$ alkyl-sulfonylamido;

$R_2$ is H or —$NH_2$;

$R_3$ is H or $C_{1-7}$ alkyl;

$R_4$ is $C_{1-7}$ alkyl, —C(=O)—$R_7$, —C(=O)—O—$R_8$, —C(=O)—N(—$R_9$)—$R_{10}$, —$CH_2$—C(=O)—NH—$R_{11}$ or —$CH_2$—C(=O)—$R_{12}$; $R_7$ to $R_{12}$ are each independently H, hydroxy, $C_{1-7}$ alkyl, substituted or unsubstituted $C_{3-10}$ cycloalkyl, substituted or unsubstituted 5- to 10-membered heterocycloalkyl or substituted or unsubstituted 5- to 13-membered heteroaryl; and each of said cycloalkyl, heterocycloalkyl and heteroaryl is optionally substituted with $C_{1-7}$ alkyl; and $R_5$ and $R_6$ are each independently H, halogen, $C_{1-7}$ alkyl or substituted or unsubstituted $C_{5-14}$ aryl; when $R_5$ and $R_6$ are $C_{1-7}$ alkyl, $R_5$ and $R_6$ are optionally connected to each other.

In accordance with another object, the present invention provides a pharmaceutical composition for the prevention or treatment of cancer, comprising the aforementioned compound and pharmaceutically acceptable additives.

A 7-azaindole or 4,7-diazaindole derivative in accordance with the present invention effectively inhibits IKKε and TBK1, and thus is useful not only as an anticancer agent for the treatment of various cancers including colorectal cancer, breast cancer, CNS cancer, colon cancer, non-small cell lung cancer, kidney cancer, prostate cancer, ovarian cancer, uterus cancer, stomach cancer, liver cancer, skin cancer, lung cancer, brain cancer, bladder cancer, esophageal cancer, pancreatic cancer, thyroid cancer, head and neck cancer, squamous cell carcinoma, osteosarcoma, B-cell or T-cell lymphoma, acute or chronic leukemia and multiple myeloma, but as a therapeutic agent for chronic inflammation.

DETAILED DESCRIPTION OF THE INVENTION

The term "halogen" as used herein, refers to fluorine, chlorine, bromine or iodine, unless otherwise specified.

The term "alkyl" as used herein, refers to linear or branched hydrocarbon chain radicals having 1 to 7 carbon atoms. Particular examples thereof may include, but not limited to, methyl, ethyl, N-propyl, i-propyl, N-butyl, i-butyl, t-butyl, N-pentyl, N-hexyl and the like.

Also, the term "cycloalkyl" refers to a saturated carbocyclic group having 3 to 10 carbon atoms which has a single ring (e.g., cyclohexyl) or a plurality of fused rings (e.g., norbornyl and adamantyl). Particular examples thereof may include, but not limited to, cyclopropyl, cyclopentyl, cyclohexyl, norbornyl, adamantyl, and the like.

Also, the term "aryl" refers to an organic radical derived from aromatic hydrocarbon by removing one hydrogen atom therefrom, which includes a substituted or unsubstituted single ring or a plurality of fused rings, wherein each ring has 5 to 20, preferably 5 to 14 atoms; it also includes a plurality of aryls which are connected via single bonds. In the present invention, aryl also includes a fused bicyclic ring system, which comprises one benzene ring and one hetero ring containing nitrogen or oxygen atom. Particular examples thereof may include, but not limited to, phenyl, naphthyl, biphenyl, terphenyl, indenyl, isoindolinyl and the like. Preferably, the aryl group may be selected from phenyl, naphthyl, and the like.

Also, the term "heteroaryl" refers to a 5- to 13-membered aromatic radical having at least one, preferably, 1 to 4, hetero atom selected from O, N and S; the heteroaryl includes monocyclic heteroaryl with 5- to 6-membered ring and polycyclic heteroaryl group condensed with at least one benzene ring; and the heteroaryl may be partially saturated. Also, in the present invention, the heteroaryl also includes a plurality of heteroaryls which are connected via single bonds. The heteroaryl group includes heteroaryl in which the hetero atom in the ring is oxidized or forms a quaternary salt. Particular examples may include, but not limited to, monocyclic heteroaryl such as furyl, thiophenyl, pyrrolyl, imidazolyl, pyrazolyl, thiazolyl, thiadiazolyl, isothiazolyl, isoxazolyl, oxazolyl, oxadizolyl, triazinyl, tetrazinyl, oxotriazolyl, tetrazolyl, furazanyl, pyridyl, pyrazinyl, pyrimidinyl, pyridazinyl, and the like; polycyclic heteroaryl such as benzofuranyl, benzothiophenyl, dibenzofuranyl, dibenzothiophenyl, isobenzofuranyl, benzoimidazolyl, benzothiazolyl, benzoisothiazolyl, benzoisoxazolyl, benzoxazolyl, benzodioxolyl, benzothiadiazolyl, dihydrobenzofuranyl, dihydrobenzoxazinyl, benzodioxinyl, dihydrobenzodioxinyl, thioxothiazolidinyl, isoindolyl, indolyl, indazolyl, quinolyl, isoquinolyl, cinnolinyl, quinazolinyl, quinoxalinyl, carbazolyl, phenanthridinyl, acridinyl, phenanthrolinyl, phenazinyl, phenothiazinyl, phenoxazinyl, and the like; N-oxides thereof (for example, pyridyl N-oxide and quinolyl N-oxide); and quaternary salts thereof. Preferably, the heteroaryl may be thiophenyl, imidazolyl, pyrazolyl, thiazolyl, oxotriazolyl, tetrazolyl, pyridyl, pyrimidinyl, pyridazinyl, benzothiophenyl, benzoimidazolyl, benzothiazolyl, benzothiadiazolyl, indolyl, indazolyl, quinolyl, isoquinolyl, benzodioxolyl, dihydrobenzofuranyl, dihydrobenzoxazinyl, benzodioxinyl, dihydrobenzodioxinyl, thioxothiazolidinyl, and the like.

Also, the term "heterocycloalkyl" refers to 5- to 10-membered mono- or poly-cyclic ring, excluding aromatic ring, having at least one, preferably, 1 to 4, hetero atom selected from O, N and S. Particular examples may include pyrrolidinyl, imidazolinyl, imidazolidinyl, pyrazolinyl, pyrazolidinyl, piperidinyl, morpholinyl, piperazinyl, tetrahydropyridinyl, and the like.

The present invention provides a compound selected from the group consisting of a 7-azaindole or 4,7-diazaindole derivative of formula (I) and a pharmaceutically acceptable salt, a hydrate and a solvate thereof:

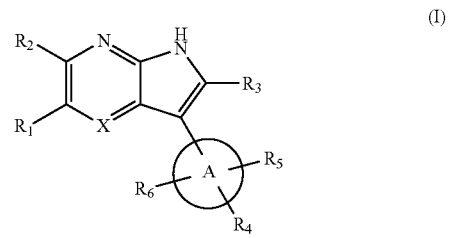

(I)

wherein,

X is C or N, ring A is $C_{6-14}$ aromatic ring, or saturated or unsaturated 5- to 7-membered heterocycle containing at least one N;

$R_1$ is H, halogen, substituted or unsubstituted $C_{5-14}$ aryl, substituted or unsubstituted 5- to 13-membered heteroaryl, or —NHY (wherein, Y is substituted or unsubstituted $C_{5-14}$ aryl; and said aryl or heteroaryl is optionally substituted with one or more substituents selected from the group consisting of 5- to 10-membered heterocycloalkyl-$C_{1-7}$ alkyl, $C_{1-7}$ alkoxy, halogen, $C_{1-7}$ alkyl, $C_{1-7}$ alkylamido, $C_{1-7}$ alkyl-5- to 10-membered heterocycloalkyl-$C_{1-7}$ alkyl, $C_{3-10}$ cycloalkyl-5- to 10-membered heterocycloalkyl-$C_{1-7}$ alkyl, 5- to 10-membered heterocycloalkyl-$C_{1-7}$ alkyl, $C_{1-7}$ alkyl-5- to 10-membered heterocycloalkyl-carbonyl, 5- to 10-membered heterocycloalkyl-amino, 5- to 10-membered heterocycloalkyl-oxy, $C_{1-7}$ alkyl-sulfonyl, $C_{3-10}$ cycloalkyl-sulfonyl, sulfamoyl, $C_{1-7}$ alkyl-sulfamoyl, 5- to 10-membered heterocycloalkyl-sulfonyl, amino, oxo, 5- to 13-membered heteroaryl-$C_{1-7}$ alkyl-carbamoyl, 5- to 10-membered heterocycloalkyl-$C_{1-7}$ alkoxy, 5- to 10-membered heterocycloalkyl-carbonyl, $C_{1-7}$ alkoxy-carbonyl-5- to 10-membered heterocycloalkyl-$C_{1-7}$ alkyl, 5- to 10-membered heterocycloalkyl, $C_{1-7}$ alkyl-carbonyl, $C_{1-7}$ alkoxy-carbonyl, cyano, $C_{1-7}$ alkyl-5- to 13-membered heteroaryl, di $C_{1-7}$ alkyl-sulfonyl, $C_{1-7}$ alkyl-amino-sulfonyl, and $C_{1-7}$ alkyl-sulfonylamido;

$R_2$ is H or —$NH_2$;

$R_3$ is H or $C_{1-7}$ alkyl;

$R_4$ is $C_{1-7}$ alkyl, —C(=O)—$R_7$, —C(=O)—O—$R_8$, —C(=O)—N(—$R_9$)—$R_{10}$, —$CH_2$—C(=O)—NH—$R_{11}$ or —$CH_2$—C(=O)—$R_{12}$; $R_7$ to $R_{12}$ are each independently H, hydroxy, $C_{1-7}$ alkyl, substituted or unsubstituted $C_{3-10}$ cycloalkyl, substituted or unsubstituted 5- to 10-membered heterocycloalkyl or substituted or unsubstituted 5- to 13-membered heteroaryl; and each of said cycloalkyl, heterocycloalkyl and heteroaryl is optionally substituted with $C_{1-7}$ alkyl; and $R_5$ and $R_6$ are each independently H, halogen, $C_{1-7}$ alkyl or substituted or unsubstituted $C_{5-14}$ aryl; when $R_5$ and $R_6$ are $C_{1-7}$ alkyl, $R_5$ and $R_6$ are optionally connected to each other.

According to one embodiment of the present invention, the ring A of the compound of formula (I) being benzene.

According to another embodiment of the present invention, the ring A of the compound of formula (I) being a heterocycle ring selected from the group consisting of:

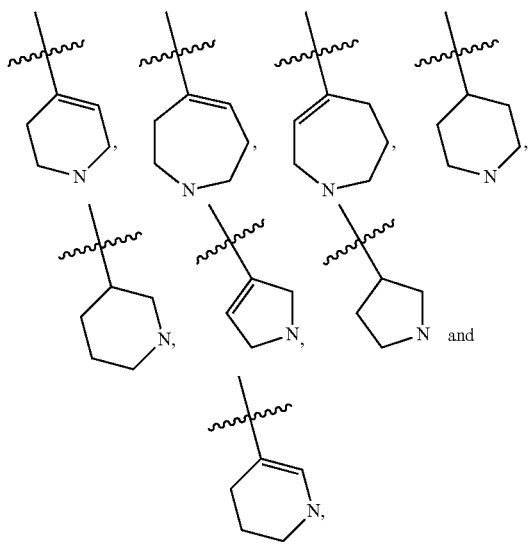

wherein, $R_4$ is substituted at N position; and each of $R_5$ and $R_6$ is optionally substituted at other positions.

According to one embodiment of the present invention, $R_1$ is H, halogen, substituted or unsubstituted phenyl, substituted or unsubstituted thiophenyl, substituted or unsubstituted isoindolinonyl, substituted or unsubstituted pyridinyl, substituted or unsubstituted furanyl, substituted or unsubstituted benzodioxolyl, substituted or unsubstituted thiadiazolyl, substituted or unsubstituted indazolyl or substituted or unsubstituted oxoisoindolinyl; and said phenyl, thiophenyl, isoindolinonyl, pyridinyl, furanyl, benzodioxolyl, thiadiazolyl, indazolyl or oxoisoindolinyl is optionally substituted with one or more substituents selected from the group consisting of 5- to 10-membered heterocycloalkyl-$C_{1-7}$ alkyl, $C_{1-7}$ alkoxy, halogen, $C_{1-7}$ alkyl, $C_{1-7}$ alkylamido, $C_{1-7}$ alkyl-5- to 10-membered heterocycloalkyl-$C_{1-7}$ alkyl, $C_{3-10}$ cycloalkyl-5- to 10-membered heterocycloalkyl-$C_{1-7}$ alkyl, 5- to 10-membered heterocycloalkyl-$C_{1-7}$ alkyl, $C_{1-7}$ alkyl-5- to 10-membered heterocycloalkyl-carbonyl, 5- to 10-membered heterocycloalkyl-amino, 5- to 10-membered heterocycloalkyl-oxy, $C_{1-7}$ alkyl-sulfonyl, $C_{3-10}$ cycloalkyl-sulfonyl, sulfamoyl, $C_{1-7}$ alkyl-sulfamoyl, 5- to 10-membered heterocycloalkyl-sulfonyl, amino, 5- to 13-memebered heteroaryl-$C_{1-7}$ alkyl-carbamoyl, 5- to 10-membered heterocycloalkyl-$C_{1-7}$ alkoxy, 5- to 10-membered heterocycloalkyl-carbonyl, $C_{1-7}$ alkoxy-carbonyl-5- to 10-membered heterocycloalkyl-$C_{1-7}$ alkyl, 5- to 10-membered heterocycloalkyl, $C_{1-7}$ alkyl-carbonyl, $C_{1-7}$ alkoxy-carbonyl, cyano, $C_{1-7}$ alkyl-5- to 13-membered heteroaryl, di $C_{1-7}$ alkyl-sulfonyl, $C_{1-7}$ alkyl-amino-sulfonyl, and $C_{1-7}$ alkyl-sulfonylamido.

According to another embodiment of the present invention, $R_1$ is H, halogen, substituted or unsubstituted phenyl, substituted or unsubstituted thiophenyl, substituted or unsubstituted isoindolinonyl, substituted or unsubstituted pyridinyl, substituted or unsubstituted furanyl, substituted or unsubstituted benzodioxolyl, substituted or unsubstituted thiadiazolyl, substituted or unsubstituted indazolyl or substituted or unsubstituted oxoisoindolinyl; and said phenyl, thiophenyl, isoindolinonyl, pyridinyl, furanyl, benzodioxolyl, thiadiazolyl, indazolyl or oxoisoindolinyl is optionally substituted with one or more substituents selected from the group consisting of fluoro, chloro, amino, tetrahydro-2H-pyran-amino, cyano, acetyl, acetamido, methyl sulfonamido, methyl, morpholinomethyl, piperazinylmethyl, methylpiperazinylmethyl, ethylpiperazinylmethyl, pyrrolidinylmethyl, cyclopropylpiperazinylmethyl, tertbutyloxycarbonylpiperazinylmethyl, morpholinoethyl, methoxy, propoxy, morpholinoethoxy, morpholinopropoxy, tetrahydro-2H-pyran-oxy, methylpiperazinylcarbonyl, methoxycarbonyl, morpholinocarbonyl, methyl sulfonyl, ethylsulfonyl, propylsulfonyl, cyclopropylsulfonyl, morpholinosulfonyl, sulfamoyl, methylsulfamoyl, dimethylsulfamoyl, furanylmethylcarbamoyl, morpholino, piperidine, and sulfonamido.

According to one embodiment of the present invention, $R_4$ is methyl, ethyl, propyl, isobutyl, —C(=O)—$R_7$, —C(=O)—O—$R_8$, —C(=O)—N(—$R_9$)—$R_{10}$, —$CH_2$—C(=O)—NH—$R_{11}$ or —$CH_2$—C(=O)—$R_{12}$; said $R_7$ to $R_{12}$ are each independently H, hydroxy, methyl, ethyl, propyl, butyl, pentyl, isobutyl, isopropyl, isopentyl, isohexyl, tert-butyl, pentan-3-yl, sec-butyl, cyclopropyl, cyclopentyl, cyclohexyl, oxetan-3-yl, tetrahydrofuran-3-yl, pyrrolidin-1-yl, cyclobutyl, thiophen-2-yl or 5-methylthiophen-2-yl.

According to preferred embodiments of the present invention, the compound of the present invention is selected from the group consisting of:

(1)

4-((5-(3-(1-methyl-1,2,3,6-tetrahydropyridin-4-yl)-1H-pyrrolo[2,3-b]pyridin-5-yl)thiophen-2-yl)methyl)morpholine;

(2)
5-(3,4-dimethoxyphenyl)-3-(1-methyl-1,2,3,6-tetrahydropyridin-4-yl)-1H-pyrrolo[2,3-b]pyridine;
(3)
5-(3,4-dimethoxyphenyl)-3-(1-ethyl-1,2,3,6-tetrahydropyridin-4-yl)-1H-pyrrolo[2,3-b]pyridine;
(4)
5-(3,4-dimethoxyphenyl)-3-(1-propyl-1,2,3,6-tetrahydropyridin-4-yl)-1H-pyrrolo[2,3-b]pyridine;
(5)
5-(3,4-dimethoxyphenyl)-3-(1-isobutyl-1,2,3,6-tetrahydropyridin-4-yl)-1H-pyrrolo[2,3-b]pyridine;
(6)
4-((5-(3-(1-ethyl-1,2,3,6-tetrahydropyridin-4-yl)-1H-pyrrolo[2,3-b]pyridin-5-yl)thiophen-2-yl)methyl)morpholine;
(7)
4-((5-(3-(1-propyl-1,2,3,6-tetrahydropyridin-4-yl)-1H-pyrrolo[2,3-b]pyridin-5-yl)thiophen-2-yl)methyl)morpholine;
(8)
1-(4-(5-(5-(morpholinomethyl)thiophen-2-yl)-1H-pyrrolo[2,3-b]pyridin-3-yl)-3,6-dihydropyridin-1(2H)-yl)ethan-1-one;
(9)
1-(4-(5-(5-(morpholinomethyl)thiophen-2-yl)-1H-pyrrolo[2,3-b]pyridin-3-yl)-3,6-dihydropyridin-1(2H)-yl)pentan-1-one;
(10)
3-methyl-1-(4-(5-(5-(morpholinomethyl)thiophen-2-yl)-1H-pyrrolo[2,3-b]pyridin-3-yl)-3,6-dihydropyridin-1(2H)-yl)butan-1-one;
(11)
N-isopropyl-4-(5-phenyl-1H-pyrrolo[2,3-b]pyridin-3-yl)-5,6-dihydropyridine-1(2H)-carboxamide;
(12)
N-isopropyl-4-(5-(4-methoxyphenyl)-1H-pyrrolo[2,3-b]pyridin-3-yl)-3,6-dihydropyridine-1(2H)-carboxamide;
(13)
4-(5-(4-fluorophenyl)-1H-pyrrolo[2,3-b]pyridin-3-yl)-N-isopropyl-3,6-dihydropyridine-1(2H)-carboxamide;
(14)
N-isopropyl-4-(5-(3-methoxyphenyl)-1H-pyrrolo[2,3-b]pyridin-3-yl)-3,6-dihydropyridine-1(2H)-carboxamide;
(15)
4-(5-(3-fluorophenyl)-1H-pyrrolo[2,3-b]pyridin-3-yl)-N-isopropyl-3,6-dihydropyridine-1(2H)-carboxamide;
(16) N-isopropyl-4-(5-(p-tolyl)-1H-pyrrolo[2,3-b]pyridin-3-yl)-3,6-dihydropyridine-1(2H)-carboxamide;
(17)
4-(5-(4-acetamidophenyl)-1H-pyrrolo[2,3-b]pyridin-3-yl)-N-isopropyl-3,6-dihydropyridine-1(2H)-carboxamide;
(18)
4-(5-(3,4-dimethoxyphenyl)-1H-pyrrolo[2,3-b]pyridin-3-yl)-N-isopropyl-5,6-dihydropyridine-1(2H)-carboxamide;
(19)
4-(5-(3-acetamidophenyl)-1H-pyrrolo[2,3-b]pyridin-3-yl)-N-isopropyl-3,6-dihydropyridine-1(2H)-carboxamide;
(20)
4-(5-(2-fluoro-4-(morpholinomethyl)phenyl)-1H-pyrrolo[2,3-b]pyridin-3-yl)-N-isopropyl-3,6-dihydropyridine-1(2H)-carboxamide;
(21)
4-(5-(2-fluoro-5-(morpholinomethyl)phenyl)-1H-pyrrolo[2,3-b]pyridin-3-yl)-N-isopropyl-3, 6-dihydropyridine-1(2H)-carboxamide;
(22)
4-(5-(4-((4-ethylpiperazin-1-yl)methyl)phenyl)-1H-pyrrolo[2,3-b]pyridin-3-yl)-N-isopropyl-3,6-dihydropyridine-1(2H)-carboxamide;
(23)
4-(5-(4-((4-cyclopropylpiperazin-1-yl)methyl)phenyl)-1H-pyrrolo[2,3-b]pyridin-3-yl)-N-isopropyl-3, 6-dihydropyridine-1(2H)-carboxamide;
(24)
4-(5-(3-((4-ethylpiperazin-1-yl)methyl)phenyl)-1H-pyrrolo[2,3-b]pyridin-3-yl)-N-isopropyl-3,6-dihydropyridine-1(2H)-carboxamide;
(25)
N-isopropyl-4-(5-(6-((4-methylpiperazin-1-yl)methyl)pyridin-3-yl)-1H-pyrrolo[2,3-b]pyridin-3-yl)-3, 6-dihydropyridine-1(2H)-carboxamide;
(26)
4-(5-(5-((4-ethylpiperazin-1-yl)methyl)thiophen-2-yl)-1H-pyrrolo[2,3-b]pyridin-3-yl)-N-isopropyl-3, 6-dihydropyridine-1(2H)-carboxamide;
(27)
N-isopropyl-4-(5-(5-(pyrrolidin-1-ylmethyl)furan-2-yl)-1H-pyrrolo[2,3-b]pyridin-3-yl)-5, 6-dihydropyridine-1(2H)-carboxamide;
(28)
N-isopropyl-4-(5-(5-(pyrrolidin-1-ylmethyl)thiophen-2-yl)-1H-pyrrolo[2,3-b]pyridin-3-yl)-5, 6-dihydropyridine-1(2H)-carboxamide;
(29)
N-isopropyl-4-(5-(3-(morpholinomethyl)phenyl)-1H-pyrrolo[2,3-b]pyridin-3-yl)-5,6-dihydropyridine-1(2H)-carboxamide;
(30)
N-isopropyl-4-(5-(4-(morpholinomethyl)phenyl)-1H-pyrrolo[2,3-b]pyridin-3-yl)-5,6-dihydropyridine-1(2H)-carboxamide;
(31)
N-isopropyl-4-(5-(3-(4-methylpiperazine-1-carbonyl)phenyl)-1H-pyrrolo[2,3-b]pyridin-3-yl)-5, 6-dihydropyridine-1(2H)-carboxamide;
(32)
N-isopropyl-4-(5-(4-(4-methylpiperazine-1-carbonyl)phenyl)-1H-pyrrolo[2,3-b]pyridin-3-yl)-5, 6-dihydropyridine-1(2H)-carboxamide;
(33)
N-isopropyl-4-(5-(5-((4-methylpiperazin-1-yl)methyl)thiophen-2-yl)-1H-pyrrolo[2,3-b]pyridin-3-yl)-5,6-dihydropyridine-1(2H)-carboxamide;
(34)
N-isopropyl-4-(5-(5-(morpholinomethyl)thiophen-2-yl)-1H-pyrrolo[2,3-b]pyridin-3-yl)-5,6-dihydropyridine-1(2H)-carboxamide;
(35)
N-isopropyl-4-(5-(5-((4-methylpiperazin-1-yl)methyl)furan-2-yl)-1H-pyrrolo[2,3-b]pyridin-3-yl)-5, 6-dihydropyridine-1(2H)-carboxamide;
(36)
N-isopropyl-4-(5-(5-(morpholinomethyl)furan-2-yl)-1H-pyrrolo[2,3-b]pyridin-3-yl)-5,6-dihydropyridine-1(2H)-carboxamide;
(37)
N-isopropyl-4-(5-(4-((tetrahydro-2H-pyran-4-yl)amino)phenyl)-1H-pyrrolo[2,3-b]pyridin-3-yl)-3, 6-dihydropyridine-1(2H)-carboxamide;

(38) N-isopropyl-4-(5-(4-((tetrahydro-2H-pyran-4-yl)oxy)phenyl)-1H-pyrrolo[2,3-b]pyridin-3-yl)-3,6-dihydropyridine-1(2H)-carboxamide;
(39) 4-(5-(7-amino-1-oxoisoindolidin-4-yl)-1H-pyrrolo[2,3-b]pyridin-3-yl)-N-isopropyl-3,6-dihydropyridine-1(2H)-carboxamide;
(40) 4-(5-(5-(morpholinomethyl)thiophen-2-yl)-1H-pyrrolo[2,3-b]pyridin-3-yl)-N-(pentan-3-yl)-3, 6-dihydropyridine-1(2H)-carboxamide;
(41) 4-(5-(5-((4-methylpiperazin-1-yl)methyl)thiophen-2-yl)-1H-pyrrolo[2,3-b]pyridin-3-yl)-N-(pentan-3-yl)-3, 6-dihydropyridine-1(2H)-carboxamide;
(42) N-(sec-butyl)-4-(5-(5-((4-methylpiperazin-1-yl)methyl)thiophen-2-yl)-1H-pyrrolo[2,3-b]pyridin-3-yl)-5, 6-dihydropyridine-1(2H)-carboxamide;
(43) N-(sec-butyl)-4-(5-(5-(morpholinomethyl)thiophen-2-yl)-1H-pyrrolo[2,3-b]pyridin-3-yl)-5, 6-dihydropyridine-1(2H)-carboxamide;
(44) N-(sec-butyl)-4-(5-(3,4-dimethoxyphenyl)-1H-pyrrolo[2,3-b]pyridin-3-yl)-5,6-dihydropyridine-1(2H)-carboxamide;
(45) N-cyclopropyl-4-(5-(5-(piperazin-1-ylmethyl)thiophen-2-yl)-1H-pyrrolo[2,3-b]pyridin-3-yl)-5, 6-dihydropyridine-1(2H)-carboxamide dihydrochloride;
(46) N-cyclopropyl-4-(5-(4-((4-methylpiperazin-1-yl)methyl)phenyl)-1H-pyrrolo[2,3-b]pyridin-3-yl)-5, 6-dihydropyridine-1(2H)-carboxamide;
(47) N-cyclopropyl-4-(5-(5-((4-methylpiperazin-1-yl)methyl)thiophen-2-yl)-1H-pyrrolo[2,3-b]pyridin-3-yl)-5, 6-dihydropyridine-1(2H)-carboxamide;
(48) N-cyclopropyl-4-(5-(5-(morpholinomethyl)thiophen-2-yl)-1H-pyrrolo[2,3-b]pyridin-3-yl)-5,6-dihydropyridine-1(2H)-carboxamide;
(49) N-cyclopentyl-4-(5-(3,4-dimethoxyphenyl)-1H-pyrrolo[2,3-b]pyridin-3-yl)-5,6-dihydropyridine-1(2H)-carboxamide;
(50) N-cyclopentyl-4-(5-(3-fluoro-4-methoxyphenyl)-1H-pyrrolo[2,3-b]pyridin-3-yl)-5,6-dihydropyridine-1(2H)-carboxamide;
(51) N-cyclopentyl-4-(5-(4-(methylsulfonyl)phenyl)-1H-pyrrolo[2,3-b]pyridin-3-yl)-5,6-dihydropyridine-1(2H)-carboxamide;
(52) N-cyclopentyl-4-(5-(3-(methylsulfonyl)phenyl)-1H-pyrrolo[2,3-b]pyridin-3-yl)-5,6-dihydropyridine-1(2H)-carboxamide;
(53) N-cyclopentyl-4-(5-(4-(ethylsulfonyl)phenyl)-1H-pyrrolo[2,3-b]pyridin-3-yl)-3,6-dihydropyridine-1(2H)-carboxamide;
(54) N-cyclopentyl-4-(5-(3-(ethylsulfonyl)phenyl)-1H-pyrrolo[2,3-b]pyridin-3-yl)-3,6-dihydropyridine-1(2H)-carboxamide;
(55) N-cyclopentyl-4-(5-(4-(propylsulfonyl)phenyl)-1H-pyrrolo[2,3-b]pyridin-3-yl)-5,6-dihydropyridine-1(2H)-carboxamide;
(56) N-cyclopentyl-4-(5-(4-(cyclopropylsulfonyl)phenyl)-1H-pyrrolo[2,3-b]pyridin-3-yl)-5,6-dihydropyridine-1(2H)-carboxamide;
(57) N-cyclopentyl-4-(5-(3-sulfamoylphenyl)-1H-pyrrolo[2,3-b]pyridin-3-yl)-5,6-dihydropyridine-1(2H)-carboxamide;
(58) N-cyclopentyl-4-(5-(4-sulfamoylphenyl)-1H-pyrrolo[2,3-b]pyridin-3-yl)-5,6-dihydropyridine-1(2H)-carboxamide;
(59) N-cyclopentyl-4-(5-(3-(N-methylsulfamoyl)phenyl)-1H-pyrrolo[2,3-b]pyridin-3-yl)-5,6-dihydropyridine-1(2H)-carboxamide;
(60) N-cyclopentyl-4-(5-(4-(N-methylsulfamoyl)phenyl)-1H-pyrrolo[2,3-b]pyridin-3-yl)-5,6-dihydropyridine-1(2H)-carboxamide;
(61) N-cyclopentyl-4-(5-(4-(morpholinosulfonyl)phenyl)-1H-pyrrolo[2,3-b]pyridin-3-yl)-5,6-dihydropyridine-1(2H)-carboxamide;
(62) N-cyclopentyl-4-(5-(3-(morpholinosulfonyl)phenyl)-1H-pyrrolo[2,3-b]pyridin-3-yl)-5,6-dihydropyridine-1(2H)-carboxamide;
(63) N-cyclopentyl-4-(5-(4-methoxy-3-(morpholinosulfonyl)phenyl)-1H-pyrrolo[2,3-b]pyridin-3-yl)-5,6-dihydropyridine-1(2H)-carboxamide;
(64) N-cyclopentyl-4-(5-(4-(2-morpholinoethyl)phenyl)-1H-pyrrolo[2,3-b]pyridin-3-yl)-5,6-dihydropyridine-1(2H)-carboxamide;
(65) 4-(5-(5-acetamido-2-aminophenyl)-1H-pyrrolo[2,3-b]pyridin-3-yl)-N-cyclopentyl-5,6-dihydropyridine-1(2H)-carboxamide;
(66) N-cyclopentyl-4-(5-(4-((furan-2-ylmethyl)carbamoyl)phenyl)-1H-pyrrolo[2,3-b]pyridin-3-yl)-5,6-dihydropyridine-1(2H)-carboxamide;
(67) N-cyclopentyl-4-(5-(3-((furan-2-ylmethyl)carbamoyl)phenyl)-1H-pyrrolo[2,3-b]pyridin-3-yl)-5,6-dihydropyridine-1(2H)-carboxamide;
(68) N-cyclopentyl-4-(5-(3-(2-morpholinoethoxy)phenyl)-1H-pyrrolo[2,3-b]pyridin-3-yl)-5,6-dihydropyridine-1(2H)-carboxamide;
(69) N-cyclopentyl-4-(5-(4-(2-morpholinoethoxy)phenyl)-1H-pyrrolo[2,3-b]pyridin-3-yl)-5,6-dihydropyridine-1(2H)-carboxamide;
(70) N-cyclopentyl-4-(5-(4-(3-morpholinopropoxy)phenyl)-1H-pyrrolo[2,3-b]pyridin-3-yl)-5, 6-dihydropyridine-1(2H)-carboxamide;
(71) N-cyclopentyl-4-(5-(5((4-methylpiperazin-1-yl)methyl)thiophen-2-yl)-1H-pyrrolo[2,3-b]pyridin-3-yl)-5,6-dihydropyridine-1(2H)-carboxamide;

(72) N-cyclopentyl-4-(5-(5-(morpholinomethyl)thiophen-2-yl)-1H-pyrrolo[2,3-b]pyridin-3-yl)-5,6-dihydropyridine-1(2H)-carboxamide;

(73) N-cyclopentyl-4-(5-(5-(morpholinomethyl)thiophen-3-yl)-1H-pyrrolo[2,3-b]pyridin-3-yl)-5,6-dihydropyridine-1(2H)-carboxamide;

(74) N-cyclopentyl-4-(5-(5-(morpholine-4-carbonyl)thiophen-2-yl)-1H-pyrrolo[2,3-b]pyridin-3-yl)-5,6-dihydropyridine-1(2H)-carboxamide;

(75) N-cyclopentyl-4-(5-(4-(morpholine-4-carbonyl)phenyl)-1H-pyrrolo[2,3-b]pyridin-3-yl)-5,6-dihydropyridine-1(2H)-carboxamide;

(76) 4-(5-(4-chloro-3-(morpholine-4-carbonyl)phenyl)-1H-pyrrolo[2,3-b]pyridin-3-yl)-N-cyclopentyl-3,6-dihydropyridine-1(2H)-carboxamide 2,2,2-trifluoroacetate;

(77) 4-(5-(3-chloro-5-(morpholine-4-carbonyl)phenyl)-1H-pyrrolo[2,3-b]pyridin-3-yl)-N-cyclopentyl-3,6-dihydropyridine-1(2H)-carboxamide 2,2,2-trifluoroacetate;

(78) 4-(5-(4-((4-methylpiperazin-1-yl)methyl)phenyl)-1H-pyrrolo[2,3-b]pyridin-3-yl)-N-(oxetan-3-yl)-5, 6-dihydropyridine-1(2H)-carboxamide;

(79) 4-(5-(5-((4-methylpiperazin-1-yl)methyl)thiophen-2-yl)-1H-pyrrolo[2,3-b]pyridin-3-yl)-N-(oxetan-3-yl)-5, 6-dihydropyridine-1(2H)-carboxamide;

(80) 4-(5-(5-(morpholinomethyl)thiophen-2-yl)-1H-pyrrolo[2,3-b]pyridin-3-yl)-N-(oxetan-3-yl)-5,6-dihydropyridine-1(2H)-carboxamide;

(81) 4-(5-(3,4-dimethoxyphenyl)-1H-pyrrolo[2,3-b]pyridin-3-yl)-N-(tetrahydrofuran-3-yl)-5, 6-dihydropyridine-1(2H)-carboxamide;

(82) 4-(5-(4-(methylsulfonyl)phenyl)-1H-pyrrolo[2,3-b]pyridin-3-yl)-N-(tetrahydrofuran-3-yl)-5,6-dihydropyridine-1(2H)-carboxamide;

(83) 4-(5-(5-((4-methylpiperazin-1-yl)methyl)thiophen-2-yl)-1H-pyrrolo[2,3-b]pyridin-3-yl)-N-(tetrahydrofuran-3-yl)-5, 6-dihydropyridine-1(2H)-carboxamide;

(84) 4-(5-(5-(morpholinomethyl)thiophen-2-yl)-1H-pyrrolo[2,3-b]pyridin-3-yl)-N-(tetrahydrofuran-3-yl)-5, 6-dihydropyridine-1(2H)-carboxamide;

(85) 4-(5-(3,4-dimethoxyphenyl)-1H-pyrrolo[2,3-b]pyridin-3-yl)-N-(pyrrolidin-1-yl)-5,6-dihydropyridine-1(2H)-carboxamide 2,2,2-trifluoroacetate;

(86) N-isopropyl-2-methyl-4-(5-(4-((4-methylpiperazin-1-yl)methyl)phenyl)-1H-pyrrolo[2,3-b]pyridin-3-yl)-5, 6-dihydropyridine-1(2H)-carboxamide;

(87) N-isopropyl-2-methyl-4-(5-(5-(morpholinomethyl)thiophen-2-yl)-1H-pyrrolo[2,3-b]pyridin-3-yl)-5, 6-dihydropyridine-1(2H)-carboxamide;

(88) N-isopropyl-2-methyl-4-(5-(5-((4-methylpiperazin-1-yl)methyl)thiophen-2-yl)-1H-pyrrolo[2,3-b]pyridin-3-yl)-5, 6-dihydropyridine-1(2H)-carboxamide;

(89) N-isopropyl-2-methyl-4-(5-(4-(4-methylpiperazine-1-carbonyl)phenyl)-1H-pyrrolo[2,3-b]pyridin-3-yl)-5, 6-dihydropyridine-1(2H)-carboxamide;

(90) N-isopropyl-2-methyl-4-(5-(4-(morpholinomethyl)phenyl)-1H-pyrrolo[2,3-b]pyridin-3-yl)-5, 6-dihydropyridine-1(2H)-carboxamide;

(91) 6-methyl-4-(5-(5-((4-methylpiperazin-1-yl)methyl)thiophen-2-yl)-1H-pyrrolo[2,3-b]pyridin-3-yl)-N-(pentan-3-yl)-3, 6-dihydropyridine-1(2H)-carboxamide;

(92) 6-methyl-4-(5-(5-(morpholinomethyl)thiophen-2-yl)-1H-pyrrolo[2,3-b]pyridin-3-yl)-N-(pentan-3-yl)-3, 6-dihydropyridine-1(2H)-carboxamide;

(93) tert-butyl 4-((5-(3-(1-(cyclopropylcarbamoyl)-6-methyl-1,2,3,6-tetrahydropyridin-4-yl)-1H-pyrrolo[2,3-b]pyridin-5-yl)thiophen-2-yl)methyl)piperazine-1-carboxylate;

(94) N-cyclopropyl-2-methyl-4-(5-(4-(4-methylpiperazine-1-carbonyl)phenyl)-1H-pyrrolo[2,3-b]pyridin-3-yl)-5, 6-dihydropyridine-1(2H)-carboxamide;

(95) N-cyclopropyl-2-methyl-4-(5-(4-((4-methylpiperazin-1-yl)methyl)phenyl)-1H-pyrrolo[2,3-b]pyridin-3-yl)-5, 6-dihydropyridine-1(2H)-carboxamide;

(96) N-cyclopropyl-2-methyl-4-(5-(5-((4-methylpiperazin-1-yl)methyl)thiophen-2-yl)-1H-pyrrolo[2,3-b]pyridin-3-yl)-5, 6-dihydropyridine-1(2H)-carboxamide;

(97) N-cyclopropyl-2-methyl-4-(5-(5-(morpholinomethyl)thiophen-2-yl)-1H-pyrrolo[2,3-b]pyridin-3-yl)-5, 6-dihydropyridine-1(2H)-carboxamide;

(98) N-cyclobutyl-2-methyl-4-(5-(4-(4-methylpiperazine-1-carbonyl)phenyl)-1H-pyrrolo[2,3-b]pyridin-3-yl)-5, 6-dihydropyridine-1(2H)-carboxamide;

(99) N-cyclobutyl-2-methyl-4-(5-(4-((4-methylpiperazin-1-yl)methyl)phenyl)-1H-pyrrolo[2,3-b]pyridin-3-yl)-5, 6-dihydropyridine-1(2H)-carboxamide;

(100) N-cyclobutyl-2-methyl-4-(5-(5-((4-methylpiperazin-1-yl)methyl)thiophen-2-yl)-1H-pyrrolo[2,3-b]pyridin-3-yl)-5, 6-dihydropyridine-1(2H)-carboxamide;

(101) N-cyclobutyl-2-methyl-4-(5-(5-(morpholinomethyl)thiophen-2-yl)-1H-pyrrolo[2,3-b]pyridin-3-yl)-5, 6-dihydropyridine-1(2H)-carboxamide;

(102) N-cyclopentyl-2-methyl-4-(5-(5-((4-methylpiperazin-1-yl)methyl)thiophen-2-yl)-1H-pyrrolo[2,3-b]pyridin-3-yl)-5, 6-dihydropyridine-1(2H)-carboxamide;

(103) N-cyclopentyl-6-methyl-4-(5-(5-((4-methylpiperazin-1-yl)methyl)thiophen-2-yl)-1H-pyrrolo[2,3-b]pyridin-3-yl)-5, 6-dihydropyridine-1(2H)-carboxamide;

(104) N-cyclopentyl-6-methyl-4-(5-(5-(morpholinomethyl)thiophen-2-yl)-1H-pyrrolo[2,3-b]pyridin-3-yl)-5, 6-dihydropyridine-1(2H)-carboxamide;
(105) N-cyclopentyl-2-methyl-4-(5-(4-(methylsulfonyl)phenyl)-1H-pyrrolo[2,3-b]pyridin-3-yl)-5,6-dihydropyridine-1(2H)-carboxamide;
(106) N-cyclopentyl-2-methyl-4-(5-(5-(morpholinomethyl)thiophen-2-yl)-1H-pyrrolo[2,3-b]pyridin-3-yl)-5, 6-dihydropyridine-1(2H)-carboxamide;
(107) N-cyclopentyl-2-methyl-4-(5-(5-((4-methylpiperazin-1-yl)methyl)thiophen-2-yl)-1H-pyrrolo[2,3-b]pyridin-3-yl)-5, 6-dihydropyridine-1(2H)-carboxamide;
(108) N-cyclopentyl-4-(5-(3,4-dimethoxyphenyl)-1H-pyrrolo[2,3-b]pyridin-3-yl)-2-methyl-5,6-dihydropyridine-1(2H)-carboxamide;
(109) 2-ethyl-N-isopropyl-4-(5-(5-(morpholinomethyl)thiophen-2-yl)-1H-pyrrolo[2,3-b]pyridin-3-yl)-5, 6-dihydropyridine-1(2H)-carboxamide;
(110) 6-ethyl-N-isopropyl-4-(5-(5-(morpholinomethyl)thiophen-2-yl)-1H-pyrrolo[2,3-b]pyridin-3-yl)-5, 6-dihydropyridine-1(2H)-carboxamide;
(111) 2-ethyl-N-isopropyl-4-(5-(5-((4-methylpiperazin-1-yl)methyl)thiophen-2-yl)-1H-pyrrolo[2,3-b]pyridin-3-yl)-5, 6-dihydropyridine-1(2H)-carboxamide;
(112) 6-ethyl-N-isopropyl-4-(5-(4-(morpholinomethyl)phenyl)-1H-pyrrolo[2,3-b]pyri din-3-yl)-3,6-dihydropyridine-1(2H)-carboxamide;
(113) 6-ethyl-N-isopropyl-4-(5-(4-(4-methylpiperazine-1-carbonyl)phenyl)-1H-pyrrolo[2,3-b]pyridin-3-yl)-3, 6-dihydropyridine-1(2H)-carboxamide;
(114) N-isopropyl-2,2-dimethyl-4-(5-(5-(morpholinomethyl)thiophen-2-yl)-1H-pyrrolo[2,3-b]pyridin-3-yl)-5, 6-dihydropyridine-1(2H)-carboxamide;
(115) N-isopropyl-2, 6-dimethyl-4-(5-(5-(morpholinomethyl)thiophen-2-yl)-1H-pyrrolo[2,3-b]pyridin-3-yl)-3, 6-dihydropyridine-1(2H)-carboxamide;
(116) N-cyclopentyl-2, 6-dimethyl-4-(5-(5-(morpholinomethyl)thiophen-2-yl)-1H-pyrrolo[2,3-b]pyridin-3-yl)-3, 6-dihydropyridine-1(2H)-carboxamide;
(117) N-isopropyl-3-(5-(5-(morpholinomethyl)thiophen-2-yl)-1H-pyrrolo[2,3-b]pyridin-3-yl)-8-azabicyclo[3.2.1]oct-3-ene-8-carboxamide;
(118) N-isopropyl-3-(5-(5-(morpholinomethyl)thiophen-2-yl)-1H-pyrrolo[2,3-b]pyridin-3-yl)-9-azabicyclo[3.3.1]non-3-ene-9-carboxamide;
(119) 4-(5-(3,4-dimethoxyphenyl)-1H-pyrrolo[2,3-b]pyridin-3-yl)-N-isopropyl-2-phenyl-5,6-dihydropyridine-1(2H)-carboxamide;
(120) N-cyclopentyl-4-(5-(3,4-dimethoxyphenyl)-1H-pyrrolo[2,3-b]pyridin-3-yl)-5-methyl-5,6-dihydropyridine-1(2H)-carboxamide;
(121) N-cyclopentyl-5-methyl-4-(5-(4-(methylsulfonyl)phenyl)-1H-pyrrolo[2,3-b]pyridin-3-yl)-5,6-dihydropyridine-1(2H)-carboxamide;
(122) N-cyclopentyl-5-methyl-4-(5-(3-(methylsulfonyl)phenyl)-1H-pyrrolo[2,3-b]pyridin-3-yl)-5,6-dihydropyridine-1(2H)-carboxamide;
(123) N-cyclopentyl-5-methyl-4-(5-(3-sulfamoylphenyl)-1H-pyrrolo[2,3-b]pyridin-3-yl)-5, 6-dihydropyridine-1(2H)-carboxamide;
(124) N-cyclopentyl-5-methyl-4-(5-(4-sulfamoylphenyl)-1H-pyrrolo[2,3-b]pyridin-3-yl)-5, 6-dihydropyridine-1(2H)-carboxamide;
(125) N-isopropyl-5-methyl-4-(5-(5-((4-methylpiperazin-1-yl)methyl)thiophen-2-yl)-1H-pyrrolo[2,3-b]pyridin-3-yl)-5, 6-dihydropyridine-1(2H)-carboxamide;
(126) N-cyclopentyl-5-methyl-4-(5-(5-((4-methylpiperazin-1-yl)methyl)thiophen-2-yl)-1H-pyrrolo[2,3-b]pyridin-3-yl)-5, 6-dihydropyridine-1(2H)-carboxamide;
(127) N-cyclopentyl-5-methyl-4-(5-(5-(morpholinomethyl)thiophen-2-yl)-1H-pyrrolo[2,3-b]pyridin-3-yl)-5, 6-dihydropyridine-1(2H)-carboxamide;
(128) N-cyclopentyl-5-ethyl-4-(5-(5-(morpholinomethyl)thiophen-2-yl)-1H-pyrrolo[2,3-b]pyridin-3-yl)-5, 6-dihydropyridine-1(2H)-carboxamide;
(129) N-cyclopentyl-4-(5-(3,4-dimethoxyphenyl)-1H-pyrrolo[2,3-b]pyridin-3-yl)-3-methyl-5,6-dihydropyridine-1(2H)-carboxamide;
(130) N-cyclopentyl-3-methyl-4-(5-(4-(methylsulfonyl)phenyl)-1H-pyrrolo[2,3-b]pyridin-3-yl)-5,6-dihydropyridine-1(2H)-carboxamide;
(131) N-cyclopentyl-3-methyl-4-(5-(5-(morpholinomethyl)thiophen-2-yl)-1H-pyrrolo[2,3-b]pyridin-3-yl)-5, 6-dihydropyridine-1(2H)-carboxamide;
(132) N-cyclopentyl-3-fluoro-4-(5-(4-(methylsulfonyl)phenyl)-1H-pyrrolo[2,3-b]pyridin-3-yl)-5,6-dihydropyridine-1(2H)-carboxamide;
(133) N-cyclopentyl-4-(5-(3,4-dimethoxyphenyl)-1H-pyrrolo[2,3-b]pyridin-3-yl)-3-fluoro-5, 6-dihydropyridine-1(2H)-carboxamide;
(134) N-cyclopentyl-3-fluoro-4-(5-(5-(morpholinomethyl)thiophen-2-yl)-1H-pyrrolo[2,3-b]pyridin-3-yl)-5, 6-dihydropyridine-1(2H)-carboxamide;
(135) ethyl 4-(1H-pyrrolo[2,3-b]pyridin-3-yl)-5, 6-dihydropyridine-1(2H)-carboxylate;
(136) pentyl 4-(1H-pyrrolo[2,3-b]pyridin-3-yl)-5,6-dihydropyridine-1(2H)-carboxylate;

(137) propyl 4-(1H-pyrrolo[2,3-b]pyridin-3-yl)-5,6-dihydropyridine-1(2H)-carboxylate;
(138) butyl 4-(1H-pyrrolo[2,3-b]pyridin-3-yl)-5,6-dihydropyridine-1(2H)-carboxylate;
(139) isopropyl 4-(1H-pyrrolo[2,3-b]pyridin-3-yl)-5,6-dihydropyridine-1(2H)-carboxylate;
(140) cyclopentyl 4-(1H-pyrrolo[2,3-b]pyridin-3-yl)-3,6-dihydropyridine-1(2H)-carboxylate;
(141) sec-butyl 4-(1H-pyrrolo[2,3-b]pyridin-3-yl)-5,6-dihydropyridine-1(2H)-carboxylate;
(142) pentan-3-yl 4-(1H-pyrrolo[2,3-b]pyridin-3-yl)-5,6-dihydropyridine-1(2H)-carboxylate;
(143) cyclohexyl 4-(1H-pyrrolo[2,3-b]pyridin-3-yl)-5,6-dihydropyridine-1(2H)-carboxylate;
(144) cyclopentyl 4-(5-(3,4-dimethoxyphenyl)-1H-pyrrolo[2,3-b]pyridin-3-yl)-5,6-dihydropyridine-1(2H)-carboxylate;
(145) cyclopentyl 4-(5-(3-sulfamoylphenyl)-1H-pyrrolo[2,3-b]pyridin-3-yl)-5,6-dihydropyridine-1(2H)-carboxylate;
(146) isopropyl 4-(5-(3-sulfamoylphenyl)-1H-pyrrolo[2,3-b]pyridin-3-yl)-5,6-dihydropyridine-1(2H)-carboxylate;
(147) isopropyl 4-(5-(3,4-dimethoxyphenyl)-1H-pyrrolo[2,3-b]pyridin-3-yl)-5,6-dihydropyridine-1(2H)-carboxylate;
(148) isopropyl 4-(5-(4-(methylsulfonyl)phenyl)-1H-pyrrolo[2,3-b]pyridin-3-yl)-5,6-dihydropyridine-1(2H)-carboxylate;
(149) isopropyl 4-(5-(3-(methylsulfonyl)phenyl)-1H-pyrrolo[2,3-b]pyridin-3-yl)-5,6-dihydropyridine-1(2H)-carboxylate;
(150) isopropyl 4-(5-(4-sulfamoylphenyl)-1H-pyrrolo[2,3-b]pyridin-3-yl)-5,6-dihydropyridine-1(2H)-carboxylate;
(151) tert-butyl 4-(5-(3-sulfamoylphenyl)-1H-pyrrolo[2,3-b]pyridin-3-yl)-5,6-dihydropyridine-1(2H)-carboxylate;
(152) tert-butyl 4-(5-(4-sulfamoylphenyl)-1H-pyrrolo[2,3-b]pyridin-3-yl)-5,6-dihydropyridine-1(2H)-carboxylate;
(153) tert-butyl 4-(5-(5-(morpholinomethyl)thiophen-2-yl)-1H-pyrrolo[2,3-b]pyridin-3-yl)-5,6-dihydropyridine-1(2H)-carboxylate;
(154) tert-butyl 4-(5-(4-(morpholinomethyl)phenyl)-1H-pyrrolo[2,3-b]pyridin-3-yl)-5,6-dihydropyridine-1(2H)-carboxylate;
(155) tert-butyl 4-(5-(4-(morpholine-4-carbonyl)phenyl)-1H-pyrrolo[2,3-b]pyridin-3-yl)-5,6-dihydropyridine-1(2H)-carboxylate;
(156) tert-butyl 4-(5-(3-(morpholinomethyl)phenyl)-1H-pyrrolo[2,3-b]pyridin-3-yl)-5,6-dihydropyridine-1(2H)-carboxylate;
(157) tert-butyl 4-(5-(6-morpholinopyridin-3-yl)-1H-pyrrolo[2,3-b]pyridin-3-yl)-5,6-dihydropyridine-1(2H)-carboxylate;
(158) tert-butyl 4-(5-(4-morpholinophenyl)-1H-pyrrolo[2,3-b]pyridin-3-yl)-5,6-dihydropyridine-1(2H)-carboxylate;
(159) tert-butyl 4-(5-(4-(piperidin-1-yl)phenyl)-1H-pyrrolo[2,3-b]pyridin-3-yl)-5,6-dihydropyridine-1(2H)-carboxylate;
(160) tert-butyl 4-(5-(benzo[d][1,3]dioxol-5-yl)-1H-pyrrolo[2,3-b]pyridin-3-yl)-5,6-dihydropyridine-1(2H)-carboxylate;
(161) tert-butyl 4-(5-(6-methoxypyridin-3-yl)-1H-pyrrolo[2,3-b]pyridin-3-yl)-5,6-dihydropyridine-1(2H)-carboxylate;
(162) tert-butyl 4-(5-(3-(methylsulfonyl)phenyl)-1H-pyrrolo[2,3-b]pyridin-3-yl)-5,6-dihydropyridine-1(2H)-carboxylate;
(163) tert-butyl 4-(5-(3-(N-methylsulfamoyl)phenyl)-1H-pyrrolo[2,3-b]pyridin-3-yl)-5,6-dihydropyridine-1(2H)-carboxylate;
(164) tert-butyl 4-(5-(4-(methylsulfonyl)phenyl)-1H-pyrrolo[2,3-b]pyridin-3-yl)-5,6-dihydropyridine-1(2H)-carboxylate;
(165) tert-butyl 4-(5-(4-(N-methylsulfamoyl)phenyl)-1H-pyrrolo[2,3-b]pyridin-3-yl)-5,6-dihydropyridine-1(2H)-carboxylate;
(166) tert-butyl 4-(5-(4-acetylphenyl)-1H-pyrrolo[2,3-b]pyridin-3-yl)-5,6-dihydropyridine-1(2H)-carboxylate;
(167) tert-butyl 4-(5-(4-(methoxycarbonyl)phenyl)-1H-pyrrolo[2,3-b]pyridin-3-yl)-5,6-dihydropyridine-1(2H)-carboxylate;
(168) tert-butyl 4-(5-(4-cyanophenyl)-1H-pyrrolo[2,3-b]pyridin-3-yl)-5,6-dihydropyridine-1(2H)-carboxylate;
(169) tert-butyl 4-(5-(3-cyanophenyl)-1H-pyrrolo[2,3-b]pyridin-3-yl)-5,6-dihydropyridine-1(2H)-carboxylate;
(170) tert-butyl 4-(5-(5-methyl-1,3,4-thiadiazol-2-yl)-1H-pyrrolo[2,3-b]pyridin-3-yl)-5,6-dihydropyridine-1(2H)-carboxylate;
(171) cyclopentyl 4-(5-(3-fluoro-4-methoxyphenyl)-1H-pyrrolo[2,3-b]pyridin-3-yl)-5,6-dihydropyridine-1(2H)-carboxylate;
(172) cyclopentyl 4-(5-(3-(methylsulfonyl)phenyl)-1H-pyrrolo[2,3-b]pyridin-3-yl)-5,6-dihydropyridine-1(2H)-carboxylate;
(173) cyclopentyl 4-(5-(4-(methylsulfonyl)phenyl)-1H-pyrrolo[2,3-b]pyridin-3-yl)-5,6-dihydropyridine-1(2H)-carboxylate;
(174) cyclopentyl 4-(5-(3-(ethylsulfonyl)phenyl)-1H-pyrrolo[2,3-b]pyridin-3-yl)-5,6-dihydropyridine-1(2H)-carboxylate;
(175) cyclopentyl 4-(5-(4-(cyclopropylsulfonyl)phenyl)-1H-pyrrolo[2,3-b]pyridin-3-yl)-5,6-dihydropyridine-1(2H)-carboxylate;
(176) cyclopentyl 4-(5-(4-sulfamoylphenyl)-1H-pyrrolo[2,3-b]pyridin-3-yl)-5,6-dihydropyridine-1(2H)-carboxylate;
(177) cyclopentyl 4-(5-(3-(N-methylsulfamoyl)phenyl)-1H-pyrrolo[2,3-b]pyridin-3-yl)-5,6-dihydropyridine-1(2H)-carboxylate;
(178) cyclopentyl 4-(5-(4-(N-methylsulfamoyl)phenyl)-1H-pyrrolo[2,3-b]pyridin-3-yl)-5,6-dihydropyridine-1(2H)-carboxylate;
(179) cyclopentyl 4-(5-(4-(N,N-dimethylsulfamoyl)phenyl)-1H-pyrrolo[2,3-b]pyridin-3-yl)-5,6-dihydropyridine-1(2H)-carboxylate;
(180) cyclopentyl 4-(5-(3-(morpholinosulfonyl)phenyl)-1H-pyrrolo[2,3-b]pyridin-3-yl)-5,6-dihydropyridine-1(2H)-carboxylate;

(181) cyclopentyl 4-(5-(4-(morpholinosulfonyl)phenyl)-1H-pyrrolo[2,3-b]pyridin-3-yl)-5,6-dihydropyridine-1(2H)-carboxylate;
(182) cyclopentyl 4-(5-(4-methoxy-3-(morpholinosulfonyl)phenyl)-1H-pyrrolo[2,3-b]pyridin-3-yl)-5,6-dihydropyridine-1(2H)-carboxylate;
(183) cyclopentyl 4-(5-(4-(morpholine-4-carbonyl)phenyl)-1H-pyrrolo[2,3-b]pyridin-3-yl)-5,6-dihydropyridine-1(2H)-carboxylate;
(184) cyclopentyl 4-(5-(3-(morpholine-4-carbonyl)phenyl)-1H-pyrrolo[2,3-b]pyridin-3-yl)-5,6-dihydropyridine-1(2H)-carboxylate;
(185) cyclopentyl 4-(5-(5-(morpholinomethyl)thiophen-3-yl)-1H-pyrrolo[2,3-b]pyridin-3-yl)-5,6-dihydropyridine-1(2H)-carboxylate;
(186) cyclopentyl 4-(5-(5-(morpholinomethyl)thiophen-2-yl)-1H-pyrrolo[2,3-b]pyridin-3-yl)-5,6-dihydropyridine-1(2H)-carboxylate;
(187) tert-butyl 4-(5-(3,4-dimethoxyphenyl)-1H-pyrrolo[2,3-b]pyridin-3-yl)-2,3,6,7-tetrahydro-1H-azepine-1-carboxylate;
(188) tert-butyl 5-(5-(3,4-dimethoxyphenyl)-1H-pyrrolo[2,3-b]pyridin-3-yl)-2,3,4,7-tetrahydro-1H-azepine-1-carboxylate;
(189) (4-(5-(3,4-difluorophenyl)-1H-pyrrolo[2,3-b]pyridin-3-yl)-5,6-dihydropyridin-1(2H)-yl) (thiophen-2-yl)methanone;
(190) (4-(5-(4-(morpholinosulfonyl)phenyl)-1H-pyrrolo[2,3-b]pyridin-3-yl)-5,6-dihydropyridin-1(2H)-yl)(thiophen-2-yl)methanone;
(191) (4-(5-(3,4-dimethoxyphenyl)-1H-pyrrolo[2,3-b]pyridin-3-yl)-5,6-dihydropyridin-1(2H)-yl)(thiophen-2-yl)methanone;
(192) (4-(5-(3-fluoro-4-methoxyphenyl)-1H-pyrrolo[2,3-b]pyridin-3-yl)-5,6-dihydropyridin-1(2H)-yl)(thiophen-2-yl)methanone;
(193) (4-(5-(3-(methylsulfonyl)phenyl)-1H-pyrrolo[2,3-b]pyridin-3-yl)-5,6-dihydropyridin-1(2H)-yl)(thiophen-2-yl)methanone;
(194) (4-(5-(4-(methylsulfonyl)phenyl)-1H-pyrrolo[2,3-b]pyridin-3-yl)-5,6-dihydropyridin-1(2H)-yl)(thiophen-2-yl)methanone;
(195) (4-(5-(3-(ethylsulfonyl)phenyl)-1H-pyrrolo[2,3-b]pyridin-3-yl)-5,6-dihydropyridin-1(2H)-yl)(thiophen-2-yl)methanone;
(196) (4-(5-(4-(cyclopropylsulfonyl)phenyl)-1H-pyrrolo[2,3-b]pyridin-3-yl)-5,6-dihydropyridin-1(2H)-yl)(thiophen-2-yl)methanone;
(197) 4-(3-(1-(thiophene-2-carbonyl)-1,2,3,6-tetrahydropyridin-4-yl)-1H-pyrrolo[2,3-b]pyridin-5-yl)benzensulfonamide;
(198) 3-(3-(1-(thiophene-2-carbonyl)-1,2,3,6-tetrahydropyridin-4-yl)-1H-pyrrolo[2,3-b]pyridin-5-yl)benzensulfonamide;
(199) N-methyl-3-(3-(1-(thiophene-2-carbonyl)-1,2,3,6-tetrahydropyridin-4-yl)-1H-pyrrolo[2,3-b]pyridin-5-yl)benzensulfonamide;
(200) N-methyl-4-(3-(1-(thiophene-2-carbonyl)-1,2,3,6-tetrahydropyridin-4-yl)-1H-pyrrolo[2,3-b]pyridin-5-yl)benzensulfonamide;
(201) N-(3-(3-(1-(thiophene-2-carbonyl)-1,2,3,6-tetrahydropyridin-4-yl)-1H-pyrrolo[2,3-b]pyridin-5-yl)phenyl)methansulfonamide;
(202) (4-(5-(3-(morpholinosulfonyl)phenyl)-1H-pyrrolo[2,3-b]pyridin-3-yl)-5,6-dihydropyridin-1(2H)-yl)(thiophen-2-yl)methanone;
(203) (4-(5-(4-methoxy-3-(morpholinosulfonyl)phenyl)-1H-pyrrolo[2,3-b]pyridin-3-yl)-5,6-di hydropyridin-1(2H)-yl)(thiophen-2-yl)methanone;
(204) (4-(5-(1H-indazol-5-yl)-1H-pyrrolo[2,3-b]pyridin-3-yl)-5,6-dihydropyridin-1(2H)-yl)(thiophen-2-yl)methanone;
(205) (4-(5-(5-((4-methylpiperazin-1-yl)methyl)thiophen-2-yl)-1H-pyrrolo[2,3-b]pyridin-3-yl)-5,6-dihydropyridin-1(2H)-yl)(thiophen-2-yl)methanone;
(206) (4-(5-(5-(morpholinomethyl)thiophen-2-yl)-1H-pyrrolo[2,3-b]pyridin-3-yl)-5,6-dihydropyridin-1(2H)-yl)(thiophen-2-yl)methanone;
(207) (4-(5-(5-(morpholinomethyl)thiophen-3-yl)-1H-pyrrolo[2,3-b]pyridin-3-yl)-5,6-dihydropyridin-1(2H)-yl)(thiophen-2-yl)methanone;
(208) (4-(5-(3-(morpholine-4-carbonyl)phenyl)-1H-pyrrolo[2,3-b]pyridin-3-yl)-5,6-dihydropyridin-1(2H)-yl)(thiophen-2-yl)methanone;
(209) (4-(5-(4-(morpholine-4-carbonyl)phenyl)-1H-pyrrolo[2,3-b]pyridin-3-yl)-5,6-dihydropyridin-1(2H)-yl)(thiophen-2-yl)methanone;
(210) (4-(5-(3,4-dimethoxyphenyl)-1H-pyrrolo[2,3-b]pyridin-3-yl)-5,6-dihydropyridin-1(2H)-yl)(5-methylthiophen-2-yl)methanone;
(211) (4-(5-(4-(methylsulfonyl)phenyl)-1H-pyrrolo[2,3-b]pyridin-3-yl)-5,6-dihydropyridin-1(2H)-yl)(5-methylthiophen-2-yl)methanone;
(212) 4-(3-(1-(5-methylthiophene-2-carbonyl)-1,2,3,6-tetrahydropyridin-4-yl)-1H-pyrrolo[2,3-b]pyridin-5-yl)benzensulfonamide;
(213) (4-(5-(3,4-dimethoxyphenyl)-1H-pyrrolo[2,3-b]pyridin-3-yl)-5-methyl-5,6-dihydropyridin-1(2H)-yl)(thiophen-2-yl)methanone;
(214) (5-methyl-4-(5-(4-(methylsulfonyl)phenyl)-1H-pyrrolo[2,3-b]pyridin-3-yl)-5,6-dihydropyridin-1(2H)-yl)(thiophen-2-yl)methanone;
(215) (4-(3-(3-methyl-1-(thiophene-2-carbonyl)-1,2,3,6-tetrahydropyridin-4-yl)-1H-pyrrolo[2,3-b]pyridin-5-yl)phenyl)(morpholino)methanone;
(216) (5-methyl-4-(5-(5-(morpholinomethyl)thiophen-2-yl)-1H-pyrrolo[2,3-b]pyridin-3-yl)-5, 6-dihydropyridin-1(2H)-yl)(thiophen-2-yl)methanone;

(217) N-cyclopentyl-N-methyl-4-(5-(3-(methylsulfonyl)phenyl)-1H-pyrrolo[2,3-b]pyridin-3-yl)-5,6-dihydropyridine-1(2H)-carboxamide;

(218) N-cyclopentyl-N-methyl-4-(5-(3-sulfamoylphenyl)-1H-pyrrolo[2,3-b]pyridin-3-yl)-5,6-dihydropyridine-1(2H)-carboxamide;

(219) N-cyclopentyl-N-methyl-4-(5-(4-sulfamoylphenyl)-1H-pyrrolo[2,3-b]pyridin-3-yl)-5,6-dihydropyridine-1(2H)-carboxamide;

(220) N-cyclopentyl-4-(5-(3,4-dimethoxyphenyl)-1H-pyrrolo[2,3-b]pyridin-3-yl)-N-methyl-5, 6-dihydropyridine-1(2H)-carboxamide;

(221) N-cyclopentyl-4-(2-methyl-5-(4-sulfamoylphenyl)-1H-pyrrolo[2,3-b]pyridin-3-yl)-5, 6-dihydropyridine-1(2H)-carboxamide;

(222) N-cyclopentyl-4-(2-methyl-5-(4-(N-methylsulfamoyl)phenyl)-1H-pyrrolo[2,3-b]pyridin-3-yl)-5,6-dihydropyridine-1(2H)-carboxamide;

(223) N-cyclopentyl-4-(2-methyl-5-(4-(morpholine-4-carbonyl)phenyl)-1H-pyrrolo[2,3-b]pyridin-3-yl)-5,6-dihydropyridine-1(2H)-carboxamide;

(224) tert-butyl 4-(6-amino-5-(3,4-dimethoxyphenyl)-1H-pyrrolo[2,3-b]pyridin-3-yl)-5,6-dihydropyridine-1(2H)-carboxylate;

(225) tert-butyl 4-(6-amino-5-(5-(morpholinomethyl)thiophen-2-yl)-1H-pyrrolo[2,3-b]pyridin-3-yl)-5,6-dihydropyridine-1(2H)-carboxylate;

(226) 4-(6-amino-5-(3,4-dimethoxyphenyl)-1H-pyrrolo[2,3-b]pyridin-3-yl)-N-cyclopentyl-5,6-dihydropyridine-1(2H)-carboxamide;

(227) 4-(6-amino-5-(5-(morpholinomethyl)thiophen-2-yl)-1H-pyrrolo[2,3-b]pyridin-3-yl)-N-cyclopentyl-5,6-dihydropyridine-1(2H)-carboxamide;

(228) N-cyclopentyl-4-(2-(3-(methylsulfonyl)phenyl)-5H-pyrrolo[2,3-b]pyrazin-7-yl)-5,6-dihydropyridine-1(2H)-carboxamide;

(229) N-cyclopentyl-4-(2-(5-(morpholinomethyl)thiophen-2-yl)-5H-pyrrolo[2,3-b]pyrazin-7-yl)-5,6-dihydropyridine-1(2H)-carboxamide;

(230) tert-butyl 4-(2-(3,4-dimethoxyphenyl)-5H-pyrrolo[2,3-b]pyrazin-7-yl)-5,6-dihydropyridine-1(2H)-carboxylate;

(231) tert-butyl 4-(2-(3-(methylsulfonyl)phenyl)-5H-pyrrolo[2,3-b]pyrazin-7-yl)-5, 6-dihydropyridine-1(2H)-carboxylate;

(232) (4-(2-(3-(methylsulfonyl)phenyl)-5H-pyrrolo[2,3-b]pyrazin-7-yl)-5, 6-dihydropyridin-1(2H)-yl)(thiophen-2-yl)methanone;

(233) (4-(2-(5-(morpholinomethyl)thiophen-2-yl)-5H-pyrrolo[2,3-b]pyrazin-7-yl)-5, 6-dihydropyridin-1(2H)-yl)(thiophen-2-yl)methanone;

(234) tert-butyl 4-(2-(5-(morpholinomethyl)thiophen-2-yl)-5H-pyrrolo[2,3-b]pyrazin-7-yl)-5, 6-dihydropyridine-1(2H)-carboxylate;

(235) 4-(5-(3,4-dimethoxyphenyl)-1H-pyrrolo[2,3-b]pyridin-3-yl)-N-isopropylpiperidine-1-carboxamide;

(236) tert-butyl 3-(5-(3,4-dimethoxyphenyl)-1H-pyrrolo[2,3-b]pyridin-3-yl)piperidine-1-carboxylate;

(237) 3-(5-(3,4-dimethoxyphenyl)-1H-pyrrolo[2,3-b]pyridin-3-yl)-N-isopropyl-2,5-dihydro-1H-pyrrol-1-carboxamide;

(238) 3-(5-(3,4-dimethoxyphenyl)-1H-pyrrolo[2,3-b]pyridin-3-yl)-N-isopropylpyrrolidine-1-carboxamide;

(239) tert-butyl 4-(5-(3,4-dimethoxyphenyl)-1H-pyrrolo[2,3-b]pyridin-3-yl)-5,6-dihydropyridine-1(2H)-carboxylate;

(240) tert-butyl 4-(5-(3-acetamidophenyl)-1H-pyrrolo[2,3-b]pyridin-3-yl)-5,6-dihydropyridine-1(2H)-carboxylate;

(241) tert-butyl 4-(5-(4-acetamidophenyl)-1H-pyrrolo[2,3-b]pyridin-3-yl)-5,6-dihydropyridine-1(2H)-carboxylate;

(242) tert-butyl 4-(5-(3-prop oxyphenyl)-1H-pyrrolo[2,3-b]pyridin-3-yl)-5, 6-dihydropyridine-1(2H)-carboxylate;

(243) tert-butyl 4-(5-(4-propoxyphenyl)-1H-pyrrolo[2,3-b]pyridin-3-yl)-5, 6-dihydropyridine-1(2H)-carboxylate;

(244) tert-butyl 4-(5-(2-methoxyphenyl)-1H-pyrrolo[2,3-b]pyridin-3-yl)-5, 6-dihydropyridine-1(2H)-carboxylate;

(245) tert-butyl 5-(5-(3,4-dimethoxyphenyl)-1H-pyrrolo[2,3-b]pyridin-3-yl)-3,4-dihydropyridine-1(2H)-carboxylate;

(246) N-cyclopentyl-2-(4-(5-(3,4-dimethoxyphenyl)-1H-pyrrolo[2,3-b]pyridin-3-yl)phenyl)acetamide 2,2,2-trifluoroacetate;

(247) 2-(4-(5-(5-(morpholinomethyl)thiophen-2-yl)-1H-pyrrolo[2,3-b]pyridin-3-yl)phenyl)acetic acid;

(248) N-cyclopentyl-2-(4-(5-(5-(morpholinomethyl)thiophen-2-yl)-1H-pyrrolo[2,3-b]pyridin-3-yl)phenyl)acetamide 2,2,2-trifluoroacetate;

(249) N-cyclopentyl-2-(4-(5-(5-(morpholine-4-carbonyl)thiophen-2-yl)-1H-pyrrolo[2,3-b]pyridin-3-yl)phenyl)acetamide; and (250) (4-(5-(4-(morpholinomethyl)phenylamino)-1H-pyrrolo[2,3-b]pyridin-3-yl)-5,6-dihydropyridin-1(2H)-yl)(thiophen-2-yl)methanone.

A 7-azaindole or 4,7-diazaindole derivative according to the present invention may exist as a pharmaceutically acceptable salt. Preferably, the pharmaceutically acceptable salt of the inventive compound may be a salt formed with an inorganic or organic acid. Examples of the inorganic acid include hydrochloric acid, sulfuric acid, nitric acid, phosphoric acid, perchloric acid, bromic acid, and the like. Also, examples of the organic acid include acetic acid, methansulfonic acid, ethansulfonic acid, p-toluensulfonic acid, fumaric acid, maleic acid, malonic acid, phthalic acid, succinic acid, lactic acid, citric acid, gluconic acid, tartaric acid, salicylic acid, malic acid, oxalic acid, benzoic acid, embonic acid, aspartic acid, glutamic acid, and the like. Examples of organic bases which can be used for preparing an organic base addition salt include tris(hydroxymethyl) methylamine, dicyclohexylamine, and the like. Examples of amino acids which can be used for preparing an amino acid addition salt include natural amino acids such as alanine, glycine, and the like.

Said salts may be prepared by conventional methods known in the art, e.g., dissolving the compound of formula (I) in a water-miscible solvent such as methanol, ethanol, acetone, 1,4-dioxane, adding with a free acid or free base thereto, and subjecting the mixture to crystallization.

Also, the compounds of the present invention may have asymmetric carbon centers and, thus, may exist as R- or S-isomer, racemic mixtures, individual enantiomers or mixtures thereof, and individual diastereomers or mixtures thereof. Such stereoisomers and mixtures thereof are all included within the scope of the present invention.

Additionally, solvates and hydrates of the 7-azaindole or 4,7-diazaindole derivative of formula (I) are also included within the scope of the present invention. Such solvates and hydrate may be prepared by conventional methods known in the art. Preferably, the solvates and hydrates may be non-toxic and water-soluble, and form 1 to 5 bonds with water or alcohol-based solvent (particularly, ethanol and the like).

Meanwhile, the present invention provides a pharmaceutical composition for the prevention or treatment of cancer, comprising a compound selected from the group consisting of the 7-azaindole or 4,7-diazaindole derivative of formula (I), and a pharmaceutically acceptable salt, a hydrate and a solvate thereof Examples of said cancer include colorectal cancer, breast cancer, CNS cancer, colon cancer, non-small cell lung cancer, kidney cancer, prostate cancer, ovarian cancer, uterus cancer, stomach cancer, liver cancer, skin cancer, lung cancer, brain cancer, bladder cancer, esophageal cancer, pancreatic cancer, thyroid cancer, head and neck cancer, squamous cell carcinoma, osteosarcoma, B-cell or T-cell lymphoma, acute or chronic leukemia and multiple myeloma.

In addition, since the inventive compound of formula (I) can inhibit IKKε and TBK1, it can also be used for the prevention or treatment of diseases associated with IKKε and TBK1 protein activation, e.g., chronic inflammation, and the like.

A pharmaceutical composition of the present invention may comprise one or more conventional non-toxic pharmaceutically acceptable additives as effective components, in addition to 7-azaindole or 4,7-diazaindole derivative of formula (I), or a pharmaceutically acceptable salt, a hydrate or a solvate thereof Examples of acceptable additives for the pharmaceutical composition of the present invention include sweeteners, binders, solubilizing agents, dissolution aids, wetting agents, emulsifiers, isotonic agents, adsorbents, disintegrants, anti-oxidants, preservatives, lubricants, fillers, fragrances, and the like, e.g., lactose, dextrose, sucrose, mannitol, sorbitol, cellulose, glycine, silica, talc, stearic acid, stearin, magnesium stearate, magnesium aluminum silicate, starch, gelatin, tragacanth gum, alginic acid, sodium alginate, methylcellulose, sodium carboxymethyl cellulose, agar, water, ethanol, polyethylene glycol, polyvinyl pyrrolidone, sodium chloride, calcium chloride, orange essence, strawberry essence, vanilla flavor, etc.

A pharmaceutical composition of the present invention may be prepared as an oral dosage form such as a tablet, a pill, powders, a capsule, a syrup or an emulsion or a parenteral dosage form for intramuscular, intravenous or subcutaneous administration. Preferably, the pharmaceutical composition may be prepared in an oral dosage form.

In the case where the pharmaceutical composition of the present invention is prepared as an oral dosage form, the inventive pharmaceutical composition may comprise additives such as cellulose, calcium silicate, corn starch, lactose, sucrose, dextrose, calcium phosphate, stearic acid, magnesium stearate, calcium stearate, gelatin, talc, a surfactant, a suspension agent, an emulsifier, a diluent, etc.

Also, in the case where the pharmaceutical composition of the present invention is prepared as an injectable dosage form, the inventive pharmaceutical composition may comprise additives such as water, brine, a glucose aqueous solution, an analog glucose aqueous solution, alcohol, glycol, ether, oil, a fatty acid, a fatty acid ester, a glyceride, a surfactant, a suspension agent, an emulsifier, etc.

Preferably, a proposed daily dose of the compound in accordance with the present invention for an adult patient (of approximately 70 kg body weight) may be in the range of 0.1 to 2,000 mg/day. The compound in accordance with the present invention may be administered in a single dose or in divided doses per day. It is understood that the daily dose should be determined in light of various relevant factors including health status, age, weight and sex of a subject to be treated, administration route and disease severity. Thus, the amount of proposed daily dose is not limited to the above-described range.

Hereinafter, the present invention is described in detail with reference to the following examples. However, these examples are merely presented to exemplify the present invention, and the scope of the present invention is not limited thereto.

The symbols and conventions used for describing the processes, schemes and examples of the present invention are consistert with those used in contemporary scientific literature, for example, the Journal of the American Chemical Society or the Journal of Biological Chemistry. Unless otherwise noted, all starting materials were obtained from commercial suppliers and used without further purification.

The following are definitions of abbreviations that are used in the examples.

Hz (Hertz)
TLC (thin layer chromatography)
$T_r$ (retertion time) RP (reverse phase)
MeOH (methanol) i-PrOH (isopropanol)
TFA (trifluoroacetic acid) TEA (triethylamine)
EtOH (ethanol) THF (tetrahydrofuran)
DMSO (dimethylsulfoxide)
EtOAc (ethyl acetate)
DCM (dichloromethane) HOAc (acetic acid)
DMF (N,N-dimethylformamide) Ac (acetyl)
HOBt (1-hydroxybenzotriazole) Bn (benzyl)
Boc (tert-butyloxy carbonyl)
mCPBA (meta-chloroperbenzoic acid)
FMOC (9-fluorenylmethoxycarbonyl)
DCC (dicyclohexylcarbodiimide)
Cbz (benzyloxycarbonyl)
NMM (N-methyl morpholine)
HOAt (1-hydroxy-7-azabenzotriazole)
TBAF (tetra-n-butylammonium fluoride)
THP (tetrahydro-2H-pyran-2-yl)
DMAP (4-dimethylaminopyridine)
HPLC (high pressure liquid chromatography)
BOP (bis(2-oxo-3-oxazolidinyl)phosphinic chloride);
EDCI (1-ethyl-3-[3-dimethylaminopropyl]carbodiimide hydrochloride)

HBTU (O-Benzotriazole-1-yl-N,N,N',N'-tetramethyluronium hexafluorophosphate)
AIBN (2,2'-azobis(2-methylpropionitrile))
MeI (iodomethane)
DIPEA (diisopropylethylamine)
NaSMe (sodium thiomethoxide)
DAST (diethylaminosulfur trifluoride)
DMAc (dimethylacetamide)
DME (dimethyl ether)
ACN (acetonitrile)

While the present invention has been described with respect to specific embodiments, it should be recognized that various modifications and changes may be made to the invention by those skilled in the art which also fall within the scope of the invention as defined by the appended claims.

All references to ether are to diethyl ether; brine refers to a saturated aqueous solution of NaCl. Unless otherwise indicated, all temperatures are expressed in ° C. (degrees Centigrade). All reactions were conducted under an inert atmosphere at room temperature unless otherwise noted, and all solvents are of the highest available purity unless otherwise indicated.

Microwave reaction was conducted with a Biotage Initiator™ microwave synthesizer.

$^1$H NMR spectra were recorded on either Bruker Ultrashield 400 plus spectrometer. Chemical shifts were expressed in parts per million (ppm, δ units). Coupling constants are in units of hertz (Hz). Splitting patterns describe apparent multiplicities and are designated as s (singlet), d (doublet), t (triplet), q (quartet), quint (quintet), m (multiplet), br (broad).

Mass spectra were obtained with either Quattro LC Triple Quadruple Tandem Mass Spectrometer (ESI: Micromass) or 1200 LC/MSD (ESI: Agilent).

For preparative HPLC, ca 100 mg of a product was injected in 1 mL of DMSO onto a SunFire™ Prep C18 OBD 5 μm 19×100 mm Column with a 10 min gradient from 10% CH$_3$CN to 90% CH$_3$CN in H$_2$O (purification systems from Gilson, Inc). Flash chromatography was carried out using Merck silica gel 60 (230-400 mesh). Biotage SP1™ FLASH Purification System and Biotage Isolera™ FLASH Purification System were used for normal phase column chromatography with ethyl acetate and hexane. Most of the reactions were monitored by thin-layer chromatography on 0.25 mm E. Merck silica gel plates (60F-254), visualized with UV light using a 5% ethanolic phosphomolybdic acid or p-anisaldehyde solution.

The following synthetic schemes are merely illustrative of the methods by which the compounds of the invention may be prepared and are not intended to limit the scope of the invention as defined in the appended claims.

PREPARATION EXAMPLE 1

Preparation of 3-(1,2,3,6-tetrahydropyridin-4-yl)-1H-pyrrolo[2,3-b]pyridine (compound 5)

Scheme 1. Total scheme for compound 5

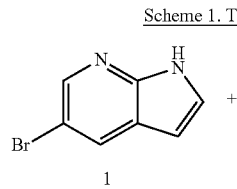

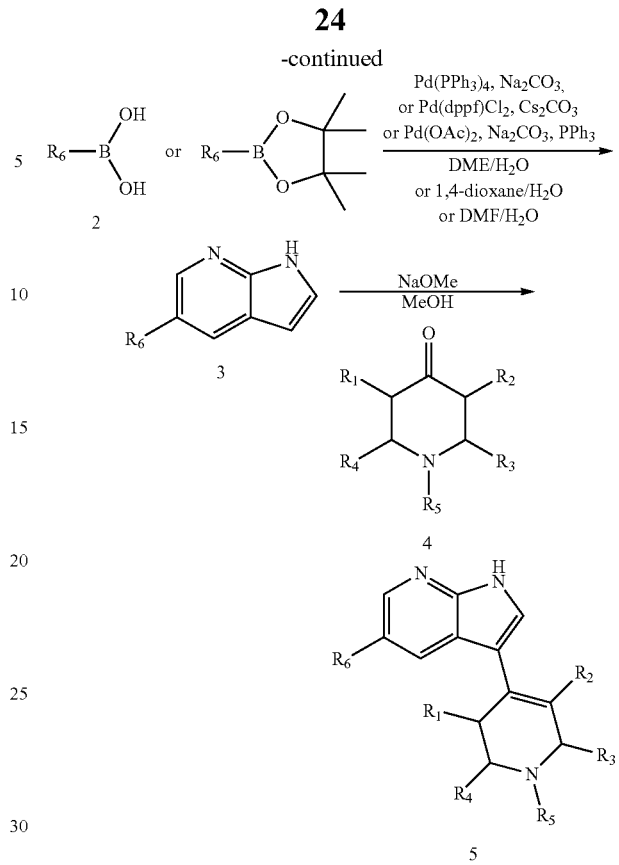

wherein,
each of $R_1$ to $R_5$ is H, methyl or ethyl, and $R_6$ is aryl or heteroaryl.

As shown in the reaction scheme, aryl or heteroaryl is introduced to the 5$^{th}$ position of azaindole via a Suzuki-coupling reaction, and introducing tetrahydropyridine to the 3$^{rd}$ position of azaindole to give the compound of formula (V).

EXAMPLE 1

4-((5-(3-(1-Methyl-1,2,3,6-tetrahydropyridin-4-yl)-1H-pyrrolo[2,3-b]pyridin-5-yl)thiophen-2-yl)methyl)morpholine Step 1: Preparation of 4-((5-(1H-pyrrolo[2,3-b]pyridin-5-yl)thiophen-2-yl)methyl)morpholine (7)

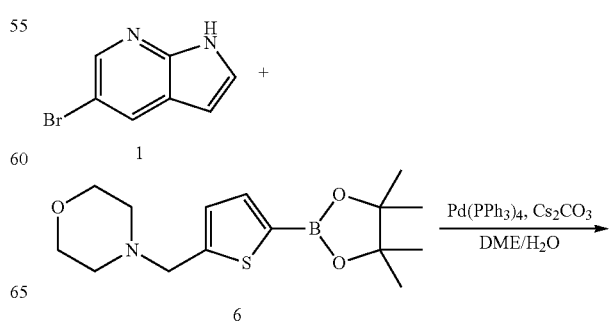

-continued

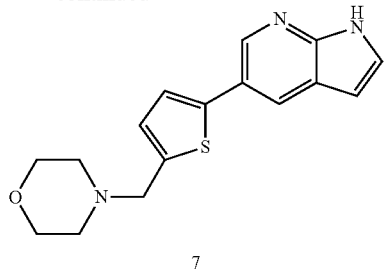

7

To a solution of DME: H₂O=4:1(v:v) (20 mL) was added 5-bromo-1H-pyrrolo[2,3-b]pyridine (1.5 g, 7.61 mmol), cesium carbonate (7.44 g, 22.84 mmol), 4-((5-(4,4,5,5-tetramethyl-1,3,2-dioxaborolan-2-yl)thiophen-2-yl)methyl)morpholine (2.82 g, 9.14 mmol) and palladium tetrakis (0.440 g, 0.381 mmol). The reaction mixture was stirred at 130° C. for 12 hours. The resulting mixture was diluted with H₂O and extracted with EtOAc. The organic layer was dried over anhydrous Na₂SO₄, filtered and concentrated in vacuo. The residue in SiO₂ phase was purified by silica chromatography to give the title compound (1.5 g, 5.01 mmol, 65% yield).

Step 2: Preparation of 4-((5-(1H-pyrrolo[2,3-b]pyridin-5-yl)thiophen-2-yl)methyl)morpholine (7)

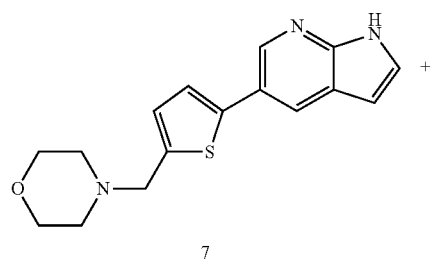

7

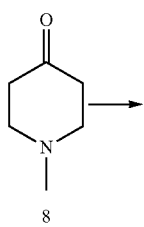

8

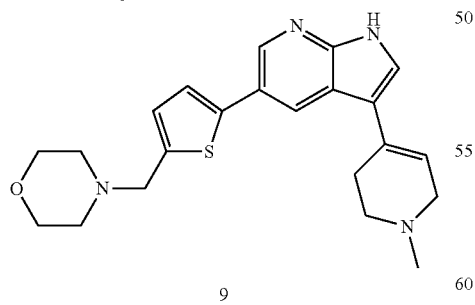

9

4-((5-(1H-pyrrolo[2,3-b]pyridin-5-yl)thiophen-2-yl)methyl)morpholine (0.10 g, 0.334 mmol), sodium methanolate (0.722 g, 3.34 mmol) and 1-methylpiperidin-4-one (0.113 g, 1.002 mmol) were added to MeOH (5 mL) The reaction mixture was stirred at 120° C. for 12 hours. The resulting mixture was diluted with H₂O and extracted with dichloromethane. The organic layer was dried over anhydrous Na₂SO₄, filtered and concentrated in vacuo. The residue in SiO₂ phase was purified by silica chromatography to give the title compound (0.02 g, 0.051 mmol, 15% yield).

¹H NMR (400 MHz, CDCl₃) δ 10.62 (br s, 1H), 8.59 (s, 1H), 8.34 (s, 1H), 7.34 (s, 1H), 7.17 (s, 1H), 6.94 (s, 1H), 6.21 (t, J=7.4 Hz, 1H), 3.79-3.75 (m, 6H), 3.23-3.22 (m, 2H), 2.76-2.73 (m, 2H), 2.65 (br s, 2H), 2.59 (br s, 4H), 2.19 (s, 3H); [M+H]⁺ 395.

EXAMPLE 2

5-(3,4-Dimethoxyphenyl)-3-(1-methyl-1,2,3,6-tetrahydropyridin-4-yl)-1H-pyrrolo[2,3-b]pyridine

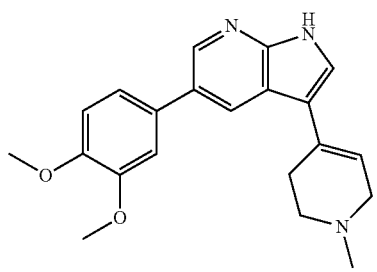 [SMILES: COc1ccc(-c2cnc3[nH]cc(C4=CCN(C)CC4)c3c2)cc1OC]

¹H NMR (400 MHz, CDCl₃) δ 9.66 (br s, 1H), 8.52 (s, 1H), 8.30 (s, 1H), 7.66 (s, 1H), 7.19-7.17 (m, 1H), 7.14 (s, 1H), 7.03-7.01 (d, J=8.3 Hz, 1H), 6.21 (br s, 1H), 4.01 (s, 3H), 3.97 (s, 3H), 3.26 (br s, 2H), 2.82-2.79 (m, 2H), 2.70 (br s,), 2.51 (s, 3H); [M+H]⁺ 350.

EXAMPLE 3

5-(3,4-Dimethoxyphenyl)-3-(1-ethyl-1,2,3,6-tetrahydropyridin-4-yl)-1H-pyrrolo[2,3-b]pyridine

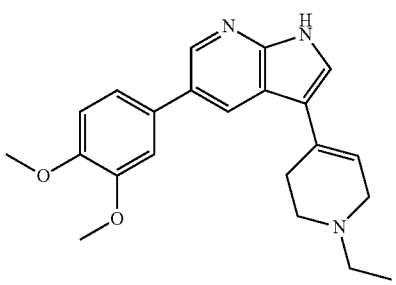 [SMILES: CCN1CC=C(c2c[nH]c3ncc(-c4ccc(OC)c(OC)c4)cc23)CC1]

¹H NMR (400 MHz, CDCl₃) δ 10.15 (br s, 1H), 8.53 (s, 1H), 8.32 (s, 1H), 7.36 (s, 1H), 7.20-7.17 (m, 1H), 7.14 (s, 1H), 7.03-7.01 (d, J=8.3 Hz, 1H), 6.23 (br s, 1H), 4.01 (s, 3H), 3.97 (s, 3H), 3.26 (br s, 2H), 2.80-2.77 (m, 2H), 2.68 (br s,), 2.62-2.57 (q, J=7.18 Hz, 2H), 1.24-1.20 (t, J=7.2 Hz, 3H); [M+H]⁺ 364.

EXAMPLE 4

5-(3,4-Dimethoxyphenyl)-3-(1-propyl-1,2,3,6-tetrahydropyridin-4-yl)-1H-pyrrolo[2,3-b]pyridine

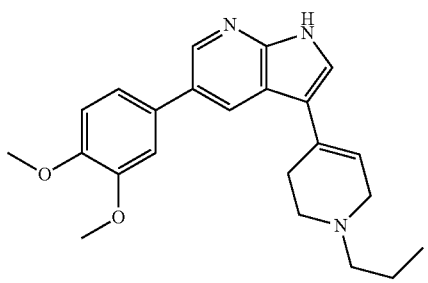 [SMILES: CCCN1CC=C(c2c[nH]c3ncc(-c4ccc(OC)c(OC)c4)cc23)CC1]

$^1$H NMR (400 MHz, CDCl$_3$) δ 9.68 (br s, 1H), 8.52 (s, 1H), 8.32 (s, 1H), 7.34 (s, 1H), 7.19-7.17 (m, 1H), 7.14 (s, 1H), 7.03-7.01 (d, J=8.3 Hz, 1H), 6.23 (br s, 1H), 4.01 (s, 3H), 3.97 (s, 3H), 2.79-2.76 (t, J=5.6 Hz, 2H), 3.26 (br s, 2H), 2.80-2.77 (m, 2H), 1.68-1.62 (q, J=7.6 Hz, 2H), 1.00-0.97 (t, J=7.3 Hz, 3H); [M+H]$^+$ 378.

EXAMPLE 5

5-(3,4-Dimethoxyphenyl)-3-(1-isobutyl-1,2,3,6-tetrahydropyridin-4-yl)-1H-pyrrolo[2,3-b]pyridine

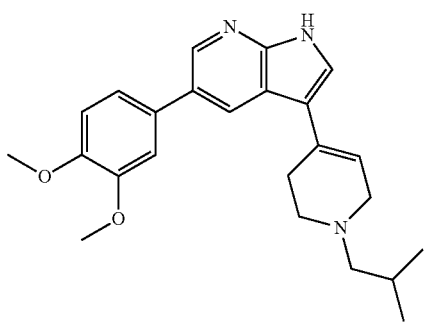 [SMILES: COc1ccc(-c2cnc3[nH]cc(C4=CCN(CC(C)C)CC4)c3c2)cc1OC]

$^1$H NMR (400 MHz, CDCl$_3$) δ 9.77 (br s, 1H), 8.52 (s, 1H), 8.33 (s, 1H), 7.35 (s, 1H), 7.20-7.17 (m, 1H), 7.14 (s, 1H), 7.03-7.01 (d, J=8.3 Hz, 1H), 6.24 (br s, 1H), 4.01 (s, 3H), 3.97 (s, 3H), 3.22 (br s, 2H), 2.74-2.72 (t, J=5.5 Hz, 2H), 2.65 (br s, 2H), 2.29-2.27 (d, J=7.2 Hz, 2H), 1.94-1.91 (m, 1H), 1.00 (s, 3H), 0.98 (s, 3H); [M+H]$^+$ 392.

EXAMPLE 6

4-((5-(3-(1-Ethyl-1,2,3,6-tetrahydropyridin-4-yl)-1H-pyrrolo[2,3-b]pyridin-5-yl)thiophen-2-yl)methyl)morpholine

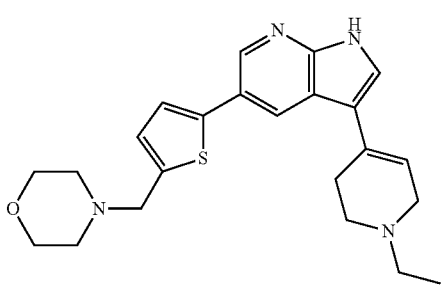 [SMILES: CCN1CC=C(c2c[nH]c3ncc(-c4ccc(CN5CCOCC5)s4)cc23)CC1]

$^1$H NMR (400 MHz, CDCl$_3$) δ 10.70 (br s, 1H), 8.58 (s, 1H), 8.34 (s, 1H), 7.34 (s, 1H), 7.17 (s, 1H), 6.94 (s, 1H), 6.22 (t, J=7.4 Hz, 1H), 3.79-3.75 (m, 6H), 3.27-3.26 (m, 2H), 2.79-2.76 (m, 2H), 2.65 (br s, 2H), 2.59-2.56 (m, 6H), 1.22-1.20 (t, J=7.3 Hz, 3H); [M+H]$^+$ 409.

EXAMPLE 7

4-((5-(3-(1-Propyl-1,2,3,6-tetrahydropyridin-4-yl)-1H-pyrrolo[2,3-b]pyridin-5-yl)thiophen-2-yl)methyl)morpholine

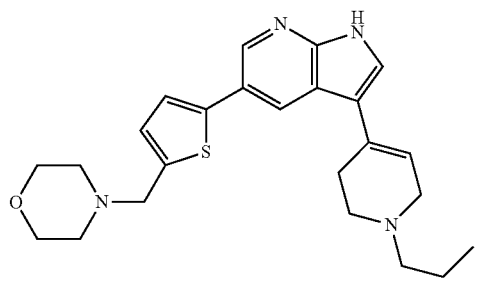 [SMILES: CCCN1CC=C(c2c[nH]c3ncc(-c4ccc(CN5CCOCC5)s4)cc23)CC1]

$^1$H NMR (400 MHz, CDCl$_3$) δ 9.50 (br s, 1H), 8.57 (s, 1H), 8.33 (s, 1H), 7.31 (s, 1H), 7.17 (s, 1H), 6.94 (s, 1H), 6.21 (t, J=7.4 Hz, 1H), 3.80-3.75 (m, 8H), 3.27-3.26 (m, 2H), 2.77-2.76 (m, 2H), 2.64 (br s, 2H), 2.58~2.57 (m, 4H), 2.49-2.47 (m, 2H), 1.01-0.97 (t, J=7.4 z, 3H); [M+H]$^+$ 423.

EXAMPLE 8

1-(4-(5-(5-(Morpholinomethyl)thiophen-2-yl)-1H-pyrrolo[2,3-b]pyridin-3-yl)-3,6-dihydropyridin-1(2H)-yl)ethan-1-one

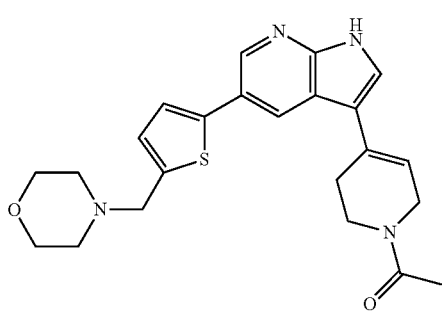 [SMILES: CC(=O)N1CC=C(c2c[nH]c3ncc(-c4ccc(CN5CCOCC5)s4)cc23)CC1]

$^1$H NMR (400 MHz, CDCl$_3$) δ 9.82 (br s, 1H), 8.62 (s, 1H), 8.32 (s, 1H), 7.38 (d, J=17.2 Hz, 1H), 7.19 (s, 1H), 6.95 (s, 1H), 6.22-6.18 (m, 1H), 4.36-4.25 (m, 2H), 3.92 (t, J=5.7 Hz, 2H), 3.80-3.74 (m, 6H), 2.66-2.58 (m, 6H), 2.23 (s, 3H); [M+H]$^+$ 423.

EXAMPLE 9

1-(4-(5-(5-(Morpholinomethyl)thiophen-2-yl)-1H-pyrrolo[2,3-b]pyridin-3-yl)-3,6-dihydropyridin-1(2H)-yl)pentan-1-one

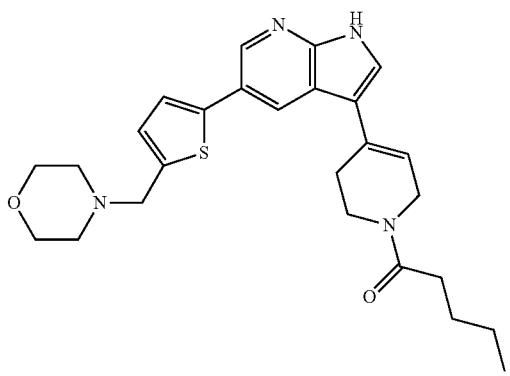 [SMILES: CCCCC(=O)N1CC=C(c2c[nH]c3ncc(-c4ccc(CN5CCOCC5)s4)cc23)CC1]

$^1$H NMR (400 MHz, CDCl$_3$) δ 10.84 (br s, 1H), 8.62 (s, 1H), 8.33 (s, 1H), 7.40 (d, J=16.5 Hz, 1H), 7.20 (s, 1H), 6.96 (s, 1H), 6.22-6.18 (m, 1H), 4.36-4.25 (m, 2H), 3.92 (t, J=5.7 Hz, 2H), 3.80-3.74 (m, 6H), 2.65-2.58 (m, 6H), 2.48-2.41 (m, 2H), 1.72-1.66 (m, 2H), 1.46-1.39 (m, 2H), 1.00 (t, J=7.3 Hz, 3H); [M+H]$^+$ 465.

EXAMPLE 10

3-Methyl-1-(4-(5-(5-(morpholinomethyl)thiophen-2-yl)-1H-pyrrolo[2,3-b]pyridin-3-yl)-3,6-dihydropyridin-1(2H)-yl)butan-1-one $^1$H NMR (400 MHz, CDCl$_3$) δ 10.81 (br s, 1H), 8.61 (s, 1H), 8.33 (s, 1H), 7.40 (d, J=16.5 Hz, 1H), 7.19 (s, 1H), 6.95 (s, 1H), 6.23-6.17 (m, 1H), 4.37-4.26 (m, 2H), 3.93 (t, J=5.7 Hz, 2H), 3.80-3.76 (m, 6H), 2.64-2.58 (m, 6H), 2.35 (m, 1H), 2.25-2.19 (m, 2H), 1.05-0.98 (m, 6H); [M+H]$^+$ 465.

PREPARATION EXAMPLE 2

Preparation of 4-(1H-pyrrolo[2,3-b]pyridin-3-yl)-5,6-dihydropyridine-1(2H)-carboxamide Scheme 2. Total scheme for compound 14

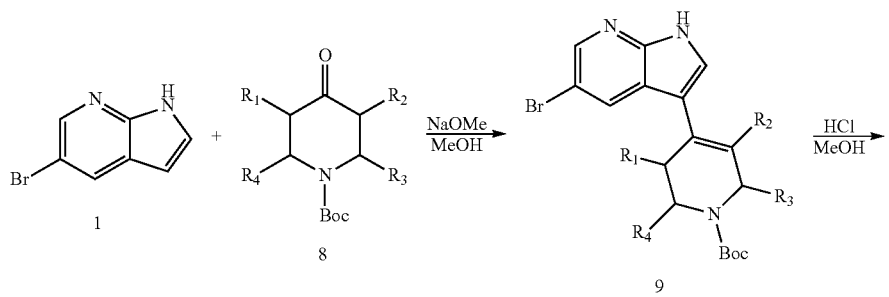

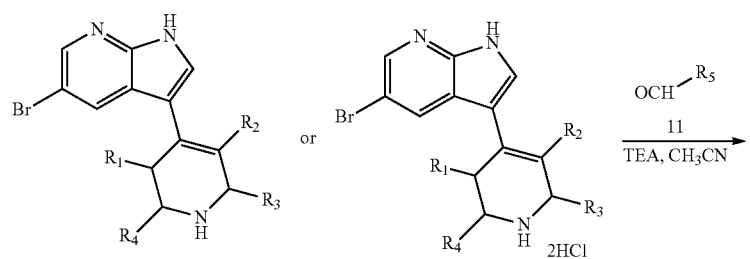

-continued

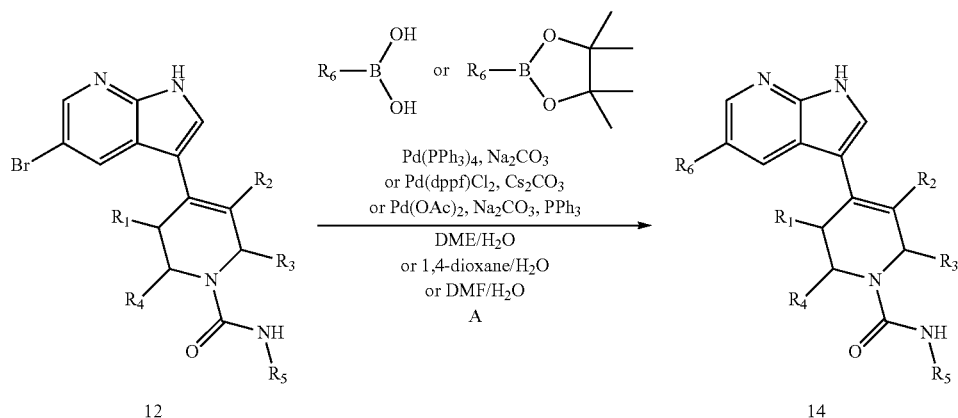

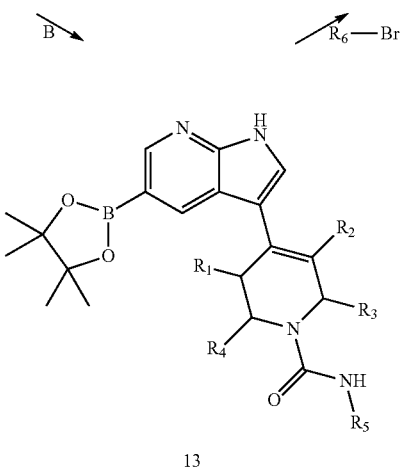

An alternative to Scheme 1, tetrahydropyridine is introduced to $3^{rd}$ position of azaindole, and then Boc is removed from tetrahydropyridine. Subsequently, by using isocyanate, a urea group is introduced and the compound thus obtained is subjected to a Suzuki-coupling reaction at $5^{th}$ position of azaindole to give compound 14.

The compounds of Examples 11 to 134 can be prepared by any of methods A, B or C below.

Method A

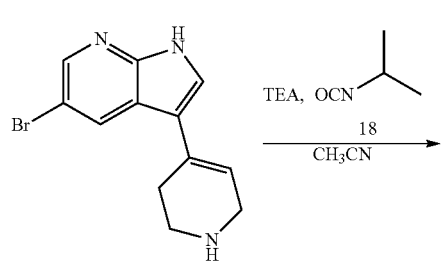

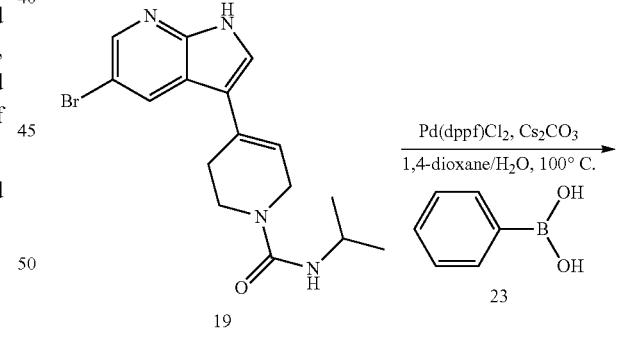

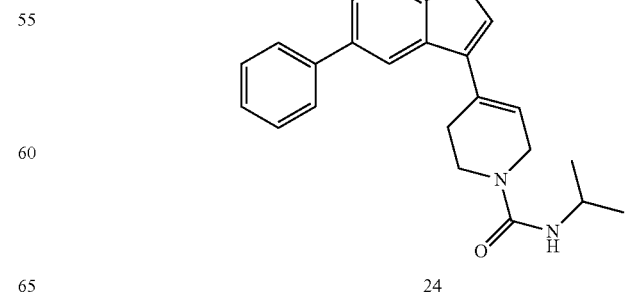

Step 1: Preparation of Compound 19

A mixture of 5-bromo-3-(1,2,3,6-tetrahydropyridin-4-yl)-1H-pyrrolo[2,3-b]pyridinedihydrochloride (360 mg, 1.02 mmol) and CH$_3$CN (6.8 mL) was slowly added with TEA (0.72 mL, 5.13 mmol) and isopropyl isocyanate (0.1 mL, 1.02 mmol) at 0° C. The resulting mixture was heated to room temperature, followed by stirring for 12 hours. The solid thus obtained was washed with water to give the title compound (264 mg, 71%) as a white solid.

[M+H]$^+$ 363.

Step 2: Preparation of Compound 24

A mixture of 4-(5-bromo-1H-pyrrolo[2,3-b]pyridin-3-yl)-N-isopropyl-5,6-dihydropyridine-1(2H)-carboxamide (100 mg, 0.275 mmol), phenylboronic acid (50 mg, 0.413 mmol), Pd(dppf)Cl$_2$ (20 mg, 0.028 mmol) and Cs$_2$CO$_3$ (270 mg, 0.826 mmol) in 1,4-dioxane/H$_2$O (2.2 mL/0.55 mL) was stirred at 100° C. for 12 hours. The resulting mixture was diluted with H$_2$O and extracted with EtOAc. The organic layer was dried over MgSO$_4$, filtered and concentrated in vacuo. The crude product was purified with prep. HPLC system (water, ACN/H$_2$O) to give the title compound (56.8 mg, 57%) as a white solid.

Method B

Step 1: N-isopropyl-4-(5-(4,4,5,5-tetramethyl-1,3,2-dioxaborolan-2-yl)-1H-pyrrolo[2,3-b]pyridin-3-yl)-5,6-dihydropyridine-1(2H)-carboxamide (20)

A mixture of 4-(5-bromo-1H-pyrrolo[2,3-b]pyridin-3-yl)-N-isopropyl-5,6-dihydropyridine-1(2H)-carboxamide (0.5 g, 1.4 mmol), bis(pinacolato)diboron (0.45 g, 1.79 mmol), PdCl$_2$(PPh$_3$)$_2$ (0.097 g, 0.14 mmol) and KOAc (0.54 g, 5.5 mmol) in 1,4-dioxane was stirred at 80° C. for 19 hours, cooled to room temperature and diluted with acetone. The resulting mixture was filtered through a Celite plug and concentrated. The residue was purified by flash chromatography using neutral silica gel and MeOH/DCM to give the title compound (0.29 g, 51%) as a yellow solid.

Step 2

A mixture of N-(4-bromophenyl)tetrahydro-2H-pyran-4-amine (0.06 g, 0.234 mmol), Pd(dppf)Cl$_2$ (0.017 g, 0.023 mmol) and cesium carbonate (0.229 g, 0.703 mmol) was added to a solution of N-isopropyl-4-(5-(4,4,5,5-tetramethyl-1,3,2-dioxaborolan-2-yl)-1H-pyrrolo[2,3-b]pyridin-3-yl)-3,6-dihydropyridine-1(2H)-carboxamide (0.115 g, 0.281 mmol) in 1,4-dioxane (1.301 mL) and water (0.260 mL) at room temperature. The mixture was stirred at 125° C. for 12 hours. The resulting mixture was concentrated in vacuo. The residue was purified by column chromatography (Biotage) and prep. HPLC (Waters) to give N-isopropyl-4-(5-(4-((tetrahydro-2H-pyran-4-yl)amino)phenyl)-1H-pyrrolo[2,3-b]pyridin-3-yl)-3,6-dihydropyridine-1(2H)-carboxamide (0.0091 g, 0.020 mmol, yield: 8.45%) as a brown solid.

Method C

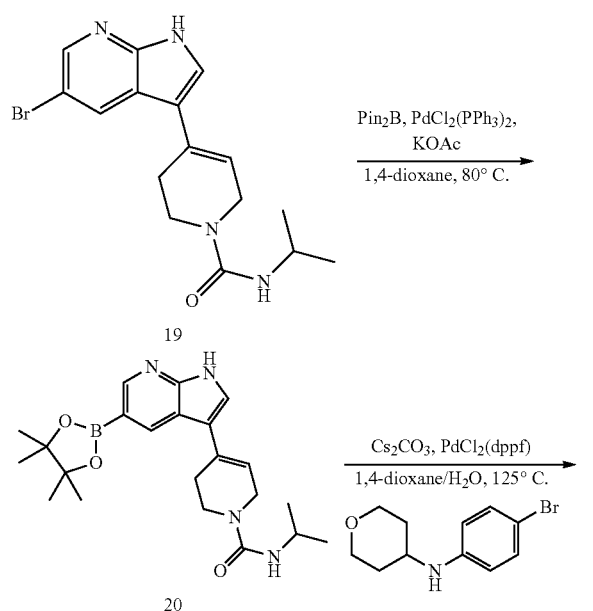

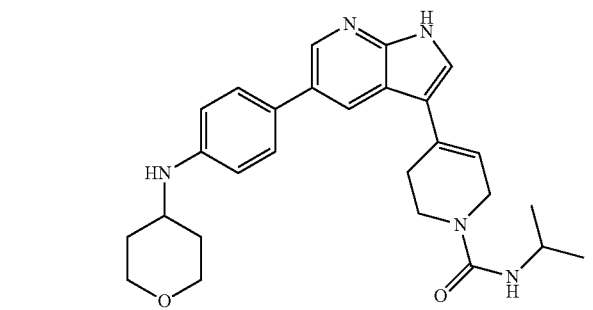

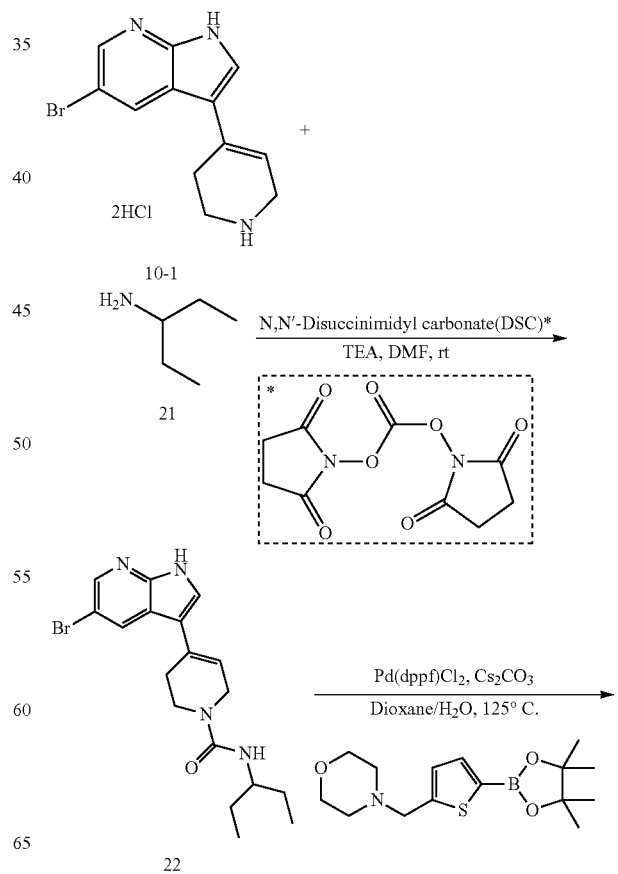

EXAMPLE 11

N-isopropyl-4-(5-phenyl-1H-pyrrolo[2,3-b]pyridin-3-yl)-5,6-dihydropyridine-1(2H)-carboxamide Step 1: Preparation of tert-butyl 4-(5-bromo-1H-pyrrolo[2,3-b]pyridin-3-yl)-5,6-dihydropyridine-1(2H)-carboxylate (16)

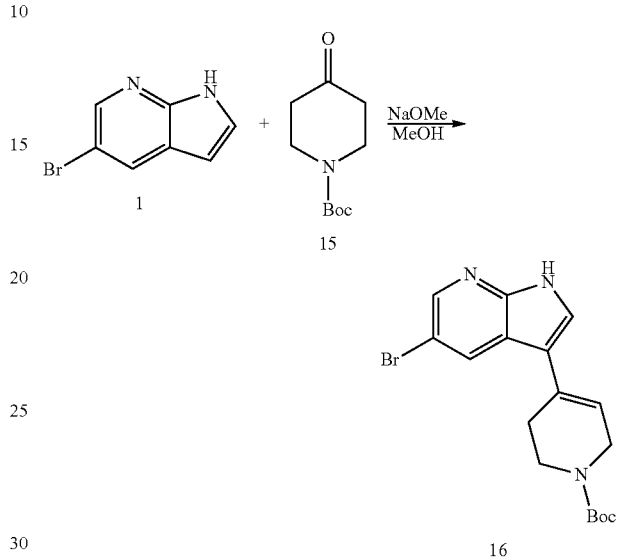

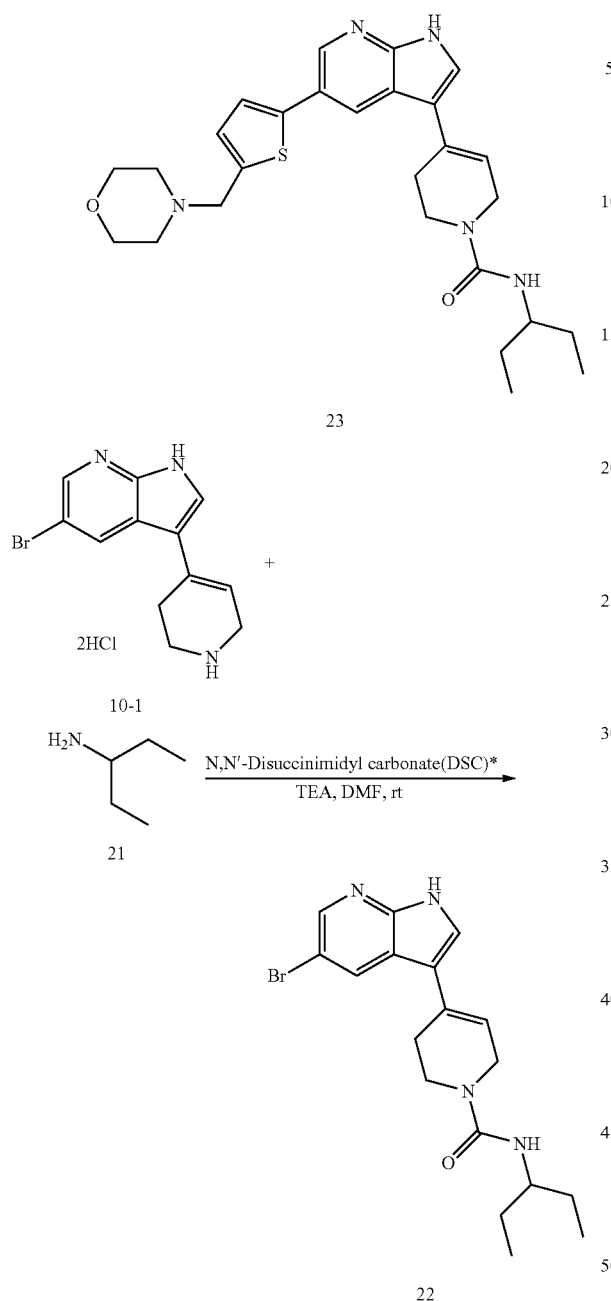

4-(5-Bromo-1H-pyrrolo[2,3-b]pyridin-3-yl)-N-(pentan-3-yl)-5,6-dihydropyridine-1(2H)-carboxamide A mixture of pentane-3-amine (0.086 mL, 0.741 mmol) and bis(2,5-dioxopyrrolidin-1-yl) carbonate (0.190 g, 0.741 mmol) in DMF (1.899 mL) was stirred at room temperature for 30 minutes, and then added with triethylamine (0.199 mL, 1.424 mmol) and 5-bromo-3-(1,2,3,6-tetrahydropyridin-4-yl)-1H-pyrrolo[2,3-b]pyridinehydrochloride (0.2 g, 0.570 mmol). The resulting mixture was stirred at room temperature for 3 hours and extracted to give the title compound (0.2 g, 0.511 mmol, 90% yield) as a white solid.

A solution of 5-bromo-1H-pyrrolo[2,3-b]pyridine (20.0 g, 101.5 mmol, 1.0 eq) and 1-Boc-4-piperidone (40.2 g, 203.0 mmol, 2.0 eq) in MeOH (200 mL) was added with NaOMe (132 mL, 25% MeOH solution). Subsequently, the mixture was heated to 90° C. and stirred for 4 hours at the above temperature. Then, the resulting mixture was added with 1 L of ice water, extracted with EtOAc (2×500 mL), washed with a saturated NaCl solution (2×300 mL), dried over anhydrous Na$_2$SO$_4$ and concentrated to give the crude product. The crude product was crystallized from N-hexane/EtOAc (v/v=10:1) (300 mL) to give the intermediate 16 (28.6 g, 75.6 mmol, 74.4%) as a yellow solid.

$^1$H NMR (400 MHz, CDCl$_3$) δ 9.15 (s, 1H), 8.37-8.36 (d, J=1.84 Hz, 1H), 8.31-8.30 (d, J=1.64 Hz, 1H), 7.31-7.28 (d, J=1.88 Hz, 1H), 6.11 (s, 1H), 4.16-4.15 (d, J=2.4 Hz, 2H), 3.71-3.68 (t, J=5.6 Hz, 2H), 2.55 (s, 2H), 1.53 (s, 9H); MS (m/z): 378.2 (MH$^+$).

Step 2: Preparation of 5-bromo-3-(1,2,3,6-tetrahydropyridin-4-yl)-1H-pyrrolo[2,3-b]pyridine (17)

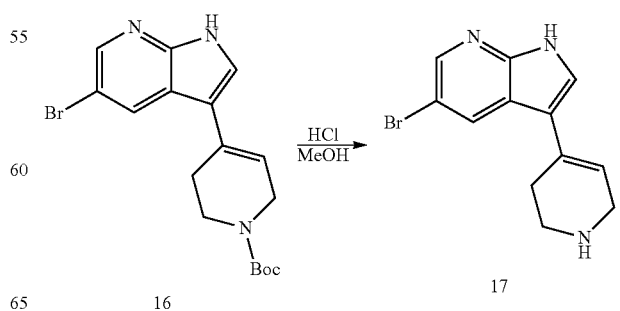

The intermediate 16 (26.8 g, 75.6 mmol, 1.0 eq) was dissolved in an HCl solution (907 mL, 1.25 M HCl in MeOH), which is then stirred at room temperature for 16 hours. Subsequently, the reaction mixture was concentrated under reduced pressure to give the crude product. The crude product was washed with hexane/EtOAc (v/v=1:1) (200 mL), filtered and dried to give the intermediate 5-bromo-3-(1,2,3,6-tetrahydropyridin-4-yl)-1H-pyrrolo[2,3-b]pyridin-edihydrochloride. Then, the intermediate was added with water (2 L) and MeOH (300 mL), adjusted to the pH of about 9 by adding Na$_2$CO$_3$, extracted with EtOAc (2 L×3), dried over anhydrous Na$_2$SO$_4$ and concentrated to give the intermediate 17 (14.5 g, 52.3 mmol, 69.1%) as a yellow solid.

$^1$H NMR (400 MHz, DMSO-d$_6$) δ 11.89 (s, 1H), 8.38-8.35 (d, J=8.8 Hz, 1H), 8.28-8.27 (d, J=2.0 Hz, 1H), 7.56 (s, 1H), 6.19 (s, 1H), 3.40 (m, 2H), 2.92 (s, 2H), 2.36 (s, 2H); MS (m/z): 278.2 (MH$^+$).

Step 3: Preparation of 4-(5-bromo-1H-pyrrolo[2,3-b]pyridin-3-yl)-N-isopropyl-5,6-dihydropyridine-1(2H)-carboxamide (19)

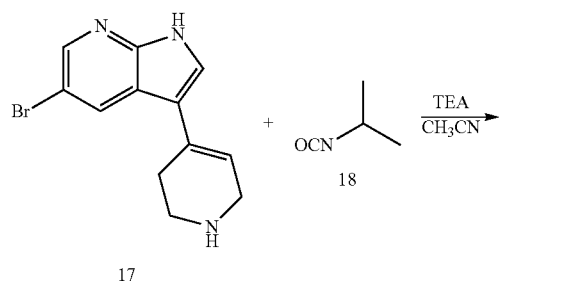

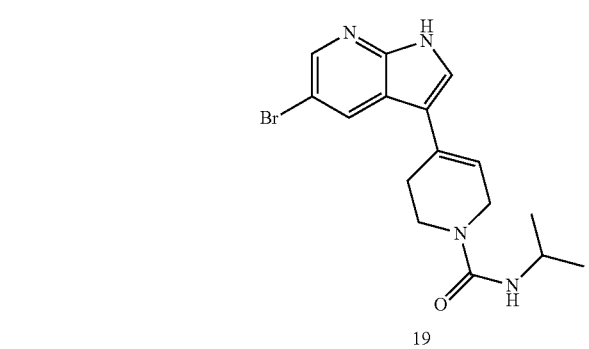

A mixture of 5-bromo-3-(1,2,3,6-tetrahydropyridin-4-yl)-1H-pyrrolo[2,3-b]pyridinedihydrochloride (360 mg, 1.02 mmol) and CH$_3$CN (6.8 mL) was slowly added with TEA (0.72 mL, 5.13 mmol) and isopropyl isocyanate (0.1 mL, 1.02 mmol) at 0° C. The resulting mixture was heated to room temperature and stirred for 12 hours. The solid thus obtained was washed with water to give the title compound (264 mg, 71%) as a white solid.

[M+H]$^+$ 363.

Step 4: Preparation of N-isopropyl-4-(5-phenyl-1H-pyrrolo[2,3-b]pyridin-3-yl)-5,6-dihydropyridine-1(2H)-carboxamide (24)

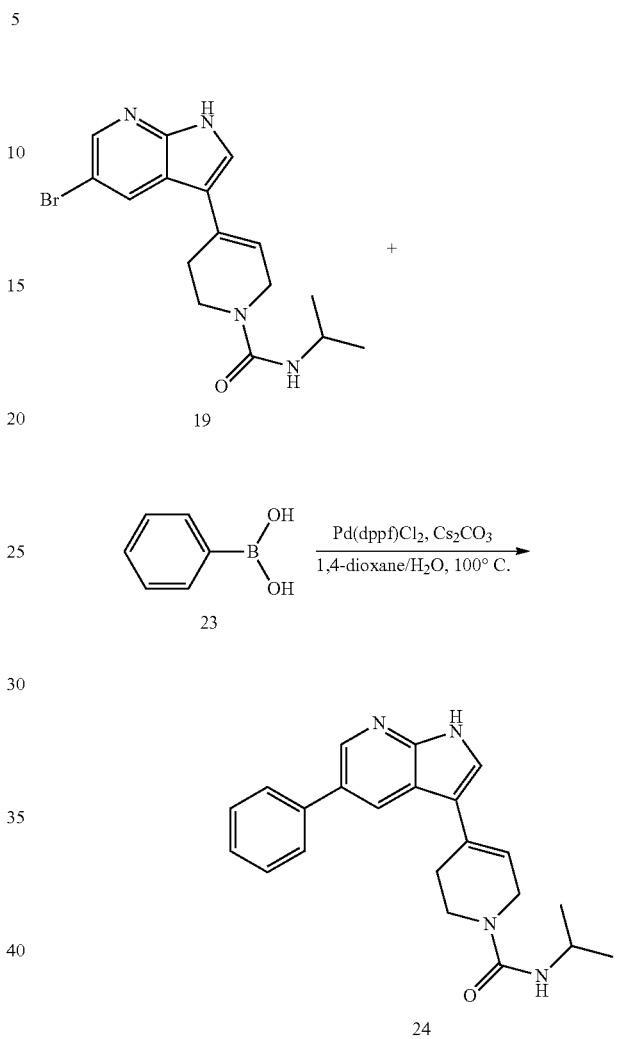

A mixture of 4-(5-bromo-1H-pyrrolo[2,3-b]pyridin-3-yl)-N-isopropyl-5,6-dihydropyridine-1(2H)-carboxamide (100 mg, 0.275 mmol), phenylboronic acid (50 mg, 0.413 mmol), Pd(dppf)Cl$_2$ (20 mg, 0.028 mmol) and Cs$_2$CO$_3$ (270 mg, 0.826 mmol) in 1,4-dioxane/H$_2$O (2.2 mL/0.55 mL) was stirred at 100° C. for 12 hours. The resulting mixture was diluted with H$_2$O and extracted with EtOAc. The organic layer was dried over MgSO$_4$, filtered and concentrated in vacuo. The crude product thus obtained was purified with prep. HPLC system (water, ACN/H$_2$O) to give the title compound (56.8 mg, 57%) as a white solid.

$^1$H NMR (400 MHz, DMSO-d$_6$) δ 11.79 (s, 1H), 8.52 (d, J=2.0 Hz, 1H), 8.39 (d, J=2.0 Hz, 1H), 7.75 (d, J=8.4 Hz, 2H), 7.61 (s, 1H), 7.48 (t, J=7.6 Hz, 2H), 7.37 (t, J=7.4 Hz, 1H), 6.27 (d, J=4.0 Hz, 1H), 6.15 (d, J=7.6 Hz, 1H), 4.02-4.01 (m, 2H), 3.81-3.76 (m, 1H), 3.56-3.52 (m, 2H), 1.09 (s, 3H), 1.07 (s, 3H); [M+H]$^+$ 361.

EXAMPLE 12

N-isopropyl-4-(5-(4-methoxyphenyl)-1H-pyrrolo[2,3-b]pyridin-3-yl)-3,6-dihydropyridine-1(2H)-carboxamide

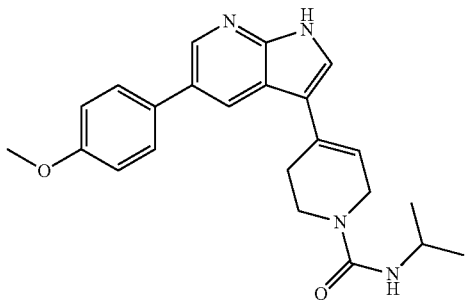 [SMILES: COc1ccc(-c2cnc3[nH]cc(C4=CCN(C(=O)NC(C)C)CC4)c3c2)cc1]

$^1$H NMR (400 MHz, DMSO-d$_6$) δ 11.73 (s, 1H), 8.47 (d, J=2.4 Hz, 1H), 8.32 (d, J=2.4 Hz, 1H), 7.67 (d, J=8.4 Hz, 2H), 7.58 (d, J=2.0 Hz, 1H), 7.04 (d, J=8.8 Hz, 1H), 6.26 (s, 1H), 6.15 (d, J=7.2 Hz, 1H), 4.02-4.01 (m, 2H), 3.81 (s, 3H), 3.54 (t, J=5.6 Hz, 1H), 1.08 (s, 3H), 1.07 (s, 3H); [M+H]$^+$ 391.

EXAMPLE 13

4-(5-(4-Fluorophenyl)-1H-pyrrolo[2,3-b]pyridin-3-yl)-N-isopropyl-3,6-dihydropyridine-1(2H)-carboxamide

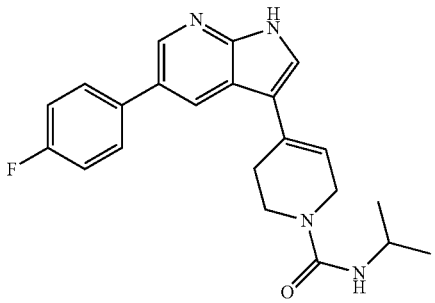 [SMILES: CC(C)NC(=O)N1CC=C(c2c[nH]c3ncc(-c4ccc(F)cc4)cc23)CC1]

$^1$H NMR (400 MHz, DMSO-d$_6$) δ 11.79 (s, 1H), 8.49 (d, J=2.4 Hz, 1H), 8.37 (d, J=2.0 Hz, 1H), 7.81-7.77 (m, 2H), 7.61 (s, 1H), 7.30 (t, J=9.0 Hz, 2H), 6.28 (s, 1H), 6.15 (d, J=7.6 Hz, 1H), 4.02-4.01 (m, 2H), 3.81-3.76 (m, 1H), 3.54 (t, J=6.0 Hz, 2H), 2.50-2.49 (m, 2H), 1.08 (s, 3H), 1.07 (s, 3H); [M+H]$^+$ 379.

EXAMPLE 14

N-isopropyl-4-(5-(3-methoxyphenyl)-1H-pyrrolo[2,3-b]pyridin-3-yl)-3,6-dihydropyridine-1(2H)-carboxamide

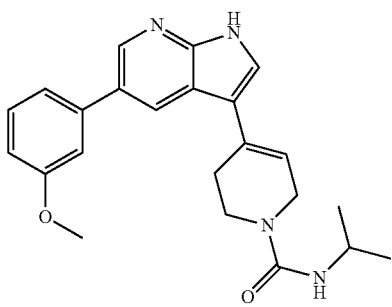 [SMILES: COc1cccc(-c2cnc3[nH]cc(C4=CCN(C(=O)NC(C)C)CC4)c3c2)c1]

$^1$H NMR (400 MHz, DMSO-d$_6$) δ 11.79 (s, 1H), 8.52 (d, J=2.0 Hz, 1H), 8.38 (d, J=2.4 Hz, 1H), 7.61 (s, 1H), 7.39 (t, J=7.8 Hz, 1H), 7.31-7.26 (m, 2H), 6.95-6.93 (m, 1H), 6.27 (s, 1H), 6.16-6.14 (m, 1H), 4.02-4.00 (m, 2H), 3.84 (s, 3H), 3.83-3.76 (m, 1H), 3.53 (t, J=6.2 Hz, 1H), 2.51-2.49 (m, 2H), 1.08 (s, 3H), 1.07 (s, 3H); [M+H]$^+$ 391.

EXAMPLE 15

4-(5-(3-Fluorophenyl)-1H-pyrrolo[2,3-b]pyridin-3-yl)-N-isopropyl-3,6-dihydropyridine-1(2H)-carboxamide

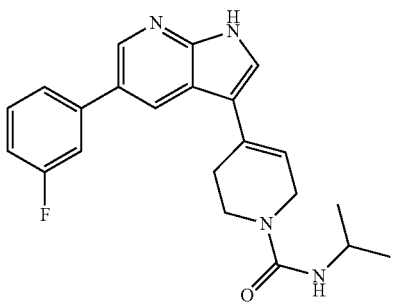 [SMILES: CC(C)NC(=O)N1CC=C(c2c[nH]c3ncc(-c4cccc(F)c4)cc23)CC1]

$^1$H NMR (400 MHz, DMSO-d$_6$) δ 11.82 (br s, 1H), 8.56 (d, J=2.0 Hz, 1H), 8.44 (d, J=2.0 Hz, 1H), 7.66-7.61 (m, 3H), 7.54-7.50 (m, 1H), 7.19-7.17 (m, 1H), 6.31 (br s, 1H), 6.16 (d, J=7.6 Hz, 1H), 4.04-4.00 (m, 2H), 3.81-3.76 (m, 1H), 3.55 (t, J=5.6 Hz, 2H), 2.51-2.49 (m, 2H), 1.09 (s, 3H), 1.07 (s, 3H); [M+H]$^+$ 379.

EXAMPLE 16

N-isopropyl-4-(5-(p-tolyl)-1H-pyrrolo[2,3-b]pyridin-3-yl)-3,6-dihydropyridine-1(2H)-carboxamide

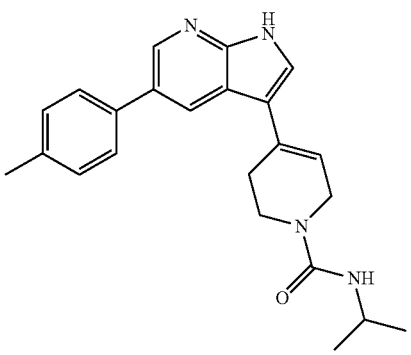 [SMILES: Cc1ccc(-c2cnc3[nH]cc(C4=CCN(C(=O)NC(C)C)CC4)c3c2)cc1]

$^1$H NMR (400 MHz, DMSO-d$_6$) δ 11.75 (s, 1H), 8.49 (s, 1H), 8.36 (s, 1H), 7.64 (d, J=8.0 Hz, 2H), 7.59 (s, 1H), 7.29 (d, J=7.6 Hz, 2H), 6.26 (br s, 1H), 6.15 (d, J=6.4 Hz, 1H), 4.02-4.00 (m, 2H), 3.81-3.75 (m, 1H), 3.54 (t, J=5.2 Hz, 2H), 2.50-2.48 (m, 2H), 2.36 (s, 3H), 1.09 (s, 3H), 1.07 (s, 3H); [M+H]$^+$ 375.

EXAMPLE 17

4-(5-(4-Acetamidophenyl)-1H-pyrrolo[2,3-b]pyridin-3-yl)-N-isopropyl-3,6-dihydropyridine-1(2H)-carboxamide

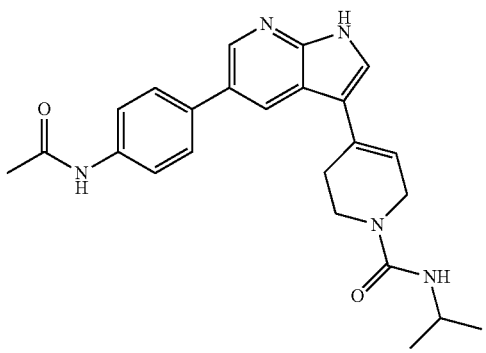 [SMILES: CC(=O)Nc1ccc(-c2cnc3[nH]cc(C4=CCN(C(=O)NC(C)C)CC4)c3c2)cc1]

$^1$H NMR (400 MHz, DMSO-d$_6$) δ 11.79 (br s, 1H), 10.02 (s, 1H), 8.49 (d, J=1.6 Hz, 1H), 8.35 (d, J=2.0 Hz, 1H), 7.68-7.67 (m, 4H), 7.58 (d, J=2.4 Hz, 1H), 6.26 (d, J=2.0 Hz, 1H), 6.15 (d, J=7.6 Hz, 1H), 4.02-4.00 (m, 2H), 3.81-3.76 (m, 1H), 3.54 (t, J=5.6 Hz, 2H), 2.50-2.48 (m, 2H), 2.07 (s, 3H), 1.09 (s, 3H), 1.07 (s, 3H); [M+H]$^+$ 418.

EXAMPLE 18

4-(5-(3,4-Dimethoxyphenyl)-1H-pyrrolo[2,3-b]pyridin-3-yl)-N-isopropyl-5,6-dihydropyridine-1(2H)-carboxamide

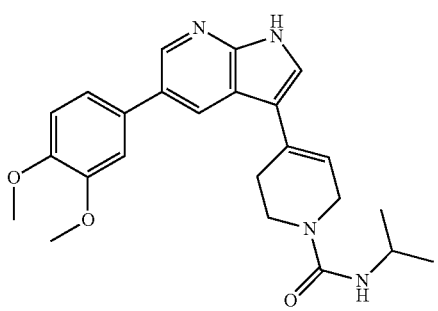 [SMILES: COc1ccc(-c2cnc3[nH]cc(C4=CCN(C(=O)NC(C)C)CC4)c3c2)cc1OC]

$^1$H NMR (400 MHz, DMSO-d$_6$) δ 11.76 (s, 1H), 8.51 (s, 1H), 8.35 (s, 1H), 7.59 (s, 1H), 7.29 (s, 1H), 7.24 (d, J=8.4 Hz, 1H), 7.05 (d, J=8.4 Hz, 1H), 6.28 (br s, 1H), 6.18 (d, J=8.0 Hz, 1H), 4.02 (br s, 2H), 3.88 (s, 3H), 3.84-3.75 (m, 6H), 3.55 (t, J=5.6 Hz, 2H), 1.08 (d, J=6.4 Hz, 6H); [M+H]$^+$ 421.

EXAMPLE 19

4-(5-(3-Acetamidophenyl)-1H-pyrrolo[2,3-b]pyridin-3-yl)-N-isopropyl-3,6-dihydropyridine-1(2H)-carboxamide

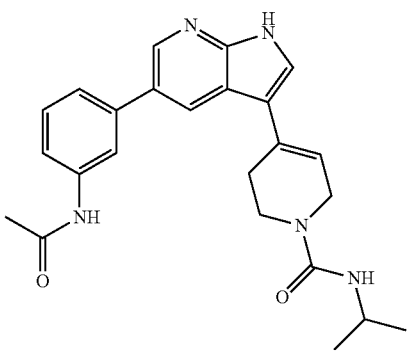 [SMILES: CC(=O)Nc1cccc(-c2cnc3[nH]cc(C4=CCN(C(=O)NC(C)C)CC4)c3c2)c1]

$^1$H NMR (400 MHz, DMSO-d$_6$) δ 11.81 (br s, 1H), 10.04 (s, 1H), 8.46 (d, J=2.0 Hz, 1H), 8.32 (d, J=2.0 Hz, 1H), 7.87 (s, 1H), 7.63-7.62 (m, 2H), 7.41-7.38 (m, 2H), 6.23 (br s, 1H), 6.16 (d, J=8.0 Hz, 1H), 4.02-4.00 (m, 2H), 3.81-3.76 (m, 1H), 3.55 (t, J=5.8 Hz, 2H), 2.52-2.49 (m, 2H), 2.07 (s, 3H), 1.09 (s, 3H), 1.07 (s, 3H); [M+H]$^+$ 418.

EXAMPLE 20

4-(5-(2-Fluoro-4-(morpholinomethyl)phenyl)-1H-pyrrolo[2,3-b]pyridin-3-yl)-N-isopropyl-3,6-dihydropyridine-1(2H)-carboxamide $^1$H NMR (400 MHz, DMSO-d$_6$) δ 11.85 (d, J=2.0 Hz, 1H), 8.38 (t, J=1.8 Hz, 1H), 8.32 (s, 1H), 7.63 (d, J=2.4 Hz, 1H), 7.59 (t, J=8.2 Hz, 1H), 6.20 (s, 1H), 6.15 (d, J=8.0 Hz, 1H), 3.99-3.98 (m, 2H), 3.82-3.74 (m, 1H), 3.60 (t, J=4.4 Hz, 4H), 3.55-3.52 (m, 4H), 2.42-2.40 (m, 4H), 1.08 (s, 3H), 1.06 (s, 3H); [M+H]$^+$ 478.

EXAMPLE 21

4-(5-(2-Fluoro-5-(morpholinomethyl)phenyl)-1H-pyrrolo[2,3-b]pyridin-3-yl)-N-isopropyl-3,6-dihydropyridine-1(2H)-carboxamide

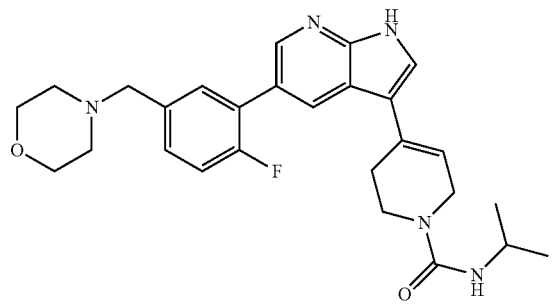 [SMILES: CC(C)NC(=O)N1CC=C(c2c[nH]c3ncc(-c4cc(CN5CCOCC5)ccc4F)cc23)CC1]

$^1$H NMR (400 MHz, DMSO-d$_6$) δ 11.86 (d, J=2.0 Hz, 1H), 8.37 (t, J=1.8 Hz, 1H), 8.32 (s, 1H), 7.63 (d, J=2.8 Hz, 1H), 7.52 (dd, J=8.0, 2.0 Hz, 1H), 7.35-7.26 (m, 2H), 6.20 (s, 1H), 6.15 (d, J=7.6 Hz, 1H), 3.99-3.98 (m, 2H), 3.81-3.76 (m, 1H), 3.58 (t, J=4.4 Hz, 4H), 3.55-3.52 (m, 4H), 2.41-2.38 (m, 4H), 1.08 (s, 3H), 1.06 (s, 3H); [M+H]$^+$ 478.

EXAMPLE 22

4-(5-(4-((4-Ethylpiperazin-1-yl)methyl)phenyl)-1H-pyrrolo[2,3-b]pyridin-3-yl)-N-isopropyl-3,6-dihydropyridine-1(2H)-carboxamide

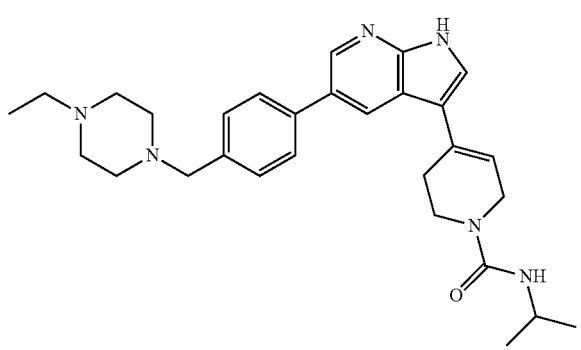 [SMILES: CCN1CCN(Cc2ccc(-c3cnc4[nH]cc(C5=CCN(C(=O)NC(C)C)CC5)c4c3)cc2)CC1]

$^1$H NMR (400 MHz, CDCl$_3$) δ 9.74 (br s, 1H), 8.57 (s, 1H), 8.34 (s, 1H), 7.61 (d, J=7.6 Hz, 2H), 7.47 (d, J=7.6 Hz, 2H), 7.38 (s, 1H), 6.20 (s, 1H), 4.30 (d, J=7.2 Hz, 1H), 4.09 (br s, 2H), 3.72 (t, J=5.6 Hz, 2H), 3.62 (s, 2H), 2.64-2.45 (m, 8H), 0.90-0.86 (m, 4H), 1.23 (m, 6H), 1.14 (t, J=7.0 Hz, 3H); [M+H]$^+$ 487.

EXAMPLE 23

4-(5-(4-((4-Cyclopropylpiperazin-1-yl)methyl)phenyl)-1H-pyrrolo[2,3-b]pyridin-3-yl)-N-isopropyl-3,6-dihydropyridine-1(2H)-carboxamide

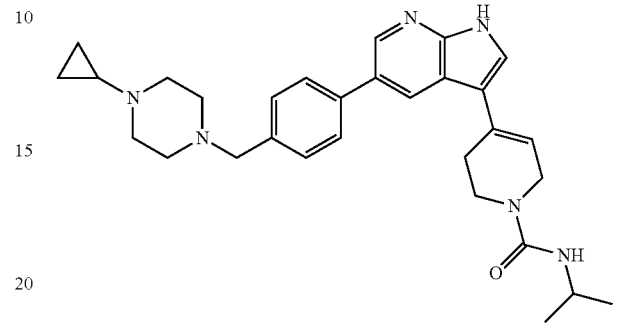

$^1$H NMR (400 MHz, CDCl$_3$) δ 9.94 (br s, 1H), 8.55 (s, 1H), 8.31 (s, 1H), 7.59 (d, J=7.6 Hz, 2H), 7.45 (d, J=7.6 Hz, 2H), 7.36 (s, 1H), 6.18 (s, 1H), 4.30 (d, J=7.2 Hz, 1H), 4.09 (br s, 2H), 3.72 (t, J=5.6 Hz, 2H), 3.62 (s, 2H), 2.72-2.55 (m, 8H), 0.90-0.86 (m, 3H), 1.23 (m, 6H), 0.490-0.455 (m, 4H); [M+H]$^+$ 499.

EXAMPLE 24

4-(5-(3-((4-Ethylpiperazin-1-yl)methyl)phenyl)-1H-pyrrolo[2,3-b]pyridin-3-yl)-N-isopropyl-3,6-dihydropyridine-1(2H)-carboxamide

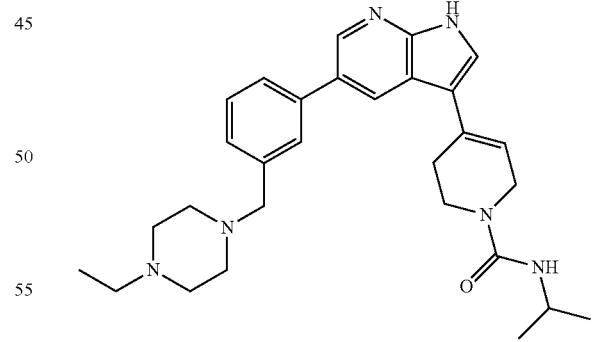

$^1$H NMR (400 MHz, CDCl$_3$) δ 10.74 (br s, 1H), 8.59 (s, 1H), 8.35 (s, 1H), 7.61 (s, 1H), 7.55 (d, J=7.6 Hz, 1H), 7.46 (t, J=7.6 Hz, 1H), 7.40 (s, 1H), 7.38 (d, J=7.2 Hz, 1H), 6.20 (s, 1H), 4.33 (d, J=7.2 Hz, 1H), 4.09 (br s, 2H), 3.73 (t, J=5.6 Hz, 1H), 3.65 (s, 2H), 2.64-2.43 (m, 8H), 1.27-1.21 (m, 4H), 1.23 (m, 6H), 1.13 (t, J=7.0 Hz, 3H); [M+H]$^+$ 487.

EXAMPLE 25

N-isopropyl-4-(5-(6-((4-methylpiperazin-1-yl)methyl)pyridin-3-yl)-1H-pyrrolo[2,3-b]pyridin-3-yl)-3,6-dihydropyridine-1(2H)-carboxamide

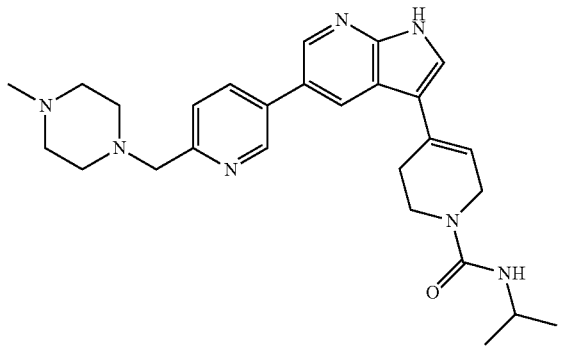 [SMILES: CC(C)NC(=O)N1CC=C(c2c[nH]c3ncc(-c4ccc(CN5CCN(C)CC5)nc4)cc23)CC1]

¹H NMR (400 MHz, CDCl₃) δ 9.71 (br s, 1H), 8.84 (s, 1H), 8.53 (s, 1H), 8.32 (s, 1H), 7.91 (d, J=7.6 Hz, 1H), 7.53 (d, J=8.0 Hz, 1H), 7.41 (s, 1H), 6.18 (s, 1H), 4.29 (d, J=7.2 Hz, 1H), 4.09-4.03 (m, 3H), 3.76 (br s, 2H), 3.72 (t, J=5.6 Hz, 2H), 2.63-2.54 (m, 9H), 2.34 (s, 3H), 1.28 (d, J=6.4 Hz, 6H); [M+H]⁺ 474.

EXAMPLE 26

4-(5-(5-((4-Ethylpiperazin-1-yl)methyl)thiophen-2-yl)-1H-pyrrolo[2,3-b]pyridin-3-yl)-N-isopropyl-3,6-dihydropyridine-1(2H)-carboxamide

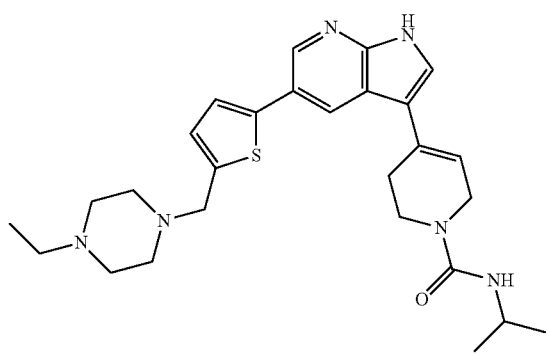 [SMILES: CCN1CCN(Cc2ccc(-c3cnc4[nH]cc(C5=CCN(C(=O)NC(C)C)CC5)c4c3)s2)CC1]

¹H NMR (400 MHz, CDCl₃) δ 9.89 (br s, 1H), 8.57 (s, 1H), 8.28 (s, 1H), 7.33 (s, 1H), 7.15 (d, J=3.6 Hz, 1H), 6.95 (s, 1H), 6.15 (s, 1H), 4.30 (d, J=7.2 Hz, 1H), 4.16 (br s, 2H), 3.71 (t, J=5.6 Hz, 1H), 3.62 (s, 2H), 2.62-2.48 (m, 8H), 1.28-1.21 (m, 4H), 1.23 (m, 6H), 1.14 (t, J=7.0 Hz, 3H); [M+H]⁺ 493.

EXAMPLE 27

N-isopropyl-4-(5-(5-(pyrrolidin-1-ylmethyl)furan-2-yl)-1H-pyrrolo[2,3-b]pyridin-3-yl)-5,6-dihydropyridine-1(2H)-carboxamide

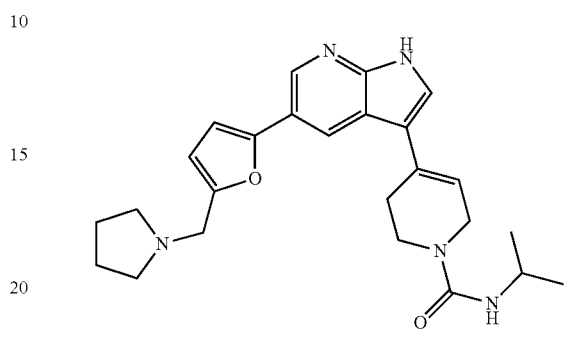

¹H NMR (400 MHz, CDCl₃) δ 9.24 (br s, 1H), 8.57 (d, J=2.0 Hz, 1H), 8.29 (d, J=1.6 Hz, 1H), 7.31 (s, 1H), 7.16 (d, J=3.6 Hz, 1H), 6.93 (d, J=3.6 Hz, 1H), 6.15 (br s, 1H), 4.27 (d, J=7.6 Hz, 1H), 4.07-4.04 (m, 2H), 3.88 (s, 2H), 3.70 (t, J=5.6 Hz, 2H), 2.66 (br s, 4H), 2.59 (s, 2H), 1.85 (br s, 2H), 1.22 (s, 3H), 1.20 (s, 3H); [M+H]⁺ 434.

EXAMPLE 28

N-isopropyl-4-(5-(5-(pyrrolidin-1-ylmethyl)thiophen-2-yl)-1H-pyrrolo[2,3-b]pyridin-3-yl)-5,6-dihydropyridine-1(2H)-carboxamide

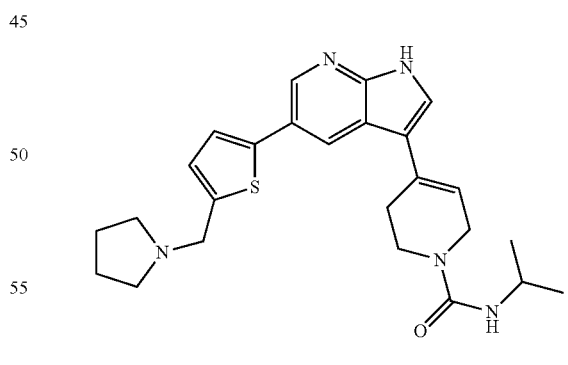

¹H NMR (400 MHz, CDCl₃) δ 9.17 (br s, 1H), 8.57 (d, J=2.0 Hz, 1H), 8.29 (d, J=1.6 Hz, 1H), 7.31 (s, 1H), 7.16 (d, J=3.6 Hz, 1H), 6.93 (d, J=3.6 Hz, 1H), 6.15 (br s, 1H), 4.27 (d, J=7.6 Hz, 1H), 4.07-4.04 (m, 2H), 3.88 (s, 2H), 3.70 (t, J=5.6 Hz, 2H), 2.66 (br s, 4H), 2.59 (s, 2H), 1.85 (br s, 2H), 1.22 (s, 3H), 1.20 (s, 3H); [M+H]⁺ 450.

EXAMPLE 29

N-isopropyl-4-(5-(3-(morpholinomethyl)phenyl)-1H-pyrrolo[2,3-b]pyridin-3-yl)-5,6-dihydropyridine-1(2H)-carboxamide

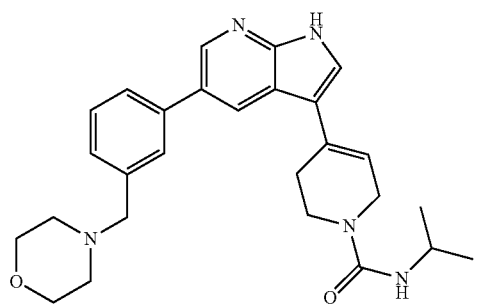 [SMILES: CC(C)NC(=O)N1CC=C(c2c[nH]c3ncc(-c4cccc(CN5CCOCC5)c4)cc23)CC1]

$^1$H NMR (400 MHz, CDCl$_3$) δ 9.58 (br s, 1H), 8.56 (d, J=2.0 Hz, 1H), 8.32 (d, J=2.0 Hz, 1H), 7.59 (s, 1H), 7.53 (d, J=7.8 Hz, 1H), 7.45 (t, J=7.6 Hz, 1H), 7.37-7.36 (m, 2H), 6.19 (s, 1H), 4.27 (d, J=7.6 Hz, 1H), 4.07-4.02 (m, 3H), 3.61 (s, 2H), 2.63 (br s, 2H), 2.52-2.51 (m, 4H), 1.21 (s, 3H), 1.19 (s, 3H); [M+H]$^+$ 460.

EXAMPLE 30

N-isopropyl-4-(5-(4-(morpholinomethyl)phenyl)-1H-pyrrolo[2,3-b]pyridin-3-yl)-5,6-dihydropyridine-1(2H)-carboxamide

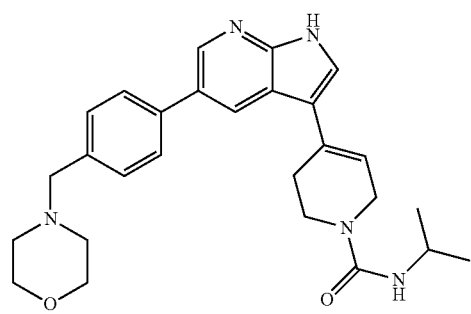 [SMILES: CC(C)NC(=O)N1CC=C(c2c[nH]c3ncc(-c4ccc(CN5CCOCC5)cc4)cc23)CC1]

$^1$H NMR (400 MHz, CDCl$_3$) δ 9.50 (br s, 1H), 8.56 (d, J=2.0 Hz, 1H), 8.31 (d, J=2.0 Hz, 1H), 7.59 (d, J=8.2 Hz, 2H), 7.45 (d, J=8.2 Hz, 2H), 7.35 (d, J=2.4 Hz, 1H), 6.19 (br s, 1H), 4.26 (d, J=7.2 Hz, 1H), 4.07-4.02 (m, 3H), 3.75 (t, J=4.6 Hz, 4H), 3.69 (t, J=5.7 Hz, 2H), 3.58 (s, 2H), 2.62 (br s, 2H), 2.50 (br s, 4H), 1.21 (s, 3H), 1.19 (s, 3H); [M+H]$^+$ 460.

EXAMPLE 31

N-isopropyl-4-(5-(3-(4-methylpiperazine-1-carbonyl)phenyl)-1H-pyrrolo[2,3-b]pyridin-3-yl)-5,6-dihydropyridine-1(2H)-carboxamide

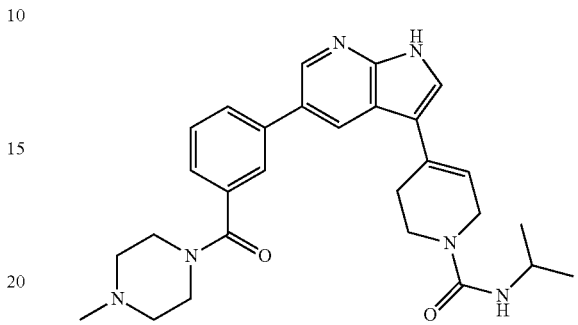

$^1$H NMR (400 MHz, DMSO-d$_6$) δ 11.83 (s, 1H), 8.55 (s, 1H), 8.42 (s, 1H), 7.86 (d, J=6.8 Hz, 1H), 7.72 (s, 1H), 7.63 (s, 1H), 7.55 (t, J=7.6 Hz, 1H), 7.36 (d, J=7.6 Hz, 1H), 6.30 (br s, 1H), 6.16 (d, J=7.6 Hz, 1H), 4.02 (br s, 2H), 3.83-3.74 (m, 1H), 3.70-3.60 (m, 2H), 3.55 (t, J=5.6 Hz, 2H), 3.45-3.35 (m, 2H), 3.32-3.30 (m, 2H), 2.52-2.28 (m, 4H), 2.21 (s, 3H), 1.08 (d, J=6.4 Hz, 6H); [M+H]$^+$ 487.

EXAMPLE 32

N-isopropyl-4-(5-(4-(4-methylpiperazine-1-carbonyl)phenyl)-1H-pyrrolo[2,3-b]pyridin-3-yl)-5,6-dihydropyridine-1(2H)-carboxamide

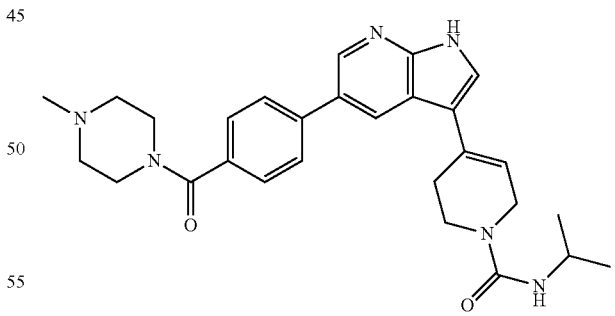

$^1$H NMR (400 MHz, DMSO-d$_6$) δ 11.83 (s, 1H), 8.57 (s, 1H), 8.45 (s, 1H), 7.83 (d, J=8.4 Hz, 2H), 7.62 (s, 1H), 7.49 (d, J=8.4 Hz, 2H), 6.30 (br s, 1H), 6.17 (d, J=7.6 Hz, 1H), 4.02 (br s, 2H), 3.84-3.75 (m, 1H), 3.70-3.59 (m, 2H), 3.55 (t, J=5.6 Hz, 2H), 3.50-3.38 (m, 2H), 3.31 (s, 1H), 2.54-2.52 (m, 1H), 2.40-2.38 (m, 2H), 2.22 (s, 3H), 1.08 (d, J=6.4 Hz, 6H); [M+H]$^+$ 487.

EXAMPLE 33

N-isopropyl-4-(5-(5-((4-methylpiperazin-1-yl)methyl)thiophen-2-yl)-1H-pyrrolo[2,3-b]pyridin-3-yl)-5,6-dihydropyridine-1(2H)-carboxamide

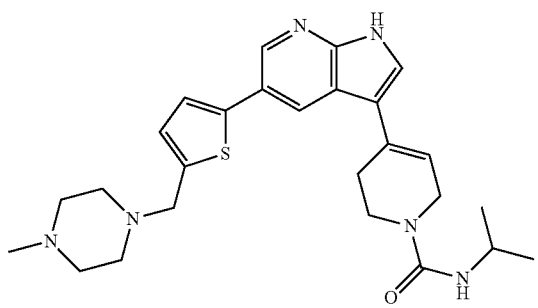 [SMILES: CC(C)NC(=O)N1CC=C(c2c[nH]c3ncc(-c4ccc(CN5CCN(C)CC5)s4)cc23)CC1]

¹H NMR (400 MHz, DMSO-d₆) δ 11.82 (s, 1H), 8.51 (s, 1H), 8.32 (s, 1H), 7.61 (s, 1H), 7.41 (d, J=3.6 Hz, 1H), 6.99 (d, J=3.6 Hz, 1H), 6.22 (br s, 1H), 6.16 (d, J=7.6 Hz, 1H), 4.03 (br s, 2H), 3.84-3.75 (m, 1H), 3.70 (s, 2H), 3.55 (t, J=5.8 Hz, 2H), 2.62-2.55 (m, 2H), 2.31 (s, 3H), 1.08 (d, J=6.4 Hz, 6H); [M+H]⁺ 479.

EXAMPLE 34

N-isopropyl-4-(5-(5-(morpholinomethyl)thiophen-2-yl)-1H-pyrrolo[2,3-b]pyridin-3-yl)-5,6-dihydropyridine-1(2H)-carboxamide

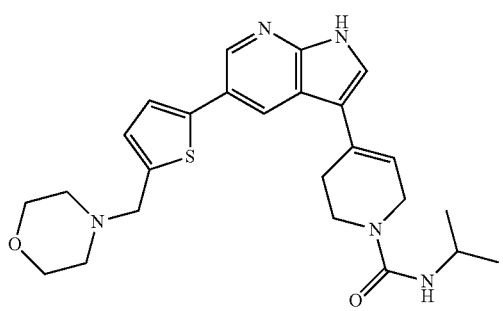 [SMILES: CC(C)NC(=O)N1CC=C(c2c[nH]c3ncc(-c4ccc(CN5CCOCC5)s4)cc23)CC1]

¹H NMR (400 MHz, DMSO-d₆) δ 11.83 (br s, 1H), 8.52 (s, 1H), 8.33 (s, 1H), 7.61 (s, 1H), 7.41 (d, J=3.6 Hz, 1H), 6.99 (d, J=3.6 Hz, 1H), 6.23 (br s, 1H), 6.17 (d, J=7.2 Hz, 1H), 4.03 (br s, 2H), 3.84-3.75 (m, 1H), 3.68 (s, 2H), 3.60 (t, J=4.4 Hz, 4H), 3.55 (t, J=5.6 Hz, 2H), 2.47-2.42 (m, 6H), 1.08 (d, J=6.8 Hz, 6H); [M+H]⁺ 466.

EXAMPLE 35

N-isopropyl-4-(5-(5-((4-methylpiperazin-1-yl)methyl)furan-2-yl)-1H-pyrrolo[2,3-b]pyridin-3-yl)-5,6-dihydropyridine-1(2H)-carboxamide

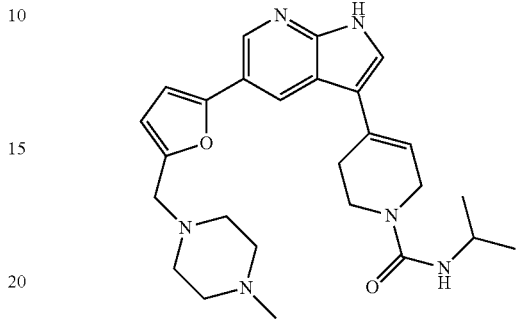

¹H NMR (400 MHz, CDCl₃) δ 9.76 (s, 1H), 8.65 (d, J=2.0 Hz, 1H), 8.37 (d, J=2.0 Hz, 1H), 7.32 (d, J=1.9 Hz, 1H), 6.61 (d, J=3.2 Hz, 1H), 6.34 (d, J=3.3 Hz, 1H), 6.20-6.18 (m, 1H), 4.30 (d, J=7.0 Hz, 1H), 4.09-4.01 (m, 3H), 3.71-3.68 (m, 2H), 2.60 (br s, 11H), 2.36 (s, 3H), 1.21 (d, J=6.5 Hz, 6H); [M+H]⁺ 463.

EXAMPLE 36

N-isopropyl-4-(5-(5-(morpholinomethyl)furan-2-yl)-1H-pyrrolo[2,3-b]pyridin-3-yl)-5,6-dihydropyridine-1(2H)-carboxamide

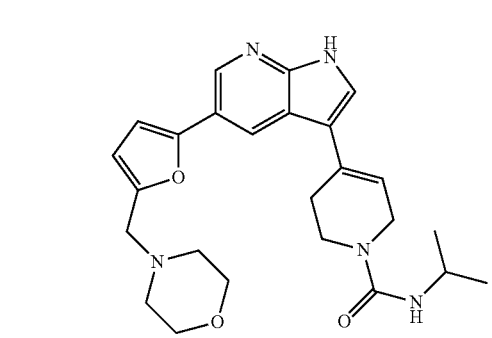 [SMILES: CC(C)NC(=O)N1CC=C(c2c[nH]c3ncc(-c4ccc(CN5CCOCC5)o4)cc23)CC1]

¹H NMR (400 MHz, CDCl₃) δ 10.58 (br s, 1H), 8.63 (d, J=1.8 Hz, 1H), 8.37 (d, J=1.8 Hz, 1H), 7.32 (s, 1H), 6.61 (d, J=3.2 Hz, 1H), 6.35 (d, J=3.2 Hz, 1H), 6.15 (br s, 1H), 4.34 (d, J=7.4 Hz, 1H), 4.08-4.02 (m, 2H), 3.78-3.73 (m, 7H), 3.70-3.65 (m, 4H), 1.87-1.84 (m, 2H), 1.21 (s, 3H), 1.19 (s, 3H); [M+H]⁺ 450.

EXAMPLE 37

N-isopropyl-4-(5-(4-(((tetrahydro-2H-pyran-4-yl)amino)phenyl)-1H-pyrrolo[2,3-b]pyridin-3-yl)-3,6-dihydropyridine-1(2H)-carboxamide

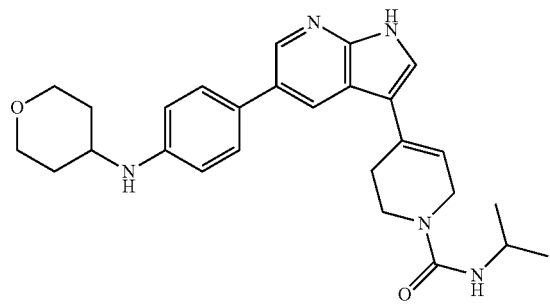 [SMILES: CC(C)NC(=O)N1CC=C(c2c[nH]c3ncc(-c4ccc(NC5CCOCC5)cc4)cc23)CC1]

$^1$H NMR (400 MHz, DMSO-d$_6$) δ 11.64 (s, 1H), 8.41 (d, J=2.0 Hz, 1H), 8.23 (d, J=1.6 Hz, 1H), 7.54 (d, J=2.4 Hz, 1H), 7.45 (d, J=8.4 Hz, 2H), 6.71 (d, J=8.4 Hz, 2H), 6.23 (s, 1H), 6.15 (d, J=7.6 Hz, 1H), 5.64 (d, J=8.8 Hz, 1H), 4.01-4.00 (m, 2H), 3.89-3.86 (m, 2H), 3.81-3.76 (m, 1H), 3.54 (t, J=5.4 Hz, 2H), 3.46-3.40 (m, 2H), 1.92-1.89 (m, 2H), 1.44-1.34 (m, 2H), 1.08 (s, 3H), 1.06 (s, 3H); [M+H]$^+$ 460.

EXAMPLE 38

N-isopropyl-4-(5-(4-(((tetrahydro-2H-pyran-4-yl)oxy)phenyl)-1H-pyrrolo[2,3-b]pyridin-3-yl)-3,6-dihydropyridine-1(2H)-carboxamide

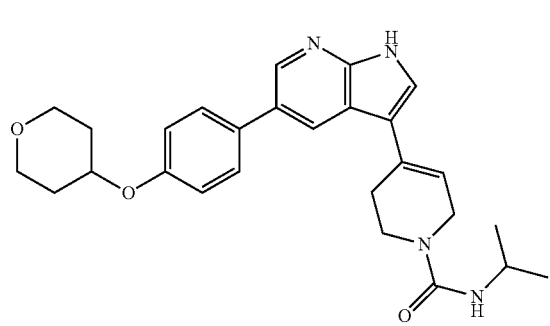 [SMILES: CC(C)NC(=O)N1CC=C(c2c[nH]c3ncc(-c4ccc(OC5CCOCC5)cc4)cc23)CC1]

$^1$H NMR (400 MHz, DMSO-d$_6$) δ 11.74 (s, 1H), 8.46 (d, J=2.4 Hz, 1H), 8.31 (d, J=2.0 Hz, 1H), 7.65 (d, J=8.8 Hz, 2H), 7.58 (s, 1H), 7.08 (d, J=8.8 Hz, 2H), 6.25 (s, 1H), 6.15 (d, J=7.6 Hz, 2H), 4.64-4.62 (m, 1H), 4.01-4.00 (m, 2H), 3.89-3.84 (m, 2H), 3.81-3.76 (m, 1H), 3.55-3.47 (m, 4H), 2.01-1.98 (m, 2H), 1.65-1.56 (m, 2H), 1.08 (s, 3H), 1.06 (s, 3H); [M+H]$^+$ 461.

EXAMPLE 39

4-(5-(7-Amino-1-oxoisoindolidin-4-yl)-1H-pyrrolo[2,3-b]pyridin-3-yl)-N-isopropyl-3,6-dihydropyridine-1(2H)-carboxamide

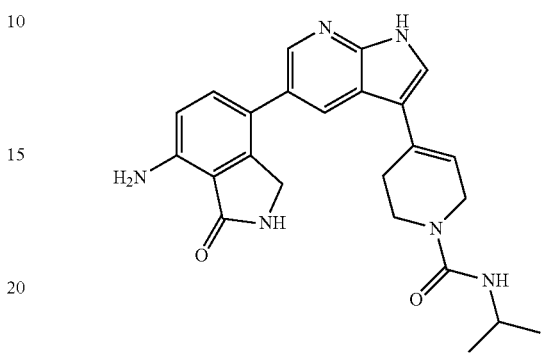

$^1$H NMR (400 MHz, DMSO-d$_6$) δ 11.73 (s, 1H), 8.32 (d, J=2.0 Hz, 1H), 8.24-8.23 (m, 2H), 7.58 (d, J=2.8 Hz, 1H), 7.36 (d, J=8.4 Hz, 1H), 6.70 (d, J=8.0 Hz, 1H), 6.21-6.19 (m, 3H), 6.15 (d, J=8.0 Hz, 1H), 4.42 (s, 2H), 3.99 (d, J=1.6 Hz, 2H), 3.82-3.76 (m, 1H), 3.53 (t, J=5.8 Hz, 2H), 2.50-2.49 (m, 2H), 1.08 (s, 3H), 1.06 (s, 3H); [M+H]±431.

EXAMPLE 40

4-(5-(5-(Morpholinomethyl)thiophen-2-yl)-1H-pyrrolo[2,3-b]pyridin-3-yl)-N-(pentan-3-yl)-3,6-dihydropyridine-1(2H)-carboxamide

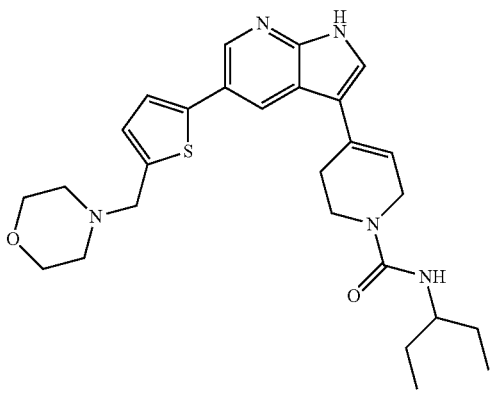 [SMILES: CCC(CC)NC(=O)N1CC=C(c2c[nH]c3ncc(-c4ccc(CN5CCOCC5)s4)cc23)CC1]

$^1$H NMR (400 MHz, DMSO-d$_6$) δ 11.83 (br s, 1H), 8.52 (s, 1H), 8.33 (s, 1H), 7.61 (s, 1H), 7.41 (s, 1H), 6.99 (s, 1H), 6.23 (br s, 1H), 6.03 (d, J=8.8 Hz, 1H), 4.07-4.03 (m, 2H), 3.69-3.66 (m, 2H), 3.59-3.54 (m, 4H), 2.44-2.43 (m, 4H), 1.44-1.36 (m, 4H), 0.82 (d, J=7.4 Hz, 6H); [M+H]$^+$ 494.

EXAMPLE 41

4-(5-(5-((4-Methylpiperazin-1-yl)methyl)thiophen-2-yl)-1H-pyrrolo[2,3-b]pyridin-3-yl)-N-(pentan-3-yl)-3,6-dihydropyridine-1(2H)-carboxamide

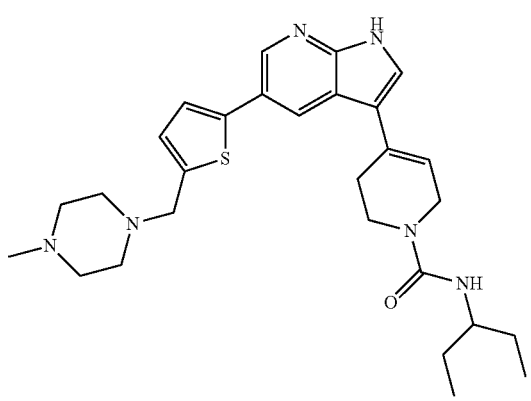

$^1$H NMR (400 MHz, DMSO-d$_6$) δ 11.82 (d, J=2.4 Hz, 1H), 8.51 (d, J=2.0 Hz, 1H), 8.32 (d, J=2.0 Hz, 1H), 7.60 (d, J=2.4 Hz, 1H), 7.39 (d, J=3.6 Hz, 1H), 6.97 (d, J=3.6 Hz, 1H), 6.23 (t, J=1.6 Hz, 1H), 6.02 (d, J=8.4 Hz, 1H), 4.07-4.03 (m, 2H), 3.67 (s, 2H), 3.56 (t, J=5.8 Hz, 1H), 3.48-3.46 (m, 1H), 3.27-3.25 (m, 1H), 2.67-2.66 (m, 1H), 2.48-2.41 (m, 7H), 2.37-2.33 (m, 1H), 2.23-2.15 (m, 3H), 1.46-1.34 (m, 4H), 0.82 (d, J=7.4 Hz, 6H); [M+H]$^+$ 507.

EXAMPLE 42

N-(sec-butyl)-4-(5-(5-((4-methylpiperazin-1-yl)methyl)thiophen-2-yl)-1H-pyrrolo[2,3-b]pyridin-3-yl)-5,6-dihydropyridine-1(2H)-carboxamide

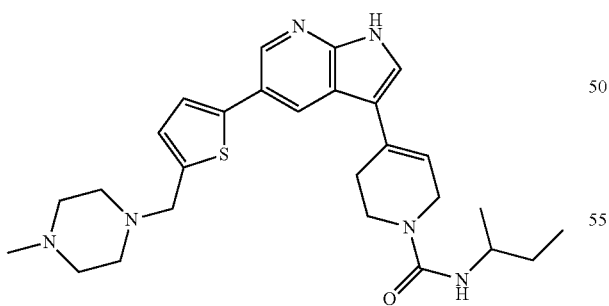

$^1$H NMR (400 MHz, DMSO-d$_6$) δ 11.82 (s, 1H), 8.51 (s, 1H), 8.32 (s, 1H), 7.61 (s, 1H), 7.41 (d, J=3.6 Hz, 1H), 6.99 (d, J=3.6 Hz, 1H), 6.23 (br s, 1H), 6.10 (d, J=8.0 Hz, 1H), 4.09-3.99 (m, 2H), 3.70 (s, 2H), 3.64-3.57 (m, 1H), 3.55 (t, J=6.2 Hz, 2H), 2.62-2.55 (m, 2H), 2.31 (s, 3H), 1.50-1.35 (m, 2H), 1.05 (d, J=6.4 Hz, 3H), 0.84 (t, J=7.2 Hz, 3H); [M+H]$^+$ 493.

EXAMPLE 43

N-(sec-butyl)-4-(5-(5-(morpholinomethyl)thiophen-2-yl)-1H-pyrrolo[2,3-b]pyridin-3-yl)-5,6-dihydropyridine-1(2H)-carboxamide

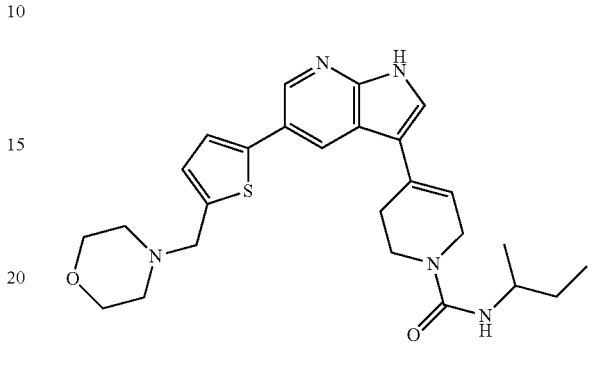

$^1$H NMR (400 MHz, DMSO-d$_6$) δ 11.83 (s, 1H), 8.52 (s, 1H), 8.33 (s, 1H), 7.61 (s, 1H), 7.46-7.41 (m, 1H), 7.01 (br s, 1H), 6.23 (br s, 1H), 6.11 (d, J=8.0 Hz, 1H), 4.09-3.99 (m, 2H), 3.67-3.53 (m, 6H), 2.45-2.41 (m, 2H), 1.50-1.35 (m, 2H), 1.05 (d, J=6.4 Hz, 3H), 0.84 (t, J=7.2 Hz, 3H); [M+H]$^+$ 480.

EXAMPLE 44

N-(sec-butyl)-4-(5-(3,4-dimethoxyphenyl)-1H-pyrrolo[2,3-b]pyridin-3-yl)-5,6-dihydropyridine-1(2H)-carboxamide

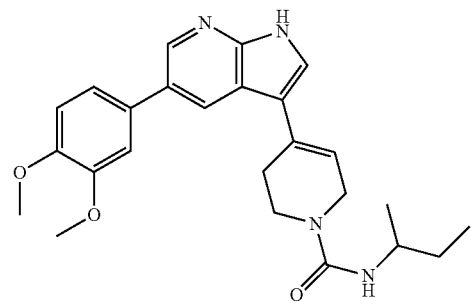 [SMILES: CCC(C)NC(=O)N1CC=C(c2c[nH]c3ncc(-c4ccc(OC)c(OC)c4)cc23)CC1]

$^1$H NMR (400 MHz, DMSO-d$_6$) δ 11.75 (s, 1H), 8.50 (s, 1H), 8.34 (s, 1H), 7.59 (s, 1H), 7.29 (s, 1H), 7.24 (d, J=8.0 Hz, 1H), 7.05 (d, J=8.4 Hz, 1H), 6.28 (br s, 1H), 6.11 (d, J=8.0 Hz, 1H), 4.06-3.98 (m, 2H), 3.87 (s, 3H), 3.80 (s, 3H), 3.64-3.58 (m, 1H), 3.55 (t, J=5.8 Hz, 2H), 1.50-1.34 (m, 2H), 1.05 (d, J=6.4 Hz, 3H), 0.83 (t, J=7.4 Hz, 3H); [M+H]$^+$ 435.

EXAMPLE 45

N-cyclopropyl-4-(5-(5-(piperazin-1-ylmethyl)thiophen-2-yl)-1H-pyrrolo[2,3-b]pyridin-3-yl)-5,6-dihydropyridine-1(2H)-carboxamide dihydrochloride

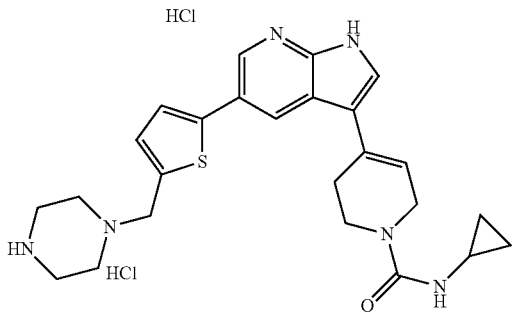 [SMILES: Cl ; O=C(NC1CC1)N1CC=C(c2c[nH]c3ncc(-c4ccc(CN5CCNCC5)s4)cc23)CC1 ; Cl]

[M+H]<sup>+</sup> 463.

EXAMPLE 46

N-cyclopropyl-4-(5-(4-((4-methylpiperazin-1-yl)methyl)phenyl)-1H-pyrrolo[2,3-b]pyridin-3-yl)-5,6-dihydropyridine-1(2H)-carboxamide

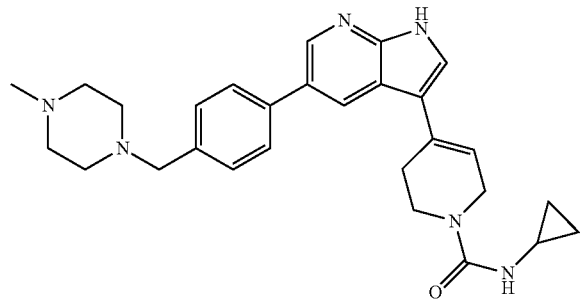

$^1$H NMR (400 MHz, DMSO-$d_6$) δ 11.83 (br s, 1H), 8.51 (s, 1H), 8.38 (s, 1H), 7.69 (d, J=8.0 Hz, 2H), 7.60 (s, 1H), 7.39 (d, J=8.0 Hz, 2H), 6.60 (d, J=2.4 Hz, 1H), 6.26 (br s, 1H), 3.96 (br s, 2H), 3.53 (t, J=5.8 Hz, 2H), 3.50 (s, 2H), 2.67 (m, 2H), 2.45-2.25 (m, 9H), 2.15 (s, 3H), 0.57-0.53 (m, 2H), 0.42-0.38 (m, 2H); [M+H]$^+$ 471.

EXAMPLE 47

N-cyclopropyl-4-(5-(5-((4-methylpiperazin-1-yl)methyl)thiophen-2-yl)-1H-pyrrolo[2,3-b]pyridin-3-yl)-5,6-dihydropyridine-1(2H)-carboxamide

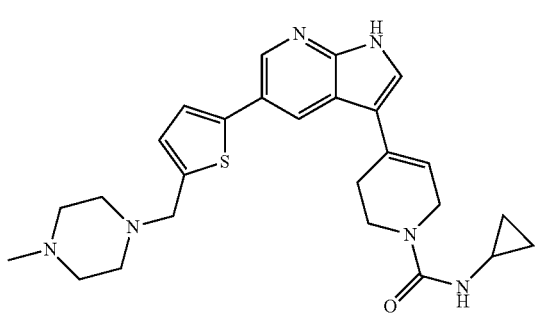 [SMILES: CN1CCN(Cc2ccc(-c3cnc4[nH]cc(C5=CCN(C(=O)NC6CC6)CC5)c4c3)s2)CC1]

$^1$H NMR (400 MHz, DMSO-$d_6$) δ 11.83 (br s, 1H), 8.51 (s, 1H), 8.32 (s, 1H), 7.60 (s, 1H), 7.40 (d, J=3.2 Hz, 1H), 6.97 (d, J=3.6 Hz, 1H), 6.60 (d, J=2.4 Hz, 1H), 6.22 (br s, 1H), 4.00 (br s, 2H), 3.67 (s, 2H), 3.52 (t, J=5.6 Hz, 2H), 3.32-3.30 (m, 1H), 2.49-2.35 (m, 10H), 2.16 (s, 3H), 0.58-0.53 (m, 2H), 0.45-0.38 (m, 2H); [M+H]$^+$ 477.

EXAMPLE 48

N-cyclopropyl-4-(5-(5-(morpholinomethyl)thiophen-2-yl)-1H-pyrrolo[2,3-b]pyridin-3-yl)-5,6-dihydropyridine-1(2H)-carboxamide

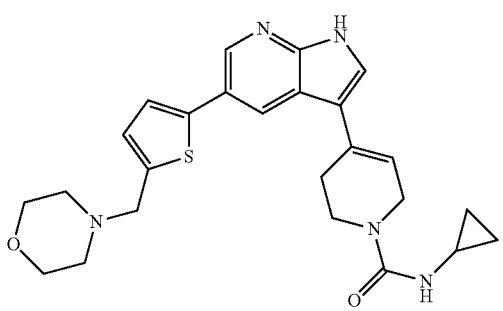 [SMILES: O=C(NC1CC1)N1CC=C(c2c[nH]c3ncc(-c4ccc(CN5CCOCC5)s4)cc23)CC1]

$^1$H NMR (400 MHz, DMSO-$d_6$) δ 11.83 (br s, 1H), 8.51 (s, 1H), 8.32 (s, 1H), 7.60 (s, 1H), 7.41 (d, J=3.2 Hz, 1H), 6.99 (d, J=3.6 Hz, 1H), 6.60 (d, J=2.8 Hz, 1H), 6.22 (br s, 1H), 4.00 (br s, 2H), 3.68 (s, 2H), 3.60 (t, J=4.4 Hz, 4H), 3.53 (t, J=5.6 Hz, 2H), 2.47-2.42 (m, 6H), 0.58-0.53 (m, 2H), 0.46-0.38 (m, 2H); [M+H]$^+$ 464.

EXAMPLE 49

N-cyclopentyl-4-(5-(3,4-dimethoxyphenyl)-1H-pyrrolo[2,3-b]pyridin-3-yl)-5,6-dihydropyridine-1(2H)-carboxamide

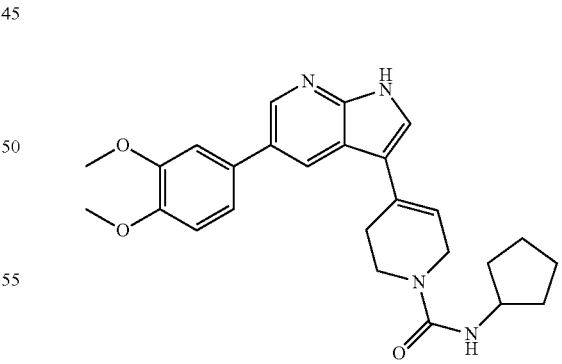

$^1$H NMR (400 MHz, DMSO-$d_6$) δ 11.88 (br s, 1H), 8.50 (s, 1H), 8.34 (s, 1H), 7.59 (s, 1H), 7.29 (s, 1H), 7.24 (d, J=8.4 Hz, 1H), 7.04 (d, J=8.4 Hz, 1H), 6.27 (br s, 1H), 6.23 (d, J=6.8 Hz, 1H), 4.02 (br s, 2H), 3.99-3.91 (m, 1H), 3.87 (s, 3H), 3.84-3.77 (m, 4H), 3.55 (t, J=5.4 Hz, 2H), 1.83-1.76 (m, 2H), 1.69-1.59 (m, 2H), 1.52-1.37 (m, 5H); [M+H]$^+$ 447.

EXAMPLE 50

N-cyclopentyl-4-(5-(3-fluoro-4-methoxyphenyl)-1H-pyrrolo[2,3-b]pyridin-3-yl)-5,6-dihydropyridine-1(2H)-carboxamide

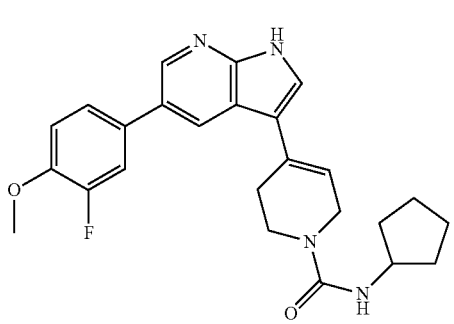 [SMILES: COc1ccc(-c2cnc3[nH]cc(C4=CCN(C(=O)NC5CCCC5)CC4)c3c2)cc1F]

$^1$H NMR (400 MHz, DMSO-d$_6$) δ 11.83 (br s, 1H), 8.53 (s, 1H), 8.39 (s, 1H), 7.61 (s, 1H), 7.48 (d, J=8.0 Hz, 1H), 7.33-7.26 (m, 2H), 6.29 (br s, 1H), 6.24 (d, J=6.8 Hz, 1H), 4.03 (br s, 2H), 3.96-3.89 (m, 4H), 3.55 (t, J=5.6 Hz, 2H), 1.83-1.75 (m, 2H), 1.67-1.57 (m, 2H), 1.52-1.37 (m, 4H); [M+H]$^+$ 435.

EXAMPLE 51

N-cyclopentyl-4-(5-(4-(methylsulfonyl)phenyl)-1H-pyrrolo[2,3-b]pyridin-3-yl)-5,6-dihydropyridine-1(2H)-carboxamide

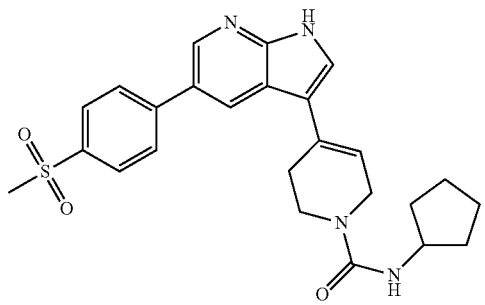

$^1$H NMR (400 MHz, DMSO-d$_6$) δ 11.88 (s, 1H), 8.62 (s, 1H), 8.51 (s, 1H), 8.07-7.99 (m, 4H), 7.64 (s, 1H), 6.31 (s, 1H), 6.21 (d, J=7.2 Hz, 1H), 4.03 (s, 2H), 3.98-3.92 (m, 1H), 3.57-3.54 (m, 2H), 3.26 (s, 3H), 1.83-1.75 (m, 2H), 1.67-1.61 (m, 2H), 1.52-1.38 (m, 4H); [M+H]$^+$ 466.

EXAMPLE 52

N-cyclopentyl-4-(5-(3-(methylsulfonyl)phenyl)-1H-pyrrolo[2,3-b]pyridin-3-yl)-5,6-dihydropyridine-1(2H)-carboxamide

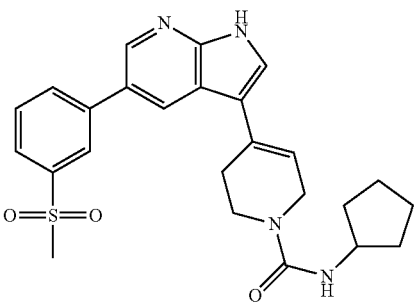

$^1$H NMR (400 MHz, DMSO-d$_6$) δ 11.89 (br s, 1H), 8.62 (s, 1H), 8.50 (s, 1H), 8.25 (m, 1H), 8.14 (d, J=8.0 Hz, 1H), 7.91 (d, J=7.6 Hz, 1H), 7.76 (t, J=7.8 Hz, 1H), 7.65 (s, 1H), 6.31 (br s, 1H), 6.24 (d, J=6.8 Hz, 1H), 4.04 (br s, 2H), 3.98-3.92 (m, 1H), 3.56 (t, J=5.6 Hz, 2H), 3.28 (s, 3H), 1.82-1.76 (m, 2H), 1.66-1.59 (m, 2H), 1.50-1.39 (m, 4H); [M+H]$^+$ 454.

EXAMPLE 53

N-cyclopentyl-4-(5-(4-(ethylsulfonyl)phenyl)-1H-pyrrolo[2,3-b]pyridin-3-yl)-3,6-dihydropyridine-1(2H)-carboxamide

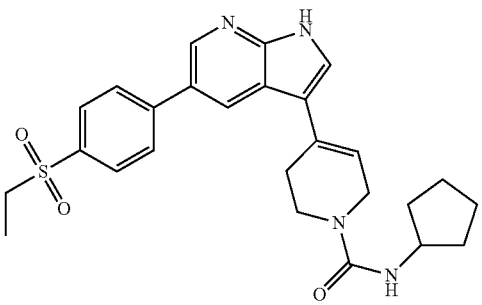 [SMILES: CCS(=O)(=O)c1ccc(-c2cnc3[nH]cc(C4=CCN(C(=O)NC5CCCC5)CC4)c3c2)cc1]

$^1$H NMR (400 MHz, DMSO-d$_6$) δ 11.87 (br s, 1H), 8.60 (s, 1H), 8.49 (s, 1H), 8.18 (s, 1H), 8.15 (d, J=8.0 Hz, 1H), 7.87 (d, J=6.8 Hz, 1H), 7.79-7.75 (m, 1H), 7.64 (s, 1H), 6.31 (s, 1H), 6.21 (d, J=6.4 Hz, 1H), 4.03 (br s, 2H), 3.99-3.92 (m, 1H), 3.57-3.54 (m, 2H), 3.45-3.39 (m, 2H), 1.86-1.74 (m, 2H), 1.70-1.56 (m, 5H), 1.54-1.36 (m, 4H), 1.16 (t, J=7.2 Hz, 3H); [M+H]$^+$ 479.

EXAMPLE 54

N-cyclopentyl-4-(5-(3-(ethylsulfonyl)phenyl)-1H-pyrrolo[2,3-b]pyridin-3-yl)-3,6-dihydropyridine-1(2H)-carboxamide

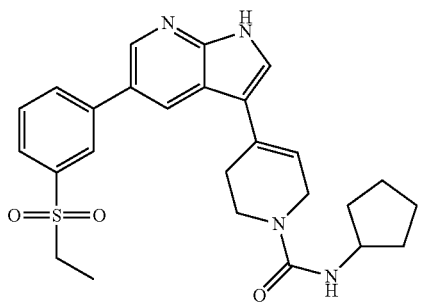 [SMILES: CCS(=O)(=O)c1cccc(-c2cnc3[nH]cc(C4=CCN(C(=O)NC5CCCC5)CC4)c3c2)c1]

$^1$H NMR (400 MHz, DMSO-d$_6$) δ 11.87 (br s, 1H), 8.60 (s, 1H), 8.49 (s, 1H), 8.18 (s, 1H), 8.15 (d, J=8.0 Hz, 1H), 7.87 (d, J=6.8 Hz, 1H), 7.77 (t, J=7.6 Hz, 1H), 7.64 (s, 1H), 6.31 (s, 1H), 6.21 (d, J=6.4 Hz, 1H), 4.03 (br s, 2H), 3.97-3.91 (m, 1H), 3.57-3.54 (m, 2H), 3.45-3.39 (m, 2H), 1.86-1.74 (m, 2H), 1.70-1.56 (m, 2H), 1.54-1.36 (m, 6H), 1.16 (t, J=7.2 Hz, 3H); [M+H]$^+$ 479.

EXAMPLE 55

N-cyclopentyl-4-(5-(4-(propylsulfonyl)phenyl)-1H-pyrrolo[2,3-b]pyridin-3-yl)-5,6-dihydropyridine-1(2H)-carboxamide

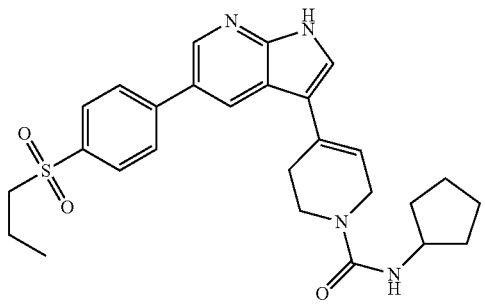 [SMILES: CCCS(=O)(=O)c1ccc(-c2cnc3[nH]cc(C4=CCN(C(=O)NC5CCCC5)CC4)c3c2)cc1]

$^1$H NMR (400 MHz, DMSO-d$_6$) δ 11.89 (br s, 1H), 8.62 (s, 1H), 8.52 (s, 1H), 8.07-7.95 (m, 4H), 7.64 (s, 1H), 6.31 (s, 1H), 6.21 (d, J=6.8 Hz, 1H), 4.03 (br s, 2H), 3.99-3.92 (m, 1H), 3.57-3.54 (m, 2H), 3.34-3.25 (m, 3H), 1.86-1.74 (m, 2H), 1.70-1.56 (m, 5H), 1.54-1.36 (m, 5H), 0.95 (t, J=7.4 Hz, 3H); [M+H]$^+$ 493.

EXAMPLE 56

N-cyclopentyl-4-(5-(4-(cyclopropylsulfonyl)phenyl)-1H-pyrrolo[2,3-b]pyridin-3-yl)-5,6-dihydropyridine-1(2H)-carboxamide

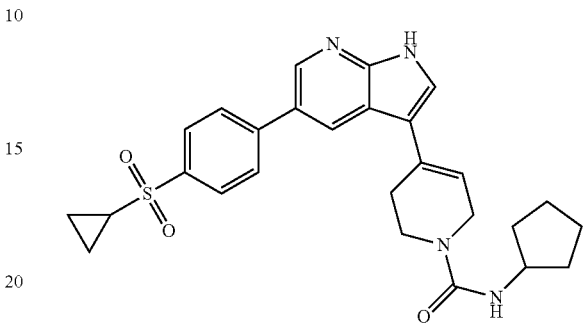

$^1$H NMR (400 MHz, DMSO-d$_6$) δ 11.89 (br s, 1H), 8.62 (s, 1H), 8.52 (s, 1H), 8.06-7.96 (m, 4H), 7.64 (s, 1H), 6.31 (s, 1H), 6.21 (d, J=6.4 Hz, 1H), 4.03 (br s, 2H), 3.99-3.92 (m, 1H), 3.57-3.54 (m, 2H), 2.93-2.88 (m, 1H), 1.81-1.76 (m, 2H), 1.71-1.56 (m, 2H), 1.52-1.36 (m, 4H), 1.19-1.14 (m, 2H), 1.11-1.05 (m, 3H); [M+H]$^+$ 491.

EXAMPLE 57

N-cyclopentyl-4-(5-(3-sulfamoylphenyl)-1H-pyrrolo[2,3-b]pyridin-3-yl)-5,6-dihydropyridine-1(2H)-carboxamide $^1$H NMR (400 MHz, DMSO-d$_6$) δ 8.56 (s, 1H), 8.44 (s, 1H), 8.18 (s, 1H), 8.00 (d, J=7.6 Hz, 1H), 8.01 (d, J=8.0 Hz, 1H), 7.81 (d, J=7.6 Hz, 1H), 7.69-7.65 (m, 2H), 6.28 (s, 1H), 6.22 (d, J=6.8 Hz, 1H), 4.04 (s, 2H), 3.97-3.92 (m, 1H), 3.57-3.54 (m, 2H), 1.83-1.75 (m, 2H), 1.67-1.61 (m, 2H), 1.52-1.38 (m, 4H); [M+H]$^+$ 466.

EXAMPLE 58

N-cyclopentyl-4-(5-(4-sulfamoylphenyl)-1H-pyrrolo[2,3-b]pyridin-3-yl)-5,6-dihydropyridine-1(2H)-carboxamide

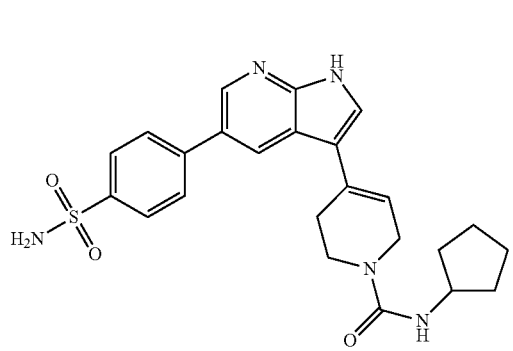 [SMILES: NS(=O)(=O)c1ccc(-c2cnc3[nH]cc(C4=CCN(C(=O)NC5CCCC5)CC4)c3c2)cc1]

¹H NMR (400 MHz, DMSO-d₆) δ 8.59 (s, 1H), 8.48 (s, 1H), 8.18 (s, 1H), 7.98-7.89 (m, 4H), 7.63 (m, 1H), 6.30 (s, 1H), 6.21 (d, J=6.4 Hz, 1H), 4.03 (s, 2H), 3.97-3.92 (m, 1H), 3.57-3.54 (m, 2H), 1.83-1.75 (m, 2H), 1.67-1.61 (m, 2H), 1.52-1.38 (m, 4H); [M+H]⁺ 466.

EXAMPLE 59

N-cyclopentyl-4-(5-(3-(N-methylsulfamoyl)phenyl)-1H-pyrrolo[2,3-b]pyridin-3-yl)-5,6-dihydropyridine-1(2H)-carboxamide

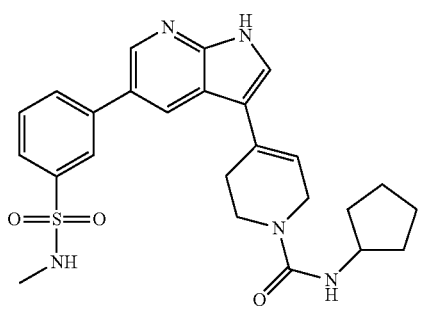

¹H NMR (400 MHz, DMSO-d₆) δ 11.87 (s, 1H), 8.56 (s, 1H), 8.44 (s, 1H), 8.08-8.04 (m, 2H), 7.78-7.70 (m, 2H), 7.65 (s, 1H), 7.51-7.47 (m, 1H), 6.28 (s, 1H), 6.21 (d, J=6.8 Hz, 1H), 4.03 (s, 2H), 3.97-3.92 (m, 1H), 3.57-3.54 (m, 2H), 2.47-2.45 (m, 3H), 1.83-1.76 (m, 2H), 1.67-1.61 (m, 2H), 1.52-1.38 (m, 4H); [M+H]⁺ 480.

EXAMPLE 60

N-cyclopentyl-4-(5-(4-(N-methylsulfamoyl)phenyl)-1H-pyrrolo[2,3-b]pyridin-3-yl)-5,6-dihydropyridine-1(2H)-carboxamide

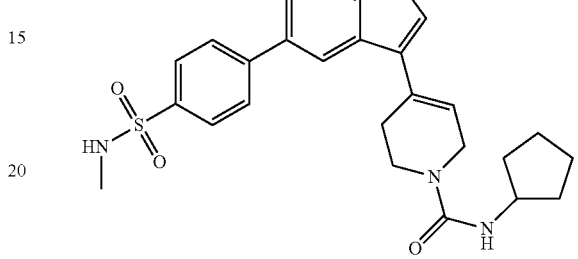

¹H NMR (400 MHz, DMSO-d₆) δ 8.60 (s, 1H), 8.50 (s, 1H), 8.01-7.85 (m, 4H), 7.63 (m, 1H), 6.30 (s, 1H), 6.20 (d, J=6.8 Hz, 1H), 4.03 (s, 2H), 3.97-3.92 (m, 1H), 3.57-3.54 (m, 2H), 2.46 (s, 3H), 1.84-1.75 (m, 2H), 1.67-1.61 (m, 2H), 1.52-1.38 (m, 4H); [M+H]⁺ 480.

EXAMPLE 61

N-cyclopentyl-4-(5-(4-(morpholinosulfonyl)phenyl)-1H-pyrrolo[2,3-b]pyridin-3-yl)-5,6-dihydropyridine-1(2H)-carboxamide

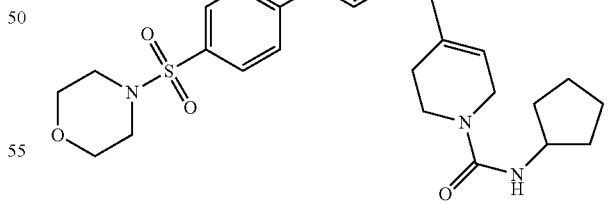

¹H NMR (400 MHz, DMSO-d₆) δ 11.89 (br s, 1H), 8.63 (s, 1H), 8.52 (s, 1H), 8.07 (d, J=7.6 Hz, 2H), 7.82 (d, J=7.6 Hz, 2H), 7.64 (s, 1H), 6.31 (br s, 1H), 6.21 (d, J=6.8 Hz, 1H), 4.03 (br s, 2H), 3.98-3.91 (m, 1H), 3.67-3.65 (m, 4H), 3.56 (t, J=5.0 Hz, 2H), 2.94-2.92 (m, 4H), 1.83-1.78 (m, 2H), 1.68-1.60 (m, 2H), 1.50-1.39 (m, 4H); [M+H]⁺ 536.

EXAMPLE 62

N-cyclopentyl-4-(5-(3-(morpholinosulfonyl)phenyl)-1H-pyrrolo[2,3-b]pyridin-3-yl)-5,6-dihydropyridine-1(2H)-carboxamide

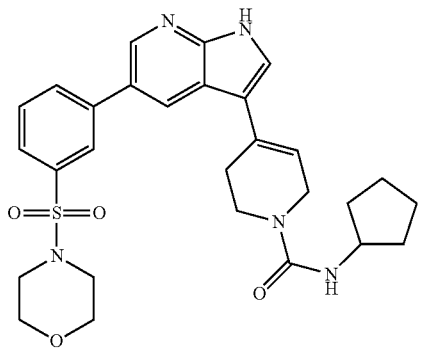 [SMILES: O=C(NC1CCCC1)N1CC=C(c2c[nH]c3ncc(-c4cccc(S(=O)(=O)N5CCOCC5)c4)cc23)CC1]

$^1$H NMR (400 MHz, DMSO-$d_6$) δ 11.88 (br s, 1H), 8.57 (s, 1H), 8.46 (s, 1H), 8.14 (d, J=8.0 Hz, 1H), 7.97 (s, 1H), 7.81-7.73 (m, 2H), 7.64 (s, 1H), 6.30 (br s, 1H), 6.21 (d, J=6.8 Hz, 1H), 4.03 (br s, 2H), 3.97-3.91 (m, 1H), 3.65-3.63 (m, 4H), 3.55 (t, J=5.2 Hz, 2H), 2.96-2.94 (m, 4H), 1.83-1.76 (m, 2H), 1.68-1.60 (m, 2H), 1.50-1.39 (m, 4H); [M+H]$^+$ 536.

EXAMPLE 63

N-cyclopentyl-4-(5-(4-methoxy-3-(morpholinosulfonyl)phenyl)-1H-pyrrolo[2,3-b]pyridin-3-yl)-5,6-dihydropyridine-1(2H)-carboxamide

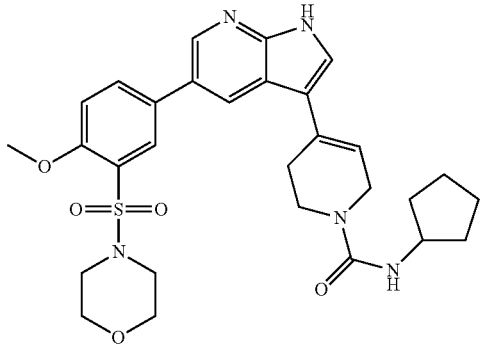

$^1$H NMR (400 MHz, DMSO-$d_6$) δ 11.82 (s, 1H), 8.48 (s, 1H), 8.36 (s, 1H), 8.04 (d, J=8.8 Hz, 1H), 7.97 (s, 1H), 7.63 (s, 1H), 7.39 (d, J=8.8 Hz, 1H), 6.26 (s, 1H), 6.23 (d, J=6.8 Hz, 1H), 4.02 (br s, 2H), 3.96 (s, 3H), 3.95-3.93 (m, 1H), 3.62-3.60 (m, 5H), 3.55 (t, J=5.4 Hz, 2H), 3.17-3.12 (m, 5H), 1.81-1.76 (m, 2H), 1.69-1.58 (m, 2H), 1.52-1.36 (m, 4H); [M+H]$^+$ 566.

EXAMPLE 64

N-cyclopentyl-4-(5-(4-(2-morpholinoethyl)phenyl)-1H-pyrrolo[2,3-b]pyridin-3-yl)-5,6-dihydropyridine-1(2H)-carboxamide

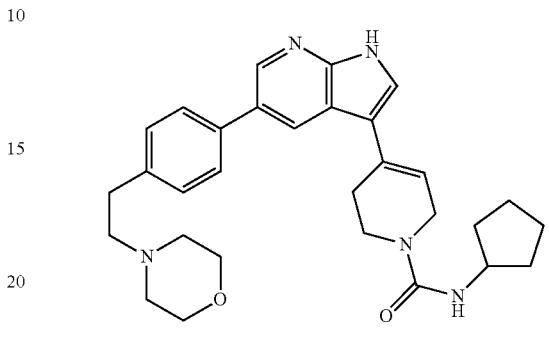

$^1$H NMR (400 MHz, DMSO-$d_6$) δ 11.80 (br s, 1H), 8.50 (s, 1H), 8.36 (s, 1H), 7.65 (d, J=8.0 Hz, 2H), 7.60 (s, 1H), 7.34 (d, J=8.0 Hz, 1H), 6.26 (br s, 1H), 6.23 (d, J=7.2 Hz, 1H), 4.02 (br s, 2H), 3.98-3.91 (m, 1H), 3.59 (t, J=4.4 Hz, 4H), 3.53 (t, J=8.0 Hz, 2H), 2.79 (t, J=7.8 Hz, 2H), 2.57-2.52 (m, 2H), 2.46-2.43 (m, 4H), 1.81-1.76 (m, 2H), 1.69-1.58 (m, 2H), 1.52-1.36 (m, 4H); [M+H]$^+$ 500.

EXAMPLE 65

4-(5-(5-Acetamido-2-aminophenyl)-1H-pyrrolo[2,3-b]pyridin-3-yl)-N-cyclopentyl-5,6-dihydropyridine-1(2H)-carboxamide

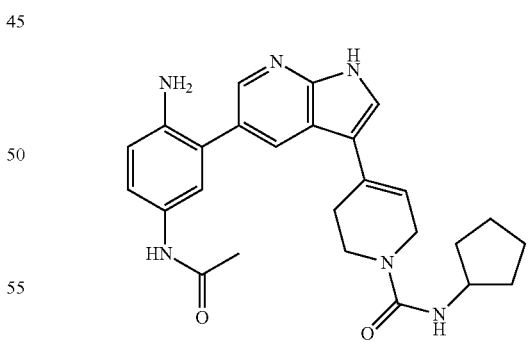

$^1$H NMR (400 MHz, DMSO-$d_6$) δ 11.77 (s, 1H), 9.61 (s, 1H), 8.22 (s, 1H), 8.16 (s, 1H), 7.60 (s, 1H), 7.23-7.25 (m, 2H), 6.71 (d, J=8.4 Hz, 1H), 6.22 (d, J=6.8 Hz, 1H), 6.14 (br s, 1H), 4.63 (br s, 2H), 3.98 (br s, 2H), 3.95-3.90 (m, 1H), 3.53 (t, J=5.4 Hz, 2H), 1.97 (s, 3H), 1.82-1.75 (m, 2H), 1.69-1.62 (m, 2H), 1.50-1.37 (m, 4H); [M+H]$^+$ 459.

EXAMPLE 66

N-cyclopentyl-4-(5-(4-((furan-2-ylmethyl)carbamoyl)phenyl)-1H-pyrrolo[2,3-b]pyridin-3-yl)-5,6-dihydropyridine-1(2H)-carboxamide

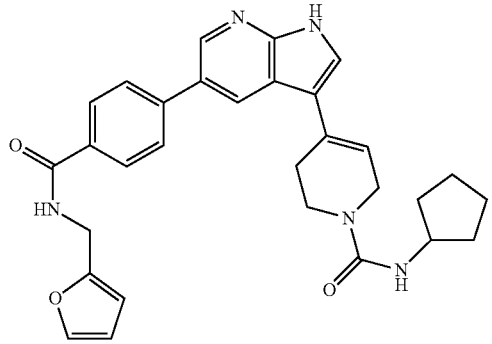 [SMILES: O=C(NCc1ccco1)c1ccc(-c2cnc3[nH]cc(C4=CCN(C(=O)NC5CCCC5)CC4)c3c2)cc1]

$^1$H NMR (400 MHz, DMSO-d$_6$) δ 11.85 (s, 1H), 9.05 (t, J=5.8 Hz, 1H), 8.60 (s, 1H), 8.48 (s, 1H), 8.23 (s, 1H), 7.94 (dd, J=46.0, 8.4 Hz, 4H), 7.63 (s, 1H), 7.60 (s, 1H), 6.43-6.41 (m, 1H), 6.31-6.29 (m, 2H), 6.24 (d, J=6.8 Hz, 1H), 4.50 (d, J=5.6 Hz, 2H), 4.03 (br s, 2H), 3.98-3.91 (m, 1H), 3.55 (t, J=5.6 Hz, 2H), 3.32 (s, 1H), 1.82-1.76 (m, 2H), 1.69-1.62 (m, 2H), 1.52-1.36 (m, 4H); [M+H]$^+$ 510.

EXAMPLE 67

N-cyclopentyl-4-(5-(3-((furan-2-ylmethyl)carbamoyl)phenyl)-1H-pyrrolo[2,3-b]pyridin-3-yl)-5,6-dihydropyridine-1(2H)-carboxamide

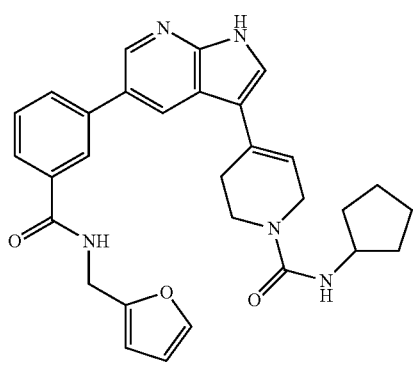 [SMILES: O=C(NCc1ccco1)c1cccc(-c2cnc3[nH]cc(C4=CCN(C(=O)NC5CCCC5)CC4)c3c2)c1]

$^1$H NMR (400 MHz, DMSO-d$_6$) δ 11.84 (s, 1H), 9.13 (t, J=5.8 Hz, 1H), 8.60 (s, 1H), 8.46 (s, 1H), 8.23 (s, 1H), 7.93 (d, J=7.6 Hz, 1H), 7.88 (d, J=8.4 Hz, 1H), 7.64-7.57 (m, 3H), 6.42-6.41 (m, 1H), 6.32-6.29 (m, 2H), 6.24 (d, J=7.2 Hz, 1H), 4.52 (d, J=5.2 Hz, 2H), 4.03 (br s, 2H), 3.98-3.90 (m, 1H), 3.55 (t, J=5.6 Hz, 2H), 1.82-1.76 (m, 2H), 1.69-1.62 (m, 2H), 1.52-1.36 (m, 4H); [M+H]$^+$ 510.

EXAMPLE 68

N-cyclopentyl-4-(5-(3-(2-morpholinoethoxy)phenyl)-1H-pyrrolo[2,3-b]pyridin-3-yl)-5,6-dihydropyridine-1(2H)-carboxamide

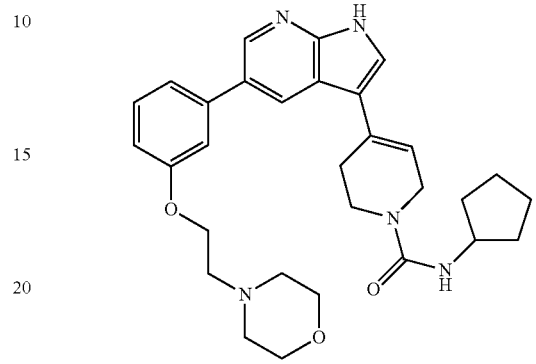

$^1$H NMR (400 MHz, DMSO-d$_6$) δ 11.80 (s, 1H), 8.53 (s, 1H), 8.38 (s, 1H), 7.61 (s, 1H), 7.38 (t, J=8.0 Hz, 1H), 7.31-7.28 (m, 2H), 6.95 (d, J=8.4 Hz, 1H), 6.28 (br s, 1H), 6.23 (d, J=6.8 Hz, 1H), 4.20 (br s, 2H), 4.02 (br s, 2H), 3.98-3.90 (m, 1H), 3.62-3.57 (m, 4H), 3.55 (t, J=5.6 Hz, 2H), 3.32 (s, 1H), 2.73 (br s, 2H), 1.82-1.76 (m, 2H), 1.69-1.58 (m, 2H), 1.52-1.36 (m, 4H); [M+H]$^+$ 516.

EXAMPLE 69

N-cyclopentyl-4-(5-(4-(2-morpholinoethoxy)phenyl)-1H-pyrrolo[2,3-b]pyridin-3-yl)-5,6-dihydropyridine-1(2H)-carboxamide

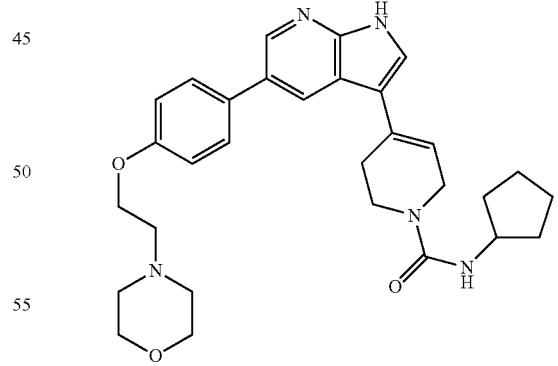

$^1$H NMR (400 MHz, DMSO-d$_6$) δ 11.73 (s, 1H), 8.47 (s, 1H), 8.32 (s, 1H), 7.66 (d, J=8.8 Hz, 2H), 7.59 (s, 1H), 7.05 (d, J=8.8 Hz, 1H), 6.26 (br s, 1H), 6.23 (d, J=7.2 Hz, 1H), 4.14 (t, J=5.6 Hz, 2H), 4.02 (br s, 2H), 3.98-3.90 (m, 1H), 3.59 (t, J=4.6 Hz, 4H), 3.55 (t, J=5.6 Hz, 2H), 3.55 (t, J=5.6 Hz, 2H), 2.72 (t, J=5.8 Hz, 2H), 1.81-1.76 (m, 2H), 1.69-1.58 (m, 2H), 1.52-1.36 (m, 4H); [M+H]$^+$ 516.

EXAMPLE 70

N-cyclopentyl-4-(5-(4-(3-morpholinopropoxy)phenyl)-1H-pyrrolo[2,3-b]pyridin-3-yl)-5,6-dihydropyridine-1(2H)-carboxamide

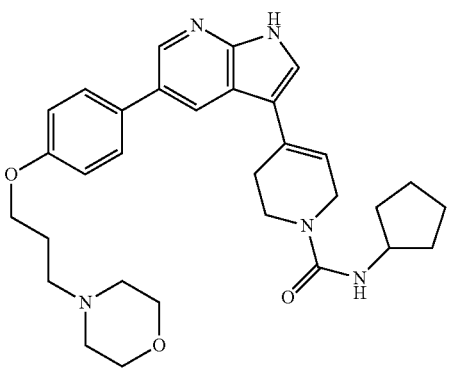 [SMILES: O=C(NC1CCCC1)N1CC=C(c2c[nH]c3ncc(-c4ccc(OCCCN5CCOCC5)cc4)cc23)CC1]

$^1$H NMR (400 MHz, DMSO-d$_6$) δ 11.74 (s, 1H), 8.47 (s, 1H), 8.32 (s, 1H), 7.67 (d, J=8.8 Hz, 2H), 7.59 (s, 1H), 7.04 (d, J=8.8 Hz, 1H), 6.26-6.23 (m, 2H), 4.07-4.05 (m, 2H), 4.02 (br s, 2H), 3.98-3.89 (m, 1H), 3.65-3.56 (m, 6H), 3.55 (t, J=5.6 Hz, 2H), 1.98-1.91 (m, 4H), 1.81-1.76 (m, 4H), 1.69-1.58 (m, 4H), 1.52-1.36 (m, 7H); [M+H]$^+$ 530.

EXAMPLE 71

N-cyclopentyl-4-(5-(5-((4-methylpiperazin-1-yl)methyl)thiophen-2-yl)-1H-pyrrolo[2,3-b]pyridin-3-yl)-5,6-dihydropyridine-1(2H)-carboxamide

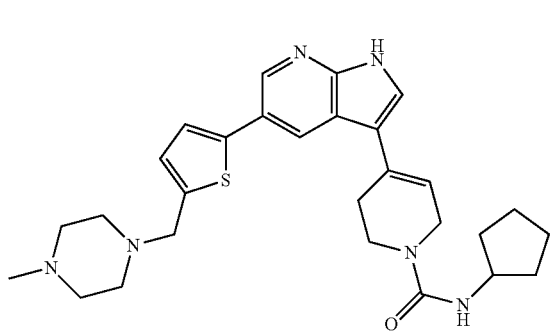

$^1$H NMR (400 MHz, DMSO-d$_6$) δ 11.84 (br s, 1H), 8.51 (s, 1H), 8.32 (s, 1H), 7.61 (s, 1H), 7.40 (d, J=3.6 Hz, 1H), 6.97 (d, J=3.6 Hz, 1H), 6.25-6.22 (m, 2H), 4.03 (br s, 2H), 3.98-3.90 (m, 1H), 3.69 (s, 2H), 3.55 (d, J=5.6 Hz, 2H), 2.15 (s, 3H), 2.49-2.25 (m, 6H), 1.84-1.76 (m, 2H), 1.69-1.60 (m, 2H), 1.52-1.37 (m, 4H); [M+H]$^+$ 505.

EXAMPLE 72

N-cyclopentyl-4-(5-(5-(morpholinomethyl)thiophen-2-yl)-1H-pyrrolo[2,3-b]pyridin-3-yl)-5,6-dihydropyridine-1(2H)-carboxamide

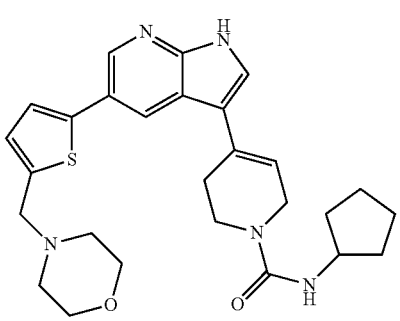 [SMILES: O=C(NC1CCCC1)N1CC=C(c2c[nH]c3ncc(-c4ccc(CN5CCOCC5)s4)cc23)CC1]

$^1$H NMR (400 MHz, DMSO-d$_6$) δ 11.82 (br s, 1H), 8.51 (s, 1H), 8.32 (s, 1H), 7.59 (s, 1H), 7.40 (s, 1H), 6.99 (s, 1H), 6.23-6.19 (m, 2H), 4.03 (br s, 2H), 3.99-3.92 (m, 1H), 3.69 (s, 2H), 3.64-3.53 (m, 6H), 2.49-2.42 (m, 6H), 1.85-1.76 (m, 2H), 1.69-1.60 (m, 2H), 1.52-1.38 (m, 4H); [M+H]$^+$ 492.

EXAMPLE 73

N-cyclopentyl-4-(5-(5-(morpholinomethyl)thiophen-3-yl)-1H-pyrrolo[2,3-b]pyridin-3-yl)-5,6-dihydropyridine-1(2H)-carboxamide

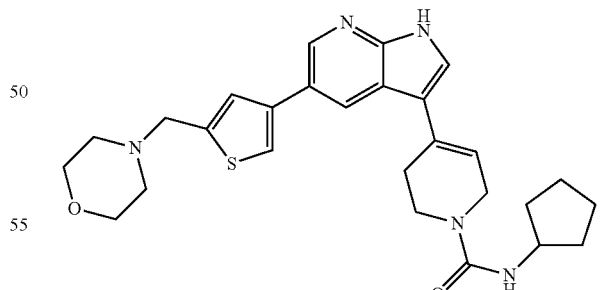

$^1$H NMR (400 MHz, DMSO-d$_6$) δ 11.71 (br s, 1H), 8.24-8.21 (m, 2H), 7.55 (s, 1H), 7.11-7.08 (m, 1H), 6.23 (d, J=6.8 Hz, 1H), 6.16 (br s, 1H), 4.0 (s, 2H), 3.96-3.90 (m, 1H), 3.53 (t, J=5.6 Hz, 2H), 2.49-2.42 (m, 7H), 1.84-1.75 (m, 3H), 1.69-1.60 (m, 3H), 1.51-1.38 (m, 5H); [M+H]$^+$ 492.

EXAMPLE 74

N-cyclopentyl-4-(5-(5-(morpholine-4-carbonyl)thiophen-2-yl)-1H-pyrrolo[2,3-b]pyridin-3-yl)-5,6-dihydropyridine-1(2H)-carboxamide

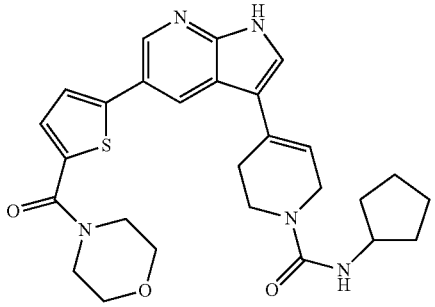 [SMILES: O=C(NC1CCCC1)N1CC=C(c2c[nH]c3ncc(-c4ccc(C(=O)N5CCOCC5)s4)cc23)CC1]

$^1$H NMR (400 MHz, DMSO-d$_6$) δ 11.83 (br s, 1H), 8.52 (s, 1H), 8.33 (s, 1H), 7.61 (s, 1H), 7.41 (s, 1H), 6.99 (s, 1H), 6.23 (br s, 1H), 6.03 (d, J=8.6 Hz, 1H), 4.34 (d, J=7.4 Hz, 1H), 4.08-4.02 (m, 2H), 3.78-3.73 (m, 4H), 3.59-3.54 (m, 4H), 2.44-2.43 (m, 4H), 1.82-1.76 (m, 4H), 1.49-1.37 (m, 4H); [M+H]$^+$ 504.

EXAMPLE 75

N-cyclopentyl-4-(5-(4-(morpholine-4-carbonyl)phenyl)-1H-pyrrolo[2,3-b]pyridin-3-yl)-5,6-dihydropyridine-1(2H)-carboxamide

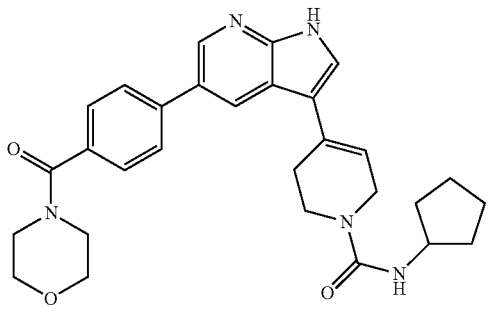 [SMILES: O=C(NC1CCCC1)N1CC=C(c2c[nH]c3ncc(-c4ccc(C(=O)N5CCOCC5)cc4)cc23)CC1]

$^1$H NMR (400 MHz, DMSO-d$_6$) δ 11.81 (br s, 1H), 8.56 (s, 1H), 8.44 (s, 1H), 7.84 (d, J=8.4 Hz, 2H), 7.61 (s, 1H), 7.52 (d, J=8.4 Hz, 2H), 6.28 (s, 1H), 6.20 (d, J=6.8 Hz, 1H), 4.03 (s, 2H), 3.97-3.91 (m, 1H), 3.69-3.49 (m, 10H), 2.48-2.45 (m, 2H), 1.83-1.77 (m, 2H), 1.68-1.61 (m, 2H), 1.55-1.39 (m, 4H); [M+H]$^+$ 500.

EXAMPLE 76

4-(5-(4-Chloro-3-(morpholine-4-carbonyl)phenyl)-1H-pyrrolo[2,3-b]pyridin-3-yl)-N-cyclopentyl-3,6-dihydropyridine-1(2H)-carboxamide 2,2,2-trifluoroacetate

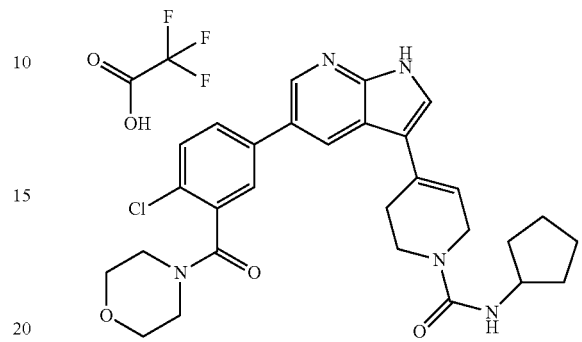

[M+H]$^+$ 534.

EXAMPLE 77

4-(5-(3-Chloro-5-(morpholine-4-carbonyl)phenyl)-1H-pyrrolo[2,3-b]pyridin-3-yl)-N-cyclopentyl-3,6-dihydropyridine-1(2H)-carboxamide 2,2,2-trifluoroacetate

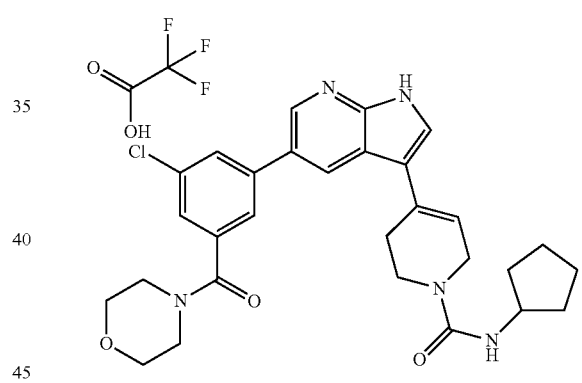

[M+H]$^+$ 534.

EXAMPLE 78

4-(5-(4-((4-Methylpiperazin-1-yl)methyl)phenyl)-1H-pyrrolo[2,3-b]pyridin-3-yl)-N-(oxetan-3-yl)-5,6-dihydropyridine-1(2H)-carboxamide

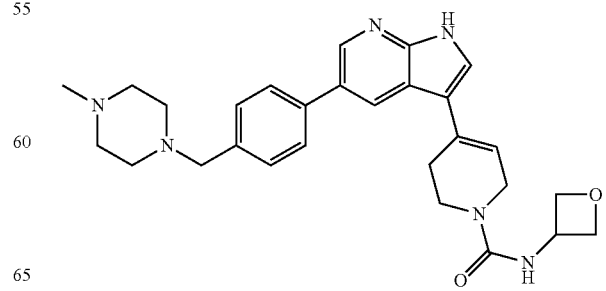

¹H NMR (400 MHz, DMSO-d₆) δ 11.81 (s, 1H), 8.53 (s, 1H), 8.40 (s, 1H), 7.74-7.72 (m, 2H), 7.62 (s, 1H), 7.48-7.39 (m, 2H), 7.18-7.14 (m, 1H), 6.29 (br s, 1H), 4.76-4.64 (m, 3H), 4.50 (t, J=6.2 Hz, 2H), 4.10-4.04 (m, 2H), 3.65-3.56 (m, 4H), 3.17 (s, 1H), 3.05-2.78 (m, 4H), 2.75-2.52 (m, 4H); [M+H]⁺ 487.

EXAMPLE 79

4-(5-(5-(((4-Methylpiperazin-1-yl)methyl)thiophen-2-yl)-1H-pyrrolo[2,3-b]pyridin-3-yl)-N-(oxetan-3-yl)-5,6-dihydropyridine-1(2H)-carboxamide

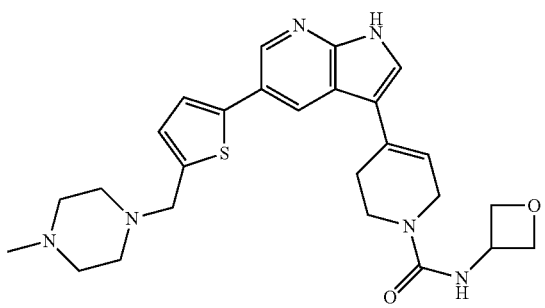 [SMILES: CN1CCN(Cc2ccc(-c3cnc4[nH]cc(C5=CCN(C(=O)NC6COC6)CC5)c4c3)s2)CC1]

¹H NMR (400 MHz, DMSO-d₆) δ 11.85 (br s, 1H), 8.51 (s, 1H), 8.33 (s, 1H), 7.61 (s, 1H), 7.40 (d, J=3.6 Hz, 1H), 7.14 (d, J=6.0 Hz, 1H), 6.97 (d, J=3.6 Hz, 1H), 6.24 (br s, 1H), 4.76-4.64 (m, 3H), 4.49 (t, J=6.2 Hz, 2H), 4.08-4.06 (m, 2H), 3.67 (s, 2H), 3.58 (t, J=5.6 Hz, 2H), 3.17 (s, 1H), 2.49-2.25 (m, 6H), 2.16 (s, 3H); [M+H]⁺ 493.

EXAMPLE 80

4-(5-(5-(Morpholinomethyl)thiophen-2-yl)-1H-pyrrolo[2,3-b]pyridin-3-yl)-N-(oxetan-3-yl)-5,6-dihydropyridine-1(2H)-carboxamide

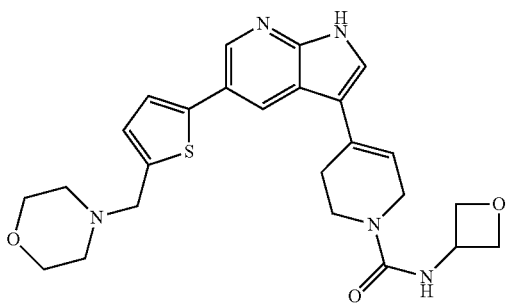 [SMILES: O=C(NC1COC1)N1CC=C(c2c[nH]c3ncc(-c4ccc(CN5CCOCC5)s4)cc23)CC1]

¹H NMR (400 MHz, DMSO-d₆) δ 11.83 (s, 1H), 8.51 (s, 1H), 8.34 (s, 1H), 7.61 (s, 1H), 7.41 (d, J=3.6 Hz, 1H), 7.13 (d, J=6.4 Hz, 1H), 6.99 (d, J=3.6 Hz, 1H), 6.27-6.24 (m, 1H), 4.75-4.65 (m, 3H), 4.49 (t, J=6.0 Hz, 2H), 4.08-4.06 (m, 2H), 3.69 (s, 2H), 3.62-3.56 (m, 6H), 2.49-2.42 (m, 5H); [M+H]⁺ 480.

EXAMPLE 81

4-(5-(3,4-Dimethoxyphenyl)-1H-pyrrolo[2,3-b]pyridin-3-yl)-N-(tetrahydrofuran-3-yl)-5,6-dihydropyridine-1(2H)-carboxamide

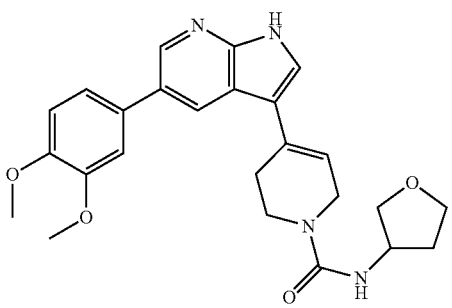 [SMILES: COc1ccc(-c2cnc3[nH]cc(C4=CCN(C(=O)NC5CCOC5)CC4)c3c2)cc1OC]

¹H NMR (400 MHz, DMSO-d₆) δ 11.72 (s, 1H), 8.50 (s, 1H), 8.34 (s, 1H), 7.59 (s, 1H), 7.29 (s, 1H), 7.24 (d, J=8.4 Hz, 1H), 7.05 (d, J=8.4 Hz, 1H), 6.49 (d, J=6.0 Hz, 1H), 6.28 (br s, 1H), 4.21-4.16 (m, 1H), 4.04 (br s, 2H), 3.87 (s, 3H), 3.85-3.75 (m, 5H), 3.69-3.62 (m, 1H), 3.57 (t, J=5.6 Hz, 2H), 3.48-3.44 (m, 1H), 2.09-2.01 (m, 1H), 1.85-1.78 (m, 1H); [M+H]⁺ 449.

EXAMPLE 82

4-(5-(4-(Methylsulfonyl)phenyl)-1H-pyrrolo[2,3-b]pyridin-3-yl)-N-(tetrahydrofuran-3-yl)-5,6-dihydropyridine-1(2H)-carboxamide

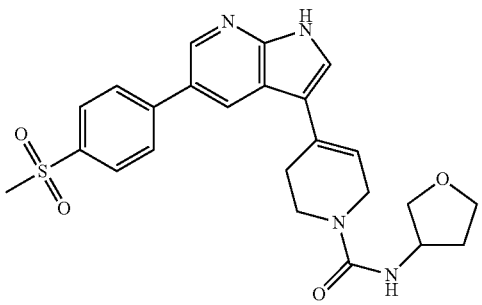 [SMILES: CS(=O)(=O)c1ccc(-c2cnc3[nH]cc(C4=CCN(C(=O)NC5CCOC5)CC4)c3c2)cc1]

¹H NMR (400 MHz, DMSO-d₆) δ 12.90 (br s, 1H), 8.62 (s, 1H), 8.52 (s, 1H), 8.04 (dd, J=23.6, 8.4 Hz, 4H), 7.66 (s, 1H), 6.50 (d, J=6.0 Hz, 1H), 6.32 (br s, 1H), 4.21-4.15 (m, 1H), 4.05 (br s, 2H), 3.83-3.76 (m, 2H), 3.69-3.63 (m, 1H), 3.57 (d, J=5.6 Hz, 2H), 3.48-3.44 (m, 2H), 3.17 (s, 3H), 2.10-2.01 (m, 1H), 1.86-1.78 (m, 1H); [M+H]⁺ 467.

EXAMPLE 83

4-(5-(5-((4-Methylpiperazin-1-yl)methyl)thiophen-2-yl)-1H-pyrrolo[2,3-b]pyridin-3-yl)-N-(tetrahydrofuran-3-yl)-5,6-dihydropyridine-1(2H)-carboxamide

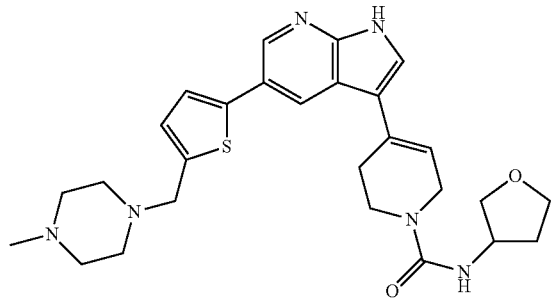 [SMILES: CN1CCN(Cc2ccc(-c3cnc4[nH]cc(C5=CCN(C(=O)NC6CCOC6)CC5)c4c3)s2)CC1]

$^1$H NMR (400 MHz, DMSO-d$_6$) δ 11.83 (br s, 1H), 8.51 (s, 1H), 8.32 (s, 1H), 7.60 (s, 1H), 7.39 (d, J=3.6 Hz, 1H), 6.97 (d, J=3.6 Hz, 1H), 6.48 (d, J=6.0 Hz, 1H), 6.23 (br s, 1H), 4.21-4.15 (m, 1H), 4.05 (br s, 2H), 3.83-3.76 (m, 2H), 3.69-3.62 (m, 4H), 3.56 (t, J=5.6 Hz, 2H), 3.48-3.45 (m, 1H), 3.17 (d, J=5.2 Hz, 1H), 2.47-2.42 (m, 4H), 2.16 (s, 3H), 2.10-2.01 (m, 1H), 1.86-1.78 (m, 1H); [M+H]$^+$ 507.

EXAMPLE 84

4-(5-(5-(Morpholinomethyl)thiophen-2-yl)-1H-pyrrolo[2,3-b]pyridin-3-yl)-N-(tetrahydrofuran-3-yl)-5,6-dihydropyridine-1(2H)-carboxamide

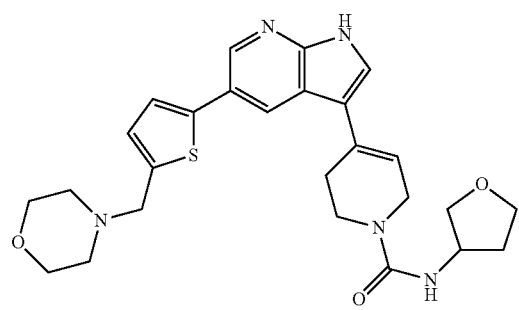 [SMILES: O=C(NC1CCOC1)N1CC=C(c2c[nH]c3ncc(-c4ccc(CN5CCOCC5)s4)cc23)CC1]

$^1$H NMR (400 MHz, DMSO-d$_6$) δ 11.83 (br s, 1H), 8.52 (s, 1H), 8.33 (s, 1H), 7.61 (s, 1H), 7.41 (br s, 1H), 7.00 (br s, 1H), 6.49 (d, J=6.0 Hz, 1H), 6.23 (br s, 1H), 4.20-4.14 (m, 1H), 4.05 (br s, 2H), 3.83-3.76 (m, 2H), 3.69-3.64 (m, 3H), 3.60-3.52 (m, 6H), 3.48-3.45 (m, 1H), 2.47-2.42 (m, 4H), 2.10-2.01 (m, 1H), 1.85-1.78 (m, 1H); [M+H]$^+$ 494.

EXAMPLE 85

4-(5-(3,4-Dimethoxyphenyl)-1H-pyrrolo[2,3-b]pyridin-3-yl)-N-(pyrrolidin-1-yl)-5,6-dihydropyridine-1(2H)-carboxamide 2,2,2-trifluoroacetate

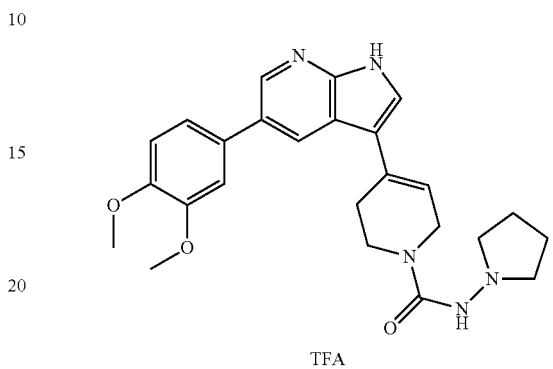

$^1$H NMR (400 MHz, DMSO-d$_6$) δ 11.85 (s, 1H), 9.80 (s, 1H), 8.53 (s, 1H), 8.38 (s, 1H), 7.65 (d, J=2.4 Hz, 1H), 7.29 (s, 1H), 7.25 (d, J=8.4 Hz, 1H), 7.06 (d, J=8.4 Hz, 1H), 6.33 (s, 1H), 4.11 (br s, 2H), 3.88 (s, 3H), 3.80 (s, 3H), 3.65-3.62 (m, 2H), 2.65-2.57 (m, 2H), 2.12-1.90 (m, 4H); [M+H]$^+$ 448.

PREPARATION Example 3

Preparation of 5-bromo-3-(6-methyl-1,2,3,6-tetrahydropyridin-4-yl)-1H-pyrrolo[2,3-b]pyridine Scheme 3. Total Scheme for Compounds 27 and 28

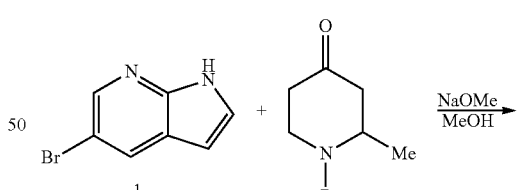

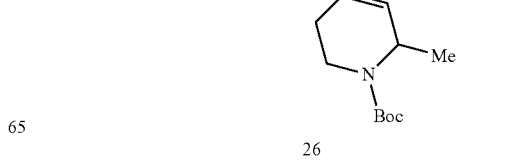

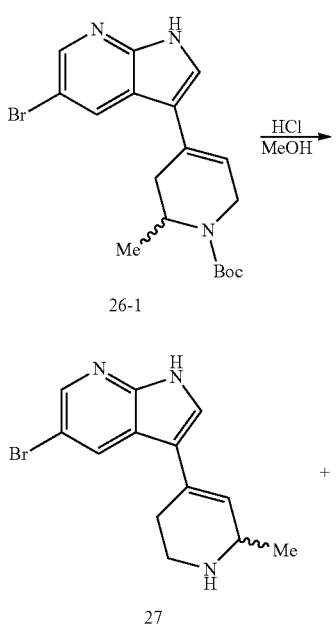

Step 1: Preparation of tert-butyl 4-(5-bromo-1H-pyrrolo[2,3-b]pyridin-3-yl)-2-methyl-5,6-dihydropyridine-1(2H)-carboxylate (26)

A mixture of 5-bromo-1H-pyrrolo[2,3-b]pyridine (2.2 g, 11.2 mmol) and tert-butyl 2-methyl-4-oxopiperidine-1-carboxylate (2.0 g, 9.38 mmol) in MeOH (16 mL) was added with NaOMe (25 wt % in MeOH, 16 mL) at room temperature. The reaction mixture was stirred at 120° C. using a pressurized container. The solvent was removed from the resulting mixture, and the mixture was diluted with $H_2O$ and extracted with $CH_2Cl_2$. The organic layer was dried over $MgSO_4$, filtered and concentrated in vacuo. The crude product was purified by silica-gel column chromatography (Biotage flash purification system, EtOAc/Hex, KP-Sil) to give a mixture of 2-methyl and 6-methyl compounds (1.62 g, 37%) as a yellow solid with high viscosity.

Step 2: Preparation of 5-bromo-3-(6-methyl-1,2,3,6-tetrahydropyridin-4-yl)-1H-pyrrolo[2,3-b]pyridine (27) and 5-bromo-3-(2-methyl-1,2,3,6-tetrahydropyridin-4-yl)-1H-pyrrolo[2,3-b]pyridine (28)

A mixture of the compound 26 (1.62 g, 4.13 mmol) and MeOH (9.9 mL) was added with HCl (1.25 M in MeOH, 9.9 mL) at room temperature, followed by stirring. The solvent was removed from the resulting mixture, and the mixture was subjected to alkalinization using 1N NaOH (aq.), followed by extraction with $CH_2Cl_2$. The organic layer was dried over $MgSO_4$, filtered and concentrated in vacuo. The crude product was purified by silica-gel column chromatography (Biotage flash purification system, $CH_2Cl_2$/MeOH, KP-Sil) to give the title compounds: 27 (470 mg, 39%) as a white solid and 28 (310 mg, 26%) as a pale yellow solid.

27: $^1H$ NMR (400 MHz, DMSO-$d_6$) δ 11.90 (br s, 1H), 8.35 (d, J=2.0 Hz, 1H), 8.27 (d, J=2.0 Hz, 1H), 7.57 (s, 1H), 6.06 (br s, 1H), 3.50-3.48 (m, 1H), 3.09-3.04 (m, 1H), 2.83-2.76 (m, 1H), 2.42-2.32 (m, 1H), 2.28-2.23 (m, 1H), 1.15 (d, J=6.8 Hz, 3H); [M+H]$^+$ 292

28: $^1H$ NMR (400 MHz, DMSO-$d_6$) δ 11.88 (br s, 1H), 8.37 (d, J=2.0 Hz, 1H), 8.27 (d, J=2.0 Hz, 1H), 7.56 (s, 1H), 6.18 (br s, 1H), 3.50-3.48 (m, 2H), 2.85-2.79 (m, 1H), 2.42-2.32 (m, 1H), 2.04-1.97 (m, 2H), 1.12 (d, J=6.4 Hz, 3H); [M+H]$^+$ 292.

Step 3-1: Preparation of 4-(5-bromo-1H-pyrrolo[2,3-b]pyridin-3-yl)-N-cyclopentyl-2-methyl-5,6-dihydropyridine-1(2H)-carboxamide

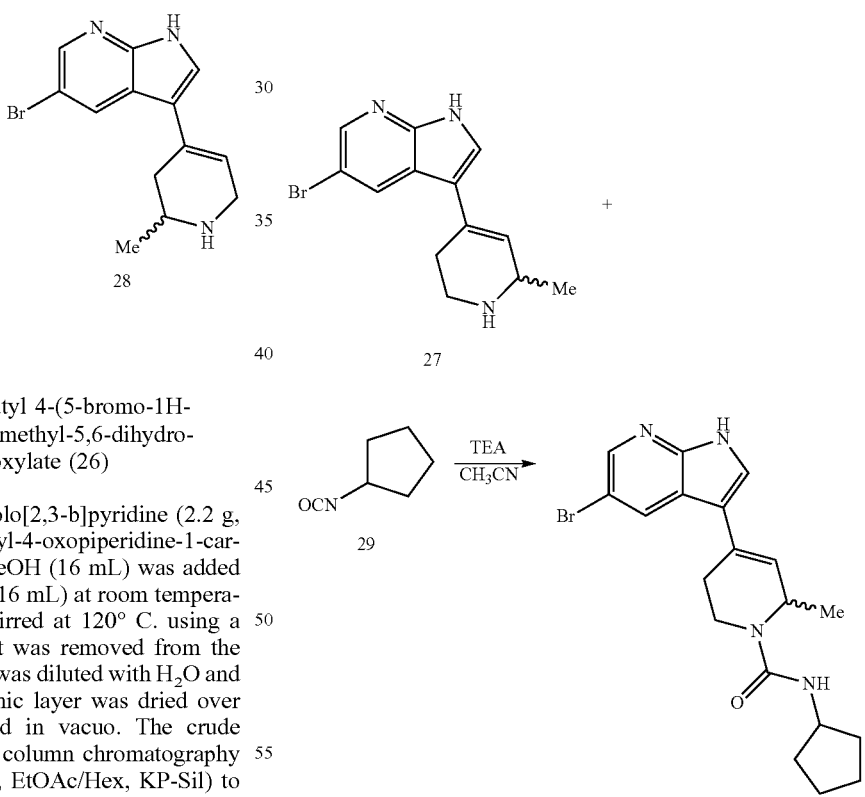

$^1H$ NMR (400 MHz, DMSO-$d_6$) δ 11.96 (br s, 1H), 8.41 (d, J=1.6 Hz, 1H), 8.28 (d, J=2.0 Hz, 1H), 7.64 (d, J=1.6 Hz, 1H), 6.16 (d, J=6.8 Hz, 1H), 6.14-6.12 (m, 1H), 4.65-4.64 (m, 1H), 4.08 (dd, J=13.0, 4.2 Hz, 1H), 3.97-3.92 (m, 1H), 2.94-2.88 (m, 1H), 2.44-2.41 (m, 2H), 1.79-1.75 (m, 2H), 1.64-1.62 (m, 2H), 1.49-1.41 (m, 4H), 1.18 (d, J=6.8 Hz, 3H); [M+H]$^+$ 403.

Step 3-2: Preparation of 4-(5-bromo-1H-pyrrolo[2,3-b]pyridin-3-yl)-N-cyclopentyl-6-methyl-5,6-dihydropyridine-1(2H)-carboxamide

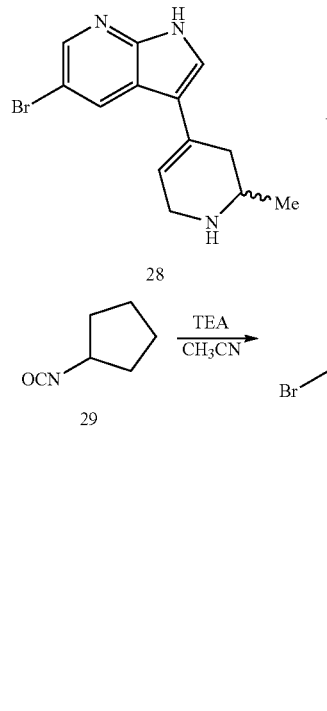

$^1$H NMR (400 MHz, DMSO-$d_6$) δ 11.95 (br s, 1H), 8.42 (d, J=1.6 Hz, 1H), 8.29 (d, J=2.0 Hz, 1H), 7.63 (d, J=2.0 Hz, 1H), 6.19-6.15 (m, 2H), 4.57-4.53 (m, 1H), 4.28-4.23 (m, 1H), 3.97-3.91 (m, 1H), 3.64-3.59 (m, 1H), 2.67-2.62 (m, 1H), 2.35-2.31 (m, 1H), 1.80-1.78 (m, 2H), 1.65-1.62 (m, 2H), 1.51-1.36 (m, 4H), 1.05 (d, J=6.8 Hz, 3H); [M+H]$^+$ 403.

EXAMPLE 86

N-isopropyl-2-methyl-4-(5-(4-((4-methylpiperazin-1-yl)methyl)phenyl)-1H-pyrrolo[2,3-b]pyridin-3-yl)-5,6-dihydropyridine-1(2H)-carboxamide

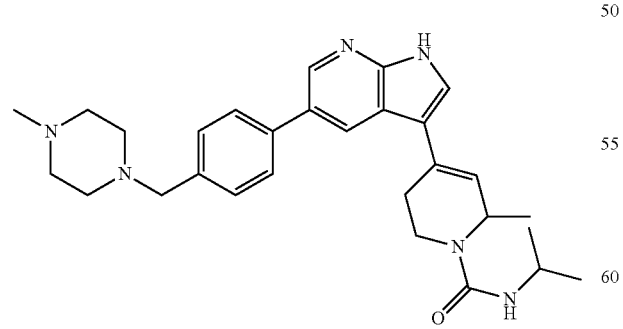

$^1$H NMR (400 MHz, DMSO-$d_6$) δ 11.78 (d, J=1.6 Hz, 1H), 8.52-8.50 (m, 1H), 8.39-8.36 (m, 1H), 7.70-7.67 (m, 2H), 7.61-7.59 (m, 1H), 7.39 (d, J=8.4 Hz, 2H), 6.26-6.22 (m, 1H), 6.10 (t, J=8.4 Hz, 1H), 4.69 (t, J=4.8 Hz, 1H), 4.56 (t, J=6.0 Hz, 1H), 4.31-4.27 (m, 1H), 4.09 (dd, J=12.8, 5.6 Hz, 1H), 3.84-3.76 (m, 1H), 3.50 (s, 2H), 2.97-2.90 (m, 1H), 2.68-2.65 (m, 1H), 2.47-2.34 (m, 8H), 2.16 (s, 3H), 1.19 (d, J=6.8 Hz, 2H), 1.07 (d, J=6.4 Hz, 6H); [M+H]$^+$ 487.

EXAMPLE 87

N-isopropyl-2-methyl-4-(5-(5-(morpholinomethyl)thiophen-2-yl)-1H-pyrrolo[2,3-b]pyridin-3-yl)-5,6-dihydropyridine-1(2H)-carboxamide

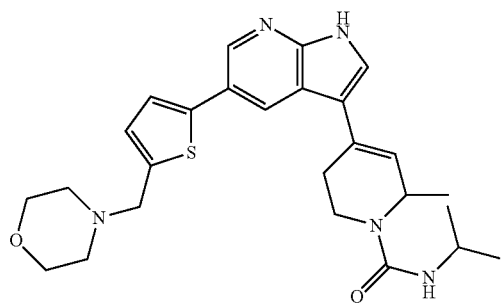 [SMILES: CC(C)NC(=O)N1CCC(c2c[nH]c3ncc(-c4ccc(CN5CCOCC5)s4)cc23)=CC1C]

$^1$H NMR (400 MHz, DMSO-$d_6$) δ 11.82 (br s, 1H), 8.52 (s, 1H), 8.31 (s, 1H), 7.61 (s, 1H), 7.40 (d, J=3.6 Hz, 1H), 6.99 (d, J=3.6 Hz, 1H), 6.17-6.16 (m, 1H), 6.09 (d, J=7.6 Hz, 1H), 4.71-4.69 (m, 1H), 4.12-4.07 (m, 1H), 3.84-3.77 (m, 1H), 3.69 (s, 2H), 3.60 (t, J=4.4 Hz, 4H), 2.97-2.90 (m, 1H), 2.47-2.42 (m, 6H), 1.20 (d, J=6.8 Hz, 3H), 1.08 (d, J=6.8 Hz, 6H); [M+H]$^+$ 480.

EXAMPLE 88

N-isopropyl-2-methyl-4-(5-(5-((4-methylpiperazin-1-yl)methyl)thiophen-2-yl)-1H-pyrrolo[2,3-b]pyridin-3-yl)-5,6-dihydropyridine-1(2H)-carboxamide $^1$H NMR (400 MHz, DMSO-$d_6$) δ 11.82 (s, 1H), 8.50 (s, 1H), 8.30 (s, 1H), 7.61 (s, 1H), 7.39 (d, J=3.6 Hz, 1H), 6.98 (d, J=3.2 Hz, 1H), 6.18-6.16 (m, 1H), 6.09 (d, J=8.0 Hz, 1H), 4.72-4.67 (m, 1H), 4.13-4.08 (m, 1H), 3.67 (s, 2H), 2.97-2.89 (m, 1H), 2.46-2.24 (m, 7H), 2.16 (s, 3H), 1.22 (d, J=8.0 Hz, 3H), 1.08 (d, J=6.4 Hz, 6H); [M+H]$^+$ 493.

EXAMPLE 89

N-isopropyl-2-methyl-4-(5-(4-(4-methylpiperazine-1-carbonyl)phenyl)-1H-pyrrolo[2,3-b]pyridin-3-yl)-5,6-dihydropyridine-1(2H)-carboxamide

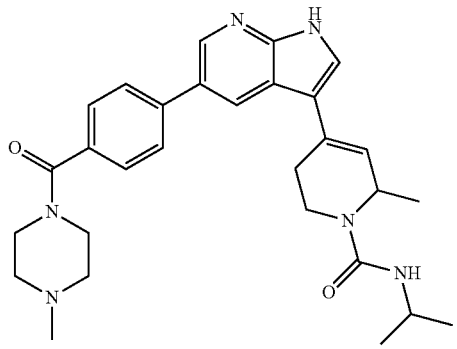 [SMILES: CC(C)NC(=O)N1CCC(c2c[nH]c3ncc(-c4ccc(C(=O)N5CCN(C)CC5)cc4)cc23)=CC1C]

$^1$H NMR (400 MHz, DMSO-$d_6$) δ 11.84 (br s, 1H), 8.55 (br s, 1H), 8.43 (br s, 1H), 7.92-7.81 (m, 2H), 7.66-7.58 (m, 1H), 7.57-7.48 (m, 2H), 6.29-6.24 (m, 1H), 6.10-6.08 (m, 1H), 4.69-4.68 (m, 1H), 4.12-4.08 (m, 1H), 3.83-3.76 (m, 1H), 3.66-3.41 (m, 6H), 2.97-2.90 (m, 1H), 2.40-2.30 (m, 4H), 2.20 (s, 3H), 1.20-1.18 (m, 3H), 1.08-1.06 (m, 6H); [M+H]$^+$ 501. (A mixture of 2-methyl and 6-methyl=9:1)

EXAMPLE 90

N-isopropyl-2-methyl-4-(5-(4-(morpholinomethyl)phenyl)-1H-pyrrolo[2,3-b]pyridin-3-yl)-5,6-dihydropyridine-1(2H)-carboxamide

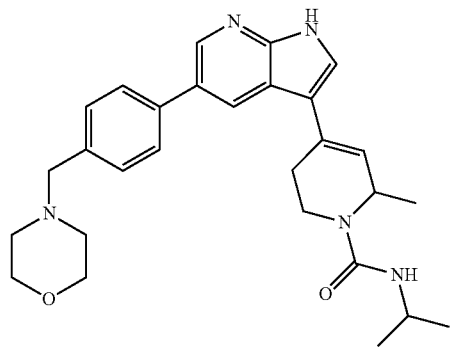 [SMILES: CC(C)NC(=O)N1CCC(c2c[nH]c3ncc(-c4ccc(CN5CCOCC5)cc4)cc23)=CC1C]

$^1$H NMR (400 MHz, DMSO-$d_6$) δ 11.79 (br s, 1H), 8.52-8.50 (m, 1H), 8.40-8.36 (m, 1H), 7.72-7.68 (m, 2H), 7.61-7.59 (m, 1H), 7.42-7.40 (m, 2H), 6.26-6.21 (m, 1H), 6.10-6.05 (m, 1H), 4.71-4.69 (m, 0.7H), 4.58-4.54 (m, 0.3H), 4.32-4.27 (m, 0.3H), 4.12-4.07 (m, 0.7H), 3.85-3.75 (m, 1H), 3.60-3.57 (m, 4H), 3.51 (s, 2H), 2.97-2.90 (m, 0.7H), 2.70-2.65 (m, 0.3H), 2.38-2.34 (m, 5H), 1.20-1.85 (m, 3H), 1.08-1.06 (d, J=6.8 Hz, 6H); [M+H]$^+$ 474. (A mixture of 2-methyl and 6-methyl=2:1)

EXAMPLE 91

6-Methyl-4-(5-(5-((4-methylpiperazin-1-yl)methyl)thiophen-2-yl)-1H-pyrrolo[2,3-b]pyridin-3-yl)-N-(pentan-3-yl)-3,6-dihydropyridine-1(2H)-carboxamide

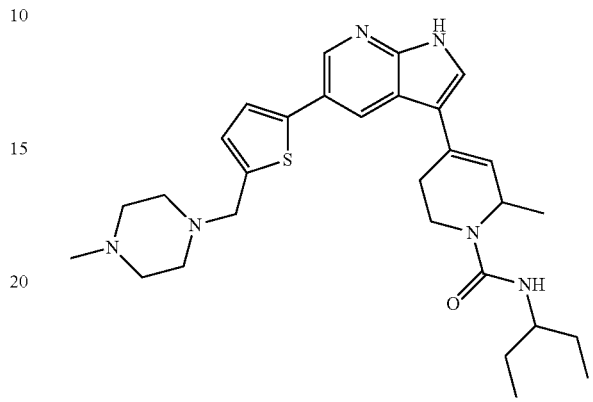

$^1$H NMR (400 MHz, DMSO-$d_6$) δ 11.82 (br s, 1H), 8.51-8.50 (m, 1H), 8.33-8.30 (m, 1H), 7.62-7.59 (m, 1H), 7.40-7.38 (m, 1H), 6.97-6.96 (m, 1H), 6.22-6.15 (m, 1H), 5.95-5.92 (m, 1H), 4.72-4.55 (m, 1H), 4.36-4.25 (m, 1H), 4.12-4.08 (m, 2H), 3.69 (s, 3H), 3.50-3.48 (m, 1H), 3.17-3.16 (m, 3H), 2.98-2.91, 2.72-2.68 (m, 1H), 2.43-2.36 (m, 8H), 2.16 (s, 3H), 1.45-1.35 (m, 4H), 1.22-1.20, 1.08-1.06 (m, 3H), 0.85-0.81 (m, 6H); [M+H]$^+$ 521. (A mixture of 2-methyl and 6-methyl=1:1)

EXAMPLE 92

6-Methyl-4-(5-(5-(morpholinomethyl)thiophen-2-yl)-1H-pyrrolo[2,3-b]pyridin-3-yl)-N-(pentan-3-yl)-3,6-dihydropyridine-1(2H)-carboxamide

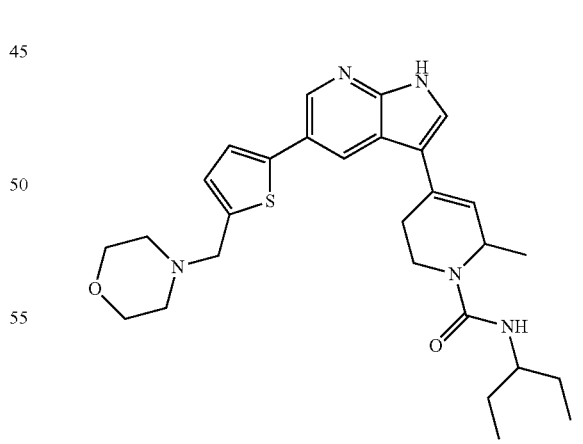

$^1$H NMR (400 MHz, DMSO-$d_6$) δ 11.83 (br s, 1H), 8.52 (d, J=1.6 Hz, 1H), 8.32 (d, J=10.8 Hz, 1H), 7.61-7.58 (m, 1H), 7.41-7.40 (m, 1H), 6.99 (d, J=2.8 Hz, 1H), 6.22-5.93 (m, 1H), 4.72-4.68 (m, 1H), 4.58-4.57 (m, 1H), 4.34-4.28 (m, 1H), 4.19-4.12 (m, 1H), 3.70-3.63 (m, 2H), 3.59-3.50 (m, 4H), 3.48-3.45 (m, 1H), 2.98-2.91 (m, 1H), 2.43-2.40

(m, 4H), 1.47-1.35 (m, 4H), 1.22-1.20 (m, 1H), 1.08-1.65 (m, 1H), 0.84-0.81 (m, 6H); [M+H]+ 507. (A mixture of 2-methyl and 6-methyl=1:1)

EXAMPLE 93 tert-Butyl 4-((5-(3-(1-(cyclopropylcarbamoyl)-6-methyl-1,2,3,6-tetrahydropyridin-4-yl)-1H-pyrrolo[2,3-b]pyridin-5-yl)thiophen-2-yl)methyl)piperazine-1-carboxylate

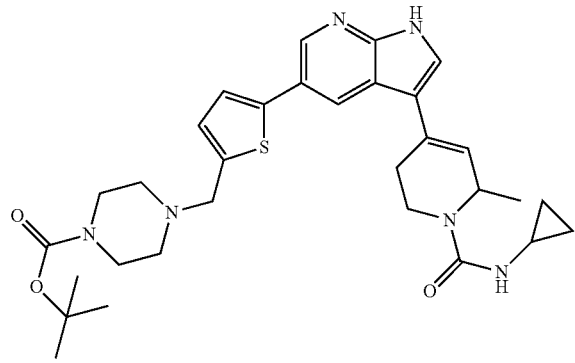 [SMILES: CC1C=C(c2c[nH]c3ncc(-c4ccc(CN5CCN(C(=O)OC(C)(C)C)CC5)s4)cc23)CCN1C(=O)NC1CC1]

[M+H]+ 577.

EXAMPLE 94

N-cyclopropyl-2-methyl-4-(5-(4-(4-methylpiperazine-1-carbonyl)phenyl)-1H-pyrrolo[2,3-b]pyridin-3-yl)-5,6-dihydropyridine-1(2H)-carboxamide

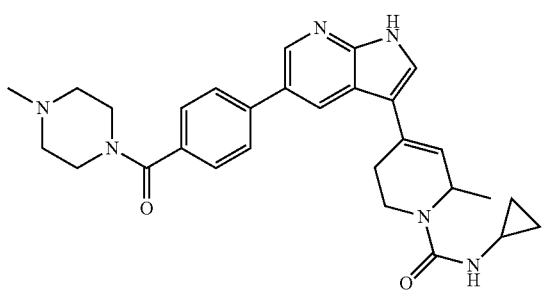 [SMILES: CC1C=C(c2c[nH]c3ncc(-c4ccc(C(=O)N5CCN(C)CC5)cc4)cc23)CCN1C(=O)NC1CC1]

¹H NMR (400 MHz, DMSO-d₆) δ 11.86 (br s, 1H), 8.60 (s, 1H), 8.43 (s, 1H), 7.83 (d, J=8.4 Hz, 2H), 7.63 (s, 1H), 7.49 (d, J=8.0 Hz, 2H), 6.55-6.52 (m, 1H), 6.24-6.21 (m, 1H), 4.68-4.62 (m, 1H), 4.08-4.02 (m, 1H), 3.68-3.58 (m, 2H), 2.99-2.92 (m, 1H), 2.56-2.52 (m, 2H), 2.45-2.26 (m, 7H), 2.21 (s, 3H), 1.19 (d, J=6.4 Hz, 3H), 0.58-0.52 (m, 2H), 0.42-0.37 (m, 2H); [M+H]+ 499.

EXAMPLE 95

N-cyclopropyl-2-methyl-4-(5-(4-((4-methylpiperazin-1-yl)methyl)phenyl)-1H-pyrrolo[2,3-b]pyridin-3-yl)-5,6-dihydropyridine-1(2H)-carboxamide

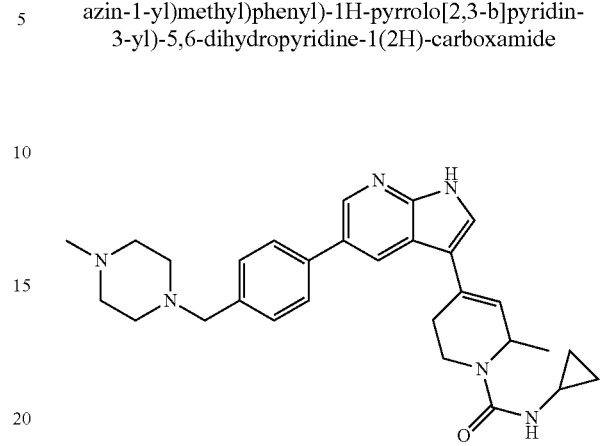

¹H NMR (400 MHz, DMSO-d₆) δ 11.81 (br s, 1H), 8.50 (s, 1H), 8.36 (s, 1H), 7.69 (d, J=5.2 Hz, 2H), 7.60 (s, 1H), 7.39 (d, J=8.0 Hz, 2H), 6.55-6.52 (m, 1H), 6.24-6.21 (m, 1H), 4.68-4.62 (m, 1H), 4.08-4.02 (m, 1H), 3.50 (s, 2H), 2.99-2.92 (m, 1H), 2.56-2.52 (m, 2H), 2.45-2.25 (m, 11H), 2.15 (s, 3H), 1.18 (d, J=6.4 Hz, 3H), 0.57-0.52 (m, 2H), 0.42-0.38 (m, 2H); [M+H]+ 485.

EXAMPLE 96

N-cyclopropyl-2-methyl-4-(5-(5-((4-methylpiperazin-1-yl)methyl)thiophen-2-yl)-1H-pyrrolo[2,3-b]pyridin-3-yl)-5,6-dihydropyridine-1(2H)-carboxamide

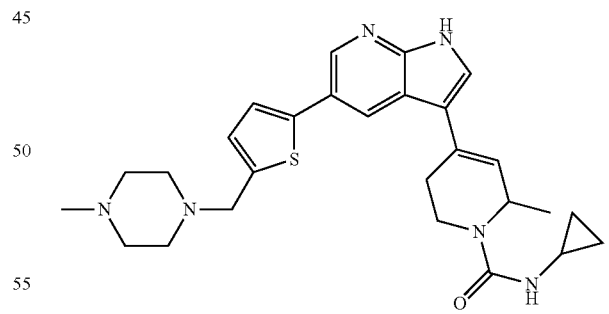

¹H NMR (400 MHz, DMSO-d₆) δ 11.83 (br s, 1H), 8.50 (s, 1H), 8.30 (s, 1H), 7.61 (s, 1H), 7.39 (d, J=3.2 Hz, 1H), 6.97 (d, J=3.2 Hz, 1H), 6.54 (d, J=2.8 Hz, 1H), 6.17-6.16 (m, 1H), 4.69-4.63 (m, 1H), 4.07-4.02 (m, 1H), 3.67 (s, 2H), 2.98-2.91 (m, 1H), 2.57-2.52 (m, 2H), 2.47-2.35 (m, 11H), 2.16 (s, 3H), 1.19 (d, J=6.8 Hz, 3H), 0.58-0.52 (m, 2H), 0.45-0.38 (m, 2H); [M+H]+ 491.

EXAMPLE 97

N-cyclopropyl-2-methyl-4-(5-(5-(morpholinomethyl)thiophen-2-yl)-1H-pyrrolo[2,3-b]pyridin-3-yl)-5,6-dihydropyridine-1(2H)-carboxamide

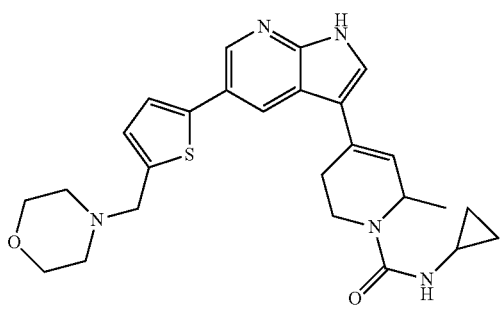 [SMILES: CC1C=C(c2c[nH]c3ncc(-c4ccc(CN5CCOCC5)s4)cc23)CCN1C(=O)NC1CC1]

$^1$H NMR (400 MHz, DMSO-d$_6$) δ 11.83 (br s, 1H), 8.51 (s, 1H), 8.31 (s, 1H), 7.61 (s, 1H), 7.40 (d, J=3.6 Hz, 1H), 6.99 (d, J=3.6 Hz, 1H), 6.54 (d, J=2.8 Hz, 1H), 6.17-6.16 (m, 1H), 4.68-4.62 (m, 1H), 4.08-4.02 (m, 1H), 3.68 (s, 2H), 3.60 (t, J=4.4 Hz, 4H), 2.99-2.91 (m, 1H), 2.58-2.55 (m, 1H), 2.47-2.35 (m, 6H), 1.19 (d, J=6.4 Hz, 3H), 0.58-0.53 (m, 2H), 0.43-0.38 (m, 2H); [M+H]$^+$ 478.

EXAMPLE 98

N-cyclobutyl-2-methyl-4-(5-(4-(4-methylpiperazine-1-carbonyl)phenyl)-1H-pyrrolo[2,3-b]pyridin-3-yl)-5,6-dihydropyridine-1(2H)-carboxamide

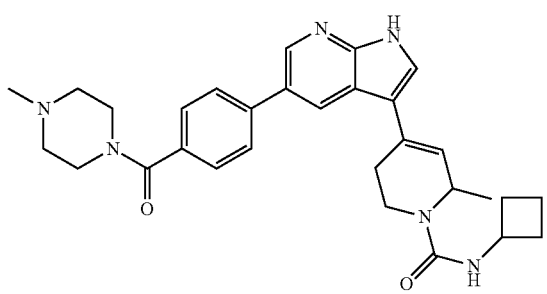 [SMILES: CC1C=C(c2c[nH]c3ncc(-c4ccc(C(=O)N5CCN(C)CC5)cc4)cc23)CCN1C(=O)NC1CCC1]

$^1$H NMR (400 MHz, DMSO-d$_6$) δ 11.85 (br s, 1H), 8.56 (s, 1H), 8.43 (s, 1H), 7.83 (d, J=8.4 Hz, 2H), 7.63 (s, 1H), 7.49 (d, J=8.0 Hz, 2H), 6.57 (d, J=7.6 Hz, 1H), 6.25-6.24 (m, 1H), 4.72-4.66 (m, 1H), 4.20-4.06 (m, 2H), 3.67-3.42 (m, 4H), 2.99-2.92 (m, 1H), 2.47-2.28 (m, 6H), 2.21 (s, 3H), 2.14-2.08 (m, 2H), 2.00-1.88 (m, 2H), 1.62-1.50 (m, 2H), 1.20 (d, J=6.4 Hz, 3H); [M+H]$^+$ 513.

EXAMPLE 99

N-cyclobutyl-2-methyl-4-(5-(4-((4-methylpiperazin-1-yl)methyl)phenyl)-1H-pyrrolo[2,3-b]pyridin-3-yl)-5,6-dihydropyridine-1(2H)-carboxamide

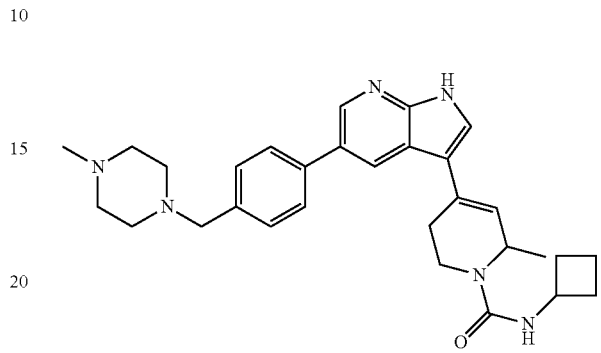

$^1$H NMR (400 MHz, DMSO-d$_6$) δ 11.81 (br s, 1H), 8.50 (s, 1H), 8.36 (s, 1H), 7.69 (d, J=12.0 Hz, 2H), 7.59 (s, 1H), 7.39 (d, J=8.0 Hz, 2H), 6.56 (d, J=7.6 Hz, 1H), 6.23-6.21 (m, 1H), 4.72-4.66 (m, 1H), 4.20-4.06 (m, 2H), 3.50 (s, 2H), 3.30-3.27 (m, 1H), 2.99-2.92 (m, 1H), 2.47-2.28 (m, 9H), 2.16 (s, 3H), 2.15 s, 3H), 2.14-2.09 (m, 2H), 2.00-1.88 (m, 2H), 1.63-1.51 (m, 2H), 1.19 (d, J=6.8 Hz, 3H); [M+H]$^+$ 499.

EXAMPLE 100

N-cyclobutyl-2-methyl-4-(5-(5-((4-methylpiperazin-1-yl)methyl)thiophen-2-yl)-1H-pyrrolo[2,3-b]pyridin-3-yl)-5,6-dihydropyridine-1(2H)-carboxamide

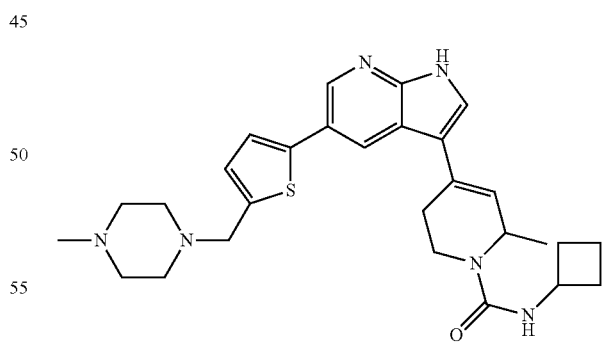

$^1$H NMR (400 MHz, DMSO-d$_6$) δ 11.85 (br s, 1H), 8.50 (s, 1H), 8.30 (s, 1H), 7.61 (s, 1H), 7.39 (d, J=3.6 Hz, 1H), 6.98 (d, J=3.6 Hz, 1H), 6.57 (d, J=7.6 Hz, 1H), 6.18-6.16 (m, 1H), 4.72-4.66 (m, 1H), 4.21-4.07 (m, 2H), 3.67 (s, 2H), 2.98-2.91 (m, 1H), 2.47-2.28 (m, 9H), 2.16 (s, 3H), 2.15-2.09 (m, 2H), 2.00-1.88 (m, 2H), 1.63-1.51 (m, 2H), 1.20 (d, J=6.8 Hz, 3H); [M+H]$^+$ 505.

EXAMPLE 101

N-cyclobutyl-2-methyl-4-(5-(5-(morpholinomethyl)thiophen-2-yl)-1H-pyrrolo[2,3-b]pyridin-3-yl)-5,6-dihydropyridine-1(2H)-carboxamide

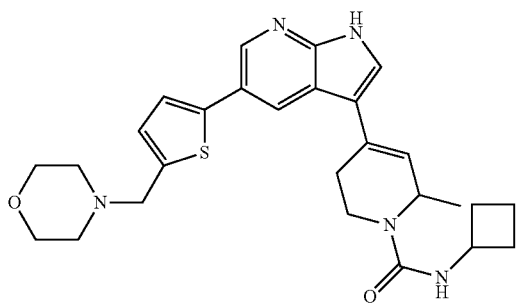 [SMILES: CC1C=C(c2c[nH]c3ncc(-c4ccc(CN5CCOCC5)s4)cc23)CCN1C(=O)NC1CCC1]

$^1$H NMR (400 MHz, DMSO-d$_6$) δ 11.83 (br s, 1H), 8.51 (s, 1H), 8.31 (s, 1H), 7.61 (s, 1H), 7.40 (d, J=3.2 Hz, 1H), 7.00 (d, J=3.6 Hz, 1H), 6.57 (d, J=7.6 Hz, 1H), 6.18-6.16 (m, 1H), 4.72-4.66 (m, 1H), 4.21-4.07 (m, 2H), 3.69 (s, 2H), 3.60 (t, J=4.4 Hz, 4H), 2.98-2.921 (m, 1H), 2.47-2.35 (m, 6H), 2.18-2.09 (m, 2H), 2.00-1.88 (m, 2H), 1.63-1.50 (m, 2H), 1.20 (d, J=6.8 Hz, 3H); [M+H]$^+$ 492.

EXAMPLE 102

N-cyclopentyl-2-methyl-4-(5-(5-((4-methylpiperazin-1-yl)methyl)thiophen-2-yl)-1H-pyrrolo[2,3-b]pyridin-3-yl)-5,6-dihydropyridine-1(2H)-carboxamide

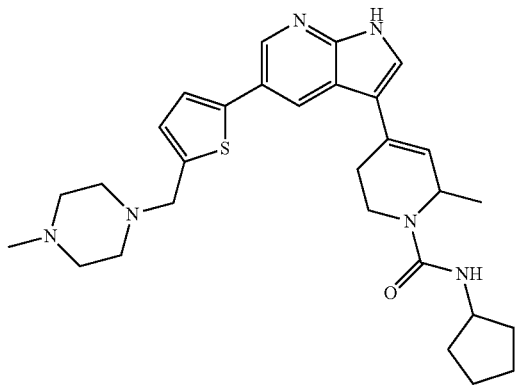 [SMILES: CC1C=C(c2c[nH]c3ncc(-c4ccc(CN5CCN(C)CC5)s4)cc23)CCN1C(=O)NC1CCCC1]

$^1$H NMR (400 MHz, DMSO-d$_6$) δ 11.84 (br s, 1H), 8.50 (d, J=2.0 Hz, 1H), 8.40 (d, J=2.0 Hz, 1H), 7.61 (br s, 1H), 7.39 (d, J=3.6 Hz, 1H), 6.97 (d, J=3.6 Hz, 1H), 6.19-6.15 (m, 2H), 4.70-4.69 (m, 1H), 4.12-4.08 (m, 1H), 4.00-3.86 (m, 1H), 3.67 (s, 2H), 3.25-3.22 (m, 1H), 2.97-2.90 (m, 1H), 2.50-2.48 (m, 1H), 2.46-2.32 (m, 8H), 2.15 (s, 3H), 1.80-1.73 (m, 2H), 1.65-1.62 (m, 2H), 1.52-1.34 (m, 4H), 1.20 (d, J=6.4 Hz, 3H); [M+H]$^+$ 519.

EXAMPLE 103

N-cyclopentyl-6-methyl-4-(5-(5-((4-methylpiperazin-1-yl)methyl)thiophen-2-yl)-1H-pyrrolo[2,3-b]pyridin-3-yl)-5,6-dihydropyridine-1(2H)-carboxamide

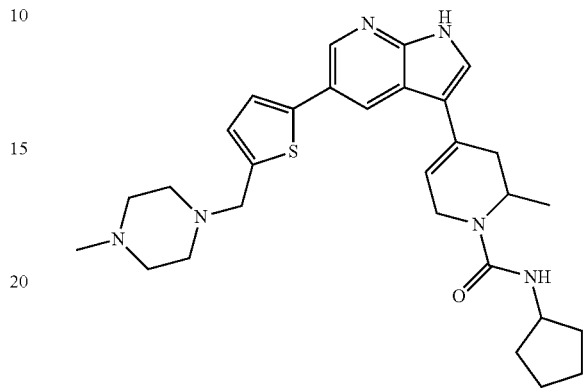

$^1$H NMR (400 MHz, DMSO-d$_6$) δ 11.83 (br s, 1H), 8.51 (d, J=2.0 Hz, 1H), 8.32 (d, J=2.0 Hz, 1H), 7.59 (br s, 1H), 7.39 (d, J=3.6 Hz, 1H), 6.97 (d, J=3.6 Hz, 1H), 6.21-6.20 (m, 1H), 6.14 (d, J=6.8 Hz, 1H), 4.59-4.55 (m, 1H), 4.34-4.29 (m, 1H), 3.98-3.92 (m, 1H), 3.67 (s, 2H), 3.67-3.63 (m, 1H), 2.69-2.64 (m, 1H), 2.50-2.48 (m, 1H), 2.40-2.31 (m, 8H), 2.15 (s, 3H), 1.83-1.75 (m, 2H), 1.65-1.62 (m, 2H), 1.51-1.37 (m, 4H), 1.07 (d, J=6.8 Hz, 3H); [M+H]$^+$ 519.

EXAMPLE 104

N-cyclopentyl-6-methyl-4-(5-(5-(morpholinomethyl)thiophen-2-yl)-1H-pyrrolo[2,3-b]pyridin-3-yl)-5,6-dihydropyridine-1(2H)-carboxamide

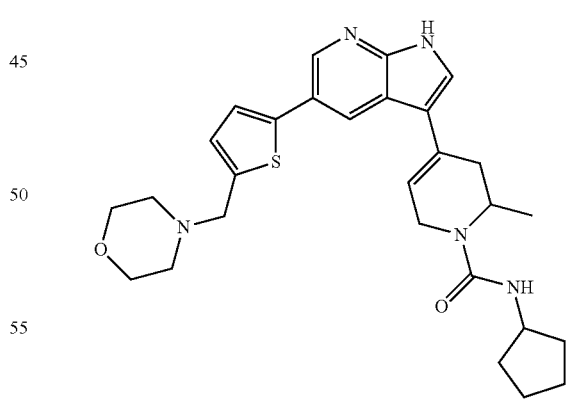

$^1$H NMR (400 MHz, DMSO-d$_6$) δ 11.83 (br s, 1H), 8.51 (d, J=2.0 Hz, 1H), 8.33 (d, J=2.0 Hz, 1H), 7.60 (br s, 1H), 7.40 (d, J=3.6 Hz, 1H), 6.99 (d, J=3.6 Hz, 1H), 6.21-6.20 (m, 1H), 6.14 (d, J=6.8 Hz, 1H), 4.59-4.55 (m, 1H), 4.34-4.27 (m, 1H), 3.98-3.92 (m, 1H), 3.68 (s, 2H), 3.64-3.63 (m, 1H), 3.61-3.58 (m, 4H), 2.68-2.64 (m, 1H), 2.43-2.39 (m, 4H), 1.81-1.76 (m, 2H), 1.66-1.63 (m, 2H), 1.50-1.37 (m, 4H), 1.07 (d, J=6.4 Hz, 3H); [M+H]$^+$ 506.

EXAMPLE 105

N-cyclopentyl-2-methyl-4-(5-(4-(methylsulfonyl)phenyl)-1H-pyrrolo[2,3-b]pyridin-3-yl)-5,6-dihydropyridine-1(2H)-carboxamide

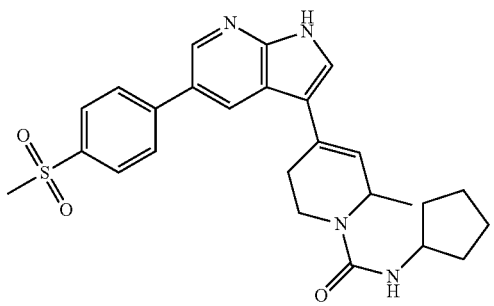 [SMILES: CC1C=C(c2c[nH]c3ncc(-c4ccc(S(C)(=O)=O)cc4)cc23)CCN1C(=O)NC1CCCC1]

$^1$H NMR (400 MHz, DMSO-d$_6$) δ 11.91 (br s, 1H), 8.61 (s, 1H), 8.49 (s, 1H), 8.09-8.00 (m, 4H), 7.66 (s, 1H), 6.28-6.26 (m, 1H), 6.18-6.14 (m, 1H), 4.72-4.68 (m, 1H), 4.13-4.08 (m, 1H), 3.99-3.94 (m, 1H), 3.38-3.28 (m, 6H), 2.99-2.92 (m, 1H), 2.45-2.38 (m, 2H), 1.83-1.76 (m, 2H), 1.67-1.61 (m, 2H), 1.52-1.36 (m, 4H), 1.20 (d, J=6.4 Hz, 3H); [M+H]$^+$ 479.

EXAMPLE 106

N-cyclopentyl-2-methyl-4-(5-(5-(morpholinomethyl)thiophen-2-yl)-1H-pyrrolo[2,3-b]pyridin-3-yl)-5,6-dihydropyridine-1(2H)-carboxamide

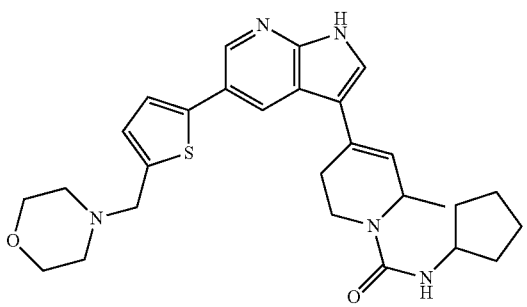 [SMILES: CC1C=C(c2c[nH]c3ncc(-c4ccc(CN5CCOCC5)s4)cc23)CCN1C(=O)NC1CCCC1]

$^1$H NMR (400 MHz, DMSO-d$_6$) δ 11.85 (s, 1H), 8.52 (s, 1H), 8.31 (s, 1H), 7.61 (s, 1H), 7.40 (d, J=3.6 Hz, 1H), 6.99 (d, J=3.6 Hz, 1H), 6.21-6.12 (m, 2H), 4.75-4.67 (m, 1H), 4.14-4.08 (m, 1H), 4.01-3.93 (m, 1H), 3.69 (s, 2H), 3.64-3.57 (m, 4H), 2.98-2.91 (m, 1H), 2.48-2.35 (m, 6H), 1.85-1.76 (m, 2H), 1.70-1.60 (m, 2H), 1.52-1.37 (m, 4H), 1.29 (d, J=6.8 Hz, 3H); [M+H]$^+$506.

EXAMPLE 107

N-cyclopentyl-2-methyl-4-(5-(5-((4-methylpiperazin-1-yl)methyl)thiophen-2-yl)-1H-pyrrolo[2,3-b]pyridin-3-yl)-5,6-dihydropyridine-1(2H)-carboxamide

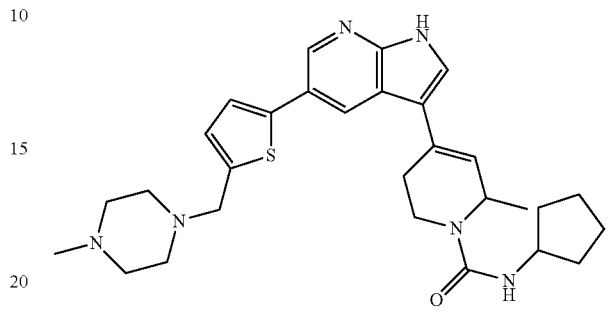

$^1$H NMR (400 MHz, DMSO-d$_6$) δ 11.84 (br s, 1H), 8.50 (d, J=2.0 Hz, 1H), 8.40 (d, J=2.0 Hz, 1H), 7.61 (br s, 1H), 7.39 (d, J=3.6 Hz, 1H), 6.97 (d, J=3.6 Hz, 1H), 6.19-6.15 (m, 2H), 4.70-4.69 (m, 1H), 4.12-4.08 (m, 1H), 4.00-3.86 (m, 1H), 3.67 (s, 2H), 3.25-3.22 (m, 1H), 2.97-2.90 (m, 1H), 2.50-2.48 (m, 1H), 2.46-2.32 (m, 8H), 2.15 (s, 3H), 1.80-1.73 (m, 2H), 1.65-1.62 (m, 2H), 1.52-1.34 (m, 4H), 1.20 (d, J=6.4 Hz, 3H); 2-메틸, $^1$H NMR (400 MHz, DMSO-d$_6$) δ 11.83 (br s, 1H), 8.51 (d, J=2.0 Hz, 1H), 8.32 (d, J=2.0 Hz, 1H), 7.59 (br s, 1H), 7.39 (d, J=3.6 Hz, 1H), 6.97 (d, J=3.6 Hz, 1H), 6.21-6.20 (m, 1H), 6.14 (d, J=6.8 Hz, 1H), 4.59-4.55 (m, 1H), 4.34-4.29 (m, 1H), 3.98-3.92 (m, 1H), 3.67 (s, 2H), 3.67-3.63 (m, 1H), 2.69-2.64 (m, 1H), 2.50-2.48 (m, 1H), 2.40-2.31 (m, 8H), 2.15 (s, 3H), 1.83-1.75 (m, 2H), 1.65-1.62 (m, 2H), 1.51-1.37 (m, 4H), 1.07 (d, J=6.8 Hz, 3H); 6-methyl; [M+H]$^+$ 519. (a mixture of 2-methyl and 6-methyl=2:1)

EXAMPLE 108

N-cyclopentyl-4-(5-(3,4-dimethoxyphenyl)-1H-pyrrolo[2,3-b]pyridin-3-yl)-2-methyl-5,6-dihydropyridine-1(2H)-carboxamide

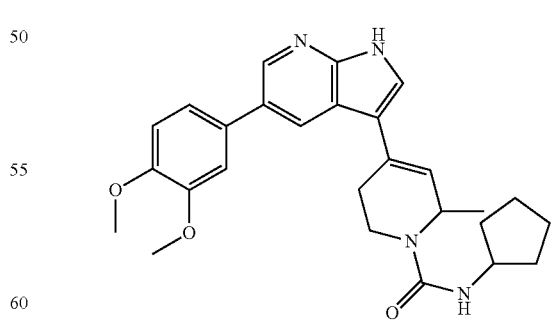

$^1$H NMR (400 MHz, DMSO-d$_6$) δ 11.77 (s, 1H), 8.50 (s, 1H), 8.32 (s, 1H), 7.59 (s, 1H), 7.28 (s, 1H), 7.23 (d, J=8.4 Hz, 1H), 7.06 (d, J=8.4 Hz, 1H), 6.26-6.12 (m, 2H), 4.72-4.62 (m, 1H), 4.15-4.08 (m, 1H), 3.99-3.93 (m, 1H), 3.87 (s, 3H), 3.80 (s, 3H), 2.98-2.91 (m, 1H), 2.49-2.34 (m, 3H), 1.85-1.74 (m, 2H), 1.67-1.62 (m, 2H), 1.52-1.38 (m, 4H), 1.19 (d, J=6.8 Hz, 3H); [M+H]+ 461.

EXAMPLE 109

2-Ethyl-N-isopropyl-4-(5-(5-(morpholinomethyl)thiophen-2-yl)-1H-pyrrolo[2,3-b]pyridin-3-yl)-5,6-dihydropyridine-1(2H)-carboxamide

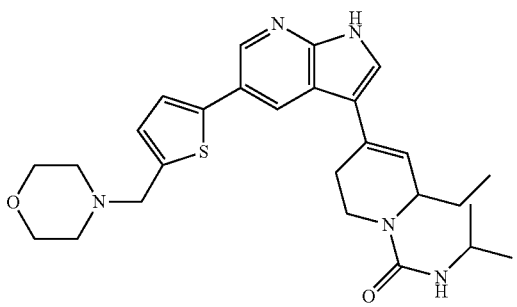 [SMILES: CCC1C=C(c2c[nH]c3ncc(-c4ccc(CN5CCOCC5)s4)cc23)CCN1C(=O)NC(C)C]

$^1$H NMR (400 MHz, DMSO-d$_6$) δ 11.82 (br s, 1H), 8.51 (s, 1H), 8.32 (s, 1H), 7.60 (s, 1H), 7.40 (d, J=3.6 Hz, 1H), 6.99 (d, J=3.6 Hz, 1H), 6.21-6.18 (m, 1H), 6.04 (d, J=7.6 Hz, 1H), 4.39-4.32 (m, 1H), 3.85-3.77 (m, 1H), 3.69 (s, 2H), 3.64-3.61 (m, 1H), 3.60 (t, J=4.4 Hz, 4H), 2.65-2.49 (m, 1H), 2.47-2.42 (m, 6H), 1.60-1.52 (m, 1H), 1.47-1.41 (m, 1H), 1.10-1.04 (m, 6H), 0.84 (d, J=7.4 Hz, 3H); [M+H]+ 494.

EXAMPLE 110

6-Ethyl-N-isopropyl-4-(5-(5-(morpholinomethyl)thiophen-2-yl)-1H-pyrrolo[2,3-b]pyridin-3-yl)-5,6-dihydropyridine-1(2H)-carboxamide

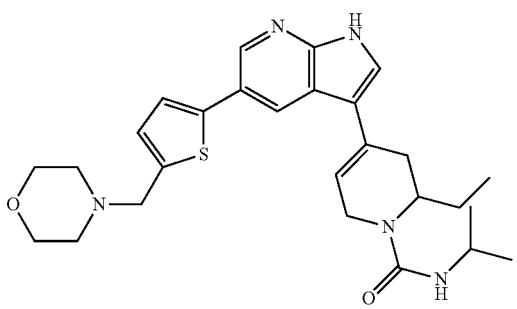 [SMILES: CCC1CC(c2c[nH]c3ncc(-c4ccc(CN5CCOCC5)s4)cc23)=CCN1C(=O)NC(C)C]

$^1$H NMR (400 MHz, DMSO-d$_6$) δ 11.82 (br s, 1H), 8.52 (s, 1H), 8.28 (s, 1H), 7.61 (s, 1H), 7.38 (d, J=3.6 Hz, 1H), 6.99 (d, J=3.6 Hz, 1H), 6.23-6.21 (m, 1H), 6.07 (d, J=11.6 Hz, 1H), 4.62-4.58 (m, 1H), 4.14-4.09 (m, 1H), 3.84-3.77 (m, 1H), 3.68 (s, 2H), 3.60 (t, J=4.4 Hz, 4H), 3.01-2.93 (m, 1H), 2.47-2.42 (m, 6H), 1.70-1.52 (m, 2H), 1.10-1.04 (m, 6H), 0.95 (d, J=7.4 Hz, 3H); [M+H]+ 494.

EXAMPLE 111

2-Ethyl-N-isopropyl-4-(5-(5-((4-methylpiperazin-1-yl)methyl)thiophen-2-yl)-1H-pyrrolo[2,3-b]pyridin-3-yl)-5,6-dihydropyridine-1(2H)-carboxamide

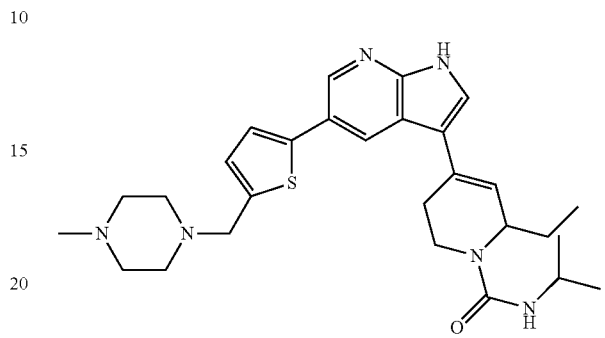

$^1$H NMR (400 MHz, DMSO-d$_6$) δ 11.82 (s, 1H), 8.51 (s, 1H), 8.31 (s, 1H), 7.60 (s, 1H), 7.39 (d, J=3.6 Hz, 1H), 6.97 (d, J=3.6 Hz, 1H), 6.20-6.17 (m, 1H), 6.08-6.05 (m, 1H), 4.40-4.32 (m, 1H), 3.86-3.78 (m, 1H), 3.67 (s, 2H), 3.66-3.57 (m, 1H), 2.67-2.52 (m, 1H), 2.46-2.24 (m, 7H), 2.16 (s, 3H), 1.61-1.52 (m, 1H), 1.48-1.41 (m, 1H), 1.10-1.06 (m, 6H), 0.84 (t, J=7.4 Hz, 3H); [M+H]+ 507.

EXAMPLE 112

6-Ethyl-N-isopropyl-4-(5-(4-(morpholinomethyl)phenyl)-1H-pyrrolo[2,3-b]pyridin-3-yl)-3,6-dihydropyridine-1(2H)-carboxamide

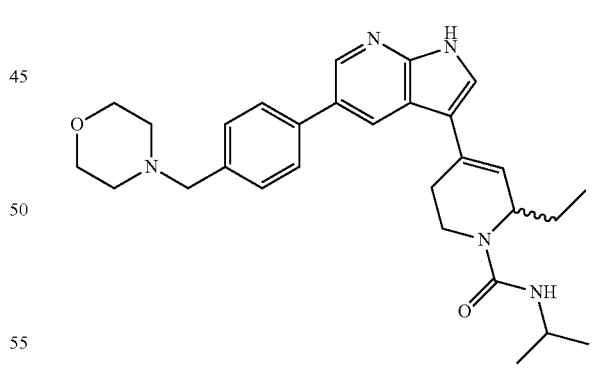

$^1$H NMR (400 MHz, CDCl$_3$) δ 10.56 (d, J=10.9 Hz, 1H), 8.59 (s, 1H), 8.35 (dd, J=7.5, 2.1 Hz, 1H), 7.65-7.59 (m, 2H), 7.48 (dd, J=8.2, 1.9 Hz, 2H), 7.40 (d, J=2.2 Hz, 1H), 6.25-6.16 (m, 1H), 4.42-4.26 (m, 5H), 4.08 (ddq, J=9.9, 6.6, 3.3 Hz, 1H), 3.78 (t, J=4.7 Hz, 4H), 3.60 (s, 2H), 2.53 (t, J=4.9 Hz, 4H), 1.82-1.67 (m, 2H), 1.22 (dt, J=6.5, 2.4 Hz, 6H), 1.09-0.96 (m, 3H); [M+H]+ 488.

EXAMPLE 113

6-Ethyl-N-isopropyl-4-(5-(4-(4-methylpiperazine-1-carbonyl)phenyl)-1H-pyrrolo[2,3-b]pyridin-3-yl)-3,6-dihydropyridine-1(2H)-carboxamide

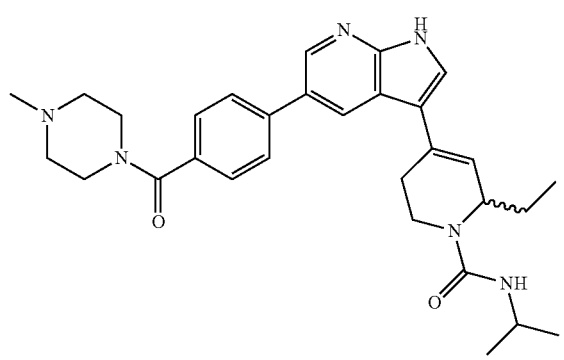 [SMILES: CCC1C=C(c2c[nH]c3ncc(-c4ccc(C(=O)N5CCN(C)CC5)cc4)cc23)CCN1C(=O)NC(C)C]

$^1$H NMR (400 MHz, CDCl$_3$) δ $^1$H NMR (400 MHz, CDCl$_3$) δ 9.75 (s, 1H), 8.57 (s, 1H), 8.35 (dd, J=7.5, 2.1 Hz, 1H), 7.65-7.59 (m, 2H), 7.48 (dd, J=8.2, 1.9 Hz, 2H), 7.40 (d, J=2.2 Hz, 1H), 6.25-6.16 (m, 1H), 4.42-4.26 (m, 3H), 4.08 (ddq, J=9.9, 6.6, 3.3 Hz, 1H), 3.78 (t, J=4.7 Hz, 4H), 3.60 (s, 2H), 2.54 (s, 3H), 2.53 (t, J=4.9 Hz, 4H), 1.82-1.67 (m, 2H), 1.22 (dt, J=6.5, 2.4 Hz, 6H), 1.09-0.96 (m, 3H); [M+H]$^+$ 515.

EXAMPLE 114

N-isopropyl-2,2-dimethyl-4-(5-(5-(morpholinomethyl)thiophen-2-yl)-1H-pyrrolo[2,3-b]pyridin-3-yl)-5,6-dihydropyridine-1(2H)-carboxamide

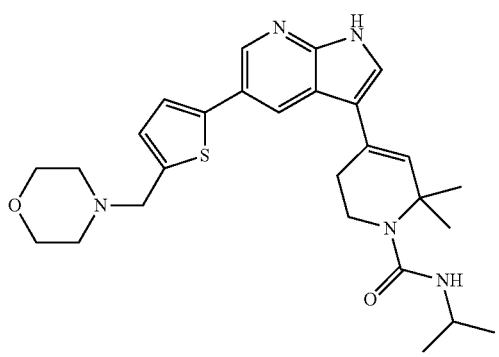 [SMILES: CC(C)NC(=O)N1CCC(c2c[nH]c3ncc(-c4ccc(CN5CCOCC5)s4)cc23)=CC1(C)C]

$^1$H NMR (400 MHz, DMSO-d$_6$) δ 11.83 (br s, 1H), 8.52-8.50 (m, 1H), 8.31-8.26 (m, 1H), 7.62 (br s, 1H), 7.42-7.35 (m, 1H), 7.00-6.99 (m, 1H), 6.19-6.08 (m, 1H), 5.90 (s, 1H), 3.96-3.95 (m, 1H), 3.75-3.73 (m, 1H), 3.68 (s, 2H), 3.60-3.58 (m, 4H), 3.43-3.40 (m, 2H), 2.44-2.43 (m, 5H), 1.54 (s, 4.8H), 1.42 (s, 1.2H), 1.07 (d, J=6.4 Hz, 6H); [M+H]$^+$ 494. (a mixture of 2,2-dimethyl and 6,6-dimethyl=4:1)

EXAMPLE 115

N-isopropyl-2,6-dimethyl-4-(5-(5-(morpholinomethyl)thiophen-2-yl)-1H-pyrrolo[2,3-b]pyridin-3-yl)-3,6-dihydropyridine-1(2H)-carboxamide

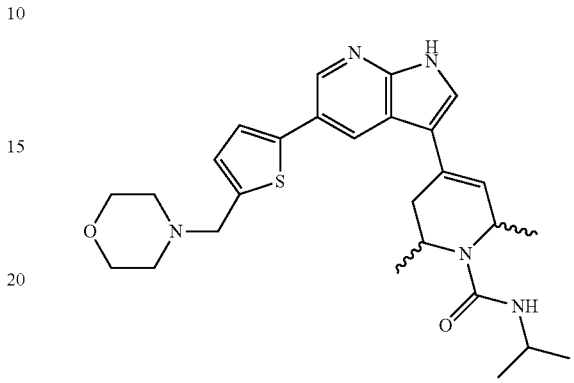

$^1$H NMR (400 MHz, CDCl$_3$) δ 8.98 (br s, 1H), 8.60 (s, 1H), 8.31 (s, 1H), 7.34 (s, 1H), 7.17 (s, 1H), 6.95 (s, 1H), 6.09-6.08 (m, 1H), 4.87-4.84 (m, 1H), 4.16-4.07 (m, 1H), 3.80-3.76 (m, 6H), 2.83-2.77 (m, 1H), 2.58 (br s, 4H), 2.39-2.04 (m, 2H), 1.48 (d, J=6.9 Hz, 3H), 1.25 (d, J=6.8 Hz, 3H), 1.21 (m, 6H); [M+H]$^+$ 494.

EXAMPLE 116

N-cyclopentyl-2,6-dimethyl-4-(5-(5-(morpholinomethyl)thiophen-2-yl)-1H-pyrrolo[2,3-b]pyridin-3-yl)-3,6-dihydropyridine-1(2H)-carboxamide

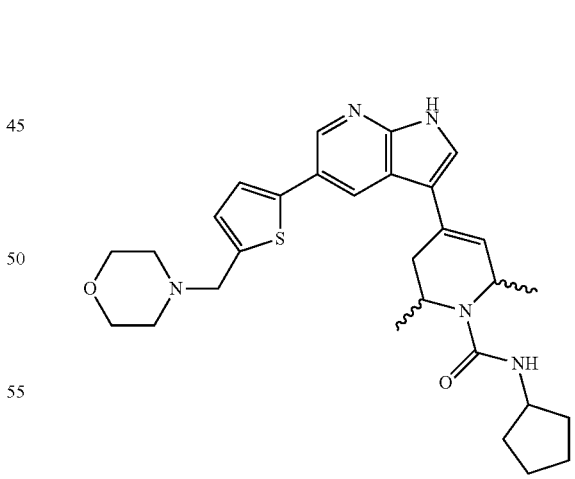

$^1$H NMR (400 MHz, CDCl$_3$) δ 10.38 (br s, 1H), 8.62 (s, 1H), 8.33 (s, 1H), 7.39 (s, 1H), 7.19 (s, 1H), 6.97 (s, 1H), 6.09-6.07 (m, 1H), 4.47-4.44 (m, 1H), 4.39 (d, J=6.8 Hz, 1H), 4.27-4.22 (m, 1H), 3.80-3.76 (m, 6H), 2.83-2.40 (m, 2H), 2.58 (br s, 4H), 2.10-2.04 (m, 2H), 1.75-1.39 (m, 6H), 1.48 (d, J=6.9 Hz, 3H), 1.33 (d, J=6.8 Hz, 3H); [M+H]$^+$ 520.

EXAMPLE 117

N-isopropyl-3-(5-(5-(morpholinomethyl)thiophen-2-yl)-1H-pyrrolo[2,3-b]pyridin-3-yl)-8-azabicyclo[3.2.1]oct-3-ene-8-carboxamide

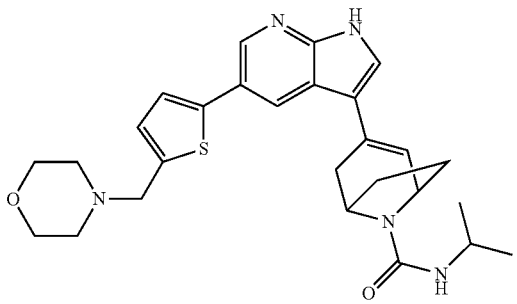 [SMILES: CC(C)NC(=O)N1C2C=C(c3c[nH]c4ncc(-c5ccc(CN6CCOCC6)s5)cc34)CC1CC2]

[M+H]+ 492.

EXAMPLE 118

N-isopropyl-3-(5-(5-(morpholinomethyl)thiophen-2-yl)-1H-pyrrolo[2,3-b]pyridin-3-yl)-9-azabicyclo[3.3.1]non-3-ene-9-carboxamide

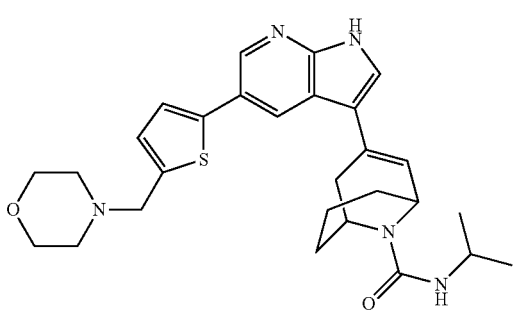 [SMILES: CC(C)NC(=O)N1C2C=C(c3c[nH]c4ncc(-c5ccc(CN6CCOCC6)s5)cc34)CC1CCC2]

$^1$H NMR (400 MHz, DMSO-d$_6$) δ 11.85 (br s, 1H), 8.52 (s, 1H), 8.30 (s, 1H), 7.60 (s, 1H), 7.40 (d, J=3.6 Hz, 1H), 6.99 (d, J=3.6 Hz, 1H), 6.26 (d, J=5.2 Hz, 1H), 6.17 (d, J=8.0 Hz, 1H), 4.76 (br s, 1H), 4.45 (br s, 1H), 3.82-3.73 (m, 1H), 3.68 (s, 2H), 3.60 (t, J=4.4 Hz, 4H), 2.81-2.74 (m, 1H), 2.45-2.35 (m, 6H), 1.80-1.72 (m, 1H), 1.69-1.52 (m, 4H), 1.50-1.44 (m, 1H), 1.06 (d, J=6.8 Hz, 6H); [M+H]+ 506.

EXAMPLE 119

4-(5-(3,4-Dimethoxyphenyl)-1H-pyrrolo[2,3-b]pyridin-3-yl)-N-isopropyl-2-phenyl-5,6-dihydropyridine-1(2H)-carboxamide

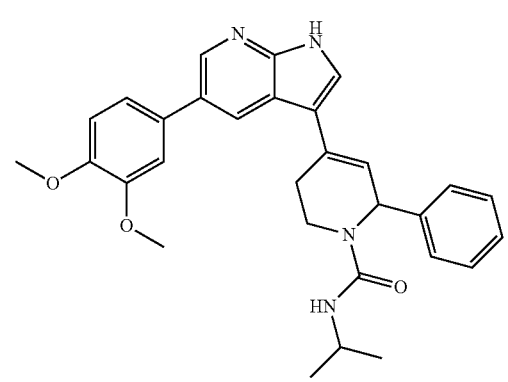 [SMILES: COc1ccc(-c2cnc3[nH]cc(C4=CC(c5ccccc5)N(C(=O)NC(C)C)CC4)c3c2)cc1OC]

$^1$H NMR (400 MHz, CDCl$_3$) δ 9.14 (s, 1H), 8.50 (s, 1H), 8.23 (s, 1H), 7.45 (d, J=7.6 Hz, 2H), 7.37 (t, J=7.4 Hz, 2H), 7.30 (d, J=6.4 Hz, 1H), 7.13 (d, J=6.8 Hz, 1H), 7.08 (s, 1H), 6.99 (d, J=8.0 Hz, 1H), 6.34 (d, J=2.8 Hz, 1H), 5.67 (br s, 1H), 4.20 (br s, 1H), 4.18-4.17 (m, 1H), 3.96 (s, 3H), 3.95 (s, 3H), 3.40-3.34 (m, 1H), 2.75-2.72 (m, 1H), 2.57 (d, J=15.6 Hz, 1H), 1.13 (d, J=6.4 Hz, 3H), 1.03 (d, J=6.4 Hz, 3H); [M+H]+ 497.

EXAMPLE 120

N-cyclopentyl-4-(5-(3,4-dimethoxyphenyl)-1H-pyrrolo[2,3-b]pyridin-3-yl)-5-methyl-5,6-dihydropyridine-1(2H)-carboxamide

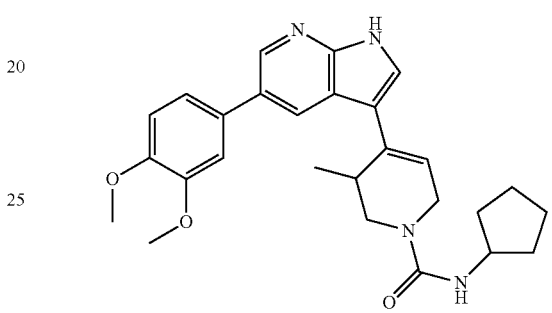

$^1$H NMR (400 MHz, DMSO-d$_6$) δ 11.77 (s, 1H), 8.50 (s, 1H), 8.29 (s, 1H), 7.60 (s, 1H), 7.28 (s, 1H), 7.23 (d, J=8.4 Hz, 1H), 7.05 (d, J=8.4 Hz, 1H), 6.16-6.12 (m, 2H), 4.35-4.30 (m, 1H), 3.99-3.93 (m, 1H), 3.87 (s, 3H), 3.85-3.72 (m, 5H), 3.11-3.07 (m, 1H), 2.90 (br s, 1H), 1.82-1.76 (m, 2H), 1.67-1.62 (m, 2H), 1.52-1.38 (m, 4H), 1.05 (d, J=6.8 Hz, 3H); [M+H]+ 461.

EXAMPLE 121

N-cyclopentyl-5-methyl-4-(5-(4-(methylsulfonyl)phenyl)-1H-pyrrolo[2,3-b]pyridin-3-yl)-5,6-dihydropyridine-1(2H)-carboxamide

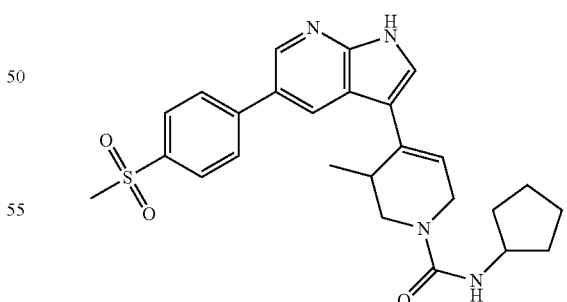

$^1$H NMR (400 MHz, DMSO-d$_6$) δ 11.91 (br s, 1H), 8.62 (s, 1H), 8.46 (s, 1H), 8.03 (dd, J=23.2, 8.4 Hz, 4H), 7.67 (s, 1H), 6.18-6.16 (m, 2H), 4.37-4.31 (m, 1H), 3.99-3.94 (m, 1H), 3.91-3.87 (m, 1H), 3.74 (d, J=18.4 Hz, 1H), 3.27 (s, 3H), 3.13-3.08 (m, 1H), 2.91 (br s, 1H), 1.83-1.76 (m, 2H), 1.67-1.61 (m, 2H), 1.52-1.36 (m, 4H), 1.04 (d, J=7.2 Hz, 3H); [M+H]+ 479.

EXAMPLE 122

N-cyclopentyl-5-methyl-4-(5-(3-(methylsulfonyl)phenyl)-1H-pyrrolo[2,3-b]pyridin-3-yl)-5,6-dihydropyridine-1(2H)-carboxamide

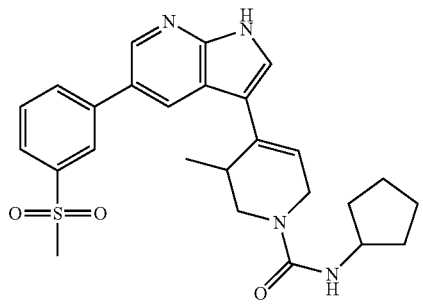 [SMILES: CC1CN(C(=O)NC2CCCC2)CC=C1c1c[nH]c2ncc(-c3cccc(S(C)(=O)=O)c3)cc12]

$^1$H NMR (400 MHz, DMSO-d$_6$) δ 11.90 (s, 1H), 8.61 (s, 1H), 8.45 (s, 1H), 8.24 (s, 1H), 8.13 (d, J=8.0 Hz, 1H), 7.91 (d, J=8.0 Hz, 1H), 7.76 (t, J=7.8 Hz, 1H), 7.67 (s, 1H), 6.18-6.16 (m, 2H), 4.36-4.31 (m, 1H), 3.99-3.87 (m, 2H), 3.75 (d, J=18.4 Hz, 1H), 3.33 (s, 3H), 3.12-3.08 (m, 1H), 2.92 (br s, 1H), 1.83-1.76 (m, 2H), 1.68-1.62 (m, 2H), 1.52-1.38 (m, 4H), 1.05 (d, J=6.8 Hz, 3H); [M+H]$^+$ 479.

EXAMPLE 123

N-cyclopentyl-5-methyl-4-(5-(3-sulfamoylphenyl)-1H-pyrrolo[2,3-b]pyridin-3-yl)-5,6-dihydropyridine-1(2H)-carboxamide

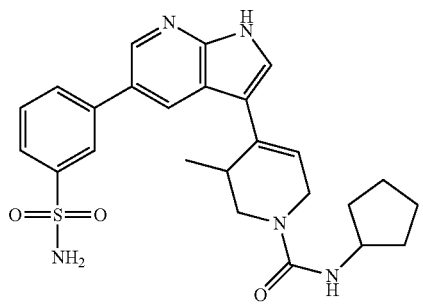 [SMILES: CC1CN(C(=O)NC2CCCC2)CC=C1c1c[nH]c2ncc(-c3cccc(S(N)(=O)=O)c3)cc12]

$^1$H NMR (400 MHz, DMSO-d$_6$) δ 8.57 (s, 1H), 8.39 (s, 1H), 8.18 (s, 1H), 8.01 (d, J=8.0 Hz, 1H), 8.01 (d, J=8.0 Hz, 1H), 7.80 (d, J=8.0 Hz, 1H), 7.69-7.65 (m, 2H), 6.19 (d, J=6.8 Hz, 1H), 6.14-6.13 (m, 1H), 4.36-4.31 (m, 1H), 3.99-3.94 (m, 1H), 3.91-3.87 (m, 1H), 3.75 (d, J=18.0 Hz, 1H), 3.12-3.08 (m, 1H), 2.92 (br s, 1H), 1.83-1.76 (m, 2H), 1.67-1.61 (m, 2H), 1.52-1.36 (m, 4H), 1.05 (d, J=6.8 Hz, 3H); [M+H]$^+$ 480.

EXAMPLE 124

N-cyclopentyl-5-methyl-4-(5-(4-sulfamoylphenyl)-1H-pyrrolo[2,3-b]pyridin-3-yl)-5,6-dihydropyridine-1(2H)-carboxamide

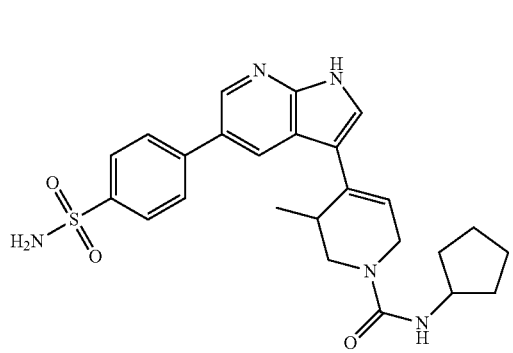 [SMILES: CC1CN(C(=O)NC2CCCC2)CC=C1c1c[nH]c2ncc(-c3ccc(S(N)(=O)=O)cc3)cc12]

$^1$H NMR (400 MHz, DMSO-d$_6$) δ 8.60 (s, 1H), 8.43 (s, 1H), 7.93 (dd, J=28.0, 8.8 Hz, 4H), 7.66 (s, 1H), 6.18-6.16 (m, 2H), 4.37-4.31 (m, 1H), 3.99-3.94 (m, 1H), 3.91-3.87 (m, 1H), 3.74 (d, J=18.4 Hz, 1H), 3.13-3.08 (m, 1H), 2.92 (br s, 1H), 1.83-1.76 (m, 2H), 1.67-1.61 (m, 2H), 1.52-1.36 (m, 4H), 1.04 (d, J=6.8 Hz, 3H); [M+H]$^+$ 480.

EXAMPLE 125

N-isopropyl-5-methyl-4-(5-(5-((4-methylpiperazin-1-yl)methyl)thiophen-2-yl)-1H-pyrrolo[2,3-b]pyridin-3-yl)-5,6-dihydropyridine-1(2H)-carboxamide

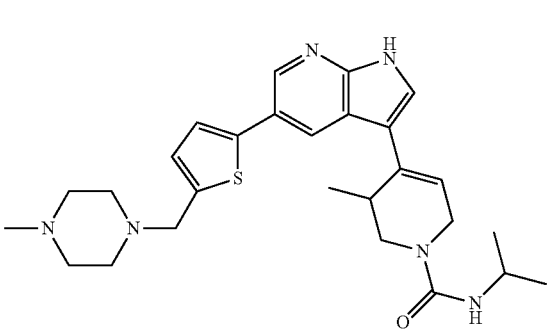 [SMILES: CC(C)NC(=O)N1CC=C(c2c[nH]c3ncc(-c4ccc(CN5CCN(C)CC5)s4)cc23)C(C)C1]

$^1$H NMR (400 MHz, DMSO-d$_6$) δ 11.82 (s, 1H), 8.26 (s, 1H), 7.61 (s, 1H), 7.38 (d, J=3.6 Hz, 1H), 6.97 (d, J=3.6 Hz, 1H), 6.08 (br s, 1H), 6.06 (d, J=2.0 Hz, 1H), 4.36-4.30 (m, 1H), 4.15-4.09 (m, 1H), 3.92-3.70 (m, 3H), 3.67 (s, 2H), 3.17 (d, J=4.4 Hz, 2H), 3.12-3.08 (m, 1H), 2.92-2.88 (m, 1H), 2.46-2.24 (m, 5H), 2.16 (s, 3H), 1.11-1.08 (m, 6H), 1.04 (d, J=6.8 Hz, 3H); [M+H]$^+$ 493.

EXAMPLE 126

N-cyclopentyl-5-methyl-4-(5-(5-((4-methylpiper-azin-1-yl)methyl)thiophen-2-yl)-1H-pyrrolo[2,3-b]pyridin-3-yl)-5,6-dihydropyridine-1(2H)-carboxamide

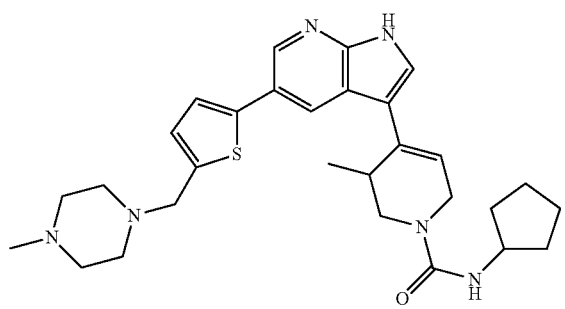 [SMILES: CC1CN(C(=O)NC2CCCC2)CC=C1c1c[nH]c2ncc(-c3ccc(CN4CCN(C)CC4)s3)cc12]

¹H NMR (400 MHz, DMSO-d₆) δ 11.82 (br s, 1H), 8.51 (s, 1H), 8.26 (s, 1H), 7.61 (s, 1H), 7.38 (d, J=3.2 Hz, 1H), 6.97 (d, J=3.6 Hz, 1H), 6.13 (d, J=7.2 Hz, 1H), 6.09-6.07 (m, 1H), 4.36-4.31 (m, 1H), 4.00-3.94 (m, 1H), 3.91-3.87 (m, 1H), 3.75 (d, J=18.4 Hz, 1H), 3.67 (s, 2H), 3.12-3.08 (m, 1H), 2.89 (br s, 1H), 2.45-2.32 (m, 4H), 2.16 (s, 3H), 1.85-1.77 (m, 2H), 1.70-1.62 (m, 2H), 1.52-1.39 (m, 4H), 1.04 (d, J=7.2 Hz, 3H); [M+H]⁺ 519.

EXAMPLE 127

N-cyclopentyl-5-methyl-4-(5-(5-(morpholinomethyl)thiophen-2-yl)-1H-pyrrolo[2,3-b]pyridin-3-yl)-5,6-dihydropyridine-1(2H)-carboxamide

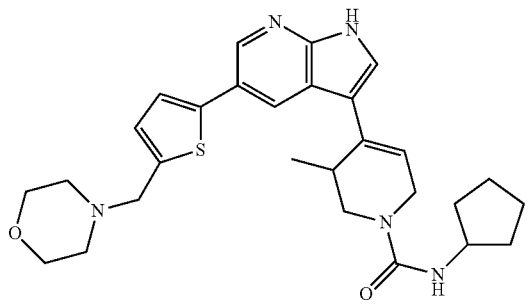 [SMILES: CC1CN(C(=O)NC2CCCC2)CC=C1c1c[nH]c2ncc(-c3ccc(CN4CCOCC4)s3)cc12]

¹H NMR (400 MHz, DMSO-d₆) δ 11.85 (br s, 1H), 8.52 (s, 1H), 8.27 (s, 1H), 7.62 (s, 1H), 7.40 (d, J=3.6 Hz, 1H), 6.99 (d, J=3.6 Hz, 1H), 6.16 (d, J=6.8 Hz, 1H), 6.08 (t, J=3.4 Hz, 1H), 4.38-4.31 (m, 1H), 3.99-3.94 (m, 1H), 3.91-3.87 (m, 1H), 3.74 (d, J=18.0 Hz, 1H), 3.68 (s, 2H), 3.61-3.57 (m, 4H), 3.11-3.07 (m, 1H), 2.89 (br s, 1H), 2.45-2.42 (m, 4H), 1.85-1.76 (m, 2H), 1.70-1.62 (m, 2H), 1.52-1.37 (m, 4H), 1.03 (d, J=6.8 Hz, 3H); [M+H]⁺ 493.

EXAMPLE 128

N-cyclopentyl-5-ethyl-4-(5-(5-(morpholinomethyl)thiophen-2-yl)-1H-pyrrolo[2,3-b]pyridin-3-yl)-5,6-dihydropyridine-1(2H)-carboxamide

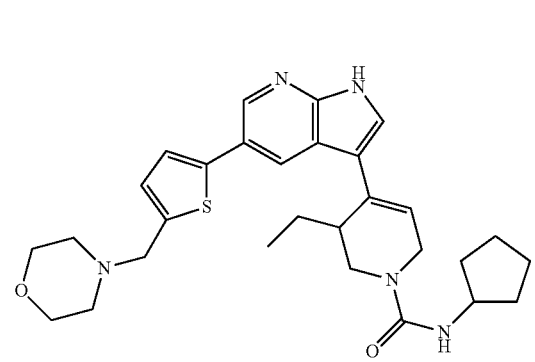 [SMILES: CCC1CN(C(=O)NC2CCCC2)CC=C1c1c[nH]c2ncc(-c3ccc(CN4CCOCC4)s3)cc12]

¹H NMR (400 MHz, DMSO-d₆) δ 11.83 (br s, 1H), 8.52 (s, 1H), 8.26 (s, 1H), 7.60 (s, 1H), 7.39 (s, 1H), 6.99 (s, 1H), 6.09 (s, 2H), 4.38-4.31 (m, 1H), 4.21-4.16 (m, 1H), 3.97-3.95 (m, 1H), 3.75-3.59 (m, 9H), 2.94-2.90 (m, 1H), 2.47-2.42 (m, 4H), 1.83-1.76 (m, 2H), 1.69-1.62 (m, 2H), 1.52-1.37 (m, 4H), 0.99-0.87 (m, 3H); [M+H]⁺ 520.

EXAMPLE 129

N-cyclopentyl-4-(5-(3,4-dimethoxyphenyl)-1H-pyrrolo[2,3-b]pyridin-3-yl)-3-methyl-5,6-dihydropyridine-1(2H)-carboxamide

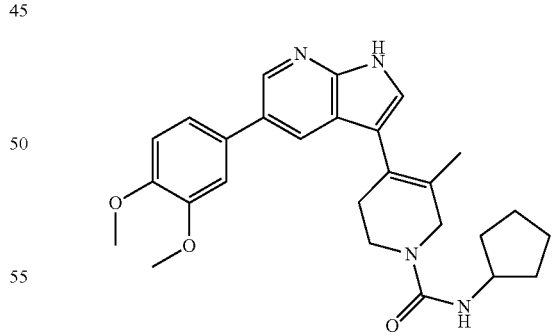

¹H NMR (400 MHz, DMSO-d₆) δ 11.74 (s, 1H), 8.49 (s, 1H), 7.93 (s, 1H), 7.43 (s, 1H), 7.24 (s, 1H), 7.20 (d, J=8.0 Hz, 1H), 7.04 (d, J=8.4 Hz, 1H), 6.23 (d, J=7.2 Hz, 1H), 4.00-3.93 (m, 1H), 3.87-3.86 (m, 4H), 3.79 (s, 3H), 3.54 (t, J=5.6 Hz, 2H), 2.46 (br s, 2H), 1.85-1.76 (m, 2H), 1.68 (s, 3H), 1.67-1.62 (m, 2H), 1.52-1.38 (m, 4H); [M+H]⁺ 461.

EXAMPLE 130

N-cyclopentyl-3-methyl-4-(5-(4-(methylsulfonyl)phenyl)-1H-pyrrolo[2,3-b]pyridin-3-yl)-5,6-dihydropyridine-1(2H)-carboxamide

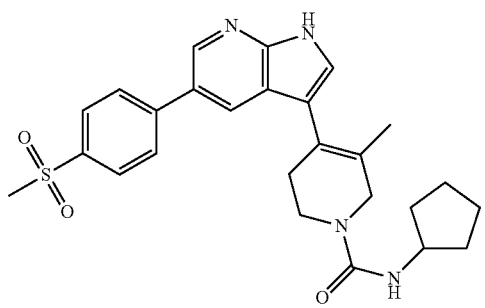 [SMILES: CC1=C(c2c[nH]c3ncc(-c4ccc(S(C)(=O)=O)cc4)cc23)CCN(C(=O)NC2CCCC2)C1]

$^1$H NMR (400 MHz, DMSO-d$_6$) δ 11.91 (br s, 1H), 8.61 (s, 1H), 8.11 (s, 1H), 8.01 (dd, J=17.2, 10.4 Hz, 4H), 7.50 (s, 1H), 6.23 (d, J=7.2 Hz, 1H), 3.98-3.91 (m, 1H), 3.87 (s, 2H), 3.54 (d, J=5.4 Hz, 2H), 3.26 (s, 3H), 2.46-2.42 (m, 2H), 1.83-1.76 (m, 2H), 1.67-1.61 (m, 5H), 1.52-1.36 (m, 4H); [M+H]$^+$ 479.

EXAMPLE 131

N-cyclopentyl-3-methyl-4-(5-(5-(morpholinomethyl)thiophen-2-yl)-1H-pyrrolo[2,3-b]pyridin-3-yl)-5,6-dihydropyridine-1(2H)-carboxamide

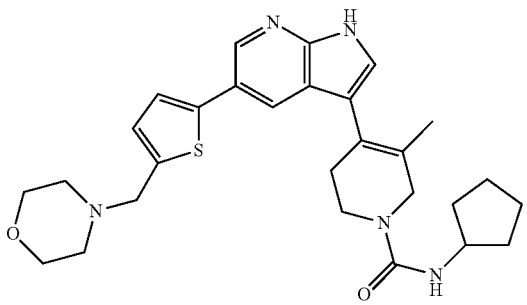 [SMILES: CC1=C(c2c[nH]c3ncc(-c4ccc(CN5CCOCC5)s4)cc23)CCN(C(=O)NC2CCCC2)C1]

$^1$H NMR (400 MHz, DMSO-d$_6$) δ 11.85 (br s, 1H), 8.51 (s, 1H), 7.90 (s, 1H), 7.46 (s, 1H), 7.37 (d, J=3.2 Hz, 1H), 6.97 (d, J=3.6 Hz, 1H), 6.26 (d, J=7.2 Hz, 1H), 4.13 (br s, 1H), 3.99-3.93 (m, 1H), 3.87 (s, 2H), 3.67 (s, 2H), 3.61-3.57 (m, 4H), 3.54 (d, J=5.6 Hz, 2H), 3.17 (s, 2H), 2.45-2.37 (m, 6H), 1.83-1.77 (m, 2H), 1.70-1.62 (m, 5H), 1.52-1.37 (m, 4H); [M+H]$^+$ 506.

EXAMPLE 132

N-cyclopentyl-3-fluoro-4-(5-(4-(methylsulfonyl)phenyl)-1H-pyrrolo[2,3-b]pyridin-3-yl)-5,6-dihydropyridine-1(2H)-carboxamide

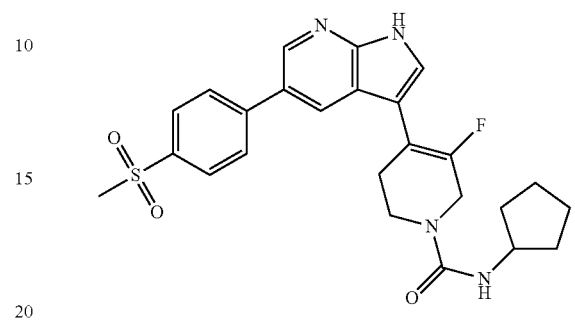

Step 1: Preparation of tert-butyl 4-((trimethylsilyl)oxy)-5,6-dihydropyridine-1(2H)-carboxylate

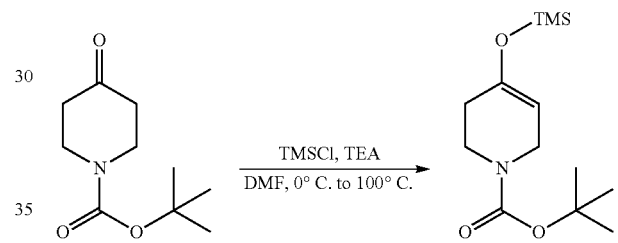

Chlorotrimethylsilane (1.68 mL, 13.2 mmol) was slowly added dropwise to a solution of 1-Boc-4-piperidone (2.19 g, 11.0 mmol) and TEA (3.68 mL, 26.4 mmol) in DMF (8 mL, anhydrous) at 0° C. Subsequently, the reaction mixture was stirred at 100° C. for 18 hours, cooled to room temperature, added with a saturated NaHCO$_3$ solution (100 mL) and extracted with EtOAc (100 mL) The organic layer was evaporated under reduced pressure to obtain the crude intermediate 2, which was used in the following step without further purification.

$^1$H NMR (400 MHz, DMSO-d$_6$) δ 4.81 (br s, 1H), 3.77 (br s, 2H), 3.42 (t, J=5.8 Hz, 2H), 2.03-1.99 (m, 2H), 1.40 (s, 9H), 0.177 (s, 9H).

Step 2: Preparation of tert-butyl 3-fluoro-4-oxopiperidine-1-carboxylate

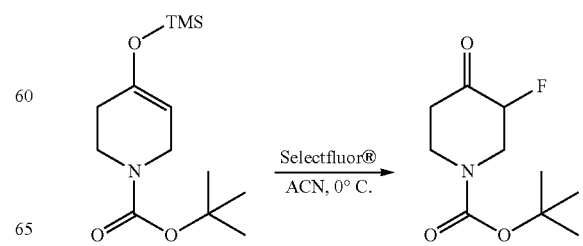

Selectfluor® (354 mg, 1 mmol) was slowly added dropwise to a solution of the crude intermediate 2 (271 mg, 1 mmol) in ACN (5 mL, anhydrous) at 0° C. Subsequently, the reaction mixture was stirred at 0° C. for 2 hours and heated for 30 minutes. The resulting reaction mixture was cooled in brine (~10 mL) and extracted with ethyl acetate (30 mL×2). The organic layer was collected and evaporated under reduced pressure to give the crude intermediate 3, which was used in the following step without further purification.

$^1$H NMR (400 MHz, DMSO-d$_6$) δ 5.19-5.03 (m, 1H), 4.45-4.25 (m, 1H), 4.09-4.00 (m, 1H), 3.60 (t, J=6.2 Hz, 1H), 2.61-2.52 (m, 1H), 2.40-2.32 (m, 2H), 1.44 (s, 9H).

Step 3: N-cyclopentyl-3-fluoro-4-(5-(4-(methylsulfonyl)phenyl)-1H-pyrrolo[2,3-b]pyridin-3-yl)-5,6-dihydropyridine-1(2H)-carboxamide

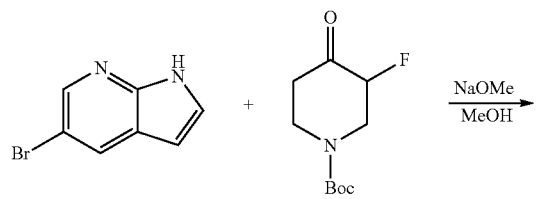

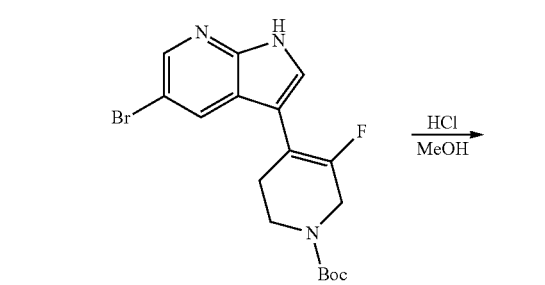

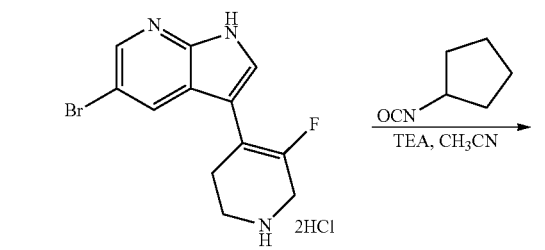

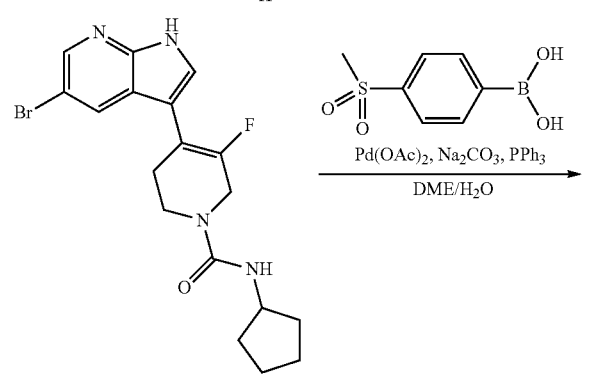

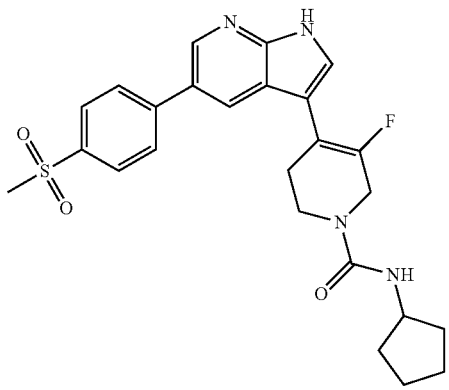

The procedures of Scheme 2 were repeated except that tert-butyl 3-fluoro-4-oxopiperidine-1-carboxylate was used instead of tert-butyl 4-oxopiperidine-1-carboxylate to give N-cyclopentyl-3-fluoro-4-(5-(4-(methylsulfonyl)phenyl)-1H-pyrrolo[2,3-b]pyridin-3-yl)-5,6-dihydropyridine-1(2H)-carboxamide.

$^1$H NMR (400 MHz, DMSO-d$_6$) δ 12.13 (br s, 1H), 8.63 (s, 1H), 8.29 (s, 1H), 8.01 (s, 4H), 7.71 (s, 1H), 6.44 (d, J=7.2 Hz, 1H), 4.12 (s, 2H), 3.99-3.90 (m, 1H), 3.56 (d, J=5.6 Hz, 2H), 3.26 (s, 3H), 2.65-2.62 (m, 2H), 1.83-1.76 (m, 2H), 1.67-1.61 (m, 2H), 1.52-1.36 (m, 4H); [M+H]$^+$ 483.

EXAMPLE 133

N-cyclopentyl-4-(5-(3,4-dimethoxyphenyl)-1H-pyrrolo[2,3-b]pyridin-3-yl)-3-fluoro-5,6-dihydropyridine-1(2H)-carboxamide

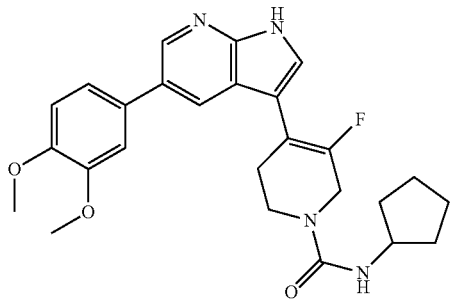 [SMILES: COc1ccc(-c2cnc3[nH]cc(C4=C(F)CN(C(=O)NC5CCCC5)CC4)c3c2)cc1OC]

$^1$H NMR (400 MHz, DMSO-d$_6$) δ 11.74 (s, 1H), 8.51 (s, 1H), 8.13 (s, 1H), 7.64 (s, 1H), 7.24 (s, 1H), 7.19 (d, J=8.4 Hz, 1H), 7.05 (d, J=8.4 Hz, 1H), 6.44 (d, J=6.8 Hz, 1H), 4.11 (s, 2H), 3.98-3.92 (m, 1H), 3.86 (s, 3H), 3.80 (s, 3H), 3.55 (t, J=5.4 Hz, 2H), 2.62 (br s, 2H), 1.84-1.76 (m, 2H), 1.68-1.62 (m, 2H), 1.52-1.38 (m, 4H); [M+H]$^+$ 465.

EXAMPLE 134

N-cyclopentyl-3-fluoro-4-(5-(5-(morpholinomethyl)thiophen-2-yl)-1H-pyrrolo[2,3-b]pyridin-3-yl)-5,6-dihydropyridine-1(2H)-carboxamide

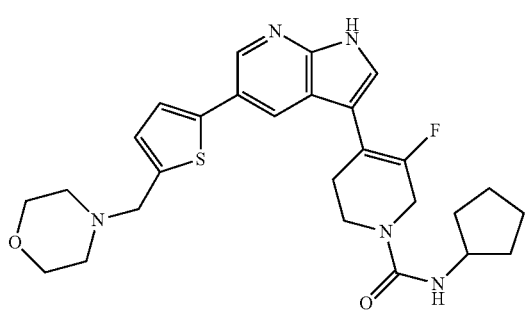 [SMILES: O=C(NC1CCCC1)N1CCC(c2c[nH]c3ncc(-c4ccc(CN5CCOCC5)s4)cc23)=C(F)C1]

$^1$H NMR (400 MHz, DMSO-d$_6$) δ 12.01 (br s, 1H), 8.55 (s, 1H), 8.12-8.10 (m, 1H), 7.65 (s, 1H), 7.34 (d, J=3.6 Hz, 1H), 7.07 (d, J=3.6 Hz, 2H), 6.98 (d, J=3.6 Hz, 1H), 6.90 (d, J=3.6 Hz, 2H), 6.43 (d, J=6.8 Hz, 1H), 4.12 (br s, 2H), 3.99-3.92 (m, 1H), 3.71 (s, 2H), 3.64 (s, 2H), 3.61-3.54 (m, 2H), 2.58 (br s, 2H), 2.46-2.40 (m, 2H), 1.83-1.77 (m, 2H), 1.70-1.62 (m, 2H), 1.52-1.40 (m, 4H); [M+H]$^+$ 510.

PREPARATION EXAMPLE 4

Preparation of 4-(1H-pyrrolo[2,3-b]pyridin-3-yl)-5,6-dihydropyridine-1(2H)-carboxylate Scheme 4. Total scheme for compound 33

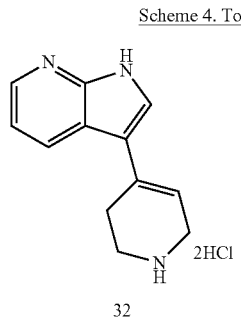

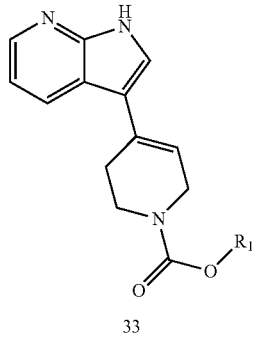

EXAMPLE 135

Ethyl 4-(1H-pyrrolo[2,3-b]pyridin-3-yl)-5,6-dihydropyridine-1(2H)-carboxylate

Scheme 5. Preparation of Example 135

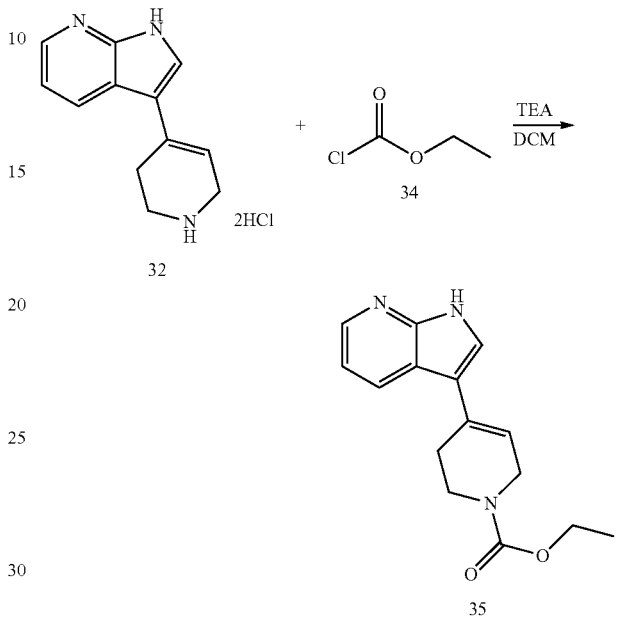

Ethyl carbonochloridate (0.5 g, 4.66 mmol, 1.1 eq) was added dropwise over 5 minutes to a solution of the intermediate 32 (1.0 g, 4.24 mmol, 1.0 eq) and TEA (1.71 g, 16.9 mmol, 4.0 eq) in DCM (20 mL) at 0° C. Then, the resulting mixture was stirred at room temperature for 2 hours. The solvent was removed from the mixture under reduced pressure, and the crude product thus obtained was purified by column chromatography (hexane: EtOAc=10:1~1:3) to give the title compound 35 (96 mg, 0.3 mmol, 8.3%).

$^1$H NMR (400 MHz, CDCl$_3$) δ 9.56 (s, 1H), 8.33-8.32 (d, J=4.56 Hz, 1H), 8.19-8.17 (d, J=8.00 Hz, 1H), 7.30 (s, 1H), 7.14-7.11 (m, 1H), 6.14 (s, 1H), 4.22-4.17 (m, 4H), 3.75-3.72 (m, 2H), 2.58 (s, 2H), 2.58 (s, 2H), 1.32-1.28 (m, 3H); MS (m/z): 272.4 (MH$^+$).

EXAMPLE 136

Pentyl 4-(1H-pyrrolo[2,3-b]pyridin-3-yl)-5,6-dihydropyridine-1(2H)-carboxylate

Scheme 6. Preparation of Example 136

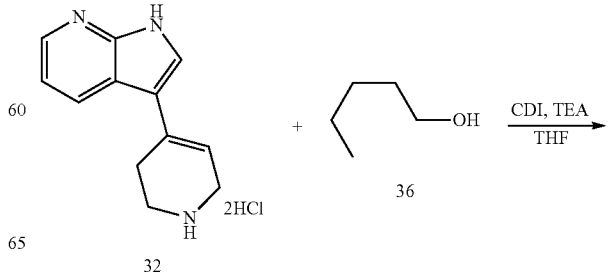

-continued

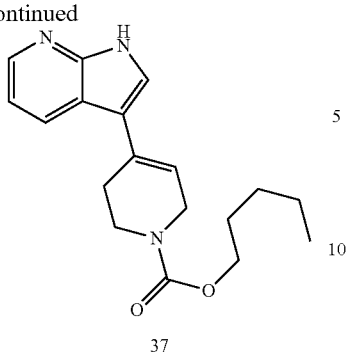

37

A solution of pentan-1-ol (1.1 g, 12.7 mmol, 3.0 eq) and CDI (1,1'-carbonyldiimidazole; 2.06 g, 12.7 mmol, 3.0 eq) in THF (40 mL) was stirred at room temperature for 1 hour, and then added with the intermediate 32 (1.0 g, 4.24 mmol, 1.0 eq) and TEA (1.72 g, 16.9 mmol, 4.0 eq). Subsequently, the suspension thus obtained was stirred at 60° C. overnight. The reaction mixture was added with water (200 mL), extracted with EtOAc (200 mL×2), washed with brine (200 mL) and concentrated to obtain the crude product. The crude product was purified by column chromatography to give the title compound 37 (1.0 g, 3.3 mmol, 79%) as a yellow solid.

$^1$H NMR (400 MHz, CDCl$_3$) δ 10.34 (s, 1H), 8.34-8.33 (m, 1H), 8.20-8.18 (m, 1H), 7.33 (s, 1H), 7.15-7.12 (m, 1H), 6.15 (s, 1H), 4.19 (s, 2H), 4.15-4.12 (m, 2H), 3.75-3.72 (m, 2H), 2.59 (s, 2H), 1.69-1.66 (m, 2H), 1.39-1.36 (m, 4H), 0.94-0.90 (m, 3H); MS (m/z): 314.4 (MH$^+$).

EXAMPLE 137

Propyl 4-(1H-pyrrolo[2,3-b]pyridin-3-yl)-5,6-dihydropyridine-1(2H)-carboxylate

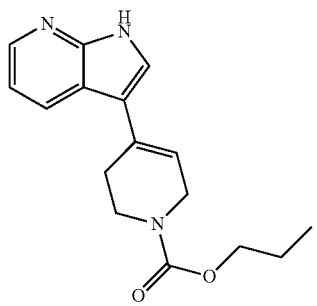 [SMILES: CCCOC(=O)N1CC=C(c2c[nH]c3ncccc23)CC1]

$^1$H NMR (400 MHz, CDCl$_3$) δ 9.73 (s, 1H), 8.36-8.34 (d, J=4.60 Hz, 1H), 8.22-8.20 (d, J=8.00 Hz, 1H), 7.33 (s, 1H), 7.17-7.14 (m, 1H), 6.17 (s, 1H), 4.21 (m, 2H), 4.14-4.10 (m, 2H), 3.78-3.75 (m, 2H), 2.61 (s, 2H), 1.76-1.71 (m, 2H), 1.02-0.98 (m, 3H); MS (m/z): 286 (MH+).

EXAMPLE 138

Butyl 4-(1H-pyrrolo[2,3-b]pyridin-3-yl)-5,6-dihydropyridine-1(2H)-carboxylate

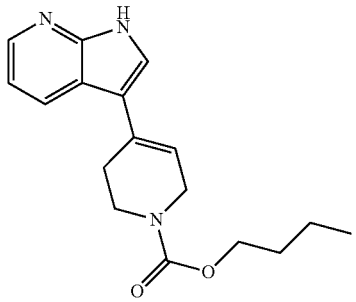 [SMILES: CCCCOC(=O)N1CC=C(c2c[nH]c3ncccc23)CC1]

$^1$H NMR (400 MHz, CDCl$_3$) δ 9.77 (s, 1H), 8.35-8.34 (m, 1H), 8.22-8.19 (dd, J=8.00 Hz, 1H), 7.33 (s, 1H), 7.17-7.14 (m, 1H), 6.17 (s, 1H), 4.21 (s, 2H), 4.18-4.15 (m, 2H), 3.77-3.74 (m, 2H), 2.60 (s, 2H), 1.68-1.66 (m, 2H), 1.47-1.42 (m, 2H), 1.00-0.96 (m, 3H), MS (m/z): 300.4 (MH+).

EXAMPLE 139

Isopropyl 4-(1H-pyrrolo[2,3-b]pyridin-3-yl)-5,6-dihydropyridine-1(2H)-carboxylate

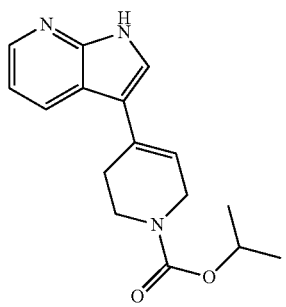 [SMILES: CC(C)OC(=O)N1CC=C(c2c[nH]c3ncccc23)CC1]

$^1$H NMR (400 MHz, CDCl$_3$) δ 9.63 (s, 1H), 8.35-8.34 (d, J=4.64 Hz, 1H), 8.22-8.20 (d, J=7.76 Hz, 1H), 7.33 (s, 1H), 7.17-7.14 (m, 1H), 6.17 (s, 1H), 5.04-4.98 (m, 1H), 4.20 (s, 2H), 3.76-3.73 (m, 2H), 2.60 (s, 2H), 1.31 (s, 3H), 1.30 (s, 3H); MS (m/z): 286.3 (MH$^+$).

EXAMPLE 140

Cyclopentyl 4-(1H-pyrrolo[2,3-b]pyridin-3-yl)-3,6-dihydropyridine-1(2H)-carboxylate

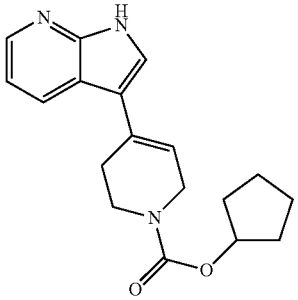 [SMILES: O=C(OC1CCCC1)N1CC=C(c2c[nH]c3ncccc23)CC1]

$^1$H NMR (400 MHz, DMSO-d$_6$) δ 11.68 (br s, 1H), 8.24-8.22 (m, 2H), 7.54 (s, 1H), 7.10-7.07 (m, 1H), 6.17 (br s, 1H), 5.03 (br s, 1H), 4.06 (s, 2H), 3.58 (t, J=5.8 Hz, 2H), 1.82-1.79 (m, 2H), 1.68-1.52 (m, 6H); [M+H]$^+$ 312.

EXAMPLE 141 sec-Butyl 4-(1H-pyrrolo[2,3-b]pyridin-3-yl)-5,6-dihydropyridine-1(2H)-carboxylate

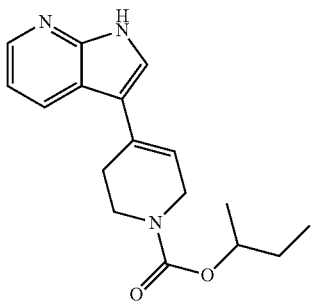 [SMILES: CCC(C)OC(=O)N1CC=C(c2c[nH]c3ncccc23)CC1]

$^1$H NMR (400 MHz, CDCl$_3$) δ 9.40 (s, 1H), 8.35-8.34 (d, J=3.76 Hz, 1H), 8.21-8.19 (d, J=8.00 Hz, 1H), 7.32 (s, 1H), 7.17-7.14 (m, 1H), 6.17 (s, 1H), 4.86-4.82 (m, 1H), 4.21 (s, 2H), 3.75-3.74 (m, 2H), 2.60 (s, 2H), 1.69-1.66 (m, 2H), 1.29-1.27 (m, 3H), 0.98-0.94 (m, 3H); MS (m/z): 300.4 (MH$^+$).

EXAMPLE 142

Pentan-3-yl 4-(1H-pyrrolo[2,3-b]pyridin-3-yl)-5,6-dihydropyridine-1(2H)-carboxylate

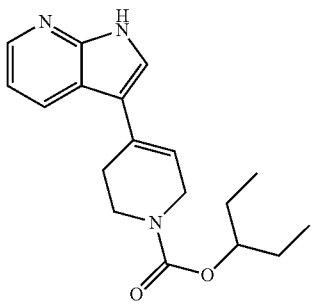 [SMILES: CCC(CC)OC(=O)N1CC=C(c2c[nH]c3ncccc23)CC1]

$^1$H NMR (400 MHz, CDCl$_3$) δ 9.57 (s, 1H), 8.35-8.34 (d, J=4.68 Hz, 1H), 8.22-8.20 (d, J=7.12 Hz, 1H), 7.33 (s, 1H), 7.17-7.14 (m, 1H), 6.18 (s, 1H), 4.75-4.72 (m, 1H), 4.22 (m, 2H), 3.78-3.75 (m, 2H), 2.60 (s, 2H), 1.66-1.60 (m, 4H), 0.96-0.93 (m, 6H); MS (m/z): 314.4 (MH$^+$).

EXAMPLE 143

Cyclohexyl 4-(1H-pyrrolo[2,3-b]pyridin-3-yl)-5,6-dihydropyridine-1(2H)-carboxylate

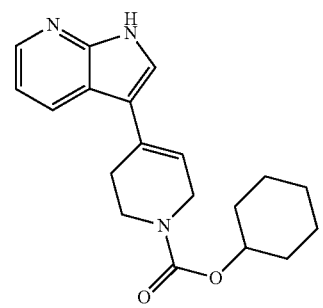 [SMILES: O=C(OC1CCCCC1)N1CC=C(c2c[nH]c3ncccc23)CC1]

$^1$H NMR (400 MHz, CDCl$_3$) δ 9.70 (s, 1H), 8.36-8.34 (d, J=4.40 Hz, 1H), 8.22-8.20 (d, J=8.0 Hz, 1H), 7.33 (s, 1H), 7.17-7.14 (m, 1H), 6.17 (s, 1H), 4.78-4.76 (m, 1H), 4.21 (m, 2H), 3.77-3.74 (m, 2H), 2.60 (s, 2H), 1.91-1.88 (m, 2H), 1.76-1.74 (s, 2H), 1.57-1.28 (m, 6H); MS (m/z): 326.4 (MH$^+$).

PREPARATION EXAMPLE 5

Preparation of Compound 40

Scheme 7. Total scheme for compound 40

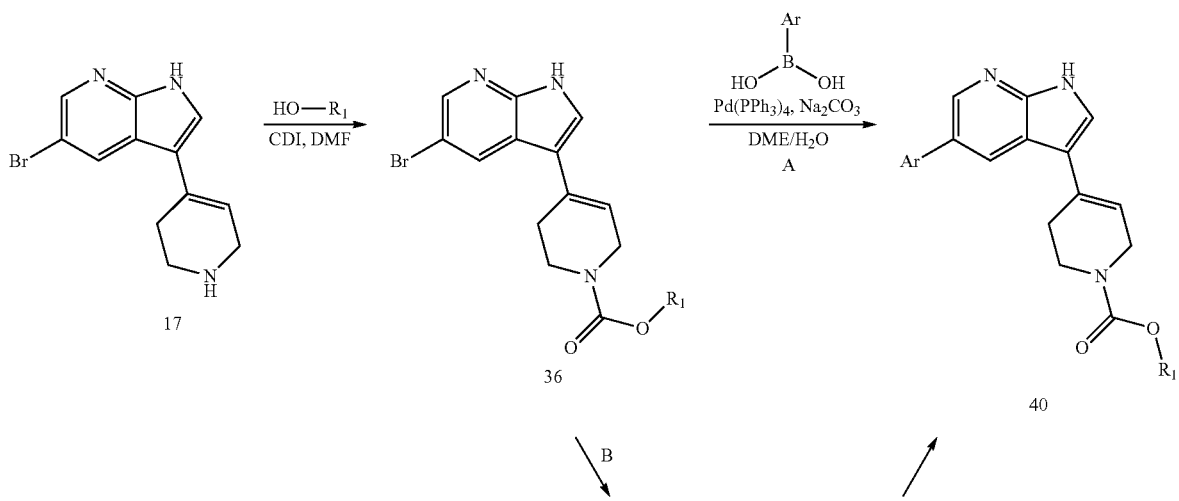

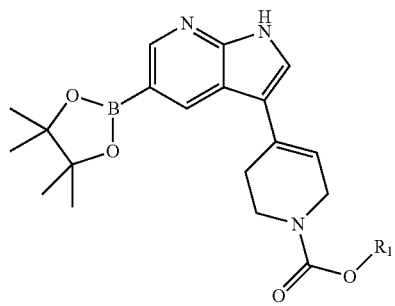

Carbamate is introduced to the 3rd position of azaindole, and then aryl or heteroaryl is introduced to the 5th position of azaindole to give the compound 40.

EXAMPLE 144

Cyclopentyl 4-(5-(3,4-dimethoxyphenyl)-1H-pyrrolo[2,3-b]pyridin-3-yl)-5,6-dihydropyridine-1(2H)-carboxylate Step 1: Preparation of cyclopentyl 4-(5-bromo-1H-pyrrolo[2,3-b]pyridin-3-yl)-5,6-dihydropyridine-1(2H)-carboxylate (42)

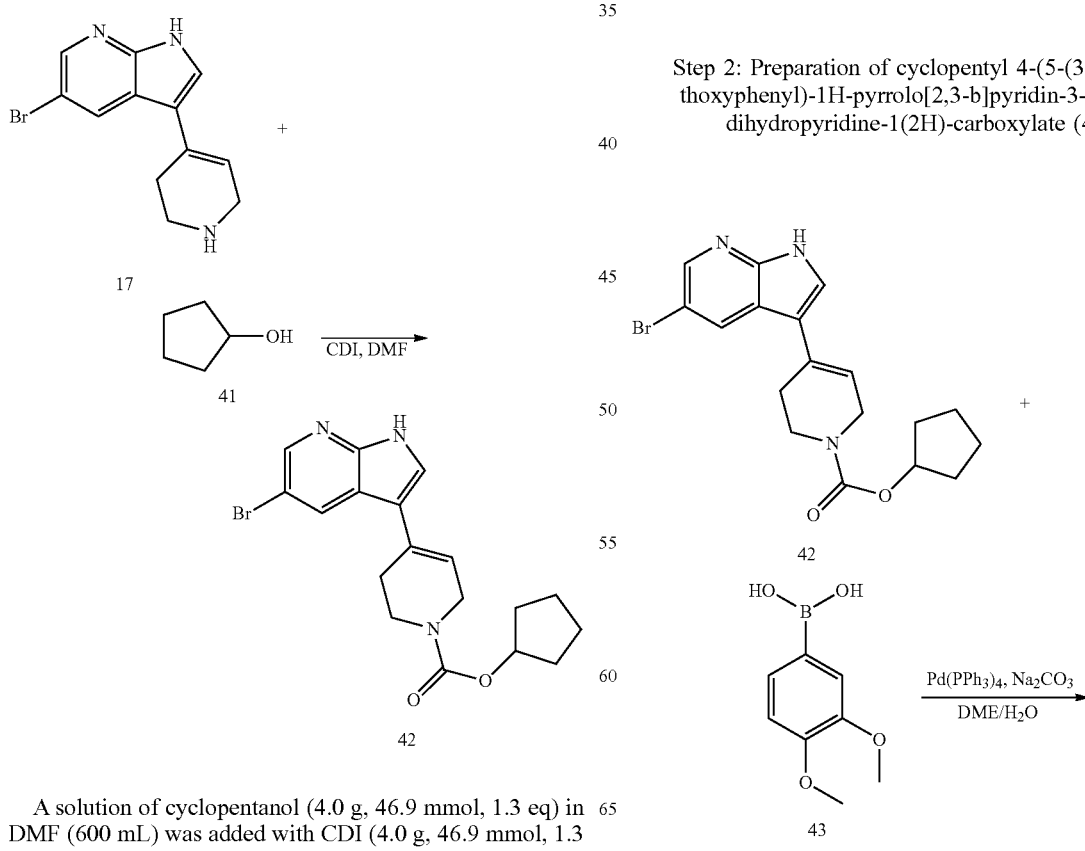

A solution of cyclopentanol (4.0 g, 46.9 mmol, 1.3 eq) in DMF (600 mL) was added with CDI (4.0 g, 46.9 mmol, 1.3 eq), which was then stirred at room temperature for 1 hour and added with the intermediate 17 (10.0 g, 36.0 mmol, 1.0 eq). The suspension thus obtained was stirred at 80° C. for 18 hours. The resulting reaction mixture was added with water (800 mL), extracted with EtOAc (500 mL×3), washed with a saturated NaCl solution (800 mL×2) and dried to give the crude product. The crude product was purified (EtOAc: hexane=5:1, 30 mL) to give the title compound 42 (11.1 g, 28.5 mmol, 79.2%) as a yellow solid.

$^1$H NMR (400 MHz, DMSO-$d_6$) δ 11.96 (s, 1H), 8.44-8.43 (d, J=1.4 Hz, 1H), 8.29-8.28 (d, J=1.7 Hz, 1H), 7.64-7.63 (m, 1H), 6.18 (s, 1H), 5.04-5.02 (m, 1H), 4.05 (s, 2H), 3.59-3.56 (t, J=5.6 Hz, 2H), 1.82-1.55 (m, 10H); MS (m/z): 390.0 (MH$^+$).

Step 2: Preparation of cyclopentyl 4-(5-(3,4-dimethoxyphenyl)-1H-pyrrolo[2,3-b]pyridin-3-yl)-5,6-dihydropyridine-1(2H)-carboxylate (44)

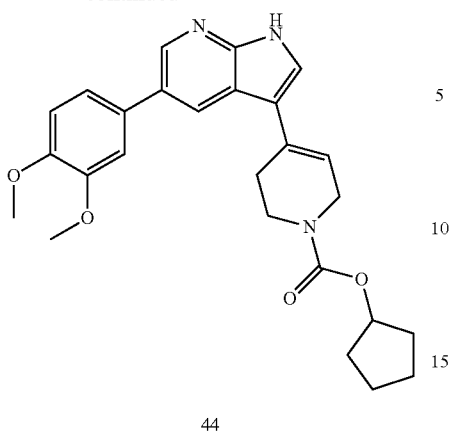

44

A suspension solution of the intermediate 42 (500 mg, 1.28 mmol, 1.0 eq), (3,4-dimethoxyphenyl)boronic acid (303 mg, 1.66 mmol, 1.3 eq) and Na₂CO₃ (542 mg, 5.12 mmol, 4.0 eq) in DME (8 mL) and water (2 mL) was subjected to purging with nitrogen, treated with Pd(PPh₃)₄ (147 mg, 0.13 mmol, 0.1 eq), and then stirred at 90° C. for 3 hours. The resulting reaction mixture was cooled to room temperature, concentrated, added with water (5 mL), filtered and washed with MeCN (5 mL) Then, the crude product thus obtained was purified by prep. HPLC to give the title compound 44 (18 mg, 0.04 mmol, 17.2%).

¹H NMR (400 MHz, DMSO-d₆) δ 11.77 (s, 1H), 8.51 (s, 1H), 8.36 (s, 1H), 7.59 (s, 1H), 7.28-7.24 (m, 2H), 7.06-7.04 (m, 1H), 6.29 (s, 1H), 5.03 (m, 1H), 4.09 (m, 2H), 3.88 (s, 3H), 3.81 (s, 3H), 3.61-3.59 (t, J=5.5 Hz, 2H), 2.54 (m, 2H), 1.82-1.56 (m, 8H); MS (m/z): 448.1 (MH+).

EXAMPLE 145

Cyclopentyl 4-(5-(3-sulfamoylphenyl)-1H-pyrrolo[2,3-b]pyridin-3-yl)-5,6-dihydropyridine-1(2H)-carboxylate Step 1: Preparation of cyclopentyl 4-(5-(4,4,5,5-tetramethyl-1,3,2-dioxaborolan-2-yl)-1H-pyrrolo[2,3-b]pyridin-3-yl)-5,6-dihydropyridine-1(2H)-carboxylate (45)

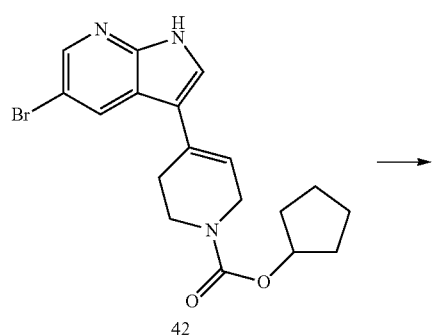

42

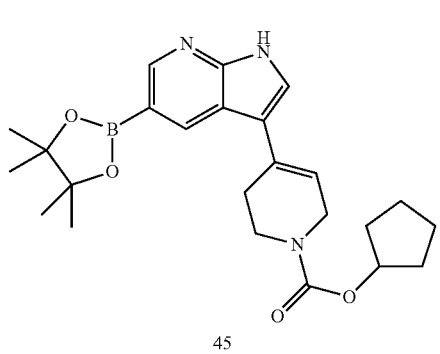

45

A suspension solution of the intermediate 42 (5.0 g, 12.8 mmol, 1.0 eq), 4,4,4',4',5,5,5',5'-octamethyl-2,2'-bi (1,3,2-dioxaborolane) (9.7 g, 38.4 mmol, 3.0 eq) and KOAc (4.39 g, 44.8 mmol, 3.5 eq) in 1,4-dioxane (50 mL) was subjected to purging with nitrogen, treated with PdCl₂(dppf) (469 mg, 0.6 mmol, 0.05 eq) and then stirred at 90° C. for 2 hours. The mixture was cooled to room temperature, filtered and concentrated. The crude product thus obtained was filtered by chromatography (EtOAc:hexane=3:1) to give the intermediate 45 (3.0 g, 6.8 mmol, 53.5%) as a yellow solid.

¹H NMR (400 MHz, DMSO-d₆) δ 11.84 (s, 1H), 8.47 (s, 1H), 8.41 (s, 1H), 7.58 (s, 1H), 6.14 (s, 1H), 5.04-5.02 (m, 1H), 4.09 (m, 2H), 3.60-3.58 (m, 2H), 1.82-1.55 (m, 8H), 1.33 (s, 12H).

Step 2: Preparation of cyclopentyl 4-(5-(3-sulfamoylphenyl)-1H-pyrrolo[2,3-b]pyridin-3-yl)-5,6-dihydropyridine-1(2H)-carboxylate (47)

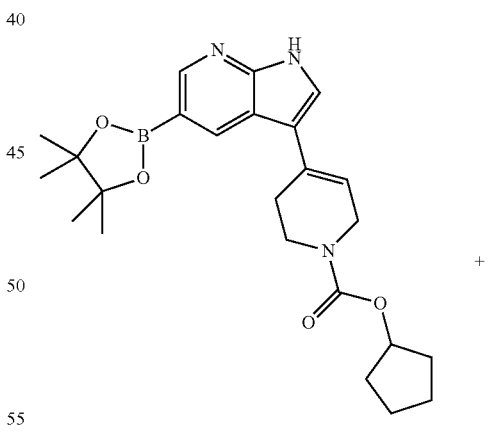

45

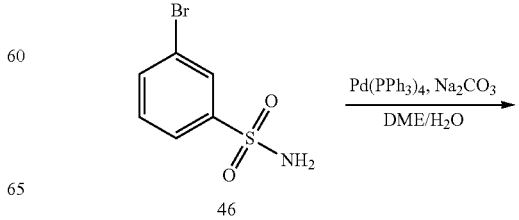

46

-continued

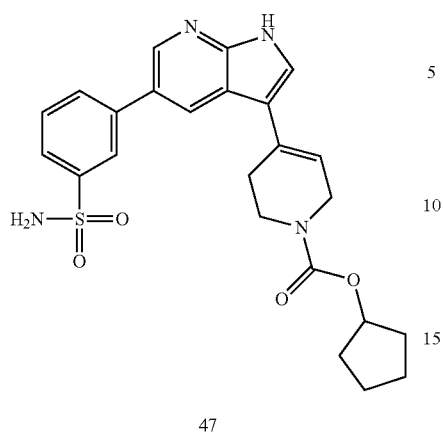

47

A suspension solution of the intermediate 45 (500 mg, 1.14 mmol, 1.3 eq), 3-bromobenzensulfonamide (205 mg, 0.87 mmol, 1.0 eq) and Na$_2$CO$_3$ (184 mg, 1.74 mmol, 2.0 eq) in DME (8 mL) and water (2 mL) was subjected to purging with nitrogen, treated with Pd(PPh$_3$)$_4$ (100 mg, 0.09 mmol, 0.1 eq) and then stirred at 90° C. for 3 hours. The reaction mixture thus obtained was cooled to room temperature, concentrated, added with water (5 mL) and EtOAc (10 mL×2), filtered and washed with MeCN (5 mL) The resulting crude product was purified by prep. HPLC to give the compound 47 (173 mg, 0.37 mmol, 42.6%) as a yellow solid.

$^1$H NMR (400 MHz, DMSO-d$_6$) δ 8.57 (s, 1H), 8.46 (s, 1H), 8.18 (s, 1H), 8.02-8.00 (d, J=7.7 Hz, 1H), 7.82-7.65 (d, J=7.8 Hz, 1H), 7.70-7.65 (m, 2H), 6.30 (s, 1H), 5.03 (s, 1H), 4.09 (m, 2H), 3.62-3.60 (m, 2H), 2.55 (s, 2H), 1.82-1.55 (m, 9H); MS (m/z): 467.1 (MH+)

EXAMPLE 146

Isopropyl 4-(5-(3-sulfamoylphenyl)-1H-pyrrolo[2,3-b]pyridin-3-yl)-5,6-dihydropyridine-1(2H)-carboxylate

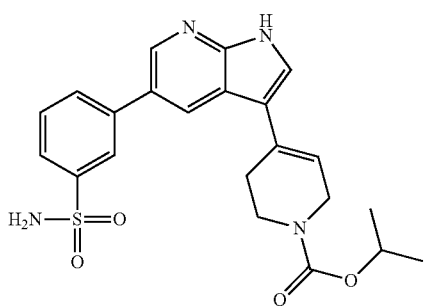 [SMILES: CC(C)OC(=O)N1CC=C(c2c[nH]c3ncc(-c4cccc(S(N)(=O)=O)c4)cc23)CC1]

$^1$H NMR (400 MHz, DMSO-d$_6$) δ 11.80 (s, 1H), 8.57-8.56 (d, J=2.0 Hz, 1H), 8.47-8.46 (d, J=2.0 Hz, 1H), 8.18 (s, 1H), 8.02-8.00 (d, J=7.8 Hz, 1H), 7.83-7.81 (d, J=7.9 Hz, 1H), 7.70-7.65 (m, 1H), 7.45 (s, 2H), 6.30 (s, 1H), 4.86-4.80 (m, 1H), 4.11 (s, 2H), 3.64-3.63 (m, 2H), 2.56 (s, 2H), 1.23 (s, 3H), 1.22 (s, 3H); MS (m/z): 441.2 (MH$^+$).

EXAMPLE 147

Isopropyl 4-(5-(3,4-dimethoxyphenyl)-1H-pyrrolo[2,3-b]pyridin-3-yl)-5,6-dihydropyridine-1(2H)-carboxylate

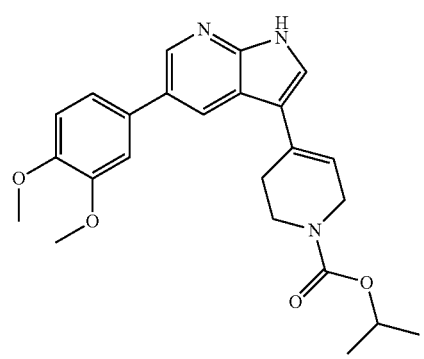 [SMILES: COc1ccc(-c2cnc3[nH]cc(C4=CCN(C(=O)OC(C)C)CC4)c3c2)cc1OC]

$^1$H NMR (400 MHz, CDCl$_3$) δ 9.71 (s, 1H), 8.55-8.54 (d, J=1.6 Hz, 1H), 8.30-8.29 (d, J=1.6 Hz, 1H), 7.37 (s, 1H), 7.20-7.17 (m, 1H), 7.15-7.14 (m, 1H), 7.03-7.01 (d, J=8.4 Hz, 1H), 6.21 (s, 1H), 5.02-4.99 (m, 1H), 4.21 (s, 2H), 4.01 (s, 3H), 3.97 (s, 3H), 3.76 (m, 2H), 2.62 (s, 2H), 1.35-1.30 (m, 6H); MS (m/z): 422.2 (MH$^+$).

EXAMPLE 148

Isopropyl 4-(5-(4-(methylsulfonyl)phenyl)-1H-pyrrolo[2,3-b]pyridin-3-yl)-5,6-dihydropyridine-1(2H)-carboxylate

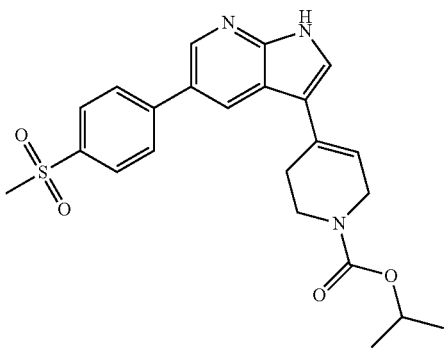 [SMILES: CC(C)OC(=O)N1CC=C(c2c[nH]c3ncc(-c4ccc(S(C)(=O)=O)cc4)cc23)CC1]

$^1$H NMR (400 MHz, DMSO-d$_6$) δ 11.92 (s, 1H), 8.63-8.62 (d, J=4.0 Hz, 1H), 8.55-8.54 (d, J=2.0 Hz, 1H), 8.08-8.06 (m, 2H), 8.02-8.00 (m, 2H), 7.66 (s, 1H), 6.34 (s, 1H), 4.84-4.81 (m, 1H), 4.10 (s, 2H), 3.63-3.60 (m, 2H), 3.30-3.27 (m, 3H), 2.55 (s, 2H), 1.23-1.21 (m, 6H); MS (m/z): 440.3 (MH$^+$).

EXAMPLE 149

Isopropyl 4-(5-(3-(methylsulfonyl)phenyl)-1H-pyrrolo[2,3-b]pyridin-3-yl)-5,6-dihydropyridine-1(2H)-carboxylate

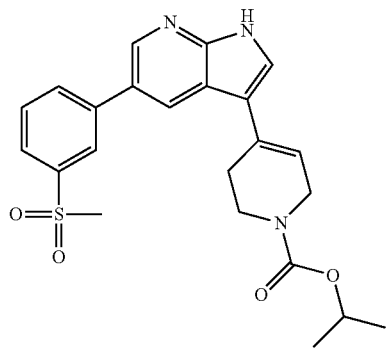 [SMILES: CC(C)OC(=O)N1CC=C(c2c[nH]c3ncc(-c4cccc(S(C)(=O)=O)c4)cc23)CC1]

$^1$H NMR (400 MHz, DMSO-d$_6$) δ 11.89 (s, 1H), 8.62-8.61 (d, J=2.0 Hz, 1H), 8.52-8.51 (d, J=2.0 Hz, 1H), 8.24 (s, 1H), 8.15-8.13 (d, J=7.6 Hz, 1H), 7.93-7.91 (d, J=7.6 Hz, 1H), 7.79-7.77 (m, 1H), 7.65 (s, 1H), 6.33 (s, 1H), 4.82-4.81 (m, 1H), 4.10 (s, 2H), 3.64-3.61 (m, 2H), 3.33 (m, 3H), 2.56 (s, 2H), 1.23-1.21 (m, 6H); MS (m/z): 440.3 (MH$^+$).

EXAMPLE 150

Isopropyl 4-(5-(4-sulfamoylphenyl)-1H-pyrrolo[2,3-b]pyridin-3-yl)-5,6-dihydropyridine-1(2H)-carboxylate

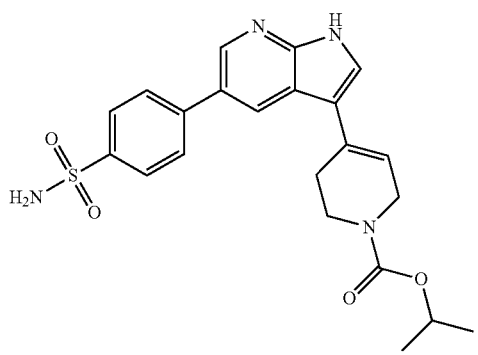 [SMILES: CC(C)OC(=O)N1CC=C(c2c[nH]c3ncc(-c4ccc(S(N)(=O)=O)cc4)cc23)CC1]

$^1$H NMR (400 MHz, DMSO-d$_6$) δ 11.87 (s, 1H), 8.61-8.60 (d, J=2.0 Hz, 1H), 8.52-8.51 (d, J=2.0 Hz, 1H), 7.99-7.97 (m, 2H), 7.94-7.92 (m, 2H), 7.64 (s, 1H), 7.40 (s, 1H), 6.34 (s, 1H), 4.86-4.80 (m, 1H), 4.10 (s, 2H), 3.64-3.61 (m, 2H), 2.55 (s, 2H), 1.23-1.22 (m, 6H); MS (m/z): 441.2 (MH$^+$).

EXAMPLE 151 tert-Butyl 4-(5-(3-sulfamoylphenyl)-1H-pyrrolo[2,3-b]pyridin-3-yl)-5,6-dihydropyridine-1(2H)-carboxylate

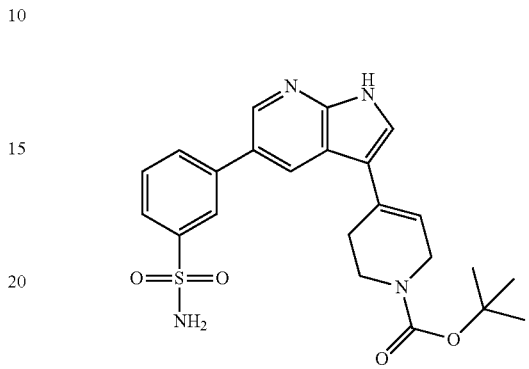

$^1$H NMR (400 MHz, DMSO-d$_6$) δ 11.92 (br s, 1H), 8.56 (s, 1H), 8.46 (s, 1H), 8.17 (s, 1H), 8.02 (d, J=7.2 Hz, 1H), 7.81 (d, J=8.0 Hz, 1H), 7.70-7.64 (m, 2H), 7.41 (br s, 2H), 6.30 (br, 1H), 4.00 (br s, 2H), 3.61-3.58 (m, 2H), 2.57-2.54 (m, 2H), 1.44 (s, 9H); [M+H]$^+$ 455.

EXAMPLE 152 tert-Butyl 4-(5-(4-sulfamoylphenyl)-1H-pyrrolo[2,3-b]pyridin-3-yl)-5,6-dihydropyridine-1(2H)-carboxylate

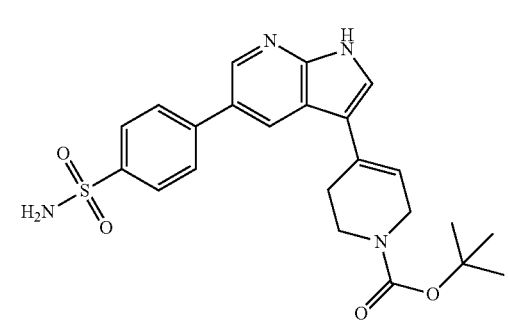 [SMILES: CC(C)(C)OC(=O)N1CC=C(c2c[nH]c3ncc(-c4ccc(S(N)(=O)=O)cc4)cc23)CC1]

$^1$H NMR (400 MHz, DMSO-d$_6$) δ 11.87 (br s, 1H), 8.60 (s, 1H), 8.52 (s, 1H), 7.99-7.89 (m, 4H), 7.63 (s, 1H), 7.40 (br s, 2H), 6.33 (br, 1H), 4.07 (br s, 2H), 3.61-3.58 (m, 2H), 2.57-2.54 (m, 2H), 1.44 (s, 9H); [M+H]$^+$ 455.

EXAMPLE 153 tert-Butyl 4-(5-(5-(morpholinomethyl)thiophen-2-yl)-1H-pyrrolo[2,3-b]pyridin-3-yl)-5,6-dihydropyridine-1(2H)-carboxylate

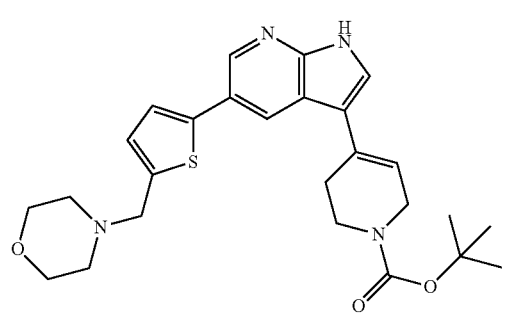 [SMILES: CC(C)(C)OC(=O)N1CC=C(c2c[nH]c3ncc(-c4ccc(CN5CCOCC5)s4)cc23)CC1]

¹H NMR (400 MHz, DMSO-d₆) δ 11.83 (br s, 1H), 8.50 (s, 1H), 8.35 (s, 1H), 7.59 (s, 1H), 7.42 (d, J=3.6 Hz, 1H), 6.99 (d, J=3.6 Hz, 1H), 6.25 (br s, 1H), 4.07 (br s, 2H), 3.68 (s, 2H), 3.61-3.56 (m, 6H), 2.46-2.42 (m, 6H), 1.44 (s, 9H); [M+H]⁺ 481.

EXAMPLE 154 tert-Butyl 4-(5-(4-(morpholinomethyl)phenyl)-1H-pyrrolo[2,3-b]pyridin-3-yl)-5,6-dihydropyridine-1(2H)-carboxylate

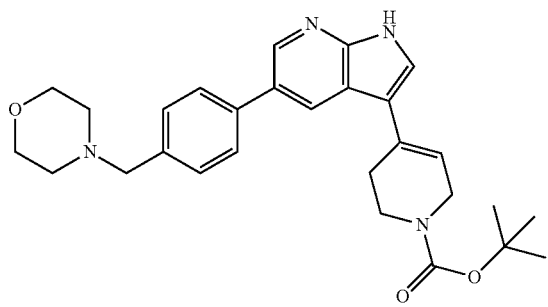 [SMILES: CC(C)(C)OC(=O)N1CC=C(c2c[nH]c3ncc(-c4ccc(CN5CCOCC5)cc4)cc23)CC1]

¹H NMR (400 MHz, DMSO-d₆) δ 11.78 (br s, 1H), 8.52 (s, 1H), 8.41 (s, 1H), 7.71 (d, J=8.0 Hz, 2H), 7.60 (s, 1H), 7.41 (d, J=8.0 Hz, 2H), 4.06 (br s, 2H), 3.61-3.56 (m, 6H), 3.51 (s, 2H), 2.57-2.54 (m, 2H), 2.41-2.37 (m, 4H), 1.41 (s, 9H); [M+H]⁺ 475.

EXAMPLE 155 tert-Butyl 4-(5-(4-(morpholine-4-carbonyl)phenyl)-1H-pyrrolo[2,3-b]pyridin-3-yl)-5,6-dihydropyridine-1(2H)-carboxylate

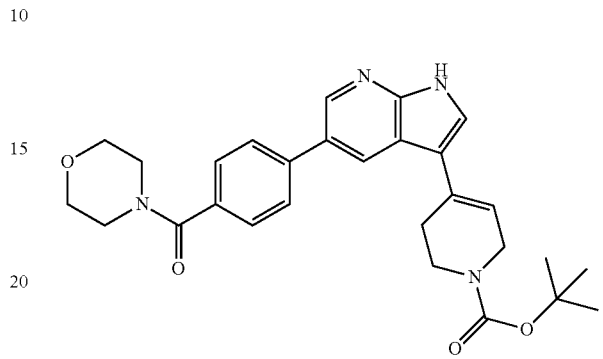

¹H NMR (400 MHz, DMSO-d₆) δ 11.82 (br s, 1H), 8.57 (s, 1H), 8.47 (s, 1H), 7.85 (d, J=7.6 Hz, 2H), 7.62 (s, 1H), 7.52 (d, J=8.0 Hz, 2H), 6.32 (br s, 1H), 4.06 (br s, 2H), 3.64-3.56 (m, 10H), 2.56-2.54 (m, 2H), 1.44 (s, 9H); [M+H]⁺ 489.

EXAMPLE 156 tert-Butyl 4-(5-(3-(morpholinomethyl)phenyl)-1H-pyrrolo[2,3-b]pyridin-3-yl)-5,6-dihydropyridine-1(2H)-carboxylate

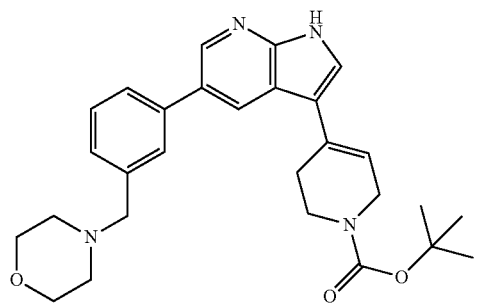 [SMILES: CC(C)(C)OC(=O)N1CC=C(c2c[nH]c3ncc(-c4cccc(CN5CCOCC5)c4)cc23)CC1]

¹H NMR (400 MHz, DMSO-d₆) δ 11.79 (br s, 1H), 8.50 (s, 1H), 8.39 (s, 1H), 7.64-7.60 (m, 3H), 7.46-7.42 (m, 1H), 7.33-7.31 (m, 1H), 6.58 (s, 1H), 4.06 (br s, 2H), 3.60-3.51 (m, 8H), 2.57-2.54 (m, 2H), 2.41-2.35 (m, 4H), 1.44 (s, 9H); [M+H]⁺ 475.

EXAMPLE 157 tert-Butyl 4-(5-(6-morpholinopyridin-3-yl)-1H-pyrrolo[2,3-b]pyridin-3-yl)-5,6-dihydropyridine-1(2H)-carboxylate

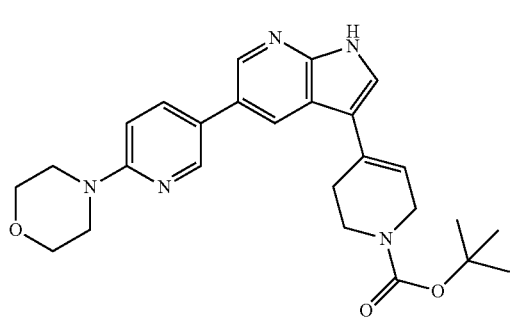 [SMILES: CC(C)(C)OC(=O)N1CC=C(c2c[nH]c3ncc(-c4ccc(N5CCOCC5)nc4)cc23)CC1]

¹H NMR (400 MHz, DMSO-d₆) δ 11.75 (br s, 1H), 8.55 (s, 1H), 8.48 (s, 1H), 8.39 (s, 1H), 8.00-7.97 (m, 1H), 7.58 (s, 1H), 6.94 (d, J=8.8 Hz, 1H), 6.31 (br s, 1H), 4.06 (br s, 2H), 3.74-3.72 (m, 4H), 3.57 (t, J=5.6 Hz, 2H), 3.51-3.48 (m, 4H), 1.44 (s, 9H); [M+H]⁺ 462.

EXAMPLE 158 tert-Butyl 4-(5-(4-morpholinophenyl)-1H-pyrrolo[2,3-b]pyridin-3-yl)-5,6-dihydropyridine-1(2H)-carboxylate

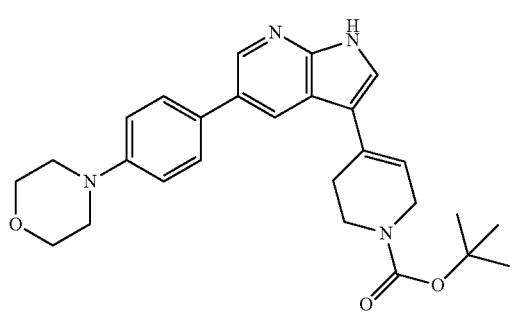 [SMILES: CC(C)(C)OC(=O)N1CC=C(c2c[nH]c3ncc(-c4ccc(N5CCOCC5)cc4)cc23)CC1]

¹H NMR (400 MHz, DMSO-d₆) δ 11.71 (br s, 1H), 8.47 (s, 1H), 8.34 (s, 1H), 7.63 (d, J=8.8 Hz, 2H), 7.57 (s, 1H), 7.05 (d, J=9.2 Hz, 2H), 6.28 (br s, 1H), 4.06 (br s, 2H), 3.78-3.76 (m, 4H), 3.57 (t, J=5.4 Hz, 2H), 3.17-3.14 (m, 4H), 1.44 (s, 9H); [M+H]⁺ 461.

EXAMPLE 159 tert-Butyl 4-(5-(4-(piperidin-1-yl)phenyl)-1H-pyrrolo[2,3-b]pyridin-3-yl)-5,6-dihydropyridine-1(2H)-carboxylate

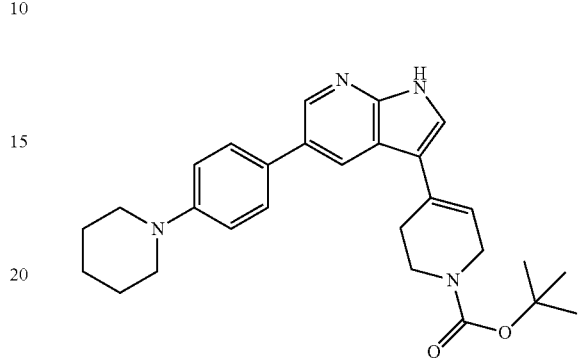

¹H NMR (400 MHz, DMSO-d₆) δ 11.68 (br s, 1H), 8.46 (s, 1H), 8.32 (s, 1H), 7.60-7.55 (m, 3H), 7.02 (d, J=8.4 Hz, 2H), 6.27 (br s, 1H), 4.06 (br s, 2H), 3.60-3.56 (m, 2H), 3.30 (s, 2H), 3.20-3.16 (m, 4H), 1.68-1.61 (m, 4H), 1.60-1.54 (m, 2H), 1.44 (s, 9H); [M+H]⁺ 459.

EXAMPLE 160 tert-Butyl 4-(5-(benzo[d][1,3]dioxol-5-yl)-1H-pyrrolo[2,3-b]pyridin-3-yl)-5,6-dihydropyridine-1(2H)-carboxylate

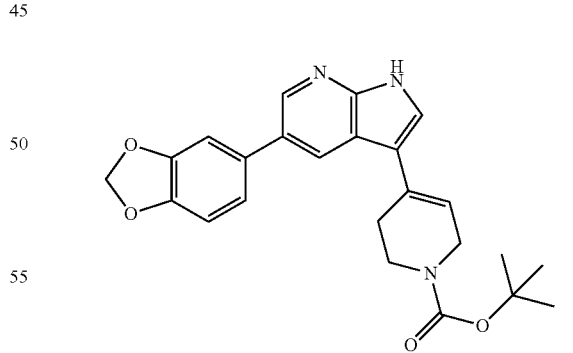

¹H NMR (400 MHz, DMSO-d₆) δ 11.75 (br s, 1H), 8.46 (s, 1H), 8.35 (s, 1H), 7.58 (s, 1H), 7.37 (s, 1H), 7.22 (d, J=8.4 Hz, 1H), 7.01 (d, J=8.0 Hz, 1H), 4.06 (br s, 2H), 3.57 (t, J=5.4 Hz, 2H), 2.56-2.53 (m, 2H), 1.44 (s, 9H); [M+H]⁺ 420.

EXAMPLE 161 tert-Butyl 4-(5-(6-methoxypyridin-3-yl)-1H-pyrrolo[2,3-b]pyridin-3-yl)-5,6-dihydropyridine-1(2H)-carboxylate

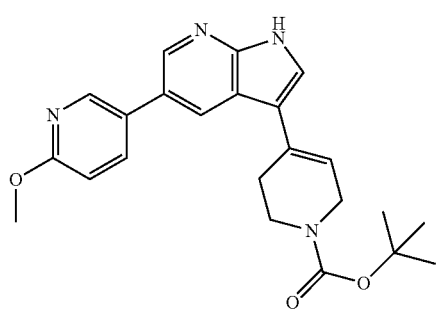 [SMILES: COc1ccc(-c2cnc3[nH]cc(C4=CCN(C(=O)OC(C)(C)C)CC4)c3c2)cn1]

¹H NMR (400 MHz, DMSO-d₆) δ 11.81 (br s, 1H), 8.57 (s, 1H), 8.51 (s, 1H), 8.44 (s, 1H), 8.13 (dd, J=8.6, 1.6 Hz, 1H), 7.60 (s, 1H), 6.93 (d, J=8.8 Hz, 1H), 6.33 (br s, 1H), 4.06 (br s, 2H), 3.91 (s, 3H), 3.59-3.55 (m, 2H), 2.57-2.52 (m, 1H), 1.44 (s, 9H); [M+H]⁺ 407.

EXAMPLE 162 tert-Butyl 4-(5-(3-(methylsulfonyl)phenyl)-1H-pyrrolo[2,3-b]pyridin-3-yl)-5,6-dihydropyridine-1(2H)-carboxylate

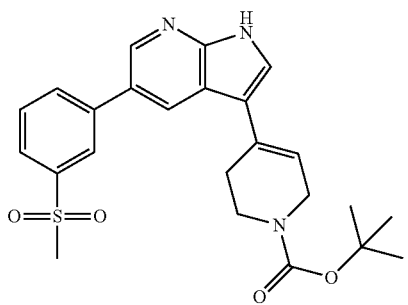 [SMILES: CC(C)(C)OC(=O)N1CC=C(c2c[nH]c3ncc(-c4cccc(S(C)(=O)=O)c4)cc23)CC1]

¹H NMR (400 MHz, DMSO-d₆) δ 11.90 (br s, 1H), 8.62 (s, 1H), 8.52 (s, 1H), 8.24-8.23 (m, 1H), 8.16-8.13 (m, 1H), 7.93-7.90 (m, 1H), 7.76 (t, J=7.8 Hz, 1H), 7.65 (s, 1H), 4.07 (br s, 2H), 3.32 (s, 3H), 3.59-3.56 (m, 2H), 2.53-2.52 (m, 3H), 1.43 (s, 9H); [M+H]⁺ 454.

EXAMPLE 163 tert-Butyl 4-(5-(3-(N-methylsulfamoyl)phenyl)-1H-pyrrolo[2,3-b]pyridin-3-yl)-5,6-dihydropyridine-1(2H)-carboxylate

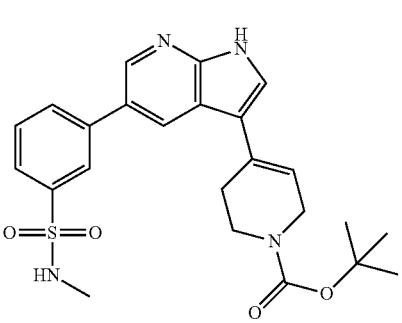 [SMILES: CNS(=O)(=O)c1cccc(-c2cnc3[nH]cc(C4=CCN(C(=O)OC(C)(C)C)CC4)c3c2)c1]

¹H NMR (400 MHz, DMSO-d₆) δ 11.88 (br s, 1H), 8.56 (s, 1H), 8.47 (s, 1H), 8.07-8.05 (m, 2H), 7.78-7.70 (m, 2H), 7.64 (s, 1H), 7.49 (br s, 1H), 6.31 (br s, 1H), 4.07 (s, 2H), 3.59-3.57 (m, 2H), 2.55-2.53 (m, 2H), 2.46 (s, 3H), 1.44 (s, 9H); [M+H]⁺ 469.

EXAMPLE 164 tert-Butyl 4-(5-(4-(methylsulfonyl)phenyl)-1H-pyrrolo[2,3-b]pyridin-3-yl)-5,6-dihydropyridine-1(2H)-carboxylate

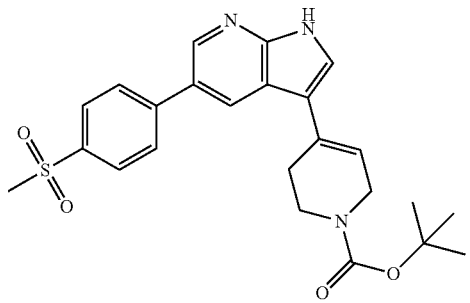 [SMILES: CC(C)(C)OC(=O)N1CC=C(c2c[nH]c3ncc(-c4ccc(S(C)(=O)=O)cc4)cc23)CC1]

¹H NMR (400 MHz, DMSO-d₆) δ 11.92 (br s, 1H), 8.63 (s, 1H), 8.55 (s, 1H), 8.09-7.99 (m, 4H), 7.65 (s, 1H), 6.34 (br s, 1H), 4.07 (br s, 2H), 3.59-3.56 (m, 2H), 3.27 (s, 3H), 2.53-2.52 (m, 3H), 1.44 (s, 9H); [M+H]⁺ 454.

EXAMPLE 165 tert-Butyl 4-(5-(4-(N-methylsulfamoyl)phenyl)-1H-pyrrolo[2,3-b]pyridin-3-yl)-5,6-dihydropyridine-1(2H)-carboxylate

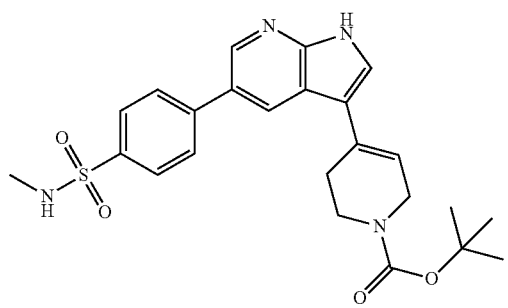 [SMILES: CNS(=O)(=O)c1ccc(-c2cnc3[nH]cc(C4=CCN(C(=O)OC(C)(C)C)CC4)c3c2)cc1]

$^1$H NMR (400 MHz, DMSO-d$_6$) δ 11.87 (br s, 1H), 8.61 (s, 1H), 8.53 (s, 1H), 8.03-7.85 (m, 2H), 7.63 (s, 1H), 7.50 (br s, 1H), 6.34 (br s, 1H), 4.07 (s, 2H), 3.59-3.57 (m, 2H), 2.55-2.53 (m, 2H), 2.46 (s, 3H), 1.44 (s, 9H); [M+H]$^+$ 469.

EXAMPLE 166 tert-Butyl 4-(5-(4-acetylphenyl)-1H-pyrrolo[2,3-b]pyridin-3-yl)-5,6-dihydropyridine-1(2H)-carboxylate

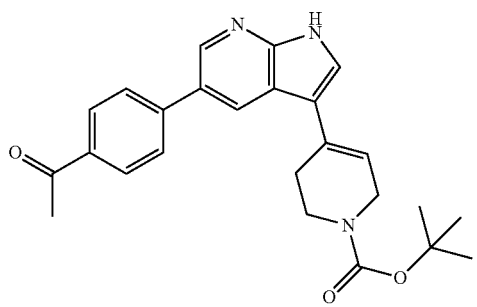 [SMILES: CC(=O)c1ccc(-c2cnc3[nH]cc(C4=CCN(C(=O)OC(C)(C)C)CC4)c3c2)cc1]

$^1$H NMR (400 MHz, DMSO-d$_6$) δ 11.89 (br s, 1H), 8.63 (s, 1H), 8.53 (s, 1H), 8.07-7.94 (m, 4H), 7.64 (s, 1H), 6.34 (br s, 1H), 4.07 (br s, 2H), 3.59-3.56 (m, 2H), 2.63 (s, 3H), 2.58-2.52 (m, 2H), 1.44 (s, 9H); [M+H]$^+$ 418.

EXAMPLE 167 tert-Butyl 4-(5-(4-(methoxycarbonyl)phenyl)-1H-pyrrolo[2,3-b]pyridin-3-yl)-5,6-dihydropyridine-1(2H)-carboxylate

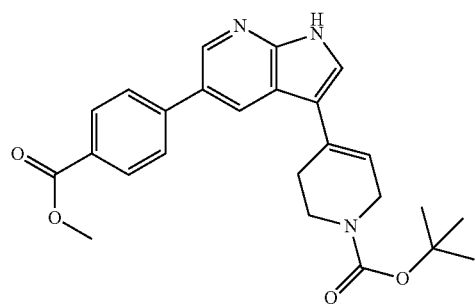 [SMILES: COC(=O)c1ccc(-c2cnc3[nH]cc(C4=CCN(C(=O)OC(C)(C)C)CC4)c3c2)cc1]

$^1$H NMR (400 MHz, DMSO-d$_6$) δ 11.88 (br s, 1H), 8.62 (s, 1H), 8.53 (s, 1H), 8.06-7.94 (m, 4H), 7.63 (s, 1H), 6.33 (br s, 1H), 4.07 (br s, 2H), 3.89 (s, 3H), 3.59-3.56 (m, 2H), 2.58-2.52 (m, 2H), 1.44 (s, 9H); [M+H]$^+$ 434.

EXAMPLE 168 tert-Butyl 4-(5-(4-cyanophenyl)-1H-pyrrolo[2,3-b]pyridin-3-yl)-5,6-dihydropyridine-1(2H)-carboxylate

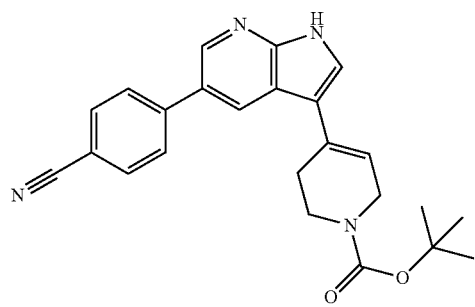 [SMILES: CC(C)(C)OC(=O)N1CC=C(c2c[nH]c3ncc(-c4ccc(C#N)cc4)cc23)CC1]

$^1$H NMR (400 MHz, DMSO-d$_6$) δ 11.89 (br s, 1H), 8.62 (s, 1H), 8.54 (s, 1H), 8.03-7.91 (m, 4H), 7.64 (s, 1H), 6.34 (br s, 1H), 4.07 (br s, 2H), 3.58-3.56 (m, 2H), 2.53-2.52 (m, 2H), 1.44 (s, 9H); [M+H]$^+$ 401.

EXAMPLE 169 tert-Butyl 4-(5-(3-cyanophenyl)-1H-pyrrolo[2,3-b]pyridin-3-yl)-5,6-dihydropyridine-1(2H)-carboxylate

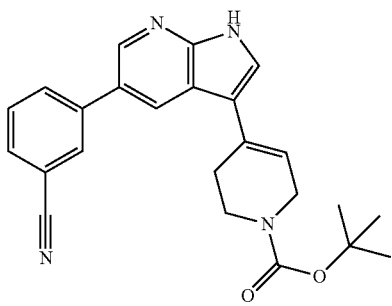 [SMILES: CC(C)(C)OC(=O)N1CC=C(c2c[nH]c3ncc(-c4cccc(C#N)c4)cc23)CC1]

$^1$H NMR (400 MHz, DMSO-d$_6$) δ 11.86 (br s, 1H), 8.60 (s, 1H), 8.53 (s, 1H), 8.30 (s, 1H), 8.14 (d, J=8.0 Hz, 1H), 7.82 (d, J=7.6 Hz, 1H), 7.68 (t, J=7.8 Hz, 1H), 7.63 (s, 1H), 6.36 (br s, 1H), 4.07 (br s, 2H), 3.58-3.56 (m, 2H), 2.53-2.52 (m, 2H), 1.44 (s, 9H); [M+H]$^+$ 401.

EXAMPLE 170 tert-Butyl 4-(5-(5-methyl-1,3,4-thiadiazol-2-yl)-1H-pyrrolo[2,3-b]pyridin-3-yl)-5,6-dihydropyridine-1(2H)-carboxylate

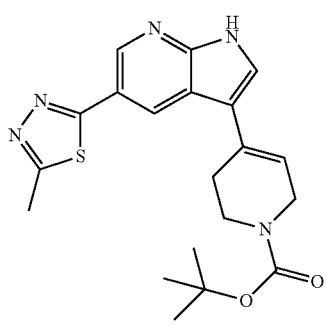 [SMILES: Cc1nnc(-c2cnc3[nH]cc(C4=CCN(C(=O)OC(C)(C)C)CC4)c3c2)s1]

Step 1: Preparation of 1H-pyrrolo[2,3-b]pyridine-5-carboxylic acid

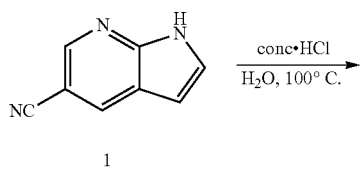

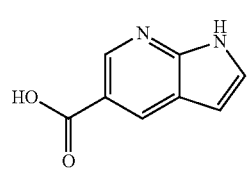

A mixture of 1H-pyrrolo[2,3-b]pyridine-5-carbonitrile (500 mg, 3.50 mmol) and concentrated HCl (3.6 mL) in H$_2$O (18 mL) was stirred at 100° C. for 12 hours. The resulting mixture was cooled to room temperature. The solid thus obtained was washed with water to give the title compound (337 mg, 29%).

Step 2: Preparation of N'-acetyl-1H-pyrrolo[2,3-b]pyridine-5-carbohydrazide

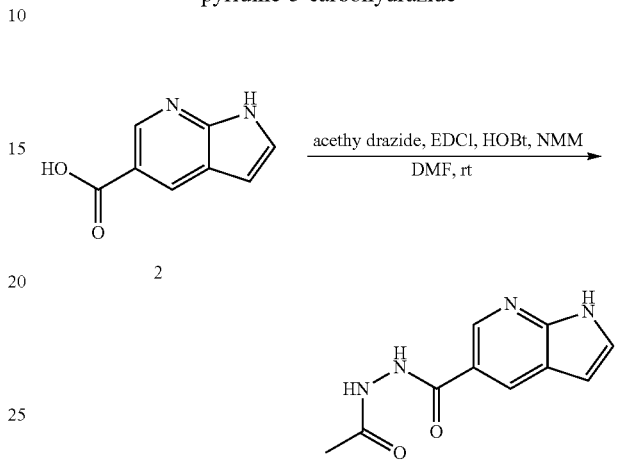

A mixture of 1H-pyrrolo[2,3-b]pyridine-5-carboxylic acid (100 mg, 0.62 mmol), acethydrazide (69 mg, 0.93 mmol), EDCI (236 mg, 1.23 mmol) and HOBt (125 mg, 0.93 mmol) in DME (6.2 mL) was added with NMM (200 μL, 1.85 mmol) at room temperature, and the reaction mixture was stirred at room temperature for 12 hours. The resulting mixture was purified with prep. HPLC system (water, ACN/H$_2$O) to give the title compound (76 mg, 56%) as a white solid.

Step 3: Preparation of 2-methyl-5-(1H-pyrrolo[2,3-b]pyridin-5-yl)-1,3,4-thiadiazole

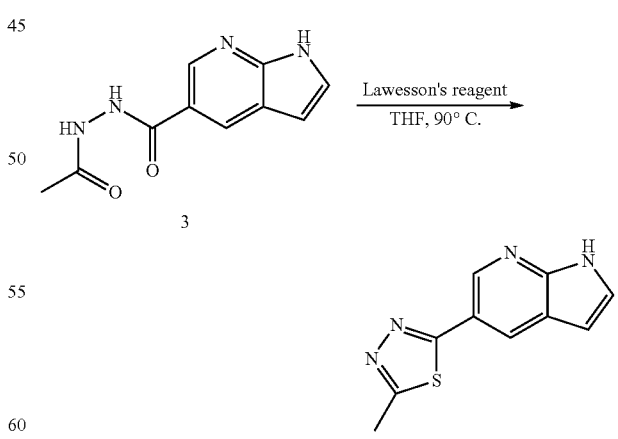

A mixture of N-acetyl-1H-pyrrolo[2,3-b]pyridine-5-carbohydrazide (70 mg, 0.32 mmol) and Lawesson's reagent (259 mg, 0.64 mmol) in THF (1.6 mL) was stirred at 90° C. for 12 hours. The resulting mixture was purified with prep.

HPLC system (water, ACN/H₂O) to give the title compound (41 mg, 60%) as a white solid.

Step 4: Preparation of tert-Butyl 4-(5-(5-methyl-1,3,4-thiadiazol-2-yl)-1H-pyrrolo[2,3-b]pyridin-3-yl)-5,6-dihydropyridine-1(2H)-carboxylate

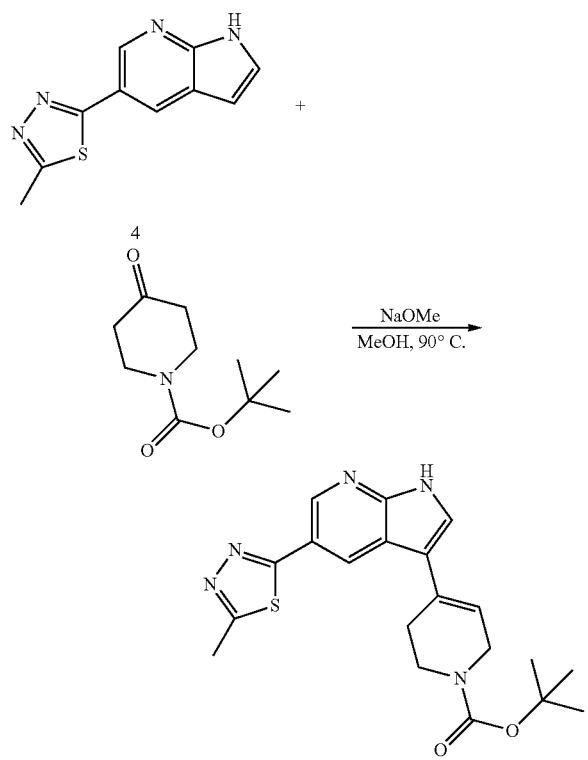

¹H NMR (400 MHz, DMSO-d₆) δ 12.13 (br s, 1H), 8.78 (d, J=2.0 Hz, 1H), 8.68 (d, J=2.0 Hz, 1H), 7.71 (br s, 1H), 6.26-6.25 (m, 1H), 4.11-4.08 (m, 2H), 3.58-3.56 (m, 2H), 2.79 (s, 3H), 2.51-2.50 (m, 2H), 1.44 (s, 9H); [M+H]⁺ 398.

EXAMPLE 171

Cyclopentyl 4-(5-(3-fluoro-4-methoxyphenyl)-1H-pyrrolo[2,3-b]pyridin-3-yl)-5,6-dihydropyridine-1(2H)-carboxylate

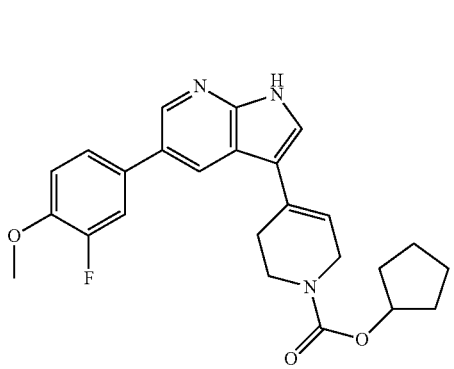

¹H NMR (400 MHz, DMSO-d₆) δ 11.84 (s, 1H), 8.54 (s, 1H), 8.41 (s, 1H), 7.62 (s, 1H), 7.47 (d, J=7.6 Hz, 1H), 7.31-7.27 (m, 2H), 6.31 (s, 1H), 5.04-5.01 (m, 1H), 4.08 (br s, 2H), 3.96 (s, 3H), 3.60 (t, J=5.8 Hz, 2H), 2.54 (br s, 1H), 1.83-1.77 (m, 2H), 1.71-1.62 (m, 5H), 1.59-1.55 (m, 2H); [M+H]⁺ 436.

EXAMPLE 172

Cyclopentyl 4-(5-(3-(methylsulfonyl)phenyl)-1H-pyrrolo[2,3-b]pyridin-3-yl)-5,6-dihydropyridine-1(2H)-carboxylate

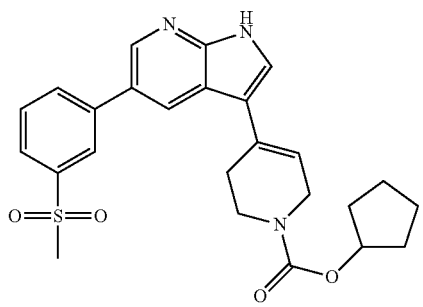 [SMILES: CS(=O)(=O)c1cccc(-c2cnc3[nH]cc(C4=CCN(C(=O)OC5CCCC5)CC4)c3c2)c1]

¹H NMR (400 MHz, DMSO-d₆) δ 11.91 (br s, 1H), 8.62 (s, 1H), 8.52 (s, 1H), 8.24 (s, 1H), 8.14 (d, J=7.2 Hz, 1H), 7.92 (d, J=7.2 Hz, 1H), 7.76 (t, J=7.62 Hz, 1H), 7.65 (s, 1H), 6.33 (br s, 1H), 5.05-5.01 (m, 1H), 4.09 (br s, 2H), 3.65-3.55 (m, 2H), 3.32 (s, 3H), 2.58-2.54 (m, 1H), 1.86-1.77 (m, 2H), 1.72-1.61 (m, 5H), 1.60-1.54 (m, 2H); [M+H]⁺ 466.

EXAMPLE 173

Cyclopentyl 4-(5-(4-(methylsulfonyl)phenyl)-1H-pyrrolo[2,3-b]pyridin-3-yl)-5,6-dihydropyridine-1(2H)-carboxylate ¹H NMR (400 MHz, DMSO-d₆) δ 11.93 (br s, 1H), 8.63 (s, 1H), 8.54 (s, 1H), 8.08-8.00 (m, 4H), 7.65 (s, 1H), 6.34 (br s, 1H), 5.03 (br s, 1H), 4.09 (m, 2H), 3.60 (m, 2H), 3.27 (s, 3H), 2.58-2.54 (m, 1H), 1.87-1.78 (m, 2H), 1.73-1.62 (m, 5H), 1.61-1.54 (m, 2H); [M+H]⁺ 466.

EXAMPLE 174

Cyclopentyl 4-(5-(3-(ethylsulfonyl)phenyl)-1H-pyrrolo[2,3-b]pyridin-3-yl)-5,6-dihydropyridine-1(2H)-carboxylate

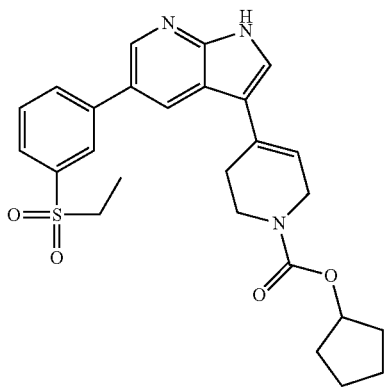 [SMILES: CCS(=O)(=O)c1cccc(-c2cnc3[nH]cc(C4=CCN(C(=O)OC5CCCC5)CC4)c3c2)c1]

$^1$H NMR (400 MHz, DMSO-d$_6$) δ 11.92 (s, 1H), 8.61 (s, 1H), 8.52 (s, 1H), 8.18 (s, 2H), 7.87-7.66 (m, 3H), 6.34 (s, 1H), 5.03 (s, 1H), 4.09 (s, 2H), 3.60 (s, 2H), 3.42 (s, 2H), 2.51 (s, 2H), 1.80-1.16 (m, 11H); MS (m/z): 480.1 (MH+).

EXAMPLE 175

Cyclopentyl 4-(5-(4-(cyclopropylsulfonyl)phenyl)-1H-pyrrolo[2,3-b]pyridin-3-yl)-5,6-dihydropyridine-1(2H)-carboxylate

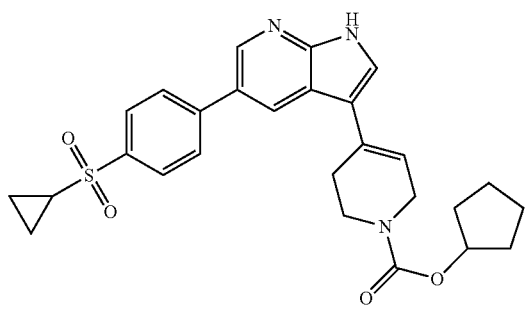 [SMILES: O=C(OC1CCCC1)N1CC=C(c2c[nH]c3ncc(-c4ccc(S(=O)(=O)C5CC5)cc4)cc23)CC1]

$^1$H NMR (400 MHz, DMSO-d$_6$) δ 11.91 (br s, 1H), 8.63 (s, 1H), 8.55 (s, 1H), 8.07-7.95 (m, 4H), 7.65 (s, 1H), 6.35 (br s, 1H), 5.05-5.02 (m, 1H), 4.09 (s, 2H), 3.60 (t, J=5.6 Hz, 2H), 2.94-2.88 (m, 1H), 2.58-2.54 (m, 1H), 1.85-1.78 (m, 2H), 1.73-1.62 (m, 5H), 1.61-1.54 (m, 2H), 1.18-1.15 (m, 2H), 1.11-1.06 (m, 2H); [M+H]$^+$ 492.

EXAMPLE 176

Cyclopentyl 4-(5-(4-sulfamoylphenyl)-1H-pyrrolo[2,3-b]pyridin-3-yl)-5,6-dihydropyridine-1(2H)-carboxylate

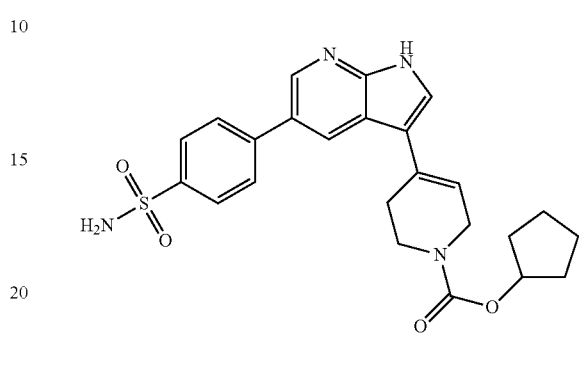

$^1$H NMR (400 MHz, DMSO-d$_6$) δ 8.60 (s, 1H), 8.51 (s, 1H), 7.99-7.89 (m, 4H), 7.64 (s, 1H), 6.34 (s, 1H), 5.05-5.01 (m, 1H), 4.09 (br s, 2H), 3.60 (t, J=5.8 Hz, 2H), 2.58-2.54 (m, 2H), 1.86-1.77 (m, 2H), 1.73-1.63 (m, 5H), 1.61-1.54 (m, 2H); [M+H]$^+$ 467.

EXAMPLE 177

Cyclopentyl 4-(5-(3-(N-methylsulfamoyl)phenyl)-1H-pyrrolo[2,3-b]pyridin-3-yl)-5,6-dihydropyridine-1(2H)-carboxylate

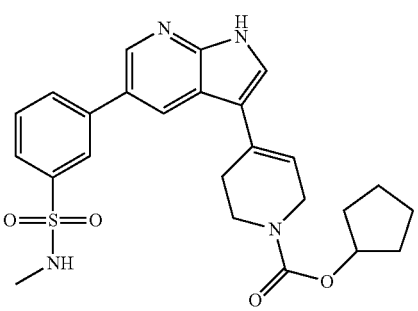 [SMILES: CNS(=O)(=O)c1cccc(-c2cnc3[nH]cc(C4=CCN(C(=O)OC5CCCC5)CC4)c3c2)c1]

$^1$H NMR (400 MHz, DMSO-d$_6$) δ 11.91 (br s, 1H), 8.56 (s, 1H), 8.47 (s, 1H), 8.07-8.05 (m, 2H), 7.78-7.70 (m, 2H), 7.65 (s, 1H), 7.49 (br s, 1H), 6.31 (br s, 1H), 5.05-5.01 (m, 1H), 4.09 (br s, 2H), 3.60 (t, J=5.8 Hz, 2H), 2.58-2.54 (m, 1H), 2.46 (s, 3H), 1.86-1.77 (m, 2H), 1.72-1.61 (m, 5H), 1.60-1.54 (m, 2H); [M+H]$^+$ 481.

EXAMPLE 178

Cyclopentyl 4-(5-(4-(N-methylsulfamoyl)phenyl)-1H-pyrrolo[2,3-b]pyridin-3-yl)-5,6-dihydropyridine-1(2H)-carboxylate

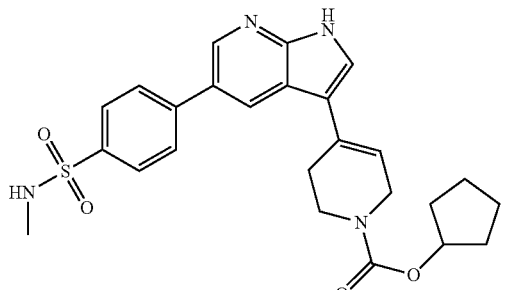

$^1$H NMR (400 MHz, DMSO-d$_6$) δ 11.90 (br s, 1H), 8.61 (s, 1H), 8.53 (s, 1H), 8.02 (d, J=8.4 Hz, 2H), 7.86 (d, J=8.4 Hz, 2H), 7.64 (s, 1H), 7.51 (br s, 1H), 6.34 (br s, 1H), 5.05-5.01 (m, 1H), 4.09 (br s, 2H), 3.60 (t, J=5.6 Hz, 2H), 2.58-2.54 (m, 1H), 2.46 (s, 3H), 1.86-1.77 (m, 2H), 1.72-1.61 (m, 5H), 1.60-1.54 (m, 2H); [M+H]$^+$ 481.

EXAMPLE 179

Cyclopentyl 4-(5-(4-(N,N-dimethylsulfamoyl)phenyl)-1H-pyrrolo[2,3-b]pyridin-3-yl)-5,6-dihydropyridine-1(2H)-carboxylate

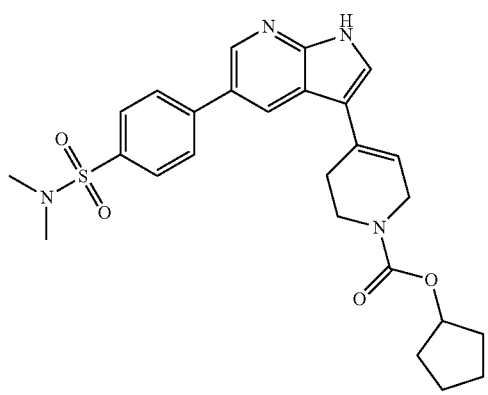 [SMILES: CN(C)S(=O)(=O)c1ccc(-c2cnc3[nH]cc(C4=CCN(C(=O)OC5CCCC5)CC4)c3c2)cc1]

$^1$H NMR (400 MHz, DMSO-d$_6$) δ 11.93 (s, 1H), 8.63 (s, 1H), 8.56 (s, 1H), 8.08-8.06 (d, J=8.2 Hz, 2H), 7.84-7.82 (d, J=8.2 Hz, 2H), 7.66 (m, 1H), 6.35 (s, 1H), 5.03 (m, 1H), 4.09 (s, 2H), 3.62-3.59 (t, J=5.3 Hz, 2H), 2.67 (s, 6H), 2.55 (m, 2H), 1.83-1.56 (m, 8H); MS (m/z): 495.1 (MH+).

EXAMPLE 180

Cyclopentyl 4-(5-(3-(morpholinosulfonyl)phenyl)-1H-pyrrolo[2,3-b]pyridin-3-yl)-5,6-dihydropyridine-1(2H)-carboxylate

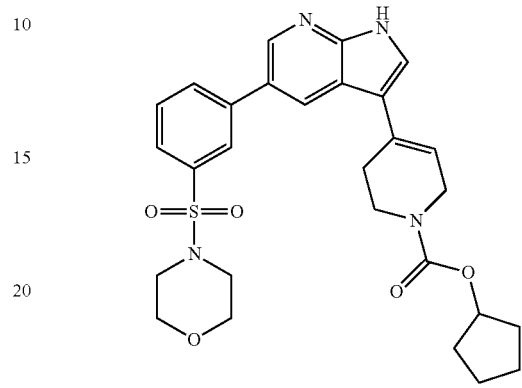

$^1$H NMR (400 MHz, DMSO-d$_6$) δ 11.93 (s, 1H), 8.58 (s, 1H), 8.50 (s, 1H), 8.16-8.15 (d, J=7.5 Hz, 1H), 7.79-7.73 (s, 2H), 7.66 (s, 1H), 6.33 (s, 1H), 5.04-5.03 (m, 1H), 4.09 (s, 2H), 3.65 (m, 4H), 3.62-3.59 (m, 2H), 2.94 (m, 4H), 2.55 (m, 2H), 1.82-1.55 (m, 9H); MS (m/z): 537.1 (MH+)

EXAMPLE 181

Cyclopentyl 4-(5-(4-(morpholinosulfonyl)phenyl)-1H-pyrrolo[2,3-b]pyridin-3-yl)-5,6-dihydropyridine-1(2H)-carboxylate

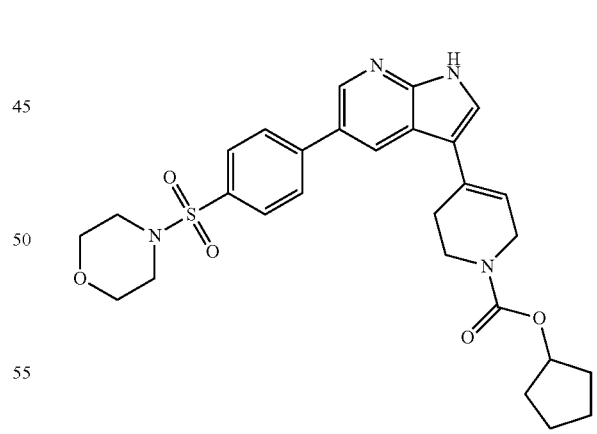

$^1$H NMR (400 MHz, DMSO-d$_6$) δ 11.92 (s, 1H), 8.64-8.63 (d, J=1.8 Hz, 1H), 8.56 (m, 1H), 8.09-8.07 (d, J=8.4 Hz, 2H), 7.83-7.81 (d, J=8.4 Hz, 2H), 7.66 (m, 1H), 6.35 (s, 1H), 5.05-5.03 (m, 1H), 4.10 (s, 2H), 3.67-3.65 (m, 4H), 3.62-3.59 (t, J=5.7 Hz, 2H), 2.55 (m, 2H), 1.83-1.56 (m, 8H); MS (m/z): 537.1 (MH+).

EXAMPLE 182

Cyclopentyl 4-(5-(4-methoxy-3-(morpholinosulfonyl)phenyl)-1H-pyrrolo[2,3-b]pyridin-3-yl)-5,6-dihydropyridine-1(2H)-carboxylate

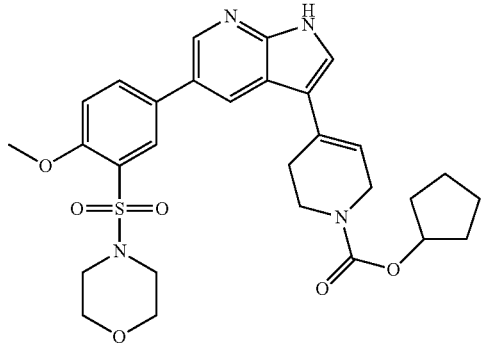 [SMILES: COc1ccc(-c2cnc3[nH]cc(C4=CCN(C(=O)OC5CCCC5)CC4)c3c2)cc1S(=O)(=O)N1CCOCC1]

$^1$H NMR (400 MHz, DMSO-$d_6$) δ 11.84 (s, 1H), 8.47 (s, 1H), 8.38 (s, 1H), 8.04 (d, J=8.8 Hz, 1H), 7.97 (s, 1H), 7.62 (s, 1H), 7.39 (d, J=8.4 Hz, 1H), 6.29 (s, 1H), 5.04-5.01 (m, 1H), 4.09 (br s, 2H), 3.96 (s, 3H), 3.62-3.59 (m, 6H), 3.17-3.13 (m, 5H), 2.54 (br s, 1H), 1.83-1.77 (m, 2H), 1.71-1.62 (m, 4H), 1.59-1.55 (m, 2H); [M+H]$^+$ 567.

EXAMPLE 183

Cyclopentyl 4-(5-(4-(morpholine-4-carbonyl)phenyl)-1H-pyrrolo[2,3-b]pyridin-3-yl)-5,6-dihydropyridine-1(2H)-carboxylate

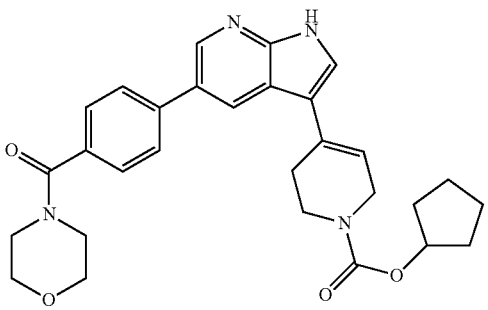 [SMILES: O=C(OC1CCCC1)N1CC=C(c2c[nH]c3ncc(-c4ccc(C(=O)N5CCOCC5)cc4)cc23)CC1]

$^1$H NMR (400 MHz, DMSO-$d_6$) δ 11.85 (br s, 1H), 8.57 (d, J=2.0 Hz, 1H), 8.47 (d, J=2.0 Hz, 1H), 7.85 (d, J=8.0 Hz, 2H), 7.62 (s, 1H), 7.52 (d, J=8.4 Hz, 2H), 6.33 (br s, 1H), 5.05-5.02 (m, 1H), 4.09-4.08 (m, 2H), 3.62-3.58 (m, 9H), 2.55-2.50 (m, 2H), 1.87-1.77 (m, 2H), 1.73-1.62 (m, 5H), 1.60-1.55 (m, 2H); [M+H]$^+$ 501.

EXAMPLE 184

Cyclopentyl 4-(5-(3-(morpholine-4-carbonyl)phenyl)-1H-pyrrolo[2,3-b]pyridin-3-yl)-5,6-dihydropyridine-1(2H)-carboxylate $^1$H NMR (400 MHz, DMSO-$d_6$) δ 11.85 (br s, 1H), 8.55 (d, J=2.7 Hz, 1H), 8.44 (d, J=2.0 Hz, 1H), 7.87-7.84 (m, 1H), 7.78-7.75 (m, 1H), 7.62 (s, 1H), 7.56 (t, J=7.8 Hz, 1H), 7.41-7.38 (m, 1H), 6.32 (br s, 1H), 5.05-5.01 (m, 1H), 4.08 (s, 2H), 3.63-3.58 (m, 2H), 2.55-2.52 (m, 2H), 1.83-1.77 (m, 2H), 1.71-1.62 (m, 5H), 1.59-1.55 (m, 2H); [M+H]$^+$ 501.

EXAMPLE 185

Cyclopentyl 4-(5-(5-(morpholinomethyl)thiophen-3-yl)-1H-pyrrolo[2,3-b]pyridin-3-yl)-5,6-dihydropyridine-1(2H)-carboxylate $^1$H NMR (400 MHz, DMSO-$d_6$) δ 11.76 (br s, 1H), 8.59 (s, 1H), 8.43 (s, 1H), 7.84 (s, 1H), 7.56 (d, J=4.8 Hz, 2H), 6.30 (s, 1H), 5.05-5.02 (m, 1H), 4.10 (s, 2H), 3.73 (s, 2H), 3.60 (t, J=4.6 Hz, 6H), 2.56-2.52 (m, 1H), 2.48-2.42 (m, 4H), 1.86-1.78 (m, 2H), 1.74-1.63 (m, 4H), 1.61-1.55 (m, 3H); [M+H]$^+$ 493.

EXAMPLE 186

Cyclopentyl 4-(5-(5-(morpholinomethyl)thiophen-2-yl)-1H-pyrrolo[2,3-b]pyridin-3-yl)-5,6-dihydropyridine-1(2H)-carboxylate <sup>1</sup>H NMR (400 MHz, DMSO-d<sub>6</sub>) δ 11.85 (br s, 1H), 8.51 (d, J=2.0 Hz, 1H), 8.35 (d, J=2.0 Hz, 1H), 7.60 (s, 1H), 7.42 (d, J=3.2 Hz, 1H), 6.99 (d, J=3.2 Hz, 1H), 6.25 (br s, 1H), 5.05-5.02 (m, 1H), 4.09 (m, 2H), 3.68 (s, 3H), 3.61-3.58 (m, 6H), 2.50-2.42 (m, 2H), 1.83-1.75 (m, 3H), 1.74-1.63 (m, 5H), 1.60-1.55 (m, 3H); [M+H]<sup>+</sup> 493.

EXAMPLE 187 tert-Butyl 4-(5-(3,4-dimethoxyphenyl)-1H-pyrrolo[2,3-b]pyridin-3-yl)-2,3,6,7-tetrahydro-1H-azepine-1-carboxylate

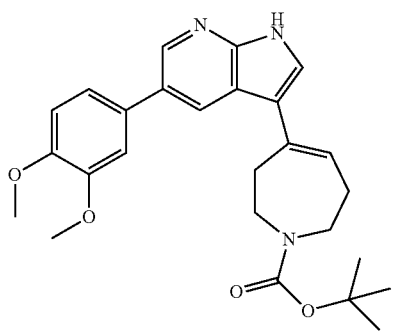 [SMILES: COc1ccc(-c2cnc3[nH]cc(C4=CCCN(C(=O)OC(C)(C)C)CC4)c3c2)cc1OC]

<sup>1</sup>H NMR (400 MHz, DMSO-d<sub>6</sub>) δ 11.70 (br s, 1H), 8.48 (s, 1H), 8.24 (s, 1H), 7.55 (s, 1H), 7.26 (s, 1H), 7.21 (d, J=8.4 Hz, 1H), 7.05 (d, J=8.4 Hz, 1H), 6.31-6.29 (m, 1H), 3.87 (s, 3H), 3.80 (s, 3H), 3.59 (t, J=5.4 Hz, 2H), 3.48 (br s, 2H), 2.75 (br s, 2H), 1.41 (s, 9H); [M+H]<sup>+</sup> 450.

EXAMPLE 188 tert-Butyl 5-(5-(3,4-dimethoxyphenyl)-1H-pyrrolo[2,3-b]pyridin-3-yl)-2,3,4,7-tetrahydro-1H-azepine-1-carboxylate

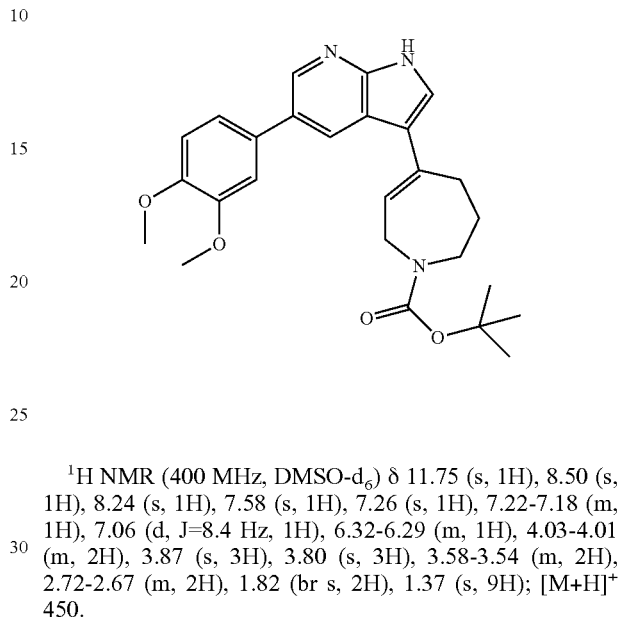

<sup>1</sup>H NMR (400 MHz, DMSO-d<sub>6</sub>) δ 11.75 (s, 1H), 8.50 (s, 1H), 8.24 (s, 1H), 7.58 (s, 1H), 7.26 (s, 1H), 7.22-7.18 (m, 1H), 7.06 (d, J=8.4 Hz, 1H), 6.32-6.29 (m, 1H), 4.03-4.01 (m, 2H), 3.87 (s, 3H), 3.80 (s, 3H), 3.58-3.54 (m, 2H), 2.72-2.67 (m, 2H), 1.82 (br s, 2H), 1.37 (s, 9H); [M+H]<sup>+</sup> 450.

PREPARATION EXAMPLE 6

Preparation of (4-(1H-pyrrolo[2,3-b]pyridin-3-yl)-5,6-dihydropyridin-1(2H)-yl)(thiophen-2-yl)methanone (50)

Scheme 8.
Total scheme for compound 50

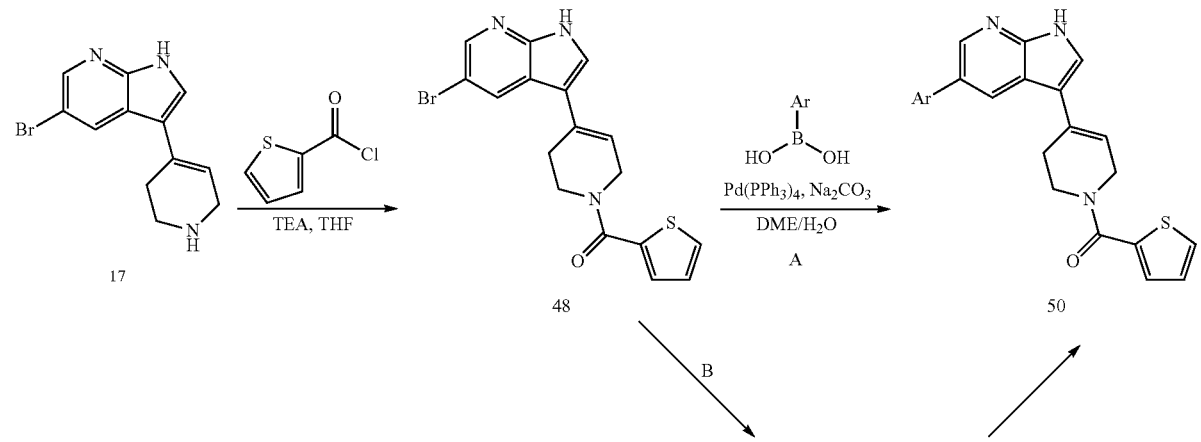

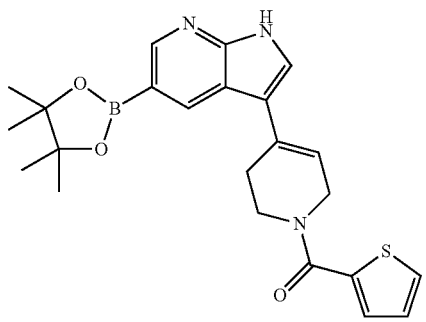

49

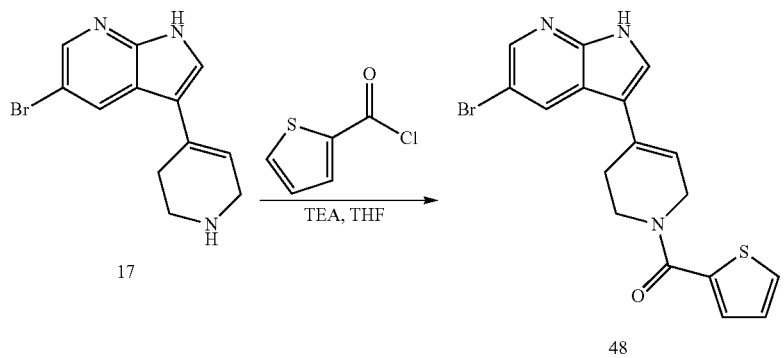

EXAMPLE 189

(4-(5-(3,4-Difluorophenyl)-1H-pyrrolo[2,3-b]pyridin-3-yl)-5,6-dihydropyridin-1(2H)-yl)(thiophen-2-yl)methanone Step 1: Preparation of (4-(5-bromo-1H-pyrrolo[2,3-b]pyridin-3-yl)-5,6-dihydropyridin-1(2H)-yl)(thiophen-2-yl)methanone (48)

A suspension solution of 5-bromo-3-(1,2,3,6-tetrahydropyridin-4-yl)-1H-pyrrolo[2,3-b]pyridine (15.0 g, 54.1 mmol, 1.0 eq) in THF (350 mL) was added with TEA (8.2 g, 81.2 mmol, 1.5 eq) at 0° C., and then added with thiophene-2-carbonyl chloride (7.9 g, 54.1 mmol, 1.0 eq). The resulting suspension was stirred at room temperature for 1 hour. The reaction mixture was concentrated, added with EtOAc and hexane (10:1, 100 mL), stirred and filtered. The solid thus obtained was dried to give the intermediate 48 (20.8 g, 53.5 mmol, 99.0%) as a white solid.

$^1$H NMR (400 MHz, DMSO-$d_6$) δ 11.99 (s, 1H), 8.46 (m, 1H), 8.30-8.29 (m, 1H), 7.79-7.78 (d, J=4.8 Hz, 1H), 7.67-7.66 (d, J=2.1 Hz, 1H), 7.52-7.51 (d, J=3.2 Hz, 1H), 7.18-7.16 (t, J=8.6 Hz, 1H), 6.22 (s, 1H), 4.37 (s, 2H), 3.87-3.84 (t, J=5.5 Hz, 2H), 2.63 (s, 2H).

Step 2: Preparation of (4-(5-(3,4-difluorophenyl)-1H-pyrrolo[2,3-b]pyridin-3-yl)-5,6-dihydropyridin-1(2H)-yl)(thiophen-2-yl)methanone

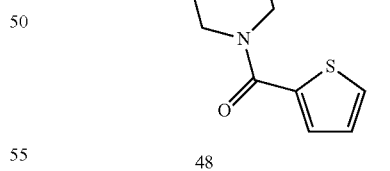

+

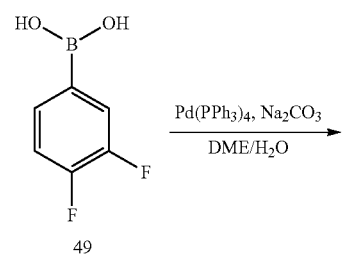

-continued

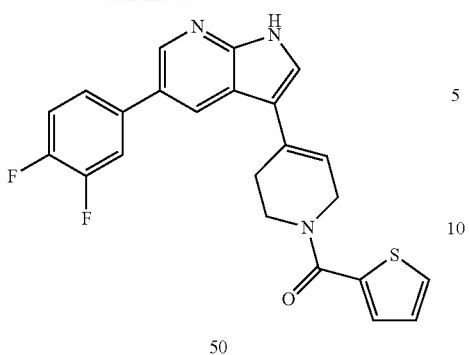

50

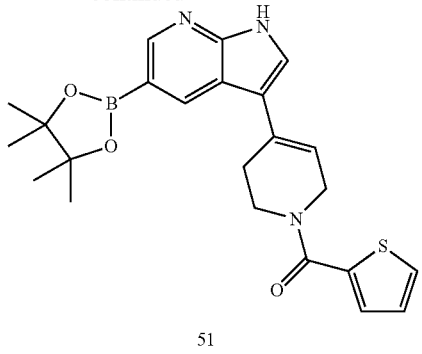

51

A suspension solution of the intermediate 48 (945 mg, 2.43 mmol, 1.0 eq), (3,4-difluorophenyl)boronic acid (500 mg, 3.16 mmol, 1.3 eq) and Na$_2$CO$_3$ (1.03 g, 9.74 mmol, 4.0 eq) in DME (16 mL) and water (4 mL) was subjected to purging with nitrogen, treated with Pd(PPh$_3$)$_4$ (281 mg, 0.24 mmol, 0.1 eq), and then stirred at 90° C. for 6 hours. The reaction mixture thus obtained was cooled to room temperature, concentrated, added with water (5 mL), filtered and then washed with MeCN (5 mL) and EtOAc (5 mL) to give the compound 50 (421 mg, 0.97 mmol, 40.2%).

$^1$H NMR (400 MHz, DMSO-d$_6$) δ 8.55-8.54 (d, J=2.0 Hz, 1H), 8.47-8.46 (d, J=1.8 Hz, 1H), 7.93-7.87 (m, 1H), 7.79-7.78 (m, 1H), 7.65-7.62 (m, 2H), 7.55-7.50 (m, 2H), 7.18-7.16 (m, 1H), 6.37 (s, 1H), 4.41 (m, 2H), 3.90-3.87 (t, J=5.7 Hz, 2H), 2.67 (m, 2H); MS (m/z): 422.0 (MH+).

EXAMPLE 190

(4-(5-(4-(Morpholinosulfonyl)phenyl)-1H-pyrrolo[2,3-b]pyridin-3-yl)-5,6-dihydropyridin-1(2H)-yl)(thiophen-2-yl)methanone Step 1: Preparation of (4-(5-(4,4,5,5-tetramethyl-1,3,2-dioxaborolan-2-yl)-1H-pyrrolo[2,3-b]pyridin-3-yl)-5,6-dihydropyridin-1(2H)-yl)(thiophen-2-yl)methanone (51)

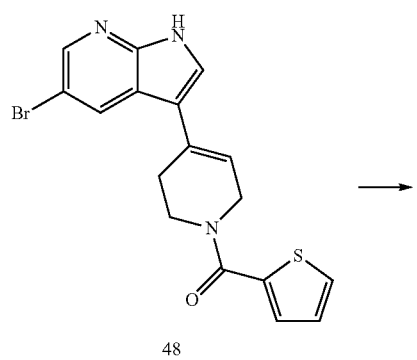

48

A suspension solution of the intermediate 48 (5.0 g, 12.8 mmol, 1.0 eq), 4,4,4',4',5,5,5',5'-octamethyl-2,2'-bi(1,3,2-dioxaborolane) (9.8 g, 38.6 mmol, 3.0 eq) and KOAc (4.48 g, 44.8 mmol, 3.5 eq) in 1,4-dioxane (50 mL) was subjected to purging with nitrogen, treated with PdCl$_2$(dppf) (471 mg, 0.6 mmol, 0.05 eq) and then stirred at 90° C. for 1 hour. The mixture thus obtained was cooled to room temperature, filtered and concentrated to give the crude product. The crude product was purified by column chromatography (EtOAc:hexane=3:1) to give the intermediate 51 (4.7 g, 10.7 mmol, 83.9%) as a yellow solid.

$^1$H NMR (400 MHz, DMSO-d$_6$) δ 11.90 (s, 1H), 8.48 (s, 1H), 8.43 (s, 1H), 7.80-7.79 (d, J=4.9 Hz, 1H), 7.63-7.62 (d, J=2.0 Hz, 1H), 7.53-7.52 (d, J=3.2 Hz, 1H), 7.18-7.16 (t, J=8.6 Hz, 1H), 6.19 (s, 1H), 4.41 (s, 2H), 3.88-3.85 (t, J=5.6 Hz, 2H), 2.64 (s, 2H), 1.32 (s, 12H).

Step 2: Preparation of (4-(5-(4-(morpholinosulfonyl)phenyl)-1H-pyrrolo[2,3-b]pyridin-3-yl)-5,6-dihydropyridin-1(2H)-yl)(thiophen-2-yl)methanone (53)

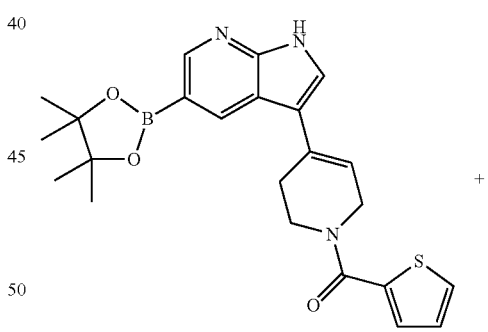

51

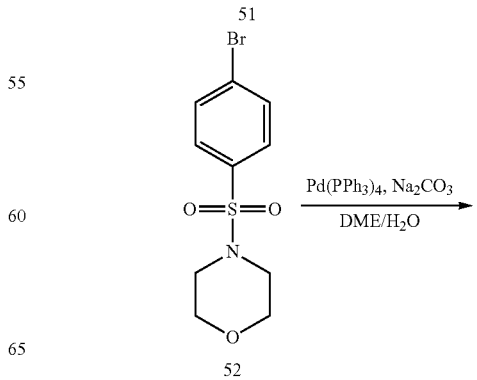

52

-continued

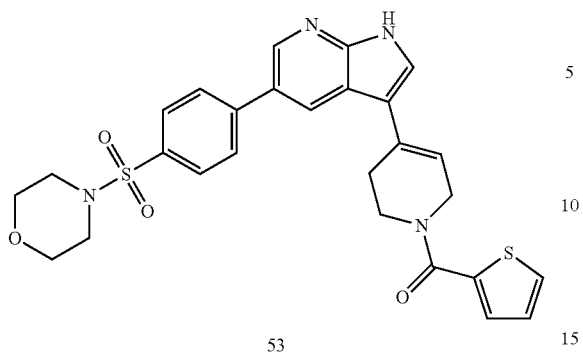

53

A suspension solution of the intermediate 51 (500 mg, 1.15 mmol, 1.1 eq), 4-((4-bromophenyl)sulfonyl)morpholine (319 mg, 1.04 mmol, 1.0 eq) and Na$_2$CO$_3$ (220 mg, 2.08 mmol, 2.0 eq) in DME (8 mL) and water (2 mL) was subjected to purging in nitrogen, treated with Pd(PPh$_3$)$_4$ (120 mg, 0.10 mmol, 0.1 eq) and stirred at 90° C. for 5 hours. The reaction mixture thus obtained was cooled to room temperature, concentrated, added with water (5 mL) and EtOAc (20 mL), filtered and washed with MeCN (5 mL), DCM and MeOH (10: 1, 5 mL) to give the compound 53 (322 mg, 0.60 mmol, 52.3%) as a yellow solid.

$^1$H NMR (400 MHz, DMSO-d$_6$) δ 11.96 (s, 1H), 8.64-8.63 (m, 1H), 8.56 (s, 1H), 8.09-8.07 (m, 2H), 7.82-7.80 (s, 2H), 7.70 (m, 1H), 7.54-7.53 (m, 1H), 7.19-7.17 (m, 1H), 6.38 (s, 1H), 4.42 (s, 2H), 3.90-3.87 (m, 2H), 3.67-3.65 (m, 4H), 2.92 (m, 4H), 2.68 (s, 2H); MS (m/z): 535.1 (MH$^+$).

EXAMPLE 191

(4-(5-(3,4-Dimethoxyphenyl)-1H-pyrrolo[2,3-b]pyridin-3-yl)-5,6-dihydropyridin-1(2H)-yl)(thiophen-2-yl)methanone

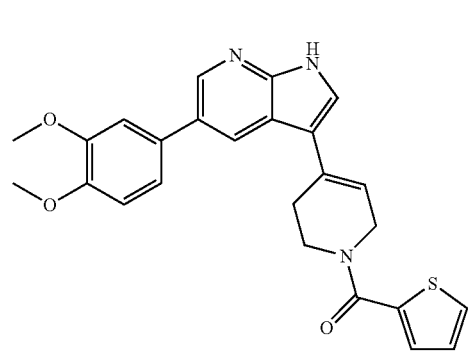 [SMILES: COc1ccc(-c2cnc3[nH]cc(C4=CCN(C(=O)c5cccs5)CC4)c3c2)cc1OC]

$^1$H NMR (400 MHz, DMSO-d$_6$) δ 11.76 (br s, 1H), 8.51 (s, 1H), 8.37 (s, 1H), 7.78 (d, J=4.8 Hz, 1H), 7.61 (s, 1H), 7.52 (s, 1H), 7.27-7.23 (m, 2H), 7.17-7.15 (m, 1H), 7.04 (d, J=8.0 Hz, 1H), 6.32 (br s, 1H), 4.40 (br s, 2H), 3.90-3.84 (m, 5H), 3.80 (s, 3H), 2.67 (s, 2H); [M+H]$^+$ 446.

EXAMPLE 192

(4-(5-(3-Fluoro-4-methoxyphenyl)-1H-pyrrolo[2,3-b]pyridin-3-yl)-5,6-dihydropyridin-1(2H)-yl)(thiophen-2-yl)methanone

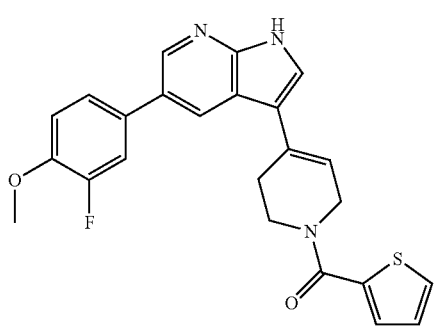 [SMILES: COc1ccc(-c2cnc3[nH]cc(C4=CCN(C(=O)c5cccs5)CC4)c3c2)cc1F]

$^1$H NMR (400 MHz, DMSO-d$_6$) δ 11.85 (s, 1H), 8.54 (s, 1H), 8.43 (s, 1H), 7.79 (d, J=5.2 Hz, 1H), 7.65 (s, 1H), 7.53 (d, J=2.8 Hz, 1H), 7.47 (d, J=8.4 Hz, 1H), 7.32-7.28 (m, 2H), 7.18-7.16 (m, 1H), 6.35 (br s, 1H), 4.40 (br s, 2H), 3.96 (s, 3H), 3.88 (t, J=5.8 Hz, 2H), 2.72-2.64 (m, 2H); [M+H]$^+$ 434.

EXAMPLE 193

(4-(5-(3-(Methylsulfonyl)phenyl)-1H-pyrrolo[2,3-b]pyridin-3-yl)-5,6-dihydropyridin-1(2H)-yl)(thiophen-2-yl)methanone

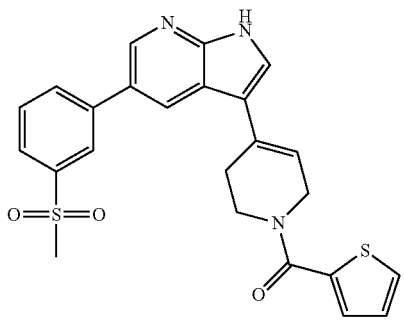 [SMILES: CS(=O)(=O)c1cccc(-c2cnc3[nH]cc(C4=CCN(C(=O)c5cccs5)CC4)c3c2)c1]

$^1$H NMR (400 MHz, DMSO-d$_6$) δ 11.91 (br s, 1H), 8.62 (s, 1H), 8.53 (s, 1H), 8.23 (s, 1H), 8.13 (d, J=7.6 Hz, 1H), 7.91 (d, J=7.6 Hz, 1H), 7.79-7.74 (m, 2H), 7.68 (s, 1H), 7.54-7.52 (m, 1H), 7.18-7.16 (m, 1H), 6.36 (br s, 1H), 4.42 (br s, 2H), 3.91-3.87 (m, 2H), 3.32 (s, 3H), 2.70-2.66 (m, 2H); [M+H]$^+$ 464.

EXAMPLE 194

(4-(5-(4-(Methylsulfonyl)phenyl)-1H-pyrrolo[2,3-b]pyridin-3-yl)-5,6-dihydropyridin-1(2H)-yl)(thiophen-2-yl)methanone

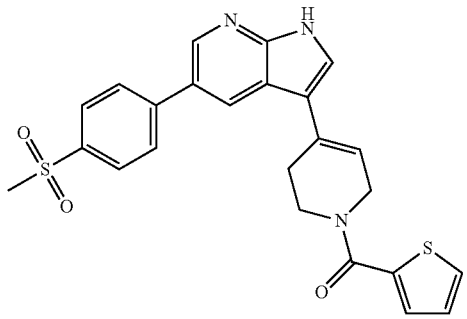 [SMILES: CS(=O)(=O)c1ccc(-c2cnc3[nH]cc(C4=CCN(C(=O)c5cccs5)CC4)c3c2)cc1]

$^1$H NMR (400 MHz, DMSO-d$_6$) δ 11.98 (s, 1H), 8.64-8.63 (m, 1H), 8.56 (m, 1H), 8.08-8.06 (m, 2H), 8.01-7.99 (m, 2H), 7.80-7.78 (d, J=5.0 Hz, 1H), 7.69 (s, 1H), 7.54-7.53 (d, J=3.5 Hz, 1H), 7.18-7.16 (m, 1H), 6.38 (s, 1H), 4.41 (s, 1H), 3.90-3.87 (t, J=5.6 Hz, 2H), 3.26 (s, 3H), 2.68 (s, 2H); MS (m/z): 464.0 (MH+).

EXAMPLE 195

(4-(5-(3-(Ethylsulfonyl)phenyl)-1H-pyrrolo[2,3-b]pyridin-3-yl)-5,6-dihydropyridin-1(2H)-yl)(thiophen-2-yl)methanone

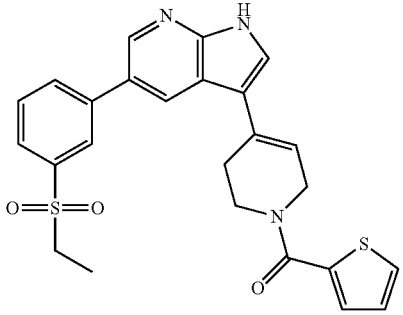 [SMILES: CCS(=O)(=O)c1cccc(-c2cnc3[nH]cc(C4=CCN(C(=O)c5cccs5)CC4)c3c2)c1]

[M+H]$^+$ 478.

EXAMPLE 196

(4-(5-(4-(Cyclopropylsulfonyl)phenyl)-1H-pyrrolo[2,3-b]pyridin-3-yl)-5,6-dihydropyridin-1(2H)-yl)(thiophen-2-yl)methanone

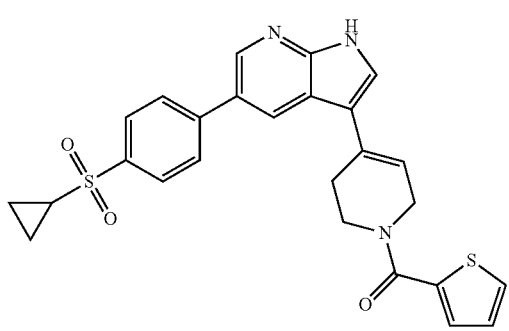 [SMILES: O=C(c1cccs1)N1CC=C(c2c[nH]c3ncc(-c4ccc(S(=O)(=O)C5CC5)cc4)cc23)CC1]

$^1$H NMR (400 MHz, DMSO-d$_6$) δ 11.92 (s, 1H), 8.63 (s, 1H), 8.57 (s, 1H), 8.07-7.95 (m, 5H), 7.79 (d, J=4.8 Hz, 1H), 7.69 (d, J=2.4 Hz, 1H), 7.53 (d, J=2.8 Hz, 1H), 7.18-7.16 (m, 1H), 6.37 (br s, 1H), 4.41 (br s, 2H), 3.90 (t, J=6.4 Hz, 1H), 2.96-2.87 (m, 1H), 2.72-2.66 (m, 2H), 1.19-1.12 (m, 2H), 1.10-1.06 (m, 2H); [M+H]$^+$ 490.

EXAMPLE 197

4-(3-(1-(Thiophene-2-carbonyl)-1,2,3,6-tetrahydropyridin-4-yl)-1H-pyrrolo[2,3-b]pyridin-5-yl)benzensulfonamide

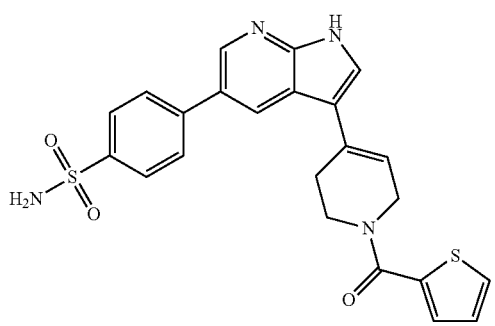 [SMILES: NS(=O)(=O)c1ccc(-c2cnc3[nH]cc(C4=CCN(C(=O)c5cccs5)CC4)c3c2)cc1]

$^1$H NMR (400 MHz, DMSO-d$_6$) δ 8.61 (s, 1H), 8.53 (s, 1H), 7.99-7.89 (m, 4H), 7.79 (d, J=5.2 Hz, 1H), 7.68 (s, 1H), 7.53 (d, J=2.8 Hz, 1H), 7.18-7.16 (m, 1H), 6.37 (br s, 1H), 4.41 (br s, 2H), 3.88 (t, J=5.8 Hz, 2H), 2.72-2.66 (m, 2H); [M+H]$^+$ 465.

EXAMPLE 198

3-(3-(1-(Thiophene-2-carbonyl)-1,2,3,6-tetrahydropyridin-4-yl)-1H-pyrrolo[2,3-b]pyridin-5-yl)benzensulfonamide

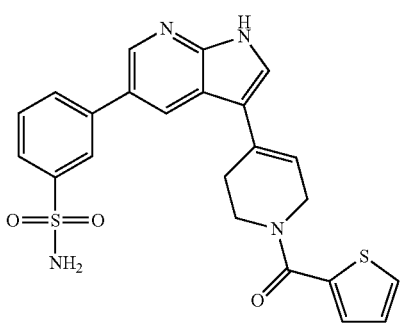 [SMILES: NS(=O)(=O)c1cccc(-c2cnc3[nH]cc(C4=CCN(C(=O)c5cccs5)CC4)c3c2)c1]

$^1$H NMR (400 MHz, DMSO-d$_6$) δ 8.57 (s, 1H), 8.48 (s, 1H), 8.17 (s, 1H), 8.01 (d, J=8.0 Hz, 1H), 7.82-7.75 (m, 2H), 7.69-7.65 (m, 2H), 7.53 (d, J=2.8 Hz, 1H), 7.18-7.16 (m, 1H), 6.34 (br s, 1H), 4.42 (br s, 2H), 3.89 (t, J=5.6 Hz, 2H), 2.72-2.66 (m, 2H); [M+H]$^+$ 465.

EXAMPLE 199

N-methyl-3-(3-(1-(thiophene-2-carbonyl)-1,2,3,6-tetrahydropyridin-4-yl)-1H-pyrrolo[2,3-b]pyridin-5-yl)benzensulfonamide

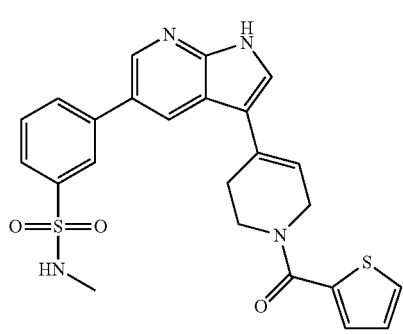 [SMILES: CNS(=O)(=O)c1cccc(-c2cnc3[nH]cc(C4=CCN(C(=O)c5cccs5)CC4)c3c2)c1]

$^1$H NMR (400 MHz, DMSO-d$_6$) δ 11.93 (br s, 1H), 8.56 (s, 1H), 8.49 (s, 1H), 8.07-8.05 (m, 2H), 7.79-7.68 (m, 4H), 7.53 (d, J=2.8 Hz, 1H), 7.18-7.16 (m, 1H), 6.35 (br s, 1H), 4.41 (br s, 2H), 3.88 (t, J=5.8 Hz, 2H), 2.72-2.66 (m, 2H), 2.47-2.43 (m, 4H); [M+H]$^+$ 479.

EXAMPLE 200

N-methyl-4-(3-(1-(thiophene-2-carbonyl)-1,2,3,6-tetrahydropyridin-4-yl)-1H-pyrrolo[2,3-b]pyridin-5-yl)benzensulfonamide

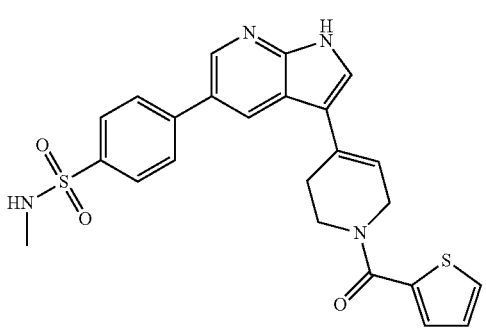 [SMILES: CNS(=O)(=O)c1ccc(-c2cnc3[nH]cc(C4=CCN(C(=O)c5cccs5)CC4)c3c2)cc1]

$^1$H NMR (400 MHz, DMSO-d$_6$) δ 11.75 (br s, 1H), 8.62 (s, 1H), 8.55 (s, 1H), 8.03-7.99 (m, 2H), 7.88-7.84 (m, 2H), 7.81-7.76 (m, 2H), 7.67 (s, 1H), 7.53 (d, J=2.8 Hz, 1H), 7.18-7.16 (m, 1H), 4.41 (br s, 2H), 3.88 (t, J=5.8 Hz, 2H), 2.72-2.66 (m, 2H), 2.47-2.43 (m, 4H); [M+H]$^+$ 479.

EXAMPLE 201

N-(3-(3-(1-(thiophene-2-carbonyl)-1,2,3,6-tetrahydropyridin-4-yl)-1H-pyrrolo[2,3-b]pyridin-5-yl)phenyl)methanesulfonamide

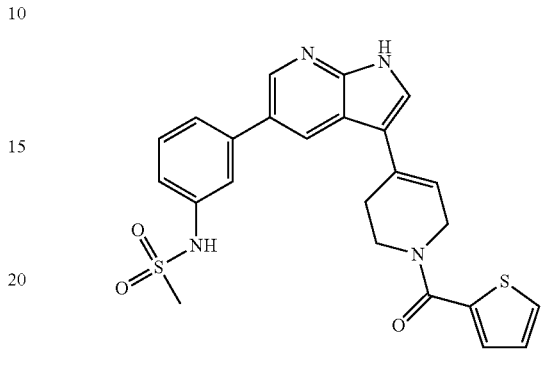

$^1$H NMR (400 MHz, DMSO-d$_6$) δ 11.83 (s, 1H), 8.43 (s, 1H), 8.33 (s, 1H), 7.79-7.78 (m, 1H), 7.63 (s, 1H), 7.53-7.52 (m, 1H), 7.22-7.17 (m, 3H), 7.04-7.00 (m, 2H), 6.29 (s, 1H), 4.40 (s, 2H), 3.88 (m, 2H), 2.75 (s, 3H), 2.67 (s, 2H); MS (m/z): 479.0 (MH$^+$).

EXAMPLE 202

(4-(5-(3-(Morpholinosulfonyl)phenyl)-1H-pyrrolo[2,3-b]pyridin-3-yl)-5,6-dihydropyridin-1(2H)-yl)(thiophen-2-yl)methanone

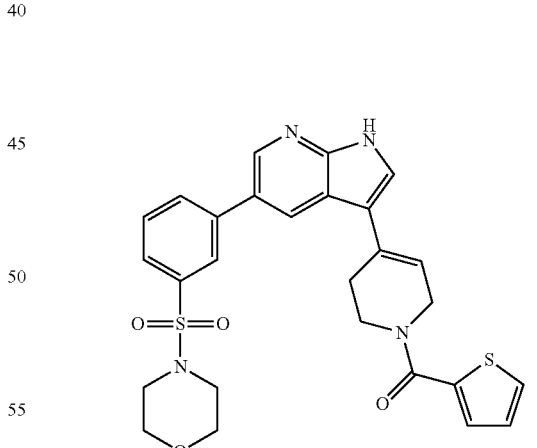

$^1$H NMR (400 MHz, DMSO-d$_6$) δ 11.95 (s, 1H), 8.58 (s, 1H), 8.51 (s, 1H), 8.16-8.14 (d, J=7.3 Hz, 1H), 7.97 (s, 1H), 7.80-7.70 (m, 4H), 7.54-7.53 (m, 1H), 7.18-7.16 (t, J=8.6 Hz, 1H), 6.37 (s, 1H), 4.41 (s, 2H), 3.90-3.87 (t, J=5.3 Hz, 2H), 3.64 (m, 4H), 2.94 (m, 4H), 2.68 (s, 2H); MS (m/z): 535.0 (MH$^+$).

EXAMPLE 203

(4-(5-(4-Methoxy-3-(morpholinosulfonyl)phenyl)-1H-pyrrolo[2,3-b]pyridin-3-yl)-5,6-dihydropyridin-1(2H)-yl)(thiophen-2-yl)methanone

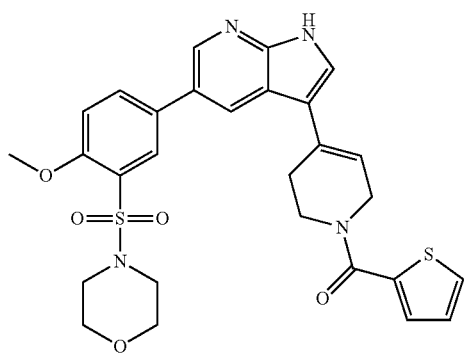 [SMILES: COc1ccc(-c2cnc3[nH]cc(C4=CCN(C(=O)c5cccs5)CC4)c3c2)cc1S(=O)(=O)N1CCOCC1]

$^1$H NMR (400 MHz, DMSO-d$_6$) δ 11.89 (br s, 1H), 8.48 (s, 1H), 8.40 (s, 1H), 8.03 (d, J=8.4 Hz, 1H), 7.96 (s, 1H), 7.79 (d, J=4.8 Hz, 1H), 7.66 (s, 1H), 7.53 (d, J=2.8 Hz, 1H), 7.38 (d, J=8.8 Hz, 1H), 7.18-7.16 (m, 1H), 6.32 (br s, 1H), 4.40 (br s, 2H), 3.96 (s, 3H), 3.88 (t, J=5.8 Hz, 2H), 3.62-3.59 (m, 4H), 3.15-3.09 (m, 4H), 2.72-2.66 (m, 2H); [M+H]$^+$ 565.

EXAMPLE 204

(4-(5-(1H-indazol-5-yl)-1H-pyrrolo[2,3-b]pyridin-3-yl)-5,6-dihydropyridin-1(2H)-yl) (thiophen-2-yl)methanone

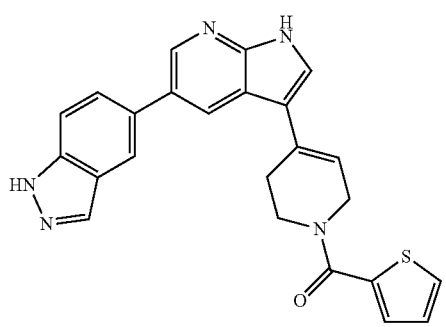 [SMILES: O=C(c1cccs1)N1CC=C(c2c[nH]c3ncc(-c4ccc5[nH]ncc5c4)cc23)CC1]

$^1$H NMR (400 MHz, MeOD) δ 8.51 (m, 2H), 8.14 (s, 1H), 8.07 (s, 1H), 7.75 (m, 1H), 7.70-7.66 (m, 2H), 7.55-7.53 (m, 2H), 7.19-7.17 (m, 1H), 6.33 (s, 1H), 4.51 (s, 2H), 4.03 (m, 2H), 2.78 (s, 2H); MS (m/z): 426.1 (MH$^+$).

EXAMPLE 205

(4-(5-(5-((4-Methylpiperazin-1-yl)methyl)thiophen-2-yl)-1H-pyrrolo[2,3-b]pyridin-3-yl)-5,6-dihydropyridin-1(2H)-yl)(thiophen-2-yl)methanone

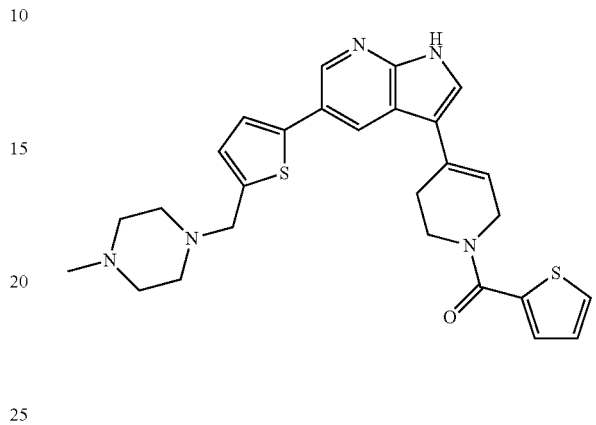

$^1$H NMR (400 MHz, DMSO-d$_6$) δ 11.90 (br s, 1H), 8.50 (s, 1H), 8.36 (s, 1H), 7.79 (d, J=4.8 Hz, 1H), 7.63 (s, 1H), 7.53 (d, J=3.6 Hz, 1H), 7.40 (d, J=3.6 Hz, 1H), 7.18-7.16 (m, 1H), 6.96 (d, J=3.6 Hz, 1H), 6.29 (br s, 1H), 3.87 (t, J=5.6 Hz, 2H), 3.66 (s, 2H), 2.68-2.63 (m, 2H), 2.45-2.28 (m, 10H), 2.15 (s, 3H); [M+H]$^+$ 504.

EXAMPLE 206

(4-(5-(5-(Morpholinomethyl)thiophen-2-yl)-1H-pyrrolo[2,3-b]pyridin-3-yl)-5,6-dihydropyridin-1(2H)-yl)(thiophen-2-yl)methanone

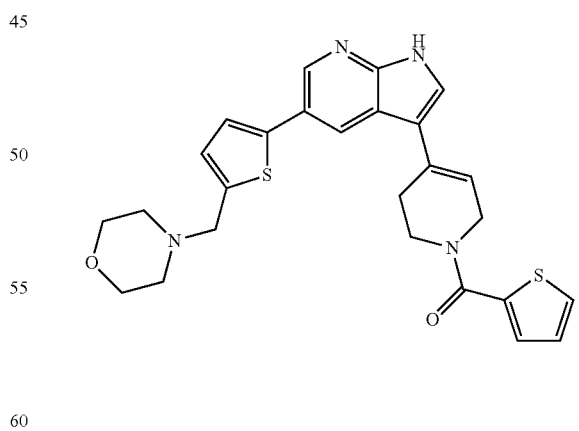

$^1$H NMR (400 MHz, DMSO-d$_6$) δ 11.89 (br s, 1H), 8.51 (s, 1H), 8.34 (s, 1H), 7.79 (d, J=4.8 Hz, 1H), 7.63 (s, 1H), 7.53 (d, J=3.6 Hz, 1H), 7.41 (d, J=3.6 Hz, 1H), 7.19-7.16 (m, 1H), 6.92 (d, J=3.6 Hz, 1H), 6.29 (br s, 1H), 3.87 (t, J=5.6 Hz, 2H), 3.68 (s, 2H), 3.63-3.56 (m, 6H), 2.68-2.63 (m, 1H), 2.45-2.40 (m, 5H); [M+H]$^+$ 491.

EXAMPLE 207

(4-(5-(5-(Morpholinomethyl)thiophen-3-yl)-1H-pyrrolo[2,3-b]pyridin-3-yl)-5,6-dihydropyridin-1(2H)-yl)(thiophen-2-yl)methanone

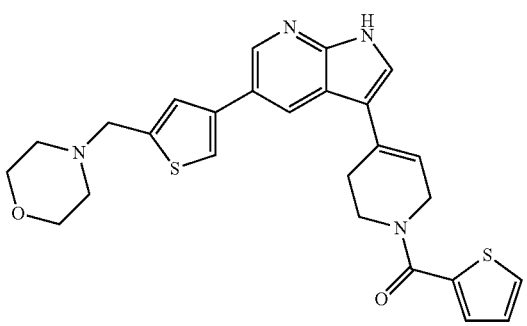 [SMILES: O=C(c1cccs1)N1CC=C(c2c[nH]c3ncc(-c4csc(CN5CCOCC5)c4)cc23)CC1]

¹H NMR (400 MHz, DMSO-d₆) δ 11.79 (br s, 1H), 8.60 (s, 1H), 8.44 (s, 1H), 7.84 (s, 1H), 7.79 (d, J=5.2 Hz, 1H), 7.60 (s, 1H), 7.56-7.53 (m, 2H), 7.19-7.16 (m, 1H), 6.34 (br s, 1H), 4.42 (br s, 2H), 3.88 (t, J=5.6 Hz, 2H), 3.72 (s, 2H), 3.61-3.57 (m, 5H), 2.68-2.63 (m, 2H), 2.46-2.39 (m, 5H); [M+H]⁺ 491.

EXAMPLE 208

(4-(5-(3-(Morpholine-4-carbonyl)phenyl)-1H-pyrrolo[2,3-b]pyridin-3-yl)-5,6-dihydropyridin-1(2H)-yl)(thiophen-2-yl)methanone

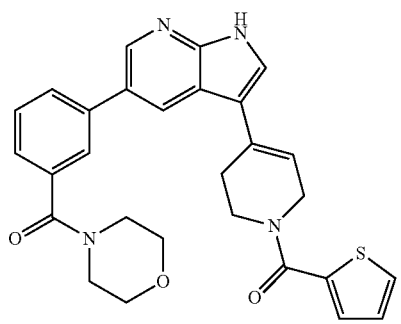 [SMILES: O=C(c1cccc(-c2cnc3[nH]cc(C4=CCN(C(=O)c5cccs5)CC4)c3c2)c1)N1CCOCC1]

[M+H]⁺ 499.

EXAMPLE 209

(4-(5-(4-(Morpholine-4-carbonyl)phenyl)-1H-pyrrolo[2,3-b]pyridin-3-yl)-5,6-dihydropyridin-1(2H)-yl)(thiophen-2-yl)methanone

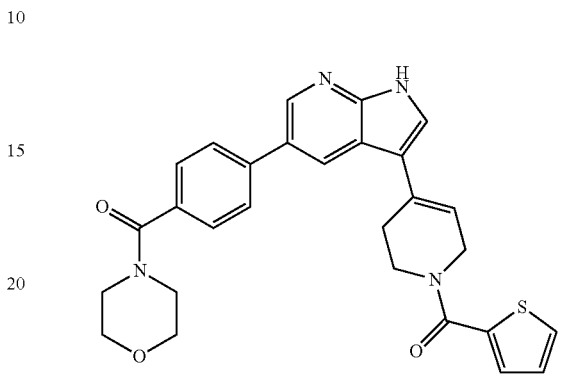

¹H NMR (400 MHz, DMSO-d₆) δ 11.85 (br s, 1H), 8.57 (s, 1H), 8.48 (s, 1H), 7.84 (d, J=7.6 Hz, 2H), 7.79-7.77 (m, 1H), 7.65 (s, 1H), 7.53-7.48 (m, 3H), 7.19-7.16 (m, 1H), 6.35 (br s, 1H), 4.49-4.40 (m, 2H), 3.91-3.85 (m, 2H), 3.70-3.42 (m, 7H), 2.72-2.63 (m, 3H); [M+H]⁺ 499.

EXAMPLE 210

(4-(5-(3,4-Dimethoxyphenyl)-1H-pyrrolo[2,3-b]pyridin-3-yl)-5,6-dihydropyridin-1(2H)-yl)(5-methylthiophen-2-yl)methanone Step 1: Preparation of 5-methylthiophene-2-carbonyl chloride (55)

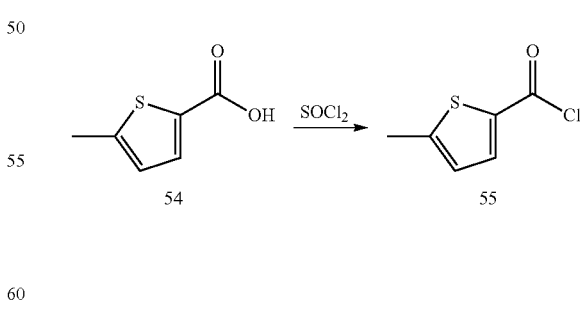

A solution of 5-methylthiophene-2-carboxylic acid (3.0 g, 21.1 mmol, 1.0 eq) in SOCl₂ (7.5 g, 63.4 mmol, 3.0 eq) was stirred at 80° C. for 2 hours. The reaction mixture was concentrated to give the crude product (3.4 g) which was used in the following step without further purification.

Step 2: Preparation of (4-(5-bromo-1H-pyrrolo[2,3-b]pyridin-3-yl)-5,6-dihydropyridin-1(2H)-yl)(5-methyl thiophen-2-yl)methanone (56)

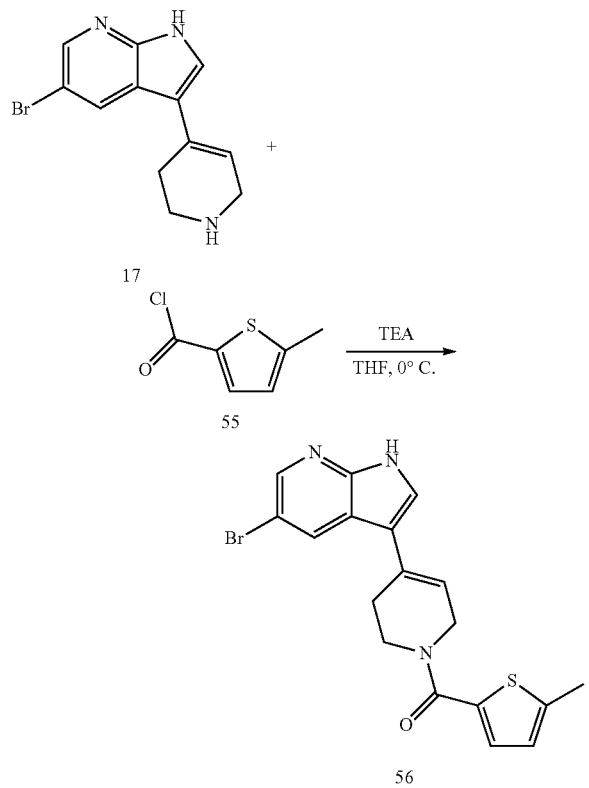

A suspension solution of 5-bromo-3-(1,2,3,6-tetrahydropyridin-4-yl)-1H-pyrrolo[2,3-b]pyridine (5.9 g, 21.2 mmol, 1.0 eq) in THF (50 mL) was added with TEA (3.2 g, 31.8 mmol, 1.5 eq) at 0° C., and then added with 5-methylthiophene-2-carbonyl chloride (3.4 g, 54.1 mmol, 1.0 eq).

The resulting suspension was stirred at room temperature for 12 hours. The reaction mixture was concentrated, and the resulting crude product was purified by chromatography (EtOAc:hexane=2:1) to give the intermediate 56 (5.0 g, 12.4 mmol, 58.6%) as a yellow solid.

$^1$H NMR (400 MHz, DMSO-d$_6$) δ 11.99 (s, 1H), 8.46 (m, 1H), 8.30-8.29 (m, 1H), 7.67-7.66 (d, J=2.4 Hz, 1H), 7.33-7.32 (d, J=3.2 Hz, 1H), 6.86-6.85 (d, J=2.8 Hz, 1H), 6.21 (s, 1H), 4.36 (s, 2H), 3.86-3.83 (t, J=5.6 Hz, 2H), 2.62 (s, 2H), 2.51-2.48 (m, 3H).

Step 3: Preparation of (4-(5-(3,4-dimethoxyphenyl)-1H-pyrrolo[2,3-b]pyridin-3-yl)-5,6-dihydropyridin-1(2H)-yl)(5-methylthiophen-2-yl)methanone

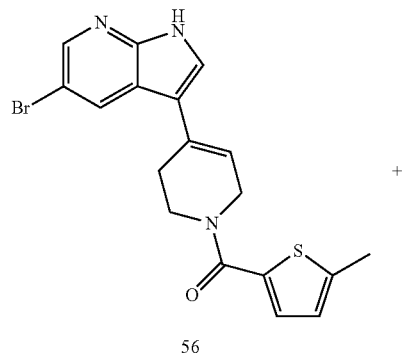

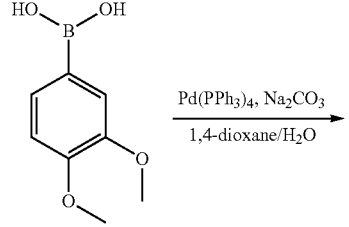

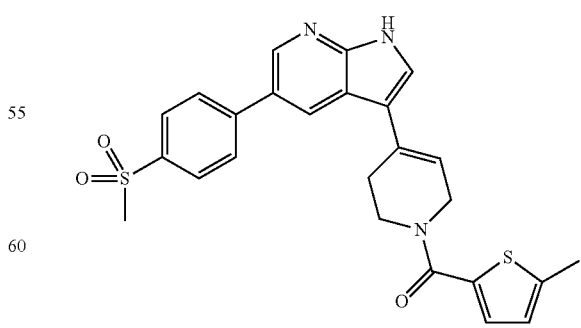

A suspension solution of the intermediate 56 (600 mg, 1.49 mmol, 1.0 eq), (3,4-difluorophenyl)boronic acid (353 mg, 1.94 mmol, 1.3 eq) and Na$_2$CO$_3$ (631 mg, 5.96 mmol, 4.0 eq) in 1,4-dioxane (12 mL) and water (3 mL) was subjected to purging with nitrogen, treated with Pd(PPh$_3$)$_4$ (344 mg, 0.30 mmol, 0.2 eq), and then stirred at 100° C. for 16 hours. The reaction mixture thus obtained was cooled to room temperature, concentrated, added with water (5 mL), filtered, extracted with EtOAc (10 mL×3), and the organic layer was collected to give the crude product. The crude product thus obtained was filtered by chromatography to give the compound 57 (52 mg, 0.11 mmol, 7.59%).

$^1$H NMR (400 MHz, DMSO-d$_6$) δ 11.78 (s, 1H), 8.51 (s, 1H), 8.37 (s, 1H), 7.62-7.61 (m, 1H), 7.34-7.33 (d, J=3.5 Hz, 1H), 7.27 (m, 1H), 7.26-7.24 (m, 2H), 6.87-6.86 (m, 1H), 6.32 (s, 1H), 4.39 (s, 2H), 3.87 (s, 6H), 3.80 (s, 3H), 2.66 (s, 2H), 32.49 (s, 3H); MS (m/z): 460.1 (MH+).

EXAMPLE 211

(4-(5-(4-(Methylsulfonyl)phenyl)-1H-pyrrolo[2,3-b]pyridin-3-yl)-5,6-dihydropyridin-1(2H)-yl)(5-methylthiophen-2-yl)methanone $^1$H NMR (400 MHz, DMSO-d$_6$) δ 11.94 (s, 1H), 8.63 (m, 1H), 8.56 (m, 1H), 8.08-8.06 (m, 2H), 8.01-7.99 (m, 2H), 7.67-7.68 (d, J=2.4 Hz, 1H), 7.34-7.33 (d, J=3.6 Hz, 1H), 6.87-6.86 (d, J=2.8 Hz, 1H), 6.37 (s, 1H), 4.40 (s, 2H), 3.89-3.87 (t, J=1.4 Hz, 2H), 3.26 (s, 3H), 2.68 (s, 2H), 2.50-2.49 (s, 3H); MS (m/z): 478.0 (MH+).

EXAMPLE 212

4-(3-(1-(5-Methylthiophene-2-carbonyl)-1,2,3,6-tetrahydropyridin-4-yl)-1H-pyrrolo[2,3-b]pyridin-5-yl)benzensulfonamide

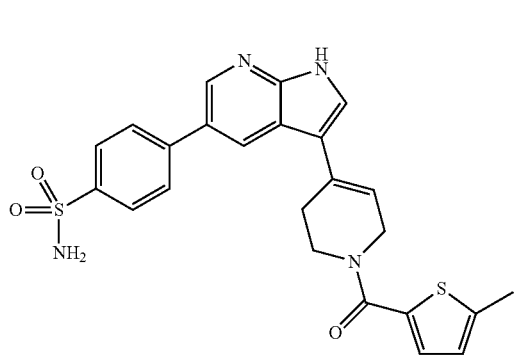 [SMILES: Cc1ccc(C(=O)N2CC=C(c3c[nH]c4ncc(-c5ccc(S(N)(=O)=O)cc5)cc34)CC2)s1]

¹H NMR (400 MHz, DMSO-d₆) δ 11.91 (s, 1H), 8.61 (m, 1H), 8.54 (m, 1H), 7.99-7.97 (m, 2H), 7.94-7.89 (m, 2H), 7.67 (s, 1H), 7.41 (m, 2H), 7.34-7.33 (m, 1H), 6.87-6.86 (d, J=2.8 Hz, 1H), 6.37 (s, 1H), 4.40 (s, 2H), 3.88-3.86 (m, 2H), 2.67 (s, 2H), 2.49 (m, 3H); MS (m/z): 479.0 (MH+).

EXAMPLE 213

(4-(5-(3,4-Dimethoxyphenyl)-1H-pyrrolo[2,3-b]pyridin-3-yl)-5-methyl-5,6-dihydropyridin-1(2H)-yl)(thiophen-2-yl)methanone

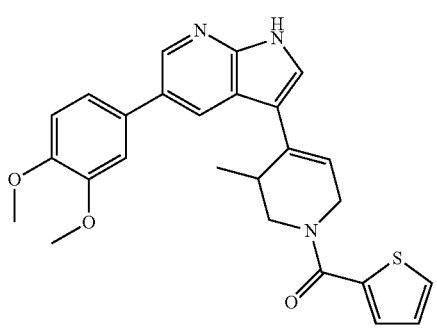 [SMILES: COc1ccc(-c2cnc3[nH]cc(C4=CCN(C(=O)c5cccs5)CC4C)c3c2)cc1OC]

¹H NMR (400 MHz, DMSO-d₆) δ 11.84 (br s, 1H), 8.50 (s, 1H), 8.33 (s, 1H), 7.79 (d, J=4.8 Hz, 1H), 7.63 (s, 1H), 7.53 (s, 1H), 7.27 (s, 1H), 7.24 (d, J=8.4 Hz, 1H), 7.18-7.16 (m, 1H), 7.04 (d, J=8.4 Hz, 1H), 6.18 (br s, 1H), 4.68-4.63 (m, 1H), 3.87 (s, 3H), 3.82-3.78 (m, 4H), 3.09-3.02 (m, 1H), 1.09 (d, J=6.8 Hz, 3H); [M+H]⁺ 460.

EXAMPLE 214

(5-Methyl-4-(5-(4-(methylsulfonyl)phenyl)-1H-pyrrolo[2,3-b]pyridin-3-yl)-5,6-dihydropyridin-1(2H)-yl)(thiophen-2-yl)methanone

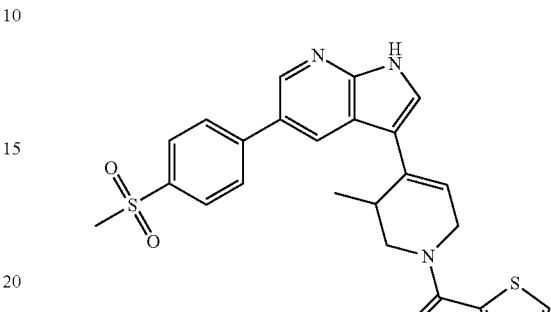

¹H NMR (400 MHz, DMSO-d₆) δ 11.90 (br s, 1H), 8.62 (s, 1H), 8.50 (s, 1H), 8.02 (dd, J=26.4, 8.8 Hz, 4H), 7.79 (d, J=6.0 Hz, 1H), 7.69 (s, 1H), 7.53 (br s, 1H), 7.19-7.17 (m, 1H), 6.21 (br s, 1H), 4.68-4.63 (m, 1H), 3.26 (s, 3H), 3.08-3.06 (br s, 1H), 1.09 (d, J=6.8 Hz, 3H); [M+H]⁺ 478.

EXAMPLE 215

(4-(3-(3-Methyl-1-(thiophene-2-carbonyl)-1,2,3,6-tetrahydropyridin-4-yl)-1H-pyrrolo[2,3-b]pyridin-5-yl)phenyl)(morpholino)methanone

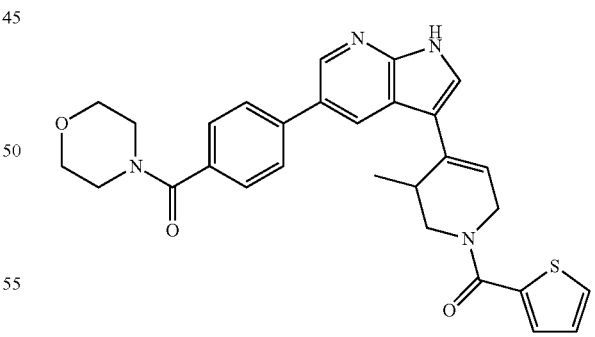

¹H NMR (400 MHz, DMSO-d₆) δ 11.87 (br s, 1H), 8.57 (s, 1H), 8.44 (s, 1H), 7.84 (d, J=8.4 Hz, 2H), 7.79-7.77 (m, 1H), 7.66 (s, 1H), 7.53-7.48 (m, 3H), 7.19-7.16 (m, 1H), 6.21 (br s, 1H), 4.67-4.63 (m, 1H), 3.87 (t, J=5.4 Hz, 1H), 3.70-3.42 (m, 9H), 3.09-3.04 (m, 1H), 2.62-2.57 (m, 1H), 1.09 (d, J=6.8 Hz, 3H); [M+H]⁺ 513.

EXAMPLE 216
(5-Methyl-4-(5-(5-(morpholinomethyl)thiophen-2-yl)-1H-pyrrolo[2,3-b]pyridin-3-yl)-5,6-dihydropyridin-1(2H)-yl)(thiophen-2-yl)methanone
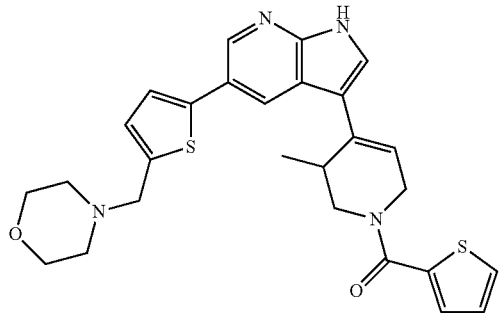 [SMILES: CC1CN(C(=O)c2cccs2)CC=C1c1c[nH]c2ncc(-c3ccc(CN4CCOCC4)s3)cc12]
$^1$H NMR (400 MHz, DMSO-d$_6$) δ 11.88 (br s, 1H), 8.51 (s, 1H), 8.32 (s, 1H), 7.79 (d, J=4.8 Hz, 1H), 7.64 (s, 1H), 7.53 (br s, 1H), 7.40 (d, J=3.6 Hz, 1H), 7.19-7.16 (m, 1H), 6.98 (d, J=3.6 Hz, 1H), 6.14 (br s, 1H), 4.69-4.64 (m, 1H), 3.68 (s, 2H), 3.60-3.58 (m, 5H), 2.46-2.38 (m, 5H), 1.08 (d, J=7.2 Hz, 3H); [M+H]$^+$ 505.
PREPARATION EXAMPLE 7
Preparation of 4-(1H-pyrrolo[2,3-b]pyridin-3-yl)-N-methyl-5,6-dihydropyridine-1(2H)-carboxamide
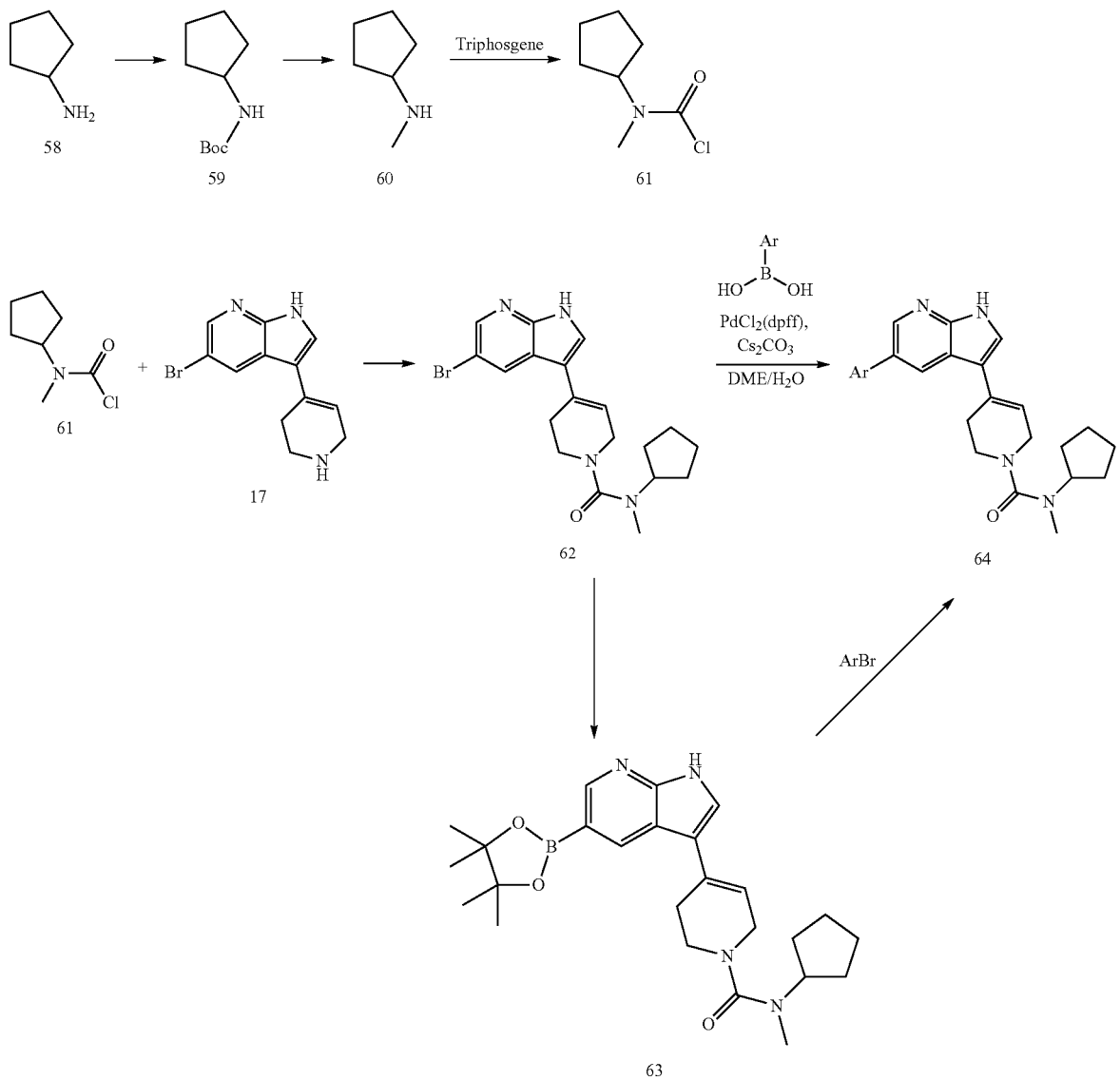

Step 1: Preparation of tert-butyl cyclopentylcarbamate (59)

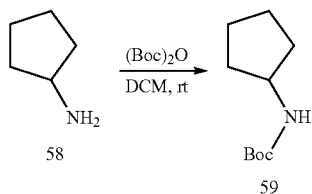 [SMILES: "(Boc)2O" ; NC1CCCC1 ; CC(C)(C)OC(=O)NC1CCCC1]

(Boc)₂O (239.6 g, 1098.0 mmol, 1.1 eq) was added dropwise to a solution of cyclopentanamine (85.0 g, 998.2 mmol, 1.0 eq) in DCM (1.5 L) at room temperature. The resulting mixture was stirred at room temperature for 1.5 hours. The mixture was concentrated to give the crude product, which was then purified by flash chromatography (hexane:EtOAc=30:1) to give tert-butyl cyclopentylcarbamate (80.4 g, 433.9 mmol, 43.4%) as a white solid.

$^1$H NMR (400 MHz, DMSO-$d_6$) δ 6.77-6.76 (d, J=6.7 Hz, 1H), 3.75-3.66 (m, 2H), 1.76-1.71 (m, 2H), 1.46-1.42 (m, 2H), 1.35-1.30 (m, 2H); MS (m/z): 208.2 (MNa⁺).

Step 2: Preparation of N-methylcyclopentanamine (60)

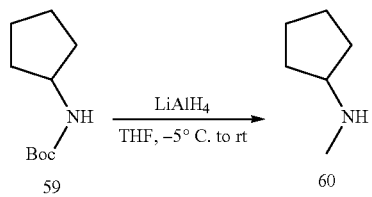

A solution of tert-butyl cyclopentylcarbamate (50.0 g, 269.8 mmol, 1.0 eq) in THF (1.5 L) was added with LiAlH₄ (15.8 g, 404.7 mmol, 1.5 eq) at −5° C. The resulting mixture was stirred for 40 hours and then added with H₂O (15 mL), 10% NaOH solution (15 mL) and H₂O (45 mL) The mixture was concentrated, added with DCM (300 mL), dried with Na₂SO₄, filtered and concentrated to give the crude product of N-methylcyclopentanamine (17.7 g).

Step 3: Preparation of cyclopentyl(methyl)carbamic chloride (61)

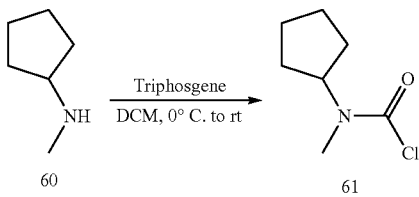

A solution of N-methylcyclopentanamine (17.7 g, 178.6 mmol, 2.0 eq) in DCM (250 mL) was added with triphosgene (26.5 g, 89.3 mmol, 1.0 eq) in DCM (100 mL) at 0° C. The mixture was stirred at room temperature for 20 hours. The resulting mixture was concentrated to give the crude product of cyclopentyl(methyl)carbamic chloride (28.8 g).

Step 4: Preparation of 4-(5-bromo-1H-pyrrolo[2,3-b]pyridin-3-yl)-N-cyclopentyl-N-methyl-5,6-dihydropyridine-1(2H)-carboxamide (62)

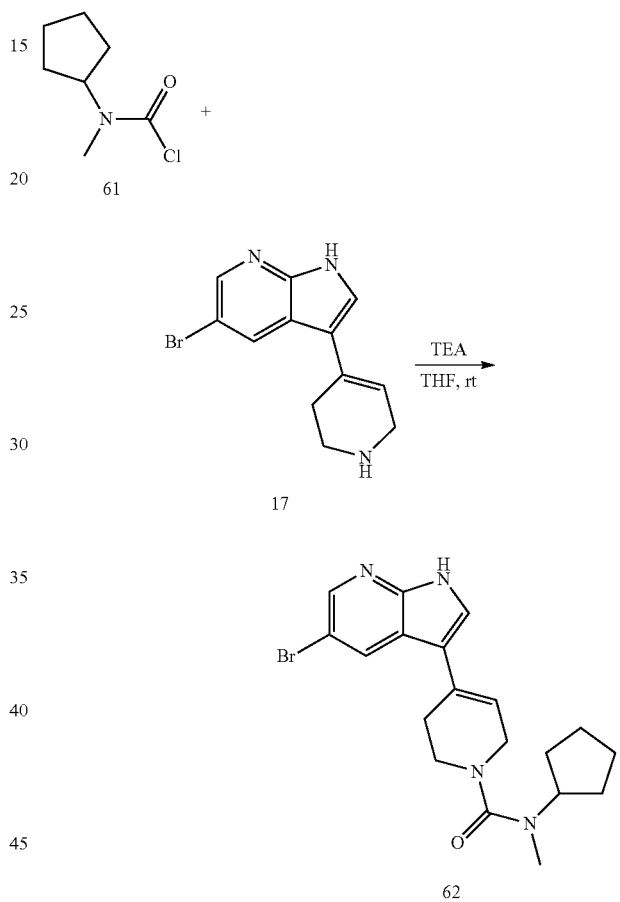

A solution of the crude product cyclopentyl(methyl)carbamic chloride (28.8 g, 178.7 mmol, 1.0 eq) and TEA (27.1 g, 268.0 mmol, 1.5 eq) in THF (600 mL) was stirred at room temperature for 0.5 hour, and then added with the intermediate 17 (29.7 g, 107.2 mmol, 1.0 eq). The resulting suspension was stirred at room temperature for 16 hours. The reaction mixture thus obtained was filtered and concentrated. The crude product was purified by chromatography (EtOAc:hexane=1:1) to give the intermediate 62 (3.0 g, 7.4 mmol) as a yellow solid.

$^1$H NMR (400 MHz, CDCl₃) δ 9.49 (s, 1H), 8.37-8.36 (m, 1H), 8.32-8.31 (m, 1H), 7.33 (s, 1H), 6.12 (s, 1H), 4.26-4.11 (m, 1H), 4.01-4.00 (d, J=2.4 Hz, 2H), 3.52-3.50 (t, J=5.5 Hz, 2H), 2.78 (s, 3H), 2.61 (s, 2H), 1.88-1.87 (m, 2H), 1.71 (m, 2H), 1.63-1.59 (m, 4H); MS (m/z): 403.0 (MH⁺).

EXAMPLE 217

N-cyclopentyl-N-methyl-4-(5-(3-(methylsulfonyl)phenyl)-1H-pyrrolo[2,3-b]pyridin-3-yl)-5,6-dihydropyridine-1(2H)-carboxamide

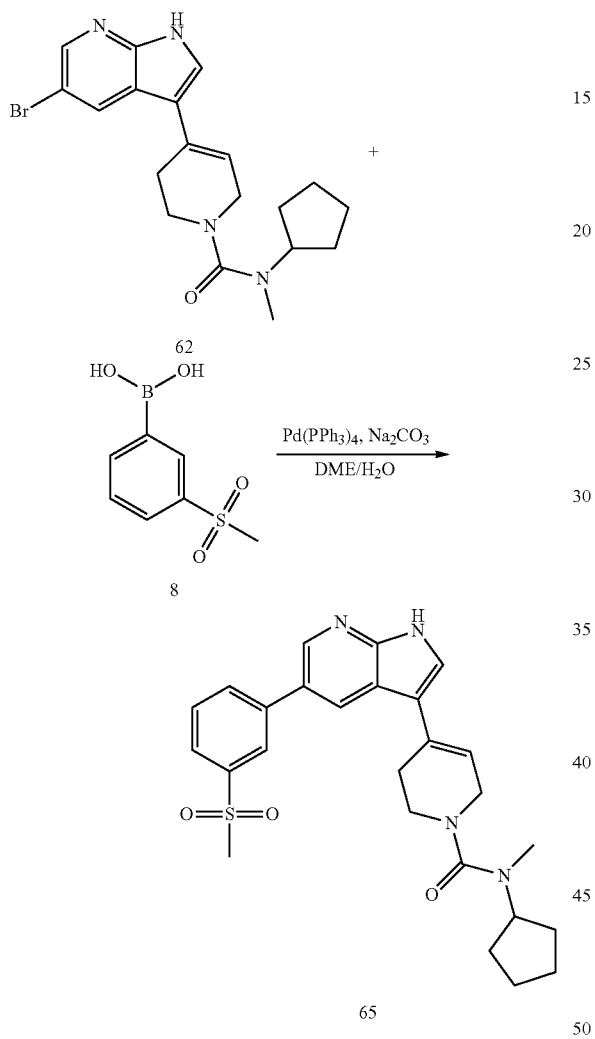

A suspension solution of 4-(5-bromo-1H-pyrrolo[2,3-b]pyridin-3-yl)-N-cyclopentyl-N-methyl-5,6-dihydropyridine-1(2H)-carboxamide (500 mg, 1.23 mmol, 1.0 eq), (3-(methylsulfonyl)phenyl)boronic acid (319 mg, 1.60 mmol, 1.3 eq) and Na$_2$CO$_3$ (521 mg, 4.92 mmol, 4.0 eq) in DME (8 mL) and water (2 mL) was subjected to purging with nitrogen, treated with Pd(PPh$_3$)$_4$ (142 mg, 0.12 mmol, 0.1 eq), and then stirred at 90° C. for 19 hours. The reaction mixture thus obtained was cooled to room temperature, added with water (5 mL), filtered, and washed with MeCN (5 mL), DCM and MeOH (5 mL) to give the title compound (317 mg, 0.6 mmol, 53.8%).

$^1$H NMR (400 MHz, DMSO-d$_6$) δ 11.91 (s, 1H), 8.61 (s, 1H), 8.52 (s, 1H), 8.24 (s, 1H), 8.15-8.13 (d, J=7.4 Hz, 1H), 7.92-7.91 (d, J=7.5 Hz, 1H), 7.78-7.77 (m, 1H), 7.66 (s, 1H), 6.34 (s, 1H), 4.07-4.06 (m, 1H), 3.91 (s, 2H), 2.68 (s, 3H), 2.59 (s, 2H), 1.74-1.52 (m, 8H); MS (m/z): 479. (MH$^+$).

EXAMPLE 218

N-cyclopentyl-N-methyl-4-(5-(3-sulfamoylphenyl)-1H-pyrrolo[2,3-b]pyridin-3-yl)-5,6-dihydropyridine-1(2H)-carboxamide

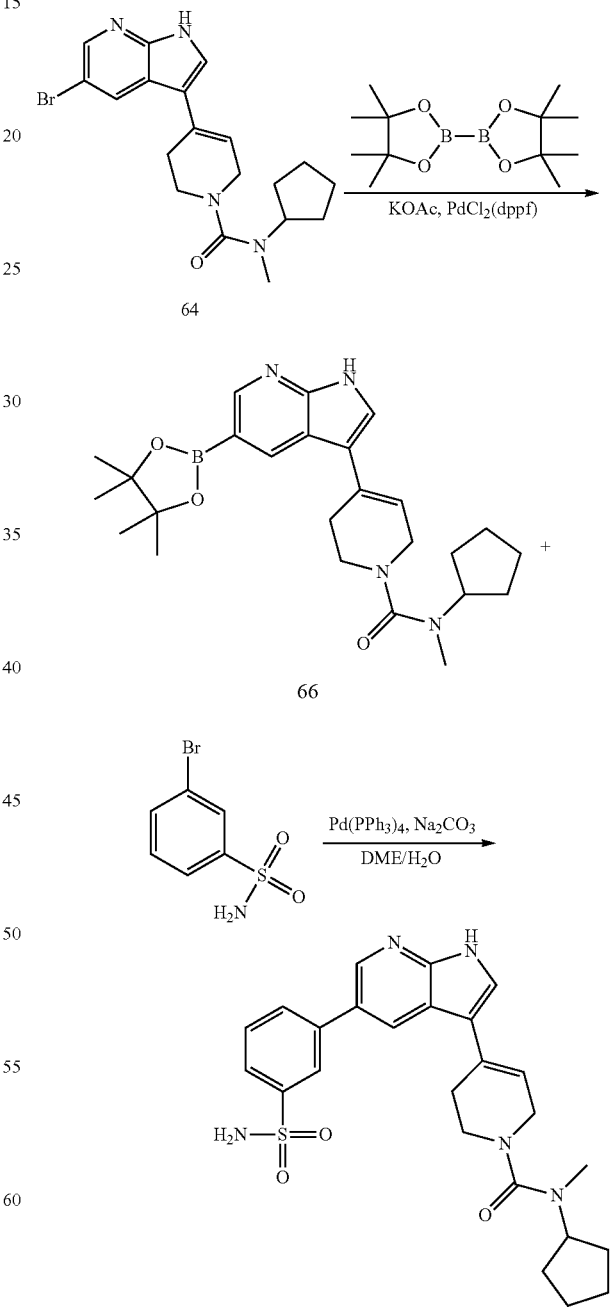

Step 1: Preparation of N-cyclopentyl-N-methyl-4-(5-(4,4,5,5-tetramethyl-1,3,2-dioxaborolan-2-yl)-1H-pyrrolo[2,3-b]pyridin-3-yl)-5,6-dihydropyridine-1(2H)-carboxamide (66)

A suspension solution of 4-(5-bromo-1H-pyrrolo[2,3-b]pyridin-3-yl)-N-cyclopentyl-N-methyl-5,6-dihydropyridine-1(2H)-carboxamide (800 mg, 1.98 mmol, 1.0 eq), 4,4,4',4',5,5,5',5'-octamethyl-2,2'-bi(1,3,2-dioxaborolane) (1.50 g, 5.95 mmol, 3.0 eq) and KOAc (680 mg, 6.93 mmol, 3.5 eq) in 1,4-dioxane (10 mL) was subjected to purging with nitrogen, treated with PdCl$_2$(dppf) (72 mg, 0.19 mmol, 0.05 eq), and then stirred at 90° C. for 2 hours. The resulting mixture was cooled to room temperature, filtered and concentrated. The crude product thus obtained was purified by chromatography (DCM:MeOH=20:1) to give the title compound (669 mg, 1.48 mmol, 75.0%) as a yellow solid.

Step 2: Preparation of N-cyclopentyl-N-methyl-4-(5-(3-sulfamoylphenyl)-1H-pyrrolo[2,3-b]pyridin-3-yl)-5,6-dihydropyridine-1(2H)-carboxamide (67)

A suspension solution of N-cyclopentyl-N-methyl-4-(5-(4,4,5,5-tetramethyl-1,3,2-dioxaborolan-2-yl)-1H-pyrrolo[2,3-b]pyridin-3-yl)-5,6-dihydropyridine-1(2H)-carboxamide (669 mg, 1.48 mmol, 1.1 eq), 3-bromobenzensulfonamide (318 mg, 1.35 mmol, 1.0 eq) and Na$_2$CO$_3$ (286 mg, 2.70 mmol, 2.0 eq) in DME (8 mL) and water (2 mL) was subjected to purging with nitrogen, treated with Pd(PPh$_3$)$_4$ (156 mg, 0.14 mmol, 0.1 eq), and then stirred at 90° C. for 19 hours. The reaction mixture thus obtained was cooled to room temperature, added with water (5 mL) and EtOAc (20 mL×2), and then filtered to give the title compound (430 mg, 0.89 mmol, 66.4%) as a yellow solid.

$^1$H NMR (400 MHz, DMSO-d$_6$) δ 11.89 (s, 1H), 8.57-8.56 (s, 1H), 8.46 (s, 1H), 8.18 (s, 1H), 8.02-8.00 (d, J=7.8 Hz, 1H), 7.82-7.80 (d, J=7.6 Hz, 1H), 7.70-7.65 (m, 2H), 7.43 (s, 1H), 6.32 (s, 1H), 4.09-4.03 (m, 1H), 3.91 (s, 1H), 3.38-3.37 (m, 2H), 2.68 (s, 3H), 2.59 (s, 2H), 1.75-1.52 (m, 8H); MS (m/z): 480. (MH$^+$).

EXAMPLE 219

N-cyclopentyl-N-methyl-4-(5-(4-sulfamoylphenyl)-1H-pyrrolo[2,3-b]pyridin-3-yl)-5,6-dihydropyridine-1(2H)-carboxamide

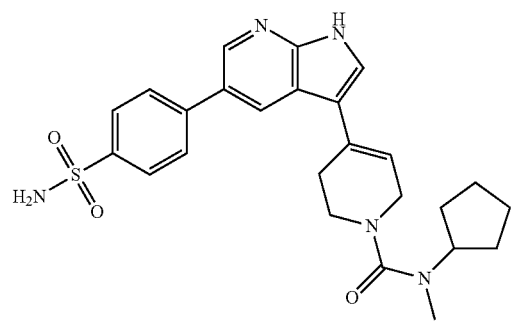 [SMILES: CN(C(=O)N1CC=C(c2c[nH]c3ncc(-c4ccc(S(N)(=O)=O)cc4)cc23)CC1)C1CCCC1]

$^1$H NMR (400 MHz, DMSO-d$_6$) δ 8.60 (s, 1H), 8.51 (s, 1H), 7.98-7.96 (m, 2H), 7.91-7.90 (m, 2H), 7.64 (s, 1H), 6.35 (s, 1H), 4.08 (m, 1H), 3.91 (s, 2H), 3.43 (s, 2H), 3.24 (s, 2H), 2.68 (s, 3H), 2.58 (s, 3H), 1.75-1.52 (m, 8H); MS (m/z): 480.2 (MH$^+$).

EXAMPLE 220

N-cyclopentyl-4-(5-(3,4-dimethoxyphenyl)-1H-pyrrolo[2,3-b]pyridin-3-yl)-N-methyl-5,6-dihydropyridine-1(2H)-carboxamide

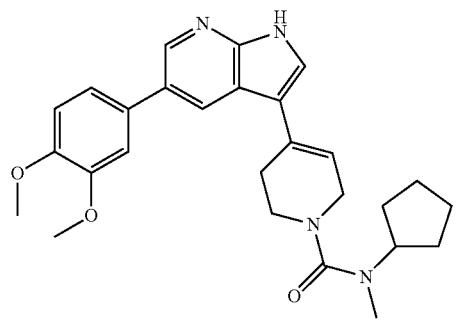 [SMILES: COc1ccc(-c2cnc3[nH]cc(C4=CCN(C(=O)N(C)C5CCCC5)CC4)c3c2)cc1OC]

$^1$H NMR (400 MHz, MeOD) δ 8.58 (s, 1H), 8.42 (s, 1H), 7.50 (s, 1H), 7.17-7.14 (m, 2H), 7.00-6.98 (m, 2H), 6.22 (s, 1H), 4.09-4.06 (m, 1H), 3.92 (m, 2H), 3.84 (s, 3H), 3.79 (s, 3H), 3.45-3.42 (m, 2H), 2.70 (s, 3H), 2.57 (s, 2H) 1.79-1.49 (m, 8H); MS (m/z): 461.1 (MH$^+$).

PREPARATION EXAMPLE 8

Preparation of tert-butyl 4-(5-bromo-2-methyl-1H-pyrrolo[2,3-b]pyridin-3-yl)-5,6-dihydropyridine-1(2H)-carboxylate (68)

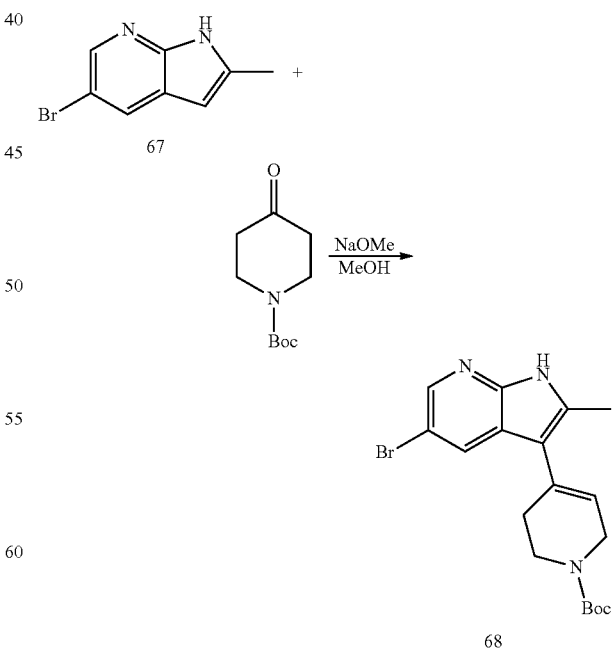

A solution of 5-bromo-2-methyl-1H-pyrrolo[2,3-b]pyridine (2.0 g, 9.5 mmol, 1.0 eq) and 1-Boc-4-piperidone (3.78 g, 19.0 mmol, 2.0 eq) in MeOH (20 mL) was added with NaOMe (12.3 mL, 25% MeOH solution). The resulting mixture was stirred at 90° C. for 17 hours. Subsequently, the reaction mixture was added to water (200 mL), extracted with EtOAc (150 mL×2), washed with a saturated NaCl solution (200 mL), dried over Na$_2$SO$_4$ and concentrated to give the crude product, which was purified by column chromatography to give the title compound (1.3 g, 3.3 mmol, 34.8%) as a yellow solid.

$^1$H NMR (400 MHz, CDCl$_3$) δ 9.61 (s, 1H), 8.25-8.24 (d, J=1.96 Hz, 1H), 7.97-7.96 (d, J=1.84 Hz, 1H), 5.74 (s, 1H), 4.13-4.12 (m, 2H), 3.71-3.68 (m, 2H), 2.52 (s, 5H), 1.54 (s, 9H);

MS (m/z): 392.29 (MH$^+$).

EXAMPLE 221

N-cyclopentyl-4-(2-methyl-5-(4-sulfamoylphenyl)-1H-pyrrolo[2,3-b]pyridin-3-yl)-5,6-dihydropyridine-1(2H)-carboxamide

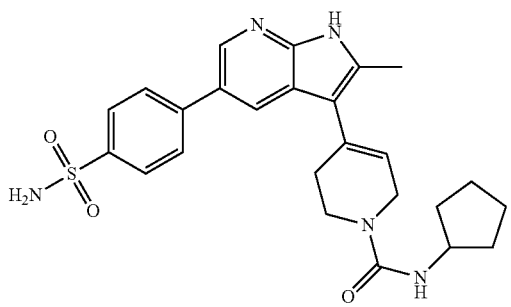 [SMILES: Cc1[nH]c2ncc(-c3ccc(S(N)(=O)=O)cc3)cc2c1C1=CCN(C(=O)NC2CCCC2)CC1]

$^1$H NMR (400 MHz, DMSO-d$_6$) δ 11.68 (br s, 1H), 8.47 (d, J=2.4 Hz, 1H), 8.14 (d, J=2.0 Hz, 1H), 7.94-7.87 (m, 4H), 7.39 (s, 2H), 6.20 (d, J=7.2 Hz, 1H), 5.76 (br s, 1H), 4.00 (br s, 2H), 3.98-3.92 (m, 1H), 3.56 (t, J=5.4 Hz, 2H), 2.44 (s, 3H), 1.83-1.77 (m, 2H), 1.68-1.60 (m, 2H), 1.52-1.47 (m, 4H); [M+H]$^+$ 480.

EXAMPLE 222

N-cyclopentyl-4-(2-methyl-5-(4-(N-methylsulfamoyl)phenyl)-1H-pyrrolo[2,3-b]pyridin-3-yl)-5,6-dihydropyridine-1(2H)-carboxamide

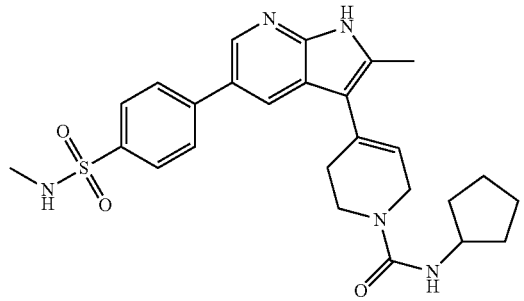 [SMILES: CNS(=O)(=O)c1ccc(-c2cnc3[nH]c(C)c(C4=CCN(C(=O)NC5CCCC5)CC4)c3c2)cc1]

$^1$H NMR (400 MHz, DMSO-d$_6$) δ 11.69 (br s, 1H), 8.49 (s, 1H), 8.16 (s, 1H), 7.97-7.83 (m, 4H), 7.51-7.47 (m, 1H), 6.20 (d, J=6.8 Hz, 1H), 5.78 (br s, 1H), 4.00 (br s, 2H), 3.98-3.92 (m, 1H), 3.56 (t, J=5.2 Hz, 2H), 2.45-2.43 (m, 7H), 1.83-1.77 (m, 2H), 1.68-1.60 (m, 2H), 1.52-1.38 (m, 4H); [M+H]$^+$ 494.

EXAMPLE 223

N-cyclopentyl-4-(2-methyl-5-(4-(morpholine-4-carbonyl)phenyl)-1H-pyrrolo[2,3-b]pyridin-3-yl)-5,6-dihydropyridine-1(2H)-carboxamide

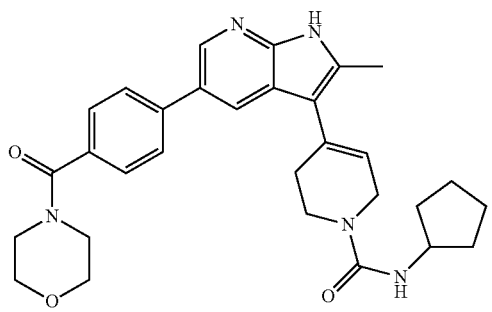 [SMILES: Cc1[nH]c2ncc(-c3ccc(C(=O)N4CCOCC4)cc3)cc2c1C1=CCN(C(=O)NC2CCCC2)CC1]

$^1$H NMR (400 MHz, DMSO-d$_6$) δ 11.66 (br s, 1H), 8.44 (s, 1H), 8.10 (s, 1H), 7.79 (d, J=8.4 Hz, 2H), 7.50 (d, J=8.4 Hz, 2H), 6.20 (d, J=6.8 Hz, 1H), 5.81-5.77 (m, 1H), 4.00 (s, 2H), 3.96-3.91 (m, 1H), 3.62-3.54 (m, 8H), 3.56 (t, J=5.6 Hz, 2H), 3.52-3.40 (m, 2H), 2.43 (s, 3H), 1.83-1.77 (m, 2H), 1.68-1.61 (m, 2H), 1.55-1.39 (m, 4H); [M+H]$^+$ 514.

PREPARATION EXAMPLE 9

Preparation of 3-(1,2,3,6-tetrahydropyridin-4-yl)-1H-pyrrolo[2,3-b]pyridine-6-amine

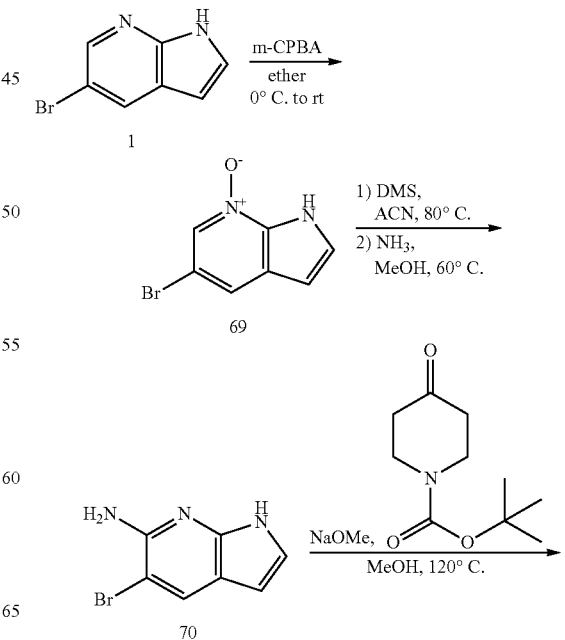

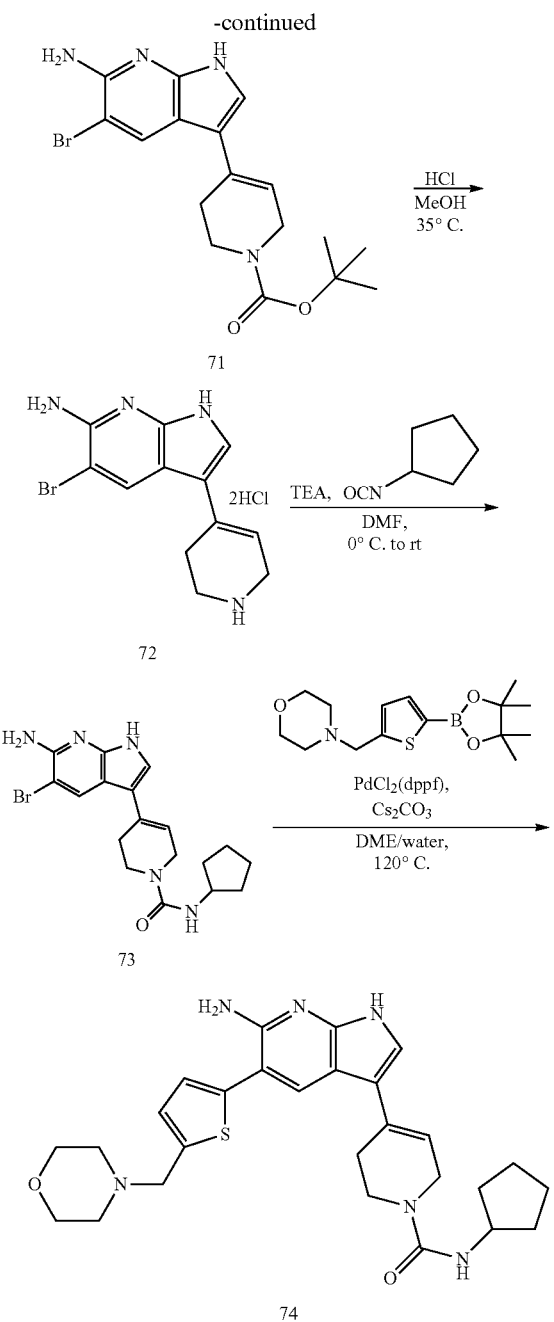

Step 1: Preparation of 5-bromo-1H-pyrrolo[2,3-b]pyridine-7-oxide (69)

A solution of 5-bromo-7-azaindole (985 mg, 5.0 mmol) in diethyl ether (25 mL) was added with m-CPBA (1.29 g, 5.8 mmol) portionwise at 0° C. The reaction mixture thus obtained was stirred at room temperature for 5 hours. The precipitated product was filtered and washed with diethyl ether. The solid thus obtained was suspended in a mixture of water (25 mL) and acetone (2.5 mL) The insoluble product was filtered and washed with water to give the title compound (1.18 g, 111%)

[M+H]$^+$ 213 and 215.

Step 2: Preparation of 5-bromo-1H-pyrrolo[2,3-b]pyridine-6-amine (70)

A suspension solution of the intermediate 69 in anhydrous ACN (10 mL) was added with dimethylsulfate (0.5 mL, 5.25 mmol). The reaction mixture was stirred at 80° C. for 8 hours and cooled to 0° C. The resulting reaction mixture was added with an ammonia solution (10 mL, 7N in MeOH), stirred at 60° C. for 2 days under nitrogen conditions, and the solvent was removed therefrom under reduced pressure. The residue was dissolved in ethyl acetate, and then washed with a saturated Na$_2$CO$_3$ solution and brine. The organic layer was evaporated and purified by silica gel column chromatography to give the intermediate 70 (570 mg, 54%).

[M+H]$^+$ 212 and 214.

Step 3: Preparation of tert-butyl 4-(6-amino-5-bromo-1H-pyrrolo[2,3-b]pyridin-3-yl)-5,6-dihydropyridine-1(2H)-carboxylate (71)

A solution of the intermediate 70 (400 mg, 1.89 mmol) and 1-Boc-4-piperidone (752 mg, 3.77 mmol, 2.0 eq) in MeOH (2.4 mL) was added with NaOMe (2.4 mL, 25% MeOH solution). Then, the mixture was heated to 120° C. and stirred for 6 hours at the above temperature. Subsequently, the resulting mixture was added to ice water (50 mL), extracted with EtOAc (2×100 mL), washed with a saturated NaCl solution (50 mL), dried over anhydrous MgSO$_4$ and concentrated to give the crude product, which was then crystallized from N-hexane/EtOAc (v/v=10:1) (50 mL) to give the crude intermediate 71 (651 mg, 1.66 mmol, 88%) as a yellow solid.

[M+H]$^+$ 393 and 395.

Step 4: Preparation of 5-bromo-3-(1,2,3,6-tetrahydropyridin-4-yl)-1H-pyrrolo[2,3-b]pyridine-6-amine dihydrochloride (72)

The intermediate 71 (390 mg, 0.99 mmol) was dissolved in an HCl solution (20 mL, 1.25 M HCl in MeOH), followed by stirring at room temperature for 16 hours. Subsequently, the reaction mixture was concentrated under reduced pressure to give the crude product 72 (351 mg, 0.96 mmol, 97%) as a yellow solid.

[M+H]$^+$ 293 and 295.

Step 5: Preparation of 4-(6-amino-5-bromo-1H-pyrrolo[2,3-b]pyridin-3-yl)-N-cyclopentyl-5,6-dihydropyridine-1(2H)-carboxamide (73)

A mixture of the intermediate 72 (351 mg, 0.96 mmol) in DMF (5.0 mL) was added with cyclopentyl isocyanate (0.097 mL, 0.86 mmol, 0.9 eq.) at 0° C. The reaction mixture was stirred at room temperature for 12 hours. The resulting reaction mixture was added to water (50 mL) The solid thus obtained was washed with water and dried to give the crude title intermediate 73 (274 mg, 0.68 mmol, 71%).

[M+H]$^+$ 404 and 406.

Step 6: Preparation of 4-(6-amino-5-(5-(morpholinomethyl)thiophen-2-yl)-1H-pyrrolo[2,3-b]pyridin-3-yl)-N-cyclopentyl-5,6-dihydropyridine-1(2H)-carboxamide (74)

A mixture of the intermediate 73 (101 mg, 0.25 mmol), 5-(morpholinomethyl)thiophene-2-boronic acid pinacol ester (123.8 mg, 0.4 mmol), PdCl$_2$(dppf) (18.3 mg, 0.025 mmol) and CS₂CO₃ (244 mg, 0.75 mmol) in DME/water (1.5 mL/1.5 mL) was subjected to purging with nitrogen, and then stirred at 100° C. for 3 hours. The reaction mixture thus obtained was cooled to room temperature, added to water (5 mL), and extracted with EtOAc (3×5 mL) The organic layer was collected and evaporated under reduced pressure. The residue was dissolved in DMF (4~5 mL) and purified by prep. HPLC (reverse phase column used, water/ACN) to give the title compound 74 (33.6 mg, 0.066 mmol, 27%).

[M+H]⁺ 507.

EXAMPLE 224 tert-Butyl 4-(6-amino-5-(3,4-dimethoxyphenyl)-1H-pyrrolo[2,3-b]pyridin-3-yl)-5,6-dihydropyridine-1(2H)-carboxylate

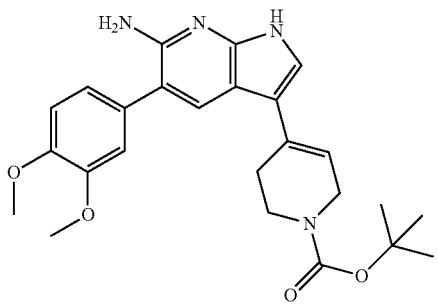 [SMILES: COc1ccc(-c2cc3c(C4=CCN(C(=O)OC(C)(C)C)CC4)c[nH]c3nc2N)cc1OC]

¹H NMR (400 MHz, DMSO-d₆) δ 10.99 (br s, 1H), 7.74 (s, 1H), 7.09 (s, 1H), 7.05-6.94 (m, 3H), 6.05 (s, 1H), 5.28 (s, 2H), 3.98 (br s, 2H), 3.52 (br s, 2H), 3.80 (s, 6H), 2.44 (br s, 2H), 1.42 (s, 9H); [M+H]⁺ 451.

EXAMPLE 225 tert-Butyl 4-(6-amino-5-(5-(morpholinomethyl)thiophen-2-yl)-1H-pyrrolo[2,3-b]pyridin-3-yl)-5,6-dihydropyridine-1(2H)-carboxylate

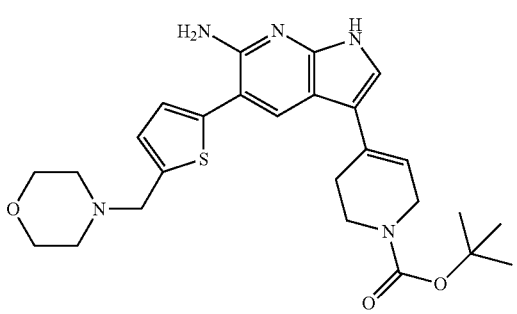 [SMILES: CC(C)(C)OC(=O)N1CC=C(c2c[nH]c3nc(N)c(-c4ccc(CN5CCOCC5)s4)cc23)CC1]

¹H NMR (400 MHz, DMSO-d₆) δ 11.08 (br s, 1H), 7.86 (s, 1H), 7.12 (s, 1H), 7.08 (d, J=3.6 Hz, 1H), 6.98 (d, J=3.6 Hz, 1H), 6.05 (br s, 1H), 5.54 (s, 2H), 4.00 (br s, 2H), 3.68 (s, 2H), 3.62-3.56 (m, 5H), 3.54-3.51 (m, 2H), 2.46-2.42 (m, 5H), 1.42 (s, 9H); [M+H]⁺ 496.

EXAMPLE 226

4-(6-Amino-5-(3,4-dimethoxyphenyl)-1H-pyrrolo[2,3-b]pyridin-3-yl)-N-cyclopentyl-5,6-dihydropyridine-1(2H)-carboxamide

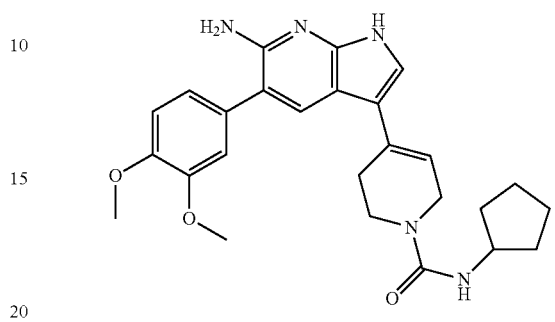

¹H NMR (400 MHz, DMSO-d₆) δ 10.99 (br s, 1H), 7.72 (s, 1H), 7.09 (s, 1H), 7.05-6.95 (m, 3H), 6.18 (d, J=7.2 Hz, 1H), 6.03 (s, 1H), 5.28 (s, 2H), 3.97-3.88 (m, 3H), 3.80 (s, 6H), 3.50 (d, J=5.6 Hz, 2H), 2.44-2.39 (m, 2H), 1.84-1.75 (m, 2H), 1.67-1.58 (m, 2H), 1.50-1.34 (m, 4H); [M+H]⁺ 462.

EXAMPLE 227

4-(6-Amino-5-(5-(morpholinomethyl)thiophen-2-yl)-1H-pyrrolo[2,3-b]pyridin-3-yl)-N-cyclopentyl-5,6-dihydropyridine-1(2H)-carboxamide

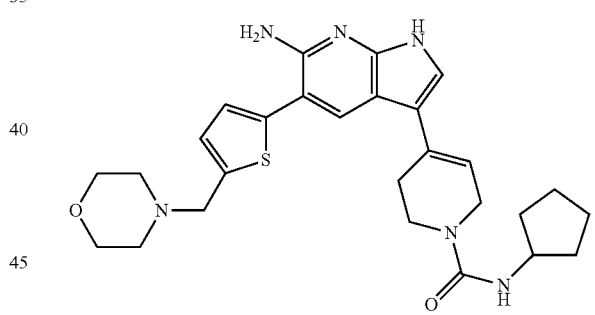

A mixture of the intermediate 73 (101 mg, 0.25 mmol), 5-(morpholinomethyl)thiophene-2-boronic acid pinacol ester (123.8 mg, 0.4 mmol), PdCl₂(dppf) (18.3 mg, 0.025 mmol) and CS₂CO₃ (244 mg, 0.75 mmol) in DME/water (1.5 mL/1.5 mL) was subjected to purging with nitrogen, followed by stirring at 100° C. for 3 hours. The reaction mixture thus obtained was cooled to room temperature, added to water (5 mL) and extracted with EtOAc (3×5 mL) The organic layer was collected and evaporated under reduced pressure. The residue thus obtained was dissolved in DMF (4~5 mL) and purified by prep. HPLC (reverse phase column used, water/ACN) to give the title compound (33.6 mg, 0.066 mmol, 27%).

¹H NMR (400 MHz, DMSO-d₆) δ 11.07 (br s, 1H), 7.85 (s, 1H), 7.13 (s, 1H), 7.09 (d, J=3.6 Hz, 1H), 6.98 (d, J=3.2 Hz, 1H), 6.19 (d, J=7.2 Hz, 1H), 6.03 (s, 1H), 5.55 (s, 2H), 3.97-3.88 (m, 3H), 3.68 (s, 2H), 3.64-3.58 (m, 4H), 3.50 (t, J=5.6 Hz, 2H), 2.45-2.39 (m, 6H), 1.81-1.75 (m, 2H), 1.68-1.58 (m, 2H), 1.50-1.35 (m, 4H); [M+H]⁺ 507.

For the compounds of Examples 228 to 234 below, the procedures of Scheme 2 were repeated except for using 2-bromo-5H-pyrrolo[2,3-b]pyrazine instead of 5-bromo-1H-pyrrolo[2,3-b]pyridine.

EXAMPLE 228

N-cyclopentyl-4-(2-(3-(methylsulfonyl)phenyl)-5H-pyrrolo[2,3-b]pyrazin-7-yl)-5,6-dihydropyridine-1(2H)-carboxamide

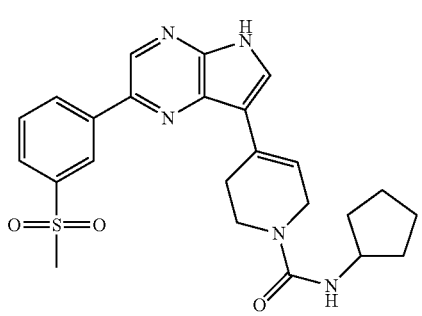 [SMILES: CS(=O)(=O)c1cccc(-c2cnc3[nH]cc(C4=CCN(C(=O)NC5CCCC5)CC4)c3n2)c1]

¹H NMR (400 MHz, DMSO-d₆) δ 12.15 (br s, 1H), 9.02 (s, 1H), 8.66-8.65 (m, 1H), 8.52 (d, J=8.0 Hz, 1H), 8.00-7.97 (m, 2H), 7.82 (d, J=7.8 Hz, 1H), 7.18 (s, 1H), 6.26 (d, J=6.8 Hz, 1H), 4.07 (br s, 2H), 4.00-3.92 (m, 1H), 3.58 (t, J=5.6 Hz, 2H), 3.32 (s, 3H), 2.55-2.52 (m, 1H), 1.84-1.73 (m, 2H), 1.69-1.60 (m, 2H), 1.52-1.36 (m, 5H); [M+H]⁺ 466.

EXAMPLE 229

N-cyclopentyl-4-(2-(5-(morpholinomethyl)thiophen-2-yl)-5H-pyrrolo[2,3-b]pyrazin-7-yl)-5,6-dihydropyridine-1(2H)-carboxamide

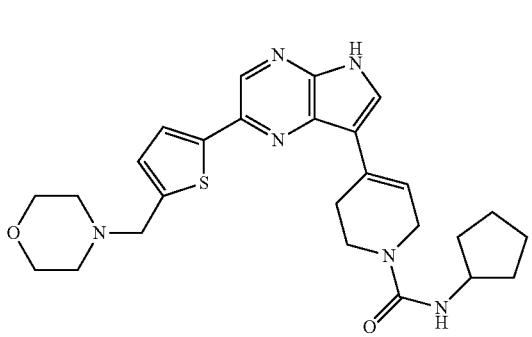 [SMILES: O=C(NC1CCCC1)N1CC=C(c2c[nH]c3ncc(-c4ccc(CN5CCOCC5)s4)nc23)CC1]

¹H NMR (400 MHz, DMSO-d₆) δ 12.03 (br s, 1H), 8.81 (s, 1H), 7.86 (s, 1H), 7.67 (d, J=3.6 Hz, 1H), 7.09 (s, 1H), 7.01 (d, J=3.2 Hz, 1H), 6.19 (d, J=7.2 Hz, 1H), 4.07 (br s, 2H), 3.98-3.94 (m, 1H), 3.69 (s, 2H), 3.60-3.52 (m, 6H), 2.49-2.42 (m, 6H), 1.85-1.76 (m, 2H), 1.71-1.60 (m, 2H), 1.52-1.37 (m, 4H); [M+H]⁺ 493.

EXAMPLE 230 tert-Butyl 4-(2-(3,4-dimethoxyphenyl)-5H-pyrrolo[2,3-b]pyrazin-7-yl)-5,6-dihydropyridine-1(2H)-carboxylate

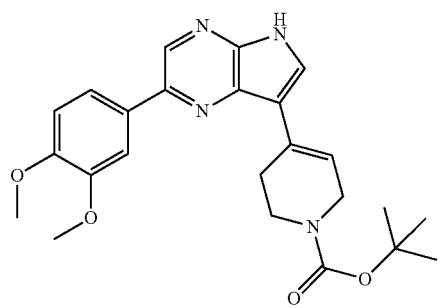 [SMILES: COc1ccc(-c2cnc3[nH]cc(C4=CCN(C(=O)OC(C)(C)C)CC4)c3n2)cc1OC]

¹H NMR (400 MHz, DMSO-d₆) δ 12.01 (br s, 1H), 8.86 (s, 1H), 7.86 (s, 1H), 7.73 (s, 2H), 7.18 (s, 1H), 7.10 (d, J=8.4 Hz, 1H), 4.10 (br s, 2H), 3.89 (s, 3H), 3.83 (s, 3H), 3.60 (s, 2H), 2.55 (br s, 2H), 1.44 (s, 9H); [M+H]⁺ 437.

EXAMPLE 231 tert-Butyl 4-(2-(3-(methylsulfonyl)phenyl)-5H-pyrrolo[2,3-b]pyrazin-7-yl)-5,6-dihydropyridine-1(2H)-carboxylate

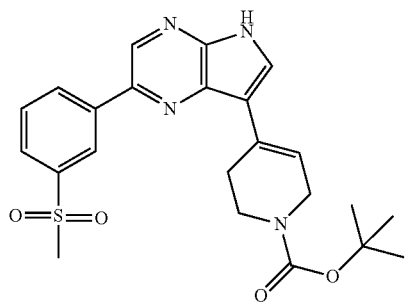 [SMILES: CC(C)(C)OC(=O)N1CC=C(c2c[nH]c3ncc(-c4cccc(S(C)(=O)=O)c4)nc23)CC1]

¹H NMR (400 MHz, DMSO-d₆) δ 12.22 (br s, 1H), 9.02 (s, 1H), 8.65 (s, 1H), 8.54 (d, J=7.2 Hz, 1H), 8.00-7.95 (m, 2H), 7.82 (t, J=7.8 Hz, 1H), 7.16 (s, 1H), 4.10 (br s, 2H), 3.60 (m, 2H), 2.57 (br s, 2H), 1.44 (s, 9H), 1.42-1.38 (m, 3H); [M+H]⁺ 455.

EXAMPLE 232

(4-(2-(3-(Methylsulfonyl)phenyl)-5H-pyrrolo[2,3-b]pyrazin-7-yl)-5,6-dihydropyridin-1(2H)-yl)(thiophen-2-yl)methanone

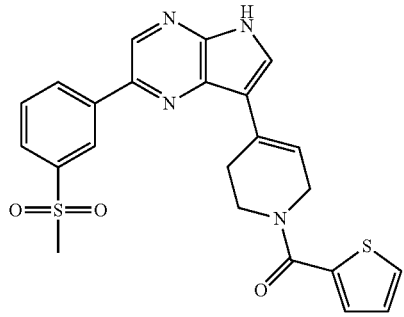 [SMILES: CS(=O)(=O)c1cccc(-c2cnc3[nH]cc(C4=CCN(C(=O)c5cccs5)CC4)c3n2)c1]

$^1$H NMR (400 MHz, DMSO-d$_6$) δ 11.98 (br s, 1H), 9.00 (s, 1H), 8.93 (s, 1H), 8.64 (s, 1H), 8.56-8.54 (m, 1H), 8.01 (s, 1H), 7.98-7.94 (m, 1H), 7.82-7.76 (m, 1H), 7.54 (d, J=3.6 Hz, 1H), 7.19-7.16 (m, 1H), 4.44 (br s, 2H), 3.90 (t, J=5.8 Hz, 2H), 3.80 (m, 1H), 3.30 (s, 3H), 3.10 (m, 1H), 2.72 (m, 1H); [M+H]$^+$ 465.

EXAMPLE 233

(4-(2-(5-(Morpholinomethyl)thiophen-2-yl)-5H-pyrrolo[2,3-b]pyrazin-7-yl)-5,6-dihydropyridin-1(2H)-yl)(thiophen-2-yl)methanone

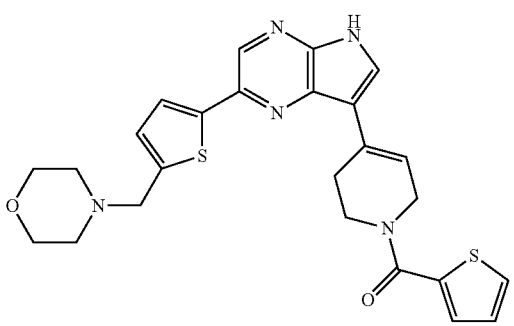 [SMILES: O=C(c1cccs1)N1CC=C(c2c[nH]c3ncc(-c4ccc(CN5CCOCC5)s4)nc23)CC1]

$^1$H NMR (400 MHz, DMSO-d$_6$) δ 12.05 (br s, 1H), 8.81 (s, 1H), 7.89 (s, 1H), 7.78 (d, J=5.2 Hz, 1H), 7.69-7.66 (m, 1H), 7.54 (s, 1H), 7.19-7.16 (m, 1H), 7.08 (s, 1H), 7.01 (s, 1H), 4.44 (br s, 2H), 3.68 (s, 2H), 3.63-3.56 (m, 5H), 2.72-2.63 (m, 3H), 2.45-2.42 (m, 4H); [M+H]$^+$ 492.

EXAMPLE 234 tert-Butyl 4-(2-(5-(morpholinomethyl)thiophen-2-yl)-5H-pyrrolo[2,3-b]pyrazin-7-yl)-5,6-dihydropyridine-1(2H)-carboxylate

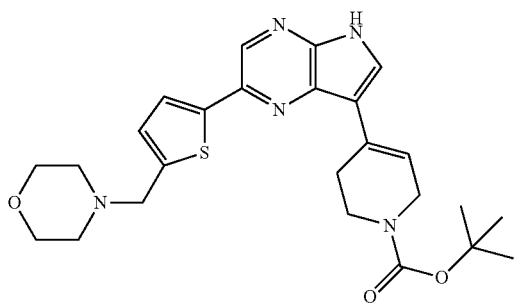 [SMILES: CC(C)(C)OC(=O)N1CC=C(c2c[nH]c3ncc(-c4ccc(CN5CCOCC5)s4)nc23)CC1]

[M+H]$^+$ 482.

EXAMPLE 235

4-(5-(3,4-Dimethoxyphenyl)-1H-pyrrolo[2,3-b]pyridin-3-yl)-N-isopropylpiperidine-1-carboxamide The compound of Example 235 was prepared by using methods similar to Steps 2 and 3 of Example 11.

Step 1: Preparation of tert-butyl 4-(5-(3,4-dimethoxyphenyl)-1H-pyrrolo[2,3-b]pyridin-3-yl)piperidine-1-carboxylate

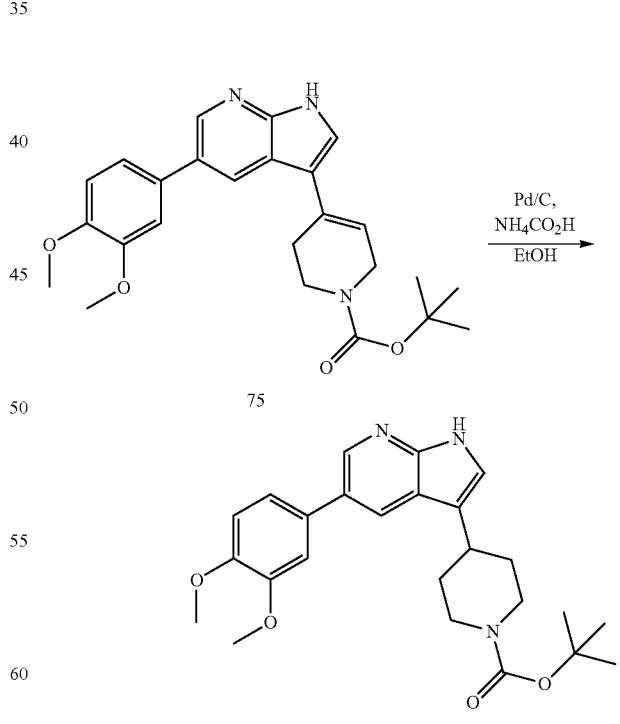

A mixture of tert-butyl 4-(5-(3,4-dimethoxyphenyl)-1H-pyrrolo[2,3-b]pyridin-3-yl)-5,6-dihydropyridine-1(2H)-carboxylate (0.27 g, 0.62 mmol, 1.0 eq.), 10% Pd/C (0.03 g, 10 wt %) and ammonium formate (0.12 g, 1.86 mmol, 3.0 eq.) was introduced to a sealed tube, and then diluted with EtOH (3.0 mL) The mixture was stirred at 50° C. for 24 hours and cooled to room temperature. The insoluble substance was removed by filtering through a Celite plug. The resulting solution was concentrated and diluted with acetone (5 mL) Then, the solution was filtered through a PTFE syringe filter, and then concentrated to give the title compound (0.26 g, 0.59 mmol, 95%) as a yellow solid.

Step 2: Preparation of 4-(5-(3,4-Dimethoxyphenyl)-1H-pyrrolo[2,3-b]pyridin-3-yl)-N-isopropylpiperidine-1-carboxamide

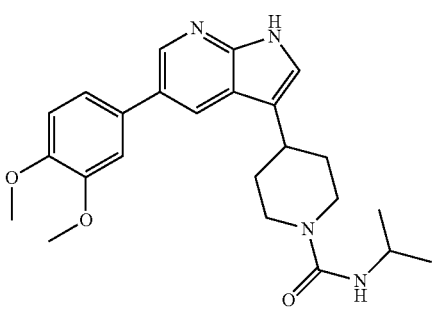 [SMILES: COc1ccc(-c2cnc3[nH]cc(C4CCN(C(=O)NC(C)C)CC4)c3c2)cc1OC]

¹H NMR (400 MHz, CDCl₃) δ 8.86 (br s, 1H), 8.52 (d, J=1.9 Hz, 1H), 8.21 (d, J=1.6 Hz, 1H), 7.19 (t, J=7.9 Hz, 1H), 7.12 (d, J=2.1 Hz, 1H), 7.05 (dd, J=7.8, 1.5 Hz, 1H), 6.99 (dd, J=8.1, 1.5 Hz, 1H), 4.29 (d, J=7.1 Hz, 1H), 4.10-4.01 (m, 3H), 3.97 (s, 3H), 3.61 (s, 3H), 3.04-2.92 (m, 3H), 2.10 (d, J=11.6 Hz, 2H), 1.76 (qd, J=12.6, 2.0 Hz, 2H), 1.21 (d, J=6.5 Hz, 6H); [M+H]⁺ 423.

EXAMPLE 236 tert-Butyl 3-(5-(3,4-dimethoxyphenyl)-1H-pyrrolo[2,3-b]pyridin-3-yl)piperidine-1-carboxylate

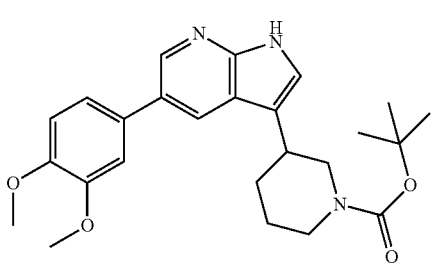 [SMILES: COc1ccc(-c2cnc3[nH]cc(C4CCCN(C(=O)OC(C)(C)C)C4)c3c2)cc1OC]

¹H NMR (400 MHz, DMSO-d₆) δ 11.48 (br s, 1H), 8.47 (s, 1H), 8.15 (s, 1H), 7.31 (s, 1H), 7.26 (s, 1H), 7.21 (d, J=8.4 Hz, 1H), 7.05 (d, J=8.4 Hz, 1H), 4.16-4.12 (m, 1H), 3.96-3.91 (m, 1H), 3.87 (s, 3H), 3.80 (s, 3H), 2.97-2.89 (m, 1H), 2.09-2.06 (m, 1H), 1.78-1.69 (m, 2H), 1.55-1.45 (m, 3H), 1.39 (s, 9H); [M+H]⁺ 438.

EXAMPLE 237

3-(5-(3,4-Dimethoxyphenyl)-1H-pyrrolo[2,3-b]pyridin-3-yl)-N-isopropyl-2,5-dihydro-1H-pyrrol-1-carboxamide

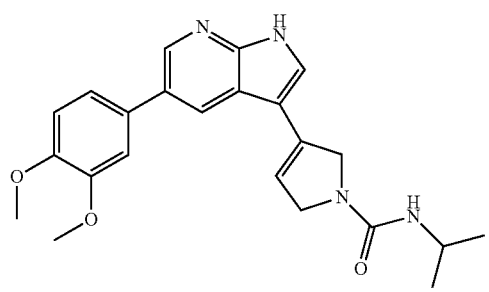 [SMILES: COc1ccc(-c2cnc3[nH]cc(C4=CCN(C(=O)NC(C)C)C4)c3c2)cc1OC]

¹H NMR (400 MHz, CDCl₃) δ 9.39 (br s, 1H), 8.55 (d, J=1.9 Hz, 1H), 8.41 (d, J=1.8 Hz, 1H), 7.31 (d, J=2.2 Hz, 1H), 7.18 (t, J=8.0 Hz, 1H), 7.04 (dd, J=7.8, 1.5 Hz, 1H), 6.98 (dd, J=8.2, 1.5 Hz, 1H), 6.16 (s, 1H), 4.58 (br s, 2H), 4.31 (br s, 2H), 4.06-4.05 (m, 2H), 3.95 (s, 3H), 3.59 (s, 3H), 1.22 (d, J=6.1 Hz, 6H); [M+H]⁺ 407.

EXAMPLE 238

3-(5-(3,4-Dimethoxyphenyl)-1H-pyrrolo[2,3-b]pyridin-3-yl)-N-isopropylpyrrolidine-1-carboxamide

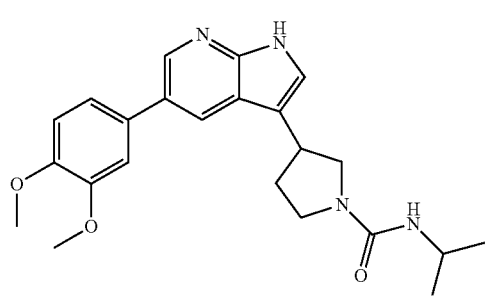 [SMILES: COc1ccc(-c2cnc3[nH]cc(C4CCN(C(=O)NC(C)C)C4)c3c2)cc1OC]

¹H NMR (400 MHz, CDCl₃) δ 10.39 (br s, 1H), 8.51 (d, J=2.0 Hz, 1H), 8.05 (d, J=2.0 Hz, 1H), 7.27 (s, 1H), 7.22 (s, 1H), 7.17 (dd, J=8.4, 2.0 Hz, 1H), 7.13 (d, J=2.0 Hz, 1H), 7.00 (d, J=8.4 Hz, 1H), 4.05-4.02 (m, 2H), 3.99 (s, 3H), 3.95 (s, 3H), 3.96-3.90 (m, 1H), 3.69 (quint, J=7.8 Hz, 1H), 3.59-3.57 (m, 1H), 3.49-3.43 (m, 2H), 2.45-2.39 (m, 1H), 2.23-2.13 (m, 1H), 1.18 (d, J=6.0 Hz, 6H); [M+H]⁺ 409.

EXAMPLE 239 tert-Butyl 4-(5-(3,4-dimethoxyphenyl)-1H-pyrrolo[2,3-b]pyridin-3-yl)-5,6-dihydropyridine-1(2H)-carboxylate

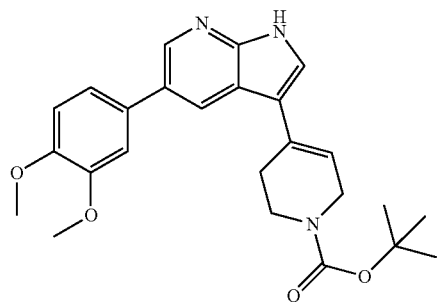 [SMILES: COc1ccc(-c2cnc3[nH]cc(C4=CCN(C(=O)OC(C)(C)C)CC4)c3c2)cc1OC]

[M+H]⁺ 436.

EXAMPLE 240 tert-Butyl 4-(5-(3-acetamidophenyl)-1H-pyrrolo[2,3-b]pyridin-3-yl)-5,6-dihydropyridine-1(2H)-carboxylate

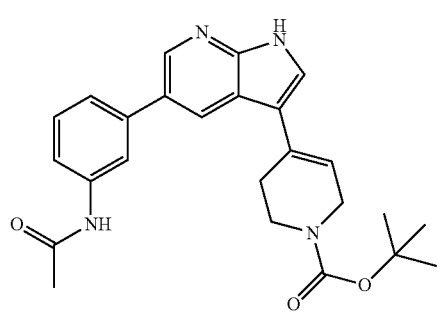 [SMILES: CC(=O)Nc1cccc(-c2cnc3[nH]cc(C4=CCN(C(=O)OC(C)(C)C)CC4)c3c2)c1]

[M+H]⁺ 433.

EXAMPLE 241 tert-Butyl 4-(5-(4-acetamidophenyl)-1H-pyrrolo[2,3-b]pyridin-3-yl)-5,6-dihydropyridine-1(2H)-carboxylate

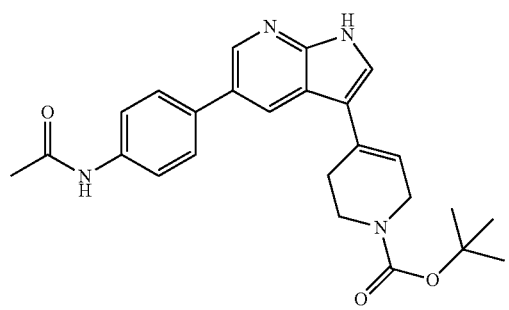 [SMILES: CC(=O)Nc1ccc(-c2cnc3[nH]cc(C4=CCN(C(=O)OC(C)(C)C)CC4)c3c2)cc1]

[M+H]⁺ 433.

EXAMPLE 242 tert-Butyl 4-(5-(3-propoxyphenyl)-1H-pyrrolo[2,3-b]pyridin-3-yl)-5,6-dihydropyridine-1(2H)-carboxylate

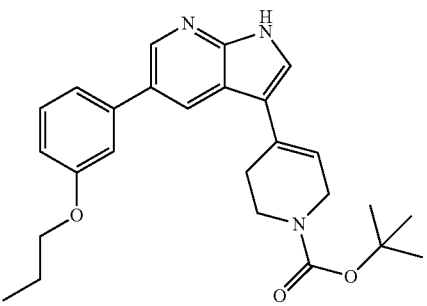 [SMILES: CCCOc1cccc(-c2cnc3[nH]cc(C4=CCN(C(=O)OC(C)(C)C)CC4)c3c2)c1]

[M+H]⁺ 434.

EXAMPLE 243 tert-Butyl 4-(5-(4-propoxyphenyl)-1H-pyrrolo[2,3-b]pyridin-3-yl)-5,6-dihydropyridine-1(2H)-carboxylate

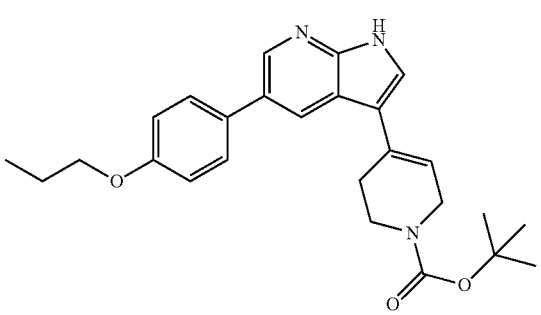 [SMILES: CCCOc1ccc(-c2cnc3[nH]cc(C4=CCN(C(=O)OC(C)(C)C)CC4)c3c2)cc1]

[M+H]⁺ 434.

EXAMPLE 244 tert-Butyl 4-(5-(2-methoxyphenyl)-1H-pyrrolo[2,3-b]pyridin-3-yl)-5,6-dihydropyridine-1(2H)-carboxylate

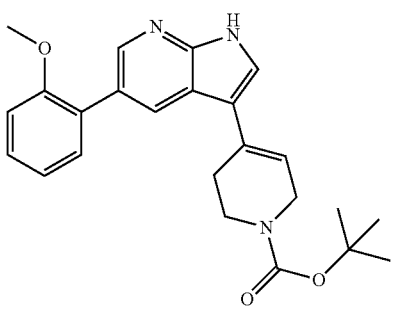 [SMILES: COc1ccccc1-c1cnc2[nH]cc(C3=CCN(C(=O)OC(C)(C)C)CC3)c2c1]

[M+H]⁺ 406.

EXAMPLE 245 tert-Butyl 5-(5-(3,4-dimethoxyphenyl)-1H-pyrrolo[2,3-b]pyridin-3-yl)-3,4-dihydropyridine-1(2H)-carboxylate

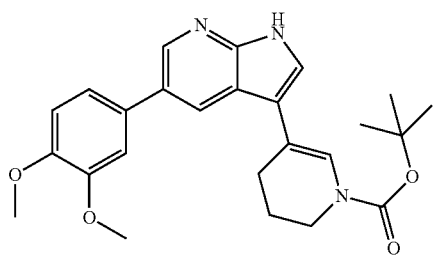 [SMILES: COc1ccc(-c2cnc3[nH]cc(C4=CN(C(=O)OC(C)(C)C)CCC4)c3c2)cc1OC]

[M+H]⁺ 436.

EXAMPLE 246

N-cyclopentyl-2-(4-(5-(3,4-dimethoxyphenyl)-1H-pyrrolo[2,3-b]pyridin-3-yl)phenyl) acetamide 2,2,2-trifluoroacetate

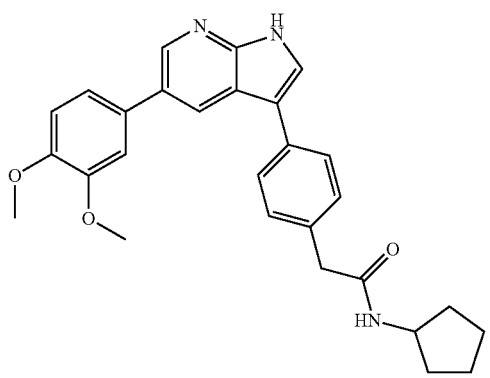 [SMILES: COc1ccc(-c2cnc3[nH]cc(-c4ccc(CC(=O)NC5CCCC5)cc4)c3c2)cc1OC]

¹H NMR (400 MHz, DMSO-d₆) δ 11.96 (s, 1H), 8.55 (d, J=2.0 Hz, 1H), 8.39 (d, J=2.0 Hz, 1H), 8.05 (d, J=7.2 Hz, 1H), 7.86 (d, J=2.4 Hz, 1H), 7.70 (d, J=8.0 Hz, 2H), 7.33-7.30 (m, 3H), 7.26 (dd, J=8.4, 2.0 Hz, 1H), 7.06 (d, J=8.4 Hz, 1H), 4.00 (q, J=6.8 Hz, 1H), 3.87 (s, 3H), 3.80 (s, 3H), 3.40 (s, 2H), 1.82-1.76 (m, 2H), 1.67-1.60 (m, 2H), 1.55-1.49 (m, 2H), 1.42-1.34 (m, 2H)); [M+H]⁺ 456.

EXAMPLE 247

2-(4-(5-(5-(Morpholinomethyl)thiophen-2-yl)-1H-pyrrolo[2,3-b]pyridin-3-yl)phenyl) acetic acid

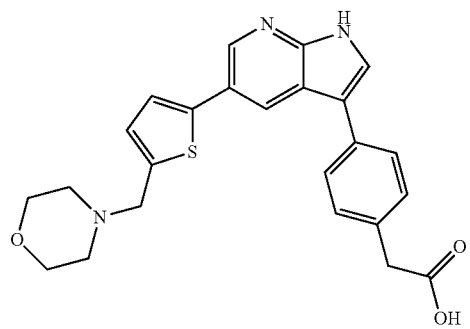 [SMILES: O=C(O)Cc1ccc(-c2c[nH]c3ncc(-c4ccc(CN5CCOCC5)s4)cc23)cc1]

¹H NMR (400 MHz, DMSO-d₆) δ 12.00 (s, 1H), 8.55 (d, J=2.0 Hz, 1H), 8.35 (d, J=2.0 Hz, 1H), 7.86 (d, J=2.4 Hz, 1H), 7.66 (d, J=8.4 Hz, 2H), 7.41 (d, J=3.6 Hz, 1H), 7.34 (d, J=8.0 Hz, 2H), 6.99 (d, J=2.0 Hz, 1H), 3.68 (s, 2H), 3.59 (t, J=4.6 Hz, 4H), 3.16 (s, 2H), 2.44 (brs, 4H); [M+H]⁺ 434.

EXAMPLE 248

N-cyclopentyl-2-(4-(5-(5-(morpholinomethyl)thiophen-2-yl)-1H-pyrrolo[2,3-b]pyridin-3-yl)phenyl) acetamide 2,2,2-trifluoroacetate

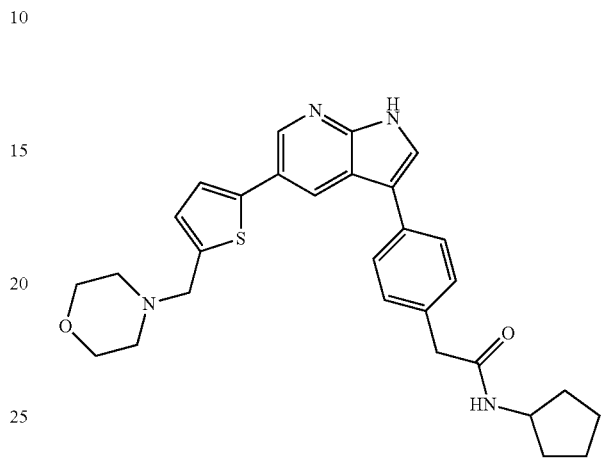

¹H NMR (400 MHz, DMSO-d₆) δ 12.18 (s, 1H), 1.16 (brs, 1H), 8.61 (d, J=2.0 Hz, 1H), 8.41 (d, J=2.4 Hz, 1H), 8.07 (d, J=7.2 Hz, 1H), 7.91 (d, J=2.4 Hz, 1H), 7.67 (d, J=8.0 Hz, 2H), 7.63 (d, J=3.6 Hz, 1H), 7.34-7.32 (m, 3H), 4.63 (s, 2H), 4.03-3.96 (m, 2H), 3.66 (brs, 2H), 3.41 (brs, 4H), 3.17 (brs, 2H), 1.84-1.77 (m, 2H), 1.67-1.63 (m, 2H), 1.56-1.48 (m, 2H), 1.42-1.36 (m, 2H); [M+H]⁺ 501.

EXAMPLE 249

N-cyclopentyl-2-(4-(5-(5-(morpholine-4-carbonyl)thiophen-2-yl)-1H-pyrrolo[2,3-b]pyridin-3-yl)phenyl)acetamide

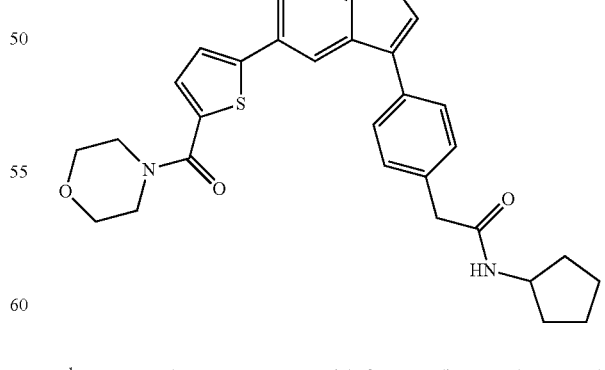

¹H NMR (400 MHz, CDCl₃) δ 9.93 (brs, 1H), 8.58 (d, J=1.6 Hz, 1H), 8.32 (d, J=2.0 Hz, 1H), 7.36 (d, J=1.2 Hz, 1H), 7.32 (d, J=4.0 Hz, 1H), 7.24 (d, J=4.0 Hz, 1H), 6.14 (s, 1H), 4.45 (d, J=6.8 Hz, 1H), 4.16 (q, J=7.3 Hz, 1H), 4.08 (d, J=2.4 Hz, 2H), 3.84 (t, J=4.8 Hz, 4H), 3.78 (t, J=4.6 Hz, 4H), 3.70

(t, J=5.6 Hz, 2H), 2.60 (s, 2H), 2.06-2.00 (m, 2H), 1.72-1.60 (m, 4H), 1.43-1.38 (m, 2H), 1.28-1.24 (m, 2H); [M+H]+ 515.

EXAMPLE 250

(4-(5-(4-(Morpholinomethyl)phenylamino)-1H-pyrrolo[2,3-b]pyridin-3-yl)-5,6-dihydropyridin-1(2H)-yl)(thiophen-2-yl)methanone

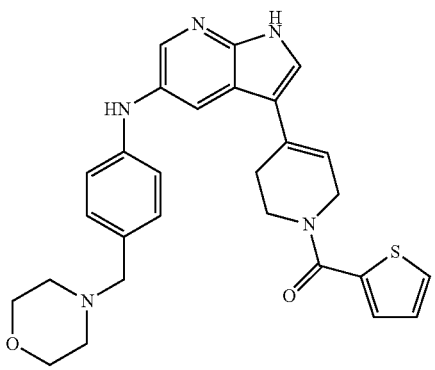 [SMILES: O=C(c1cccs1)N1CC=C(c2c[nH]c3ncc(Nc4ccc(CN5CCOCC5)cc4)cc23)CC1]

1H NMR (400 MHz, DMSO-d6) δ 11.74 (s, 1H), 9.63 (brs, 1H), 8.23 (brs, 1H), 8.11 (d, J=2.4 Hz, 1H), 8.00 (d, J=0.8 Hz, 1H), 7.79 (dd, J=5.0, 1.0 Hz, 1H), 7.62 (d, J=2.8 Hz, 1H), 7.50 (dd, J=3.8, 1.0 Hz, 1H), 7.25 (d, J=8.8 Hz, 2H), 7.16 (dd, J=4.8, 3.6 Hz, 1H), 6.90 (d, J=8.4 Hz, 2H), 6.10 (s, 1H), 4.35 (brs, 2H), 4.20 (d, J=4.8 Hz, 2H), 3.96 (t, J=5.0 Hz, 1H), 3.86 (t, J=5.6 Hz, 2H), 3.60 (t, J=12.0 Hz, 2H), 3.26 (d, J=12.0 Hz, 2H), 3.09-3.02 (m, 2H), 2.68-2.65 (m, 2H); [M+H]+ 500.

Inhibition activities on IKKε and TBK1 were evaluated using the compounds of Examples 1 to 250.

The inhibition activities on IKKε and TBK1 were measured by a luminometer, IKKε/TBK1 Kinase Enzyme System (Promega, Ca# V4158; Invitrogen, PR8031B, Promega, Ca# V3991) and ADP-Glo Kinase Assay using ADP-Glo™ Kinase Analysis Kit (Promega, Ca# V9101) and a kinase reaction buffer [40 mM Tris(pH 7.5), 20 mM MgCl$_2$, 0.1 mg/mL BSA] in accordance with the manufacturer's protocol.

The results of the inhibition activities of the compounds of Examples 1 to 250 against TBK1 and IKKε are shown in Table 1 below.

TABLE 1

| Example | Name | TBK1 (μM) | IKKε (μM) |
|---|---|---|---|
| 1 | 4-((5-(3-(1-methyl-1,2,3,6-tetrahydropyridin-4-yl)-1H-pyrrolo[2,3-b]pyridin-5-yl)thiophen-2-yl)methyl)morpholine | 6.86 | >10 |
| 2 | 5-(3,4-dimethoxyphenyl)-3-(1-methyl-1,2,3,6-tetrahydropyridin-4-yl)-1H-pyrrolo[2,3-b]pyridine | 9.04 | >10 |
| 3 | 5-(3,4-dimethoxyphenyl)-3-(1-ethyl-1,2,3,6-tetrahydropyridin-4-yl)-1H-pyrrolo[2,3-b]pyridine | 5.93 | >10 |
| 4 | 5-(3,4-dimethoxyphenyl)-3-(1-propyl-1,2,3,6-tetrahydropyridin-4-yl)-1H-pyrrolo[2,3-b]pyridine | 3.23 | 5.14 |
| 5 | 5-(3,4-dimethoxyphenyl)-3-(1-isobutyl-1,2,3,6-tetrahydropyridin-4-yl)-1H-pyrrolo[2,3-b]pyridine | 1.56 | 2.75 |
| 6 | 4-((5-(3-(1-ethyl-1,2,3,6-tetrahydropyridin-4-yl)-1H-pyrrolo[2,3-b]pyridin-5-yl)thiophen-2-yl)methyl)morpholine | 4.08 | 8.90 |
| 7 | 4-((5-(3-(1-propyl-1,2,3,6-tetrahydropyridin-4-yl)-1H-pyrrolo[2,3-b]pyridin-5-yl)thiophen-2-yl)methyl)morpholine | 1.91 | 4.25 |
| 8 | 1-(4-(5-(5-(morpholinomethyl)thiophen-2-yl)-1H-pyrrolo[2,3-b]pyridin-3-yl)-3,6-dihydropyridin-1(2H)-yl)ethan-1-one | 0.14 | 0.66 |
| 9 | 1-(4-(5-(5-(morpholinomethyl)thiophen-2-yl)-1H-pyrrolo[2,3-b]pyridin-3-yl)-3,6-dihydropyridin-1(2H)-yl)pentan-1-one | 0.33 | 0.51 |
| 10 | 3-methyl-1-(4-(5-(5-(morpholinomethyl)thiophen-2-yl)-1H-pyrrolo[2,3-b]pyridin-3-yl)-3,6-dihydropyridin-1(2H)-yl)butan-1-one | 0.075 | 0.13 |
| 11 | N-isopropyl-4-(5-phenyl-1H-pyrrolo[2,3-b]pyridin-3-yl)-5,6-dihydropyridine-1(2H)-carboxamide | 0.024 | 8.20 |
| 12 | N-isopropyl-4-(5-(4-methoxyphenyl)-1H-pyrrolo[2,3-b]pyridin-3-yl)-3,6-dihydropyridine-1(2H)-carboxamide | 0.029 | 2.20 |
| 13 | 4-(5-(4-fluorophenyl)-1H-pyrrolo[2,3-b]pyridin-3-yl)-N-isopropyl-3,6-dihydropyridine-1(2H)-carboxamide | 0.031 | 6.80 |
| 14 | N-isopropyl-4-(5-(3-methoxyphenyl)-1H-pyrrolo[2,3-b]pyridin-3-yl)-3,6-dihydropyridine-1(2H)-carboxamide | 0.015 | >10 |
| 15 | 4-(5-(3-fluorophenyl)-1H-pyrrolo[2,3-b]pyridin-3-yl)-N-isopropyl-3,6-dihydropyridine-1(2H)-carboxamide | 0.011 | >10 |
| 16 | N-isopropyl-4-(5-(p-tolyl)-1H-pyrrolo[2,3-b]pyridin-3-yl)-3,6-dihydropyridine-1(2H)-carboxamide | 0.036 | 0.28 |
| 17 | 4-(5-(4-acetamidophenyl)-1H-pyrrolo[2,3-b]pyridin-3-yl)-N-isopropyl-3,6-dihydropyridine-1(2H)-carboxamide | 0.0078 | 0.021 |
| 18 | 4-(5-(3,4-dimethoxyphenyl)-1H-pyrrolo[2,3-b]pyridin-3-yl)-N-isopropyl-5,6-dihydropyridine-1(2H)-carboxamide | 0.0025 | 0.045 |
| 19 | 4-(5-(3-acetamidophenyl)-1H-pyrrolo[2,3-b]pyridin-3-yl)-N-isopropyl-3,6-dihydropyridine-1(2H)-carboxamide | 0.0064 | 0.0070 |
| 20 | 4-(5-(2-fluoro-4-(morpholinomethyl)phenyl)-1H-pyrrolo[2,3-b]pyridin-3-yl)-N-isopropyl-3,6-dihydropyridine-1(2H)-carboxamide | 0.032 | 0.046 |
| 21 | 4-(5-(2-fluoro-5-(morpholinomethyl)phenyl)-1H-pyrrolo[2,3-b]pyridin-3-yl)-N-isopropyl-3,6-dihydropyridine-1(2H)-carboxamide | 0.071 | 0.16 |

TABLE 1-continued

| Example | Name | TBK1 (µM) | IKKε (µM) |
|---|---|---|---|
| 22 | 4-(5-(4-((4-ethylpiperazin-1-yl)methyl)phenyl)-1H-pyrrolo[2,3-b]pyridin-3-yl)-N-isopropyl-3,6-dihydropyridine-1(2H)-carboxamide | 0.010 | 0.020 |
| 23 | 4-(5-(4-((4-cyclopropylpiperazin-1-yl)methyl)phenyl)-1H-pyrrolo[2,3-b]pyridin-3-yl)-N-isopropyl-3,6-dihydropyridine-1(2H)-carboxamide | 0.0057 | 0.0066 |
| 24 | 4-(5-(3-((4-ethylpiperazin-1-yl)methyl)phenyl)-1H-pyrrolo[2,3-b]pyridin-3-yl)-N-isopropyl-3,6-dihydropyridine-1(2H)-carboxamide | 0.012 | 0.041 |
| 25 | N-isopropyl-4-(5-(6-((4-methylpiperazin-1-yl)methyl)pyridin-3-yl)-1H-pyrrolo[2,3-b]pyridin-3-yl)-3,6-dihydropyridine-1(2H)-carboxamide | 0.016 | 0.051 |
| 26 | 4-(5-(5-((4-ethylpiperazin-1-yl)methyl)thiophen-2-yl)-1H-pyrrolo[2,3-b]pyridin-3-yl)-N-isopropyl-3,6-dihydropyridine-1(2H)-carboxamide | 0.0077 | 0.025 |
| 27 | N-isopropyl-4-(5-(5-(pyrrolidin-1-ylmethyl)furan-2-yl)-1H-pyrrolo[2,3-b]pyridin-3-yl)-5,6-dihydropyridine-1(2H)-carboxamide | 0.57 | 1.98 |
| 28 | N-isopropyl-4-(5-(5-(pyrrolidin-1-ylmethyl)thiophen-2-yl)-1H-pyrrolo[2,3-b]pyridin-3-yl)-5,6-dihydropyridine-1(2H)-carboxamide | 0.018 | 0.058 |
| 29 | N-isopropyl-4-(5-(3-(morpholinomethyl)phenyl)-1H-pyrrolo[2,3-b]pyridin-3-yl)-5,6-dihydropyridine-1(2H)-carboxamide | 0.016 | 0.029 |
| 30 | N-isopropyl-4-(5-(4-(morpholinomethyl)phenyl)-1H-pyrrolo[2,3-b]pyridin-3-yl)-5,6-dihydropyridine-1(2H)-carboxamide | 0.0045 | 0.0088 |
| 31 | N-isopropyl-4-(5-(3-(4-methylpiperazine-1-carbonyl)phenyl)-1H-pyrrolo[2,3-b]pyridin-3-yl)-5,6-dihydropyridine-1(2H)-carboxamide | 0.015 | 0.046 |
| 32 | N-isopropyl-4-(5-(4-(4-methylpiperazine-1-carbonyl)phenyl)-1H-pyrrolo[2,3-b]pyridin-3-yl)-5,6-dihydropyridine-1(2H)-carboxamide | 0.0070 | 0.013 |
| 33 | N-isopropyl-4-(5-(5-((4-methylpiperazin-1-yl)methyl)thiophen-2-yl)-1H-pyrrolo[2,3-b]pyridin-3-yl)-5,6-dihydropyridine-1(2H)-carboxamide | 0.0011 | 0.0069 |
| 34 | N-isopropyl-4-(5-(5-(morpholinomethyl)thiophen-2-yl)-1H-pyrrolo[2,3-b]pyridin-3-yl)-5,6-dihydropyridine-1(2H)-carboxamide | 0.00073 | |
| 35 | N-isopropyl-4-(5-(5-((4-methylpiperazin-1-yl)methyl)furan-2-yl)-1H-pyrrolo[2,3-b]pyridin-3-yl)-5,6-dihydropyridine-1(2H)-carboxamide | 0.018 | 0.11 |
| 36 | N-isopropyl-4-(5-(5-(morpholinomethyl)furan-2-yl)-1H-pyrrolo[2,3-b]pyridin-3-yl)-5,6-dihydropyridine-1(2H)-carboxamide | | 0.0093 |
| 37 | N-isopropyl-4-(5-(4-((tetrahydro-2H-pyran-4-yl)amino)phenyl)-1H-pyrrolo[2,3-b]pyridin-3-yl)-3,6-dihydropyridine-1(2H)-carboxamide | 0.010 | 0.013 |
| 38 | N-isopropyl-4-(5-(4-((tetrahydro-2H-pyran-4-yl)oxy)phenyl)-1H-pyrrolo[2,3-b]pyridin-3-yl)-3,6-dihydropyridine-1(2H)-carboxamide | 0.029 | 0.021 |
| 39 | 4-(5-(7-amino-1-oxoisoindolidin-4-yl)-1H-pyrrolo[2,3-b]pyridin-3-yl)-N-isopropyl-3,6-dihydropyridine-1(2H)-carboxamide | 0.035 | 0.035 |
| 40 | 4-(5-(5-(morpholinomethyl)thiophen-2-yl)-1H-pyrrolo[2,3-b]pyridin-3-yl)-N-(pentan-3-yl)-3,6-dihydropyridine-1(2H)-carboxamide | 0.074 | 0.17 |
| 41 | 4-(5-(5-((4-methylpiperazin-1-yl)methyl)thiophen-2-yl)-1H-pyrrolo[2,3-b]pyridin-3-yl)-N-(pentan-3-yl)-3,6-dihydropyridine-1(2H)-carboxamide | 0.047 | 0.22 |
| 42 | N-(sec-butyl)-4-(5-(5-((4-methylpiperazin-1-yl)methyl)thiophen-2-yl)-1H-pyrrolo[2,3-b]pyridin-3-yl)-5,6-dihydropyridine-1(2H)-carboxamide | 0.0019 | 0.062 |
| 43 | N-(sec-butyl)-4-(5-(5-(morpholinomethyl)thiophen-2-yl)-1H-pyrrolo[2,3-b]pyridin-3-yl)-5,6-dihydropyridine-1(2H)-carboxamide | 0.0055 | |
| 44 | N-(sec-butyl)-4-(5-(3,4-dimethoxyphenyl)-1H-pyrrolo[2,3-b]pyridin-3-yl)-5,6-dihydropyridine-1(2H)-carboxamide | 0.0075 | |
| 45 | N-cyclopropyl-4-(5-(5-(piperazin-1-ylmethyl)thiophen-2-yl)-1H-pyrrolo[2,3-b]pyridin-3-yl)-5,6-dihydropyridine-1(2H)-carboxamide dihydrochloride | 0.0033 | 0.024 |
| 46 | N-cyclopropyl-4-(5-(4-((4-methylpiperazin-1-yl)methyl)phenyl)-1H-pyrrolo[2,3-b]pyridin-3-yl)-5,6-dihydropyridine-1(2H)-carboxamide | 0.014 | 0.025 |
| 47 | N-cyclopropyl-4-(5-(5-((4-methylpiperazin-1-yl)methyl)thiophen-2-yl)-1H-pyrrolo[2,3-b]pyridin-3-yl)-5,6-dihydropyridine-1(2H)-carboxamide | 0.0036 | 0.012 |
| 48 | N-cyclopropyl-4-(5-(5-(morpholinomethyl)thiophen-2-yl)-1H-pyrrolo[2,3-b]pyridin-3-yl)-5,6-dihydropyridine-1(2H)-carboxamide | 0.0082 | 0.01 |
| 49 | N-cyclopentyl-4-(5-(3,4-dimethoxyphenyl)-1H-pyrrolo[2,3-b]pyridin-3-yl)-5,6-dihydropyridine-1(2H)-carboxamide | 0.032 | |
| 50 | N-cyclopentyl-4-(5-(3-fluoro-4-methoxyphenyl)-1H-pyrrolo[2,3-b]pyridin-3-yl)-5,6-dihydropyridine-1(2H)-carboxamide | 0.33 | 0.41 |
| 51 | N-cyclopentyl-4-(5-(4-(methylsulfonyl)phenyl)-1H-pyrrolo[2,3-b]pyridin-3-yl)-5,6-dihydropyridine-1(2H)-carboxamide | 0.051 | |
| 52 | N-cyclopentyl-4-(5-(3-(methylsulfonyl)phenyl)-1H-pyrrolo[2,3-b]pyridin-3-yl)-5,6-dihydropyridine-1(2H)-carboxamide | 0.023 | 0.048 |
| 53 | N-cyclopentyl-4-(5-(4-(ethylsulfonyl)phenyl)-1H-pyrrolo[2,3-b]pyridin-3-yl)-3,6-dihydropyridine-1(2H)-carboxamide | 0.066 | |
| 54 | N-cyclopentyl-4-(5-(3-(ethylsulfonyl)phenyl)-1H-pyrrolo[2,3-b]pyridin-3-yl)-3,6-dihydropyridine-1(2H)-carboxamide | 0.032 | 0.084 |
| 55 | N-cyclopentyl-4-(5-(4-(propylsulfonyl)phenyl)-1H-pyrrolo[2,3-b]pyridin-3-yl)-5,6-dihydropyridine-1(2H)-carboxamide | 0.051 | 0.6 |
| 56 | N-cyclopentyl-4-(5-(4-(cyclopropylsulfonyl)phenyl)-1H-pyrrolo[2,3-b]pyridin-3-yl)-5,6-dihydropyridine-1(2H)-carboxamide | 0.058 | 0.19 |
| 57 | N-cyclopentyl-4-(5-(3-sulfamoylphenyl)-1H-pyrrolo[2,3-b]pyridin-3-yl)-5,6-dihydropyridine-1(2H)-carboxamide | 0.031 | |
| 58 | N-cyclopentyl-4-(5-(4-sulfamoylphenyl)-1H-pyrrolo[2,3-b]pyridin-3-yl)-5,6-dihydropyridine-1(2H)-carboxamide | 0.061 | |

TABLE 1-continued

| Example | Name | TBK1 (μM) | IKKε (μM) |
|---|---|---|---|
| 59 | N-cyclopentyl-4-(5-(3-(N-methylsulfamoyl)phenyl)-1H-pyrrolo[2,3-b]pyridin-3-yl)-5,6-dihydropyridine-1(2H)-carboxamide | 0.03 | |
| 60 | N-cyclopentyl-4-(5-(4-(N-methylsulfamoyl)phenyl)-1H-pyrrolo[2,3-b]pyridin-3-yl)-5,6-dihydropyridine-1(2H)-carboxamide | 0.038 | |
| 61 | N-cyclopentyl-4-(5-(4-(morpholinosulfonyl)phenyl)-1H-pyrrolo[2,3-b]pyridin-3-yl)-5,6-dihydropyridine-1(2H)-carboxamide | 0.086 | |
| 62 | N-cyclopentyl-4-(5-(3-(morpholinosulfonyl)phenyl)-1H-pyrrolo[2,3-b]pyridin-3-yl)-5,6-dihydropyridine-1(2H)-carboxamide | 0.091 | |
| 63 | N-cyclopentyl-4-(5-(4-methoxy-3-(morpholinosulfonyl)phenyl)-1H-pyrrolo[2,3-b]pyridin-3-yl)-5,6-dihydropyridine-1(2H)-carboxamide | 0.029 | 0.44 |
| 64 | N-cyclopentyl-4-(5-(4-(2-morpholinoethyl)phenyl)-1H-pyrrolo[2,3-b]pyridin-3-yl)-5,6-dihydropyridine-1(2H)-carboxamide | 0.11 | |
| 65 | 4-(5-(5-acetamido-2-aminophenyl)-1H-pyrrolo[2,3-b]pyridin-3-yl)-N-cyclopentyl-5,6-dihydropyridine-1(2H)-carboxamide | 1.90 | |
| 66 | N-cyclopentyl-4-(5-(4-((furan-2-ylmethyl)carbamoyl)phenyl)-1H-pyrrolo[2,3-b]pyridin-3-yl)-5,6-dihydropyridine-1(2H)-carboxamide | 0.25 | |
| 67 | N-cyclopentyl-4-(5-(3-((furan-2-ylmethyl)carbamoyl)phenyl)-1H-pyrrolo[2,3-b]pyridin-3-yl)-5,6-dihydropyridine-1(2H)-carboxamide | 0.41 | |
| 68 | N-cyclopentyl-4-(5-(3-(2-morpholinoethoxy)phenyl)-1H-pyrrolo[2,3-b]pyridin-3-yl)-5,6-dihydropyridine-1(2H)-carboxamide | 0.064 | |
| 69 | N-cyclopentyl-4-(5-(4-(2-morpholinoethoxy)phenyl)-1H-pyrrolo[2,3-b]pyridin-3-yl)-5,6-dihydropyridine-1(2H)-carboxamide | 0.065 | |
| 70 | N-cyclopentyl-4-(5-(4-(3-morpholinopropoxy)phenyl)-1H-pyrrolo[2,3-b]pyridin-3-yl)-5,6-dihydropyridine-1(2H)-carboxamide | 0.4 | |
| 71 | N-cyclopentyl-4-(5-(5-((4-methylpiperazin-1-yl)methyl)thiophen-2-yl)-1H-pyrrolo[2,3-b]pyridin-3-yl)-5,6-dihydropyridine-1(2H)-carboxamide | 0.005 | |
| 72 | N-cyclopentyl-4-(5-(5-(morpholinomethyl)thiophen-2-yl)-1H-pyrrolo[2,3-b]pyridin-3-yl)-5,6-dihydropyridine-1(2H)-carboxamide | 0.028 | 0.038 |
| 73 | N-cyclopentyl-4-(5-(5-(morpholinomethyl)thiophen-3-yl)-1H-pyrrolo[2,3-b]pyridin-3-yl)-5,6-dihydropyridine-1(2H)-carboxamide | 0.62 | |
| 74 | N-cyclopentyl-4-(5-(5-(morpholine-4-carbonyl)thiophen-2-yl)-1H-pyrrolo[2,3-b]pyridin-3-yl)-5,6-dihydropyridine-1(2H)-carboxamide | 0.053 | |
| 75 | N-cyclopentyl-4-(5-(4-(morpholine-4-carbonyl)phenyl)-1H-pyrrolo[2,3-b]pyridin-3-yl)-5,6-dihydropyridine-1(2H)-carboxamide | 0.025 | |
| 76 | 4-(5-(4-chloro-3-(morpholine-4-carbonyl)phenyl)-1H-pyrrolo[2,3-b]pyridin-3-yl)-N-cyclopentyl-3,6-dihydropyridine-1(2H)-carboxamide 2,2,2-trifluoroacetate | 0.29 | |
| 77 | 4-(5-(3-chloro-5-(morpholine-4-carbonyl)phenyl)-1H-pyrrolo[2,3-b]pyridin-3-yl)-N-cyclopentyl-3,6-dihydropyridine-1(2H)-carboxamide 2,2,2-trifluoroacetate | 0.25 | |
| 78 | 4-(5-(4-((4-methylpiperazin-1-yl)methyl)phenyl)-1H-pyrrolo[2,3-b]pyridin-3-yl)-N-(oxetan-3-yl)-5,6-dihydropyridine-1(2H)-carboxamide | 0.015 | 0.055 |
| 79 | 4-(5-(5-((4-methylpiperazin-1-yl)methyl)thiophen-2-yl)-1H-pyrrolo[2,3-b]pyridin-3-yl)-N-(oxetan-3-yl)-5,6-dihydropyridine-1(2H)-carboxamide | 0.32 | 0.028 |
| 80 | 4-(5-(5-(morpholinomethyl)thiophen-2-yl)-1H-pyrrolo[2,3-b]pyridin-3-yl)-N-(oxetan-3-yl)-5,6-dihydropyridine-1(2H)-carboxamide | 0.0012 | 0.0034 |
| 81 | 4-(5-(3,4-dimethoxyphenyl)-1H-pyrrolo[2,3-b]pyridin-3-yl)-N-(tetrahydrofuran-3-yl)-5,6-dihydropyridine-1(2H)-carboxamide | 0.021 | |
| 82 | 4-(5-(4-(methylsulfonyl)phenyl)-1H-pyrrolo[2,3-b]pyridin-3-yl)-N-(tetrahydrofuran-3-yl)-5,6-dihydropyridine-1(2H)-carboxamide | 0.035 | |
| 83 | 4-(5-(5-((4-methylpiperazin-1-yl)methyl)thiophen-2-yl)-1H-pyrrolo[2,3-b]pyridin-3-yl)-N-(tetrahydroruran-3-yl)-5,6-dihydropyridine-1(2H)-carboxamide | 0.013 | |
| 84 | 4-(5-(5-(morpholinomethyl)thiophen-2-yl)-1H-pyrrolo[2,3-b]pyridin-3-yl)-N-(tetrahydroruran-3-yl)-5,6-dihydropyridine-1(2H)-carboxamide | 0.016 | |
| 85 | 4-(5-(3,4-dimethoxyphenyl)-1H-pyrrolo[2,3-b]pyridin-3-yl)-N-(pyrrolidin-1-yl)-5,6-dihydropyridine-1(2H)-carboxamide 2,2,2-trifluoroacetate | 0.11 | |
| 86 | N-isopropyl-2-methyl-4-(5-(4-((4-methylpiperazin-1-yl)methyl)phenyl)-1H-pyrrolo[2,3-b]pyridin-3-yl)-5,6-dihydropyridine-1(2H)-carboxamide | 0.0028 | 0.0035 |
| 87 | N-isopropyl-2-methyl-4-(5-(5-(morpholinomethyl)thiophen-2-yl)-1H-pyrrolo[2,3-b]pyridin-3-yl)-5,6-dihydropyridine-1(2H)-carboxamide | 0.0010 | 0.0015 |
| 88 | N-isopropyl-2-methyl-4-(5-(5-((4-methylpiperazin-1-yl)methyl)thiophen-2-yl)-1H-pyrrolo[2,3-b]pyridin-3-yl)-5,6-dihydropyridine-1(2H)-carboxamide | 0.0008 | 0.0032 |
| 89 | N-isopropyl-2-methyl-4-(5-(4-(4-methylpiperazine-1-carbonyl)phenyl)-1H-pyrrolo[2,3-b]pyridin-3-yl)-5,6-dihydropyridine-1(2H)-carboxamide | 0.0028 | 0.0033 |
| 90 | N-isopropyl-2-methyl-4-(5-(4-(morpholinomethyl)phenyl)-1H-pyrrolo[2,3-b]pyridin-3-yl)-5,6-dihydropyridine-1(2H)-carboxamide | 0.0052 | 0.0055 |
| 91 | 6-methyl-4-(5-(5-((4-methylpiperazin-1-yl)methyl)thiophen-2-yl)-1H-pyrrolo[2,3-b]pyridin-3-yl)-N-(pentan-3-yl)-3,6-dihydropyridine-1(2H)-carboxamide | 0.046 | 0.18 |
| 92 | 6-methyl-4-(5-(5-(morpholinomethyl)thiophen-2-yl)-1H-pyrrolo[2,3-b]pyridin-3-yl)-N-(pentan-3-yl)-3,6-dihydropyridine-1(2H)-carboxamide | 0.035 | 0.13 |

TABLE 1-continued

| Example | Name | TBK1 (μM) | IKKε (μM) |
|---|---|---|---|
| 93 | tert-butyl 4-((5-(3-(1-(cyclopropylcarbamoyl)-6-methyl-1,2,3,6-tetrahydropyridin-4-yl)-1H-pyrrolo[2,3-b]pyridin-5-yl)thiophen-2-yl)methyl)piperazine-1-carboxylate | 0.018 | 0.048 |
| 94 | N-cyclopropyl-2-methyl-4-(5-(4-(4-methylpiperazine-1-carbonyl)phenyl)-1H-pyrrolo[2,3-b]pyridin-3-yl)-5,6-dihydropyridine-1(2H)-carboxamide | 0.0039 | 0.010 |
| 95 | N-cyclopropyl-2-methyl-4-(5-(4-((4-methylpiperazin-1-yl)methyl)phenyl)-1H-pyrrolo[2,3-b]pyridin-3-yl)-5,6-dihydropyridine-1(2H)-carboxamide | 0.0074 | 0.014 |
| 96 | N-cyclopropyl-2-methyl-4-(5-(5-((4-methylpiperazin-1-yl)methyl)thiophen-2-yl)-1H-pyrrolo[2,3-b]pyridin-3-yl)-5,6-dihydropyridine-1(2H)-carboxamide | 0.0031 | 0.0065 |
| 97 | N-cyclopropyl-2-methyl-4-(5-(5-(morpholinomethyl)thiophen-2-yl)-1H-pyrrolo[2,3-b]pyridin-3-yl)-5,6-dihydropyridine-1(2H)-carboxamide | 0.0017 | 0.0025 |
| 98 | N-cyclobutyl-2-methyl-4-(5-(4-(4-methylpiperazine-1-carbonyl)phenyl)-1H-pyrrolo[2,3-b]pyridin-3-yl)-5,6-dihydropyridine-1(2H)-carboxamide | 0.015 | 0.022 |
| 99 | N-cyclobutyl-2-methyl-4-(5-(4-((4-methylpiperazin-1-yl)methyl)phenyl)-1H-pyrrolo[2,3-b]pyridin-3-yl)-5,6-dihydropyridine-1(2H)-carboxamide | 0.028 | 0.064 |
| 100 | N-cyclobutyl-2-methyl-4-(5-(5-((4-methylpiperazin-1-yl)methyl)thiophen-2-yl)-1H-pyrrolo[2,3-b]pyridin-3-yl)-5,6-dihydropyridine-1(2H)-carboxamide | 0.0056 | 0.035 |
| 101 | N-cyclobutyl-2-methyl-4-(5-(5-(morpholinomethyl)thiophen-2-yl)-1H-pyrrolo[2,3-b]pyridin-3-yl)-5,6-dihydropyridine-1(2H)-carboxamide | 0.010 | 0.029 |
| 102 | N-cyclopentyl-2-methyl-4-(5-(5-((4-methylpiperazin-1-yl)methyl)thiophen-2-yl)-1H-pyrrolo[2,3-b]pyridin-3-yl)-5,6-dihydropyridine-1(2H)-carboxamide | 0.0044 | 0.013 |
| 103 | N-cyclopentyl-6-methyl-4-(5-(5-((4-methylpiperazin-1-yl)methyl)thiophen-2-yl)-1H-pyrrolo[2,3-b]pyridin-3-yl)-5,6-dihydropyridine-1(2H)-carboxamide | 0.058 | 0.15 |
| 104 | N-cyclopentyl-6-methyl-4-(5-(5-(morpholinomethyl)thiophen-2-yl)-1H-pyrrolo[2,3-b]pyridin-3-yl)-5,6-dihydropyridine-1(2H)-carboxamide | 0.11 | 0.19 |
| 105 | N-cyclopentyl-2-methyl-4-(5-(4-(methylsulfonyl)phenyl)-1H-pyrrolo[2,3-b]pyridin-3-yl)-5,6-dihydropyridine-1(2H)-carboxamide | 0.025 | 0.022 |
| 106 | N-cyclopentyl-2-methyl-4-(5-(5-(morpholinomethyl)thiophen-2-yl)-1H-pyrrolo[2,3-b]pyridin-3-yl)-5,6-dihydropyridine-1(2H)-carboxamide | 0.0031 | 0.0047 |
| 107 | N-cyclopentyl-2-methyl-4-(5-(5-((4-methylpiperazin-1-yl)methyl)thiophen-2-yl)-1H-pyrrolo[2,3-b]pyridin-3-yl)-5,6-dihydropyridine-1(2H)-carboxamide | 0.0027 | 0.0032 |
| 108 | N-cyclopentyl-4-(5-(3,4-dimethoxyphenyl)-1H-pyrrolo[2,3-b]pyridin-3-yl)-2-methyl-5,6-dihydropyridine-1(2H)-carboxamide | 0.023 | 0.029 |
| 109 | 2-ethyl-N-isopropyl-4-(5-(5-(morpholinomethyl)thiophen-2-yl)-1H-pyrrolo[2,3-b]pyridin-3-yl)-5,6-dihydropyridine-1(2H)-carboxamide | 0.22 | 0.39 |
| 110 | 6-ethyl-N-isopropyl-4-(5-(5-(morpholinomethyl)thiophen-2-yl)-1H-pyrrolo[2,3-b]pyridin-3-yl)-5,6-dihydropyridine-1(2H)-carboxamide | 0.031 | 0.043 |
| 111 | 2-ethyl-N-isopropyl-4-(5-(5-((4-methylpiperazin-1-yl)methyl)thiophen-2-yl)-1H-pyrrolo[2,3-b]pyridin-3-yl)-5,6-dihydropyridine-1(2H)-carboxamide | 0.018 | 0.077 |
| 112 | 6-ethyl-N-isopropyl-4-(5-(4-(morpholinomethyl)phenyl)-1H-pyrrolo[2,3-b]pyridin-3-yl)-3,6-dihydropyridine-1(2H)-carboxamide | 0.056 | 0.062 |
| 113 | 6-ethyl-N-isopropyl-4-(5-(4-(4-methylpiperazine-1-carbonyl)phenyl)-1H-pyrrolo[2,3-b]pyridin-3-yl)-3,6-dihydropyridine-1(2H)-carboxamide | 0.018 | 0.046 |
| 114 | N-isopropyl-2,2-dimethyl-4-(5-(5-(morpholinomethyl)thiophen-2-yl)-1H-pyrrolo[2,3-b]pyridin-3-yl)-5,6-dihydropyridine-1(2H)-carboxamide | 0.0059 | 0.0080 |
| 115 | N-isopropyl-2,6-dimethyl-4-(5-(5-(morpholinomethyl)thiophen-2-yl)-1H-pyrrolo[2,3-b]pyridin-3-yl)-3,6-dihydropyridine-1(2H)-carboxamide | 0.36 | 0.43 |
| 116 | N-cyclopentyl-2,6-dimethyl-4-(5-(5-(morpholinomethyl)thiophen-2-yl)-1H-pyrrolo[2,3-b]pyridin-3-yl)-3,6-dihydropyridine-1(2H)-carboxamide | 1.28 | 1.52 |
| 117 | N-isopropyl-3-(5-(5-(morpholinomethyl)thiophen-2-yl)-1H-pyrrolo[2,3-b]pyridin-3-yl)-8-azabicyclo[3.2.1]oct-3-ene-8-carboxamide | 2.70 | 4.79 |
| 118 | N-isopropyl-3-(5-(5-(morpholinomethyl)thiophen-2-yl)-1H-pyrrolo[2,3-b]pyridin-3-yl)-9-azabicyclo[3.3.1]non-3-ene-9-carboxamide | 0.34 | 0.61 |
| 119 | 4-(5-(3,4-dimethoxyphenyl)-1H-pyrrolo[2,3-b]pyridin-3-yl)-N-isopropyl-2-phenyl-5,6-dihydropyridine-1(2H)-carboxamide | 5.41 | 3.47 |
| 120 | N-cyclopentyl-4-(5-(3,4-dimethoxyphenyl)-1H-pyrrolo[2,3-b]pyridin-3-yl)-5-methyl-5,6-dihydropyridine-1(2H)-carboxamide | 0.084 | |
| 121 | N-cyclopentyl-5-methyl-4-(5-(4-(methylsulfonyl)phenyl)-1H-pyrrolo[2,3-b]pyridin-3-yl)-5,6-dihydropyridine-1(2H)-carboxamide | 0.097 | 0.33 |
| 122 | N-cyclopentyl-5-methyl-4-(5-(3-(methylsulfonyl)phenyl)-1H-pyrrolo[2,3-b]pyridin-3-yl)-5,6-dihydropyridine-1(2H)-carboxamide | 0.036 | 0.097 |
| 123 | N-cyclopentyl-5-methyl-4-(5-(3-sulfamoylphenyl)-1H-pyrrolo[2,3-b]pyridin-3-yl)-5,6-dihydropyridine-1(2H)-carboxamide | 0.028 | 0.080 |
| 124 | N-cyclopentyl-5-methyl-4-(5-(4-sulfamoylphenyl)-1H-pyrrolo[2,3-b]pyridin-3-yl)-5,6-dihydropyridine-1(2H)-carboxamide | 0.051 | |
| 125 | N-isopropyl-5-methyl-4-(5-(5-((4-methylpiperazin-1-yl)methyl)thiophen-2-yl)-1H-pyrrolo[2,3-b]pyridin-3-yl)-5,6-dihydropyridine-1(2H)-carboxamide | 0.0036 | 0.027 |

TABLE 1-continued

| Example | Name | TBK1 (μM) | IKKε (μM) |
|---|---|---|---|
| 126 | N-cyclopentyl-5-methyl-4-(5-(5-((4-methylpiperazin-1-yl)methyl)thiophen-2-yl)-1H-pyrrolo[2,3-b]pyridin-3-yl)-5,6-dihydropyridine-1(2H)-carboxamide | 0.015 | 0.033 |
| 127 | N-cyclopentyl-5-methyl-4-(5-(5-(morpholinomethyl)thiophen-2-yl)-1H-pyrrolo[2,3-b]pyridin-3-yl)-5,6-dihydropyridine-1(2H)-carboxamide | 0.0040 | 0.10 |
| 128 | N-cyclopentyl-5-ethyl-4-(5-(5-(morpholinomethyl)thiophen-2-yl)-1H-pyrrolo[2,3-b]pyridin-3-yl)-5,6-dihydropyridine-1(2H)-carboxamide | 0.071 | |
| 129 | N-cyclopentyl-4-(5-(3,4-dimethoxyphenyl)-1H-pyrrolo[2,3-b]pyridin-3-yl)-3-methyl-5,6-dihydropyridine-1(2H)-carboxamide | 0.24 | |
| 130 | N-cyclopentyl-3-methyl-4-(5-(4-(methylsulfonyl)phenyl)-1H-pyrrolo[2,3-b]pyridin-3-yl)-5,6-dihydropyridine-1(2H)-carboxamide | 0.55 | |
| 131 | N-cyclopentyl-3-methyl-4-(5-(5-(morpholinomethyl)thiophen-2-yl)-1H-pyrrolo[2,3-b]pyridin-3-yl)-5,6-dihydropyridine-1(2H)-carboxamide | 0.22 | |
| 132 | N-cyclopentyl-3-fluoro-4-(5-(4-(methylsulfonyl)phenyl)-1H-pyrrolo[2,3-b]pyridin-3-yl)-5,6-dihydropyridine-1(2H)-carboxamide | 0.25 | |
| 133 | N-cyclopentyl-4-(5-(3,4-dimethoxyphenyl)-1H-pyrrolo[2,3-b]pyridin-3-yl)-3-fluoro-5,6-dihydropyridine-1(2H)-carboxamide | 0.22 | |
| 134 | N-cyclopentyl-3-fluoro-4-(5-(5-(morpholinomethyl)thiophen-2-yl)-1H-pyrrolo[2,3-b]pyridin-3-yl)-5,6-dihydropyridine-1(2H)-carboxamide | | |
| 135 | ethyl 4-(1H-pyrrolo[2,3-b]pyridin-3-yl)-5,6-dihydropyridine-1(2H)-carboxylate | 1.1 | |
| 136 | pentyl 4-(1H-pyrrolo[2,3-b]pyridin-3-yl)-5,6-dihydropyridine-1(2H)-carboxylate | 10.6 | |
| 137 | propyl 4-(1H-pyrrolo[2,3-b]pyridin-3-yl)-5,6-dihydropyridine-1(2H)-carboxylate | 0.44 | |
| 138 | butyl 4-(1H-pyrrolo[2,3-b]pyridin-3-yl)-5,6-dihydropyridine-1(2H)-carboxylate | 5.2 | |
| 139 | isopropyl 4-(1H-pyrrolo[2,3-b]pyridin-3-yl)-5,6-dihydropyridine-1(2H)-carboxylate | 0.32 | |
| 140 | cyclopentyl 4-(1H-pyrrolo[2,3-b]pyridin-3-yl)-3,6-dihydropyridine-1(2H)-carboxylate | 0.31 | |
| 141 | sec-butyl 4-(1H-pyrrolo[2,3-b]pyridin-3-yl)-5,6-dihydropyridine-1(2H)-carboxylate | 0.5 | |
| 142 | pentan-3-yl 4-(1H-pyrrolo[2,3-b]pyridin-3-yl)-5,6-dihydropyridine-1(2H)-carboxylate | 3 | |
| 143 | cyclohexyl 4-(1H-pyrrolo[2,3-b]pyridin-3-yl)-5,6-dihydropyridine-1(2H)-carboxylate | 1 | |
| 144 | cyclopentyl 4-(5-(3,4-dimethoxyphenyl)-1H-pyrrolo[2,3-b]pyridin-3-yl)-5,6-dihydropyridine-1(2H)-carboxylate | 0.46 | |
| 145 | cyclopentyl 4-(5-(3-sulfamoylphenyl)-1H-pyrrolo[2,3-b]pyridin-3-yl)-5,6-dihydropyridine-1(2H)-carboxylate | 0.033 | 0.12 |
| 146 | isopropyl 4-(5-(3-sulfamoylphenyl)-1H-pyrrolo[2,3-b]pyridin-3-yl)-5,6-dihydropyridine-1(2H)-carboxylate | >10 | |
| 147 | isopropyl 4-(5-(3,4-dimethoxyphenyl)-1H-pyrrolo[2,3-b]pyridin-3-yl)-5,6-dihydropyridine-1(2H)-carboxylate | 0.11 | |
| 148 | isopropyl 4-(5-(4-(methylsulfonyl)phenyl)-1H-pyrrolo[2,3-b]pyridin-3-yl)-5,6-dihydropyridine-1(2H)-carboxylate | 0.054 | 0.25 |
| 149 | isopropyl 4-(5-(3-(methylsulfonyl)phenyl)-1H-pyrrolo[2,3-b]pyridin-3-yl)-5,6-dihydropyridine-1(2H)-carboxylate | 0.030 | |
| 150 | isopropyl 4-(5-(4-sulfamoylphenyl)-1H-pyrrolo[2,3-b]pyridin-3-yl)-5,6-dihydropyridine-1(2H)-carboxylate | 0.036 | |
| 151 | tert-butyl 4-(5-(3-sulfamoylphenyl)-1H-pyrrolo[2,3-b]pyridin-3-yl)-5,6-dihydropyridine-1(2H)-carboxylate | 0.042 | |
| 152 | tert-butyl 4-(5-(4-sulfamoylphenyl)-1H-pyrrolo[2,3-b]pyridin-3-yl)-5,6-dihydropyridine-1(2H)-carboxylate | 0.081 | |
| 153 | tert-butyl 4-(5-(5-(morpholinomethyl)thiophen-2-yl)-1H-pyrrolo[2,3-b]pyridin-3-yl)-5,6-dihydropyridine-1(2H)-carboxylate | 0.8 | |

TABLE 1-continued

| Example | Name | TBK1 (μM) | IKKε (μM) |
|---|---|---|---|
| 154 | tert-butyl 4-(5-(4-(morpholinomethyl)phenyl)-1H-pyrrolo[2,3-b]pyridin-3-yl)-5,6-dihydropyridine-1(2H)-carboxylate | 0.32 | |
| 155 | tert-butyl 4-(5-(4-(morpholine-4-carbonyl)phenyl)-1H-pyrrolo[2,3-b]pyridin-3-yl)-5,6-dihydropyridine-1(2H)-carboxylate | 0.039 | |
| 156 | tert-butyl 4-(5-(3-(morpholinomethyl)phenyl)-1H-pyrrolo[2,3-b]pyridin-3-yl)-5,6-dihydropyridine-1(2H)-carboxylate | 0.26 | |
| 157 | tert-butyl 4-(5-(6-morpholinopyridin-3-yl)-1H-pyrrolo[2,3-b]pyridin-3-yl)-5,6-dihydropyridine-1(2H)-carboxylate | 0.36 | |
| 158 | tert-butyl 4-(5-(4-morpholinophenyl)-1H-pyrrolo[2,3-b]pyridin-3-yl)-5,6-dihydropyridine-1(2H)-carboxylate | 0.41 | |
| 159 | tert-butyl 4-(5-(4-(piperidin-1-yl)phenyl)-1H-pyrrolo[2,3-b]pyridin-3-yl)-5,6-dihydropyridine-1(2H)-carboxylate | 0.6 | |
| 160 | tert-butyl 4-(5-(benzo[d][1,3]dioxol-5-yl)-1H-pyrrolo[2,3-b]pyridin-3-yl)-5,6-dihydropyridine-1(2H)-carboxylate | 2 | |
| 161 | tert-butyl 4-(5-(6-methoxypyridin-3-yl)-1H-pyrrolo[2,3-b]pyridin-3-yl)-5,6-dihydropyridine-1(2H)-carboxylate | 0.6 | |
| 162 | tert-butyl 4-(5-(3-(methylsulfonyl)phenyl)-1H-pyrrolo[2,3-b]pyridin-3-yl)-5,6-dihydropyridine-1(2H)-carboxylate | 0.078 | |
| 163 | tert-butyl 4-(5-(3-(N-methylsulfamoyl)phenyl)-1H-pyrrolo[2,3-b]pyridin-3-yl)-5,6-dihydropyridine-1(2H)-carboxylate | 0.059 | |
| 164 | tert-butyl 4-(5-(4-(methylsulfonyl)phenyl)-1H-pyrrolo[2,3-b]pyridin-3-yl)-5,6-dihydropyridine-1(2H)-carboxylate | 0.25 | |
| 165 | tert-butyl 4-(5-(4-(N-methylsulfamoyl)phenyl)-1H-pyrrolo[2,3-b]pyridin-3-yl)-5,6-dihydropyridine-1(2H)-carboxylate | 0.028 | |
| 166 | tert-butyl 4-(5-(4-acetylphenyl)-1H-pyrrolo[2,3-b]pyridin-3-yl)-5,6-dihydropyridine-1(2H)-carboxylate | 0.95 | |
| 167 | tert-butyl 4-(5-(4-(methoxycarbonyl)phenyl)-1H-pyrrolo[2,3-b]pyridin-3-yl)-5,6-dihydropyridine-1(2H)-carboxylate | 1.6 | |
| 168 | tert-butyl 4-(5-(4-cyanophenyl)-1H-pyrrolo[2,3-b]pyridin-3-yl)-5,6-dihydropyridine-1(2H)-carboxylate | 1.3 | |
| 169 | tert-butyl 4-(5-(3-cyanophenyl)-1H-pyrrolo[2,3-b]pyridin-3-yl)-5,6-dihydropyridine-1(2H)-carboxylate | 4.5 | |
| 170 | tert-butyl 4-(5-(5-methyl-1,3,4-thiadiazol-2-yl)-1H-pyrrolo[2,3-b]pyridin-3-yl)-5,6-dihydropyridine-1(2H)-carboxylate | 0.032 | 0.28 |
| 171 | cyclopentyl 4-(5-(3-fluoro-4-methoxyphenyl)-1H-pyrrolo[2,3-b]pyridin-3-yl)-5,6-dihydropyridine-1(2H)-carboxylate | 0.88 | |
| 172 | cyclopentyl 4-(5-(3-(methylsulfonyl)phenyl)-1H-pyrrolo[2,3-b]pyridin-3-yl)-5,6-dihydropyridine-1(2H)-carboxylate | 0.055 | |
| 173 | cyclopentyl 4-(5-(4-(methylsulfonyl)phenyl)-1H-pyrrolo[2,3-b]pyridin-3-yl)-5,6-dihydropyridine-1(2H)-carboxylate | 0.12 | |
| 174 | cyclopentyl 4-(5-(3-(ethylsulfonyl)phenyl)-1H-pyrrolo[2,3-b]pyridin-3-yl)-5,6-dihydropyridine-1(2H)-carboxylate | 0.19 | |
| 175 | cyclopentyl 4-(5-(4-(cyclopropylsulfonyl)phenyl)-1H-pyrrolo[2,3-b]pyridin-3-yl)-5,6-dihydropyridine-1(2H)-carboxylate | 0.35 | |
| 176 | cyclopentyl 4-(5-(4-sulfamoylphenyl)-1H-pyrrolo[2,3-b]pyridin-3-yl)-5,6-dihydropyridine-1(2H)-carboxylate | 0.052 | |
| 177 | cyclopentyl 4-(5-(3-(N-methylsulfamoyl)phenyl)-1H-pyrrolo[2,3-b]pyridin-3-yl)-5,6-dihydropyridine-1(2H)-carboxylate | 0.097 | |
| 178 | cyclopentyl 4-(5-(4-(N-methylsulfamoyl)phenyl)-1H-pyrrolo[2,3-b]pyridin-3-yl)-5,6-dihydropyridine-1(2H)-carboxylate | 0.17 | |

TABLE 1-continued

| Example | Name | TBK1 (μM) | IKKε (μM) |
|---|---|---|---|
| 179 | cyclopentyl 4-(5-(4-(N,N-dimethylsulfamoyl)phenyl)-1H-pyrrolo[2,3-b]pyridin-3-yl)-5,6-dihydropyridine-1(2H)-carboxylate | 0.34 | 0.50 |
| 180 | cyclopentyl 4-(5-(3-(morpholinosulfonyl)phenyl)-1H-pyrrolo[2,3-b]pyridin-3-yl)-5,6-dihydropyridine-1(2H)-carboxylate | 0.40 | |
| 181 | cyclopentyl 4-(5-(4-(morpholinosulfonyl)phenyl)-1H-pyrrolo[2,3-b]pyridin-3-yl)-5,6-dihydropyridine-1(2H)-carboxylate | 0.37 | |
| 182 | cyclopentyl 4-(5-(4-methoxy-3-(morpholinosulfonyl)phenyl)-1H-pyrrolo[2,3-b]pyridin-3-yl)-5,6-dihydropyridine-1(2H)-carboxylate | 0.18 | |
| 183 | cyclopentyl 4-(5-(4-(morpholine-4-carbonyl)phenyl)-1H-pyrrolo[2,3-b]pyridin-3-yl)-5,6-dihydropyridine-1(2H)-carboxylate | 0.039 | |
| 184 | cyclopentyl 4-(5-(3-(morpholine-4-carbonyl)phenyl)-1H-pyrrolo[2,3-b]pyridin-3-yl)-5,6-dihydropyridine-1(2H)-carboxylate | 0.1 | |
| 185 | cyclopentyl 4-(5-(5-(morpholinomethyl)thiophen-3-yl)-1H-pyrrolo[2,3-b]pyridin-3-yl)-5,6-dihydropyridine-1(2H)-carboxylate | 0.081 | |
| 186 | cyclopentyl 4-(5-(5-(morpholinomethyl)thiophen-2-yl)-1H-pyrrolo[2,3-b]pyridin-3-yl)-5,6-dihydropyridine-1(2H)-carboxylate | 0.16 | |
| 187 | tert-butyl 4-(5-(3,4-dimethoxyphenyl)-1H-pyrrolo[2,3-b]pyridin-3-yl)-2,3,6,7-tetrahydro-1H-azepine-1-carboxylate | 3.30 | |
| 188 | tert-butyl 5-(5-(3,4-dimethoxyphenyl)-1H-pyrrolo[2,3-b]pyridin-3-yl)-2,3,4,7-tetrahydro-1H-azepine-1-carboxylate | 4.90 | |
| 189 | (4-(5-(3,4-difluorophenyl)-1H-pyrrolo[2,3-b]pyridin-3-yl)-5,6-dihydropyridin-1(2H)-yl)(thiophen-2-yl)methanone | >10 | |
| 190 | (4-(5-(4-(morpholinosulfonyl)phenyl)-1H-pyrrolo[2,3-b]pyridin-3-yl)-5,6-dihydropyridin-1(2H)-yl)(thiophen-2-yl)methanone | 0.14 | 0.39 |
| 191 | (4-(5-(3,4-dimethoxyphenyl)-1H-pyrrolo[2,3-b]pyridin-3-yl)-5,6-dihydropyridin-1(2H)-yl)(thiophen-2-yl)methanone | 0.11 | |
| 192 | (4-(5-(3-fluoro-4-methoxyphenyl)-1H-pyrrolo[2,3-b]pyridin-3-yl)-5,6-dihydropyridin-1(2H)-yl)(thiophen-2-yl)methanone | 0.46 | |
| 193 | (4-(5-(3-(methylsulfonyl)phenyl)-1H-pyrrolo[2,3-b]pyridin-3-yl)-5,6-dihydropyridin-1(2H)-yl)(thiophen-2-yl)methanone | 0.036 | |
| 194 | (4-(5-(4-(methylsulfonyl)phenyl)-1H-pyrrolo[2,3-b]pyridin-3-yl)-5,6-dihydropyridin-1(2H)-yl)(thiophen-2-yl)methanone | >10 | |
| 195 | (4-(5-(3-(ethylsulfonyl)phenyl)-1H-pyrrolo[2,3-b]pyridin-3-yl)-5,6-dihydropyridin-1(2H)-yl)(thiophen-2-yl)methanone | 0.061 | |
| 196 | (4-(5-(4-(cyclopropylsulfonyl)phenyl)-1H-pyrrolo[2,3-b]pyridin-3-yl)-5,6-dihydropyridin-1(2H)-yl)(thiophen-2-yl)methanone | 0.25 | |
| 197 | 4-(3-(1-(thiophene-2-carbonyl)-1,2,3,6-tetrahydropyridin-4-yl)-1H-pyrrolo[2,3-b]pyridin-5-yl)benzensulfonamide | 0.028 | |
| 198 | 3-(3-(1-(thiophene-2-carbonyl)-1,2,3,6-tetrahydropyridin-4-yl)-1H-pyrrolo[2,3-b]pyridin-5-yl)benzensulfonamide | 0.015 | |
| 199 | N-methyl-3-(3-(1-(thiophene-2-carbonyl)-1,2,3,6-tetrahydropyridin-4-yl)-1H-pyrrolo[2,3-b]pyridin-5-yl)benzensulfonamide | 0.034 | |
| 200 | N-methyl-4-(3-(1-(thiophene-2-carbonyl)-1,2,3,6-tetrahydropyridin-4-yl)-1H-pyrrolo[2,3-b]pyridin-5-yl)benzensulfonamide | 0.045 | |
| 201 | N-(3-(3-(1-(thiophene-2-carbonyl)-1,2,3,6-tetrahydropyridin-4-yl)-1H-pyrrolo[2,3-b]pyridin-5-yl)phenyl)methansulfonamide | >10 | |
| 202 | (4-(5-(3-(morpholinosulfonyl)phenyl)-1H-pyrrolo[2,3-b]pyridin-3-yl)-5,6-dihydropyridin-1(2H)-yl)(thiophen-2-yl)methanone | 0.23 | |
| 203 | (4-(5-(4-methoxy-3-(morpholinosulfonyl)phenyl)-1H-pyrrolo[2,3-b]pyridin-3-yl)-5,6-dihydropyridin-1(2H)-yl)(thiophen-2-yl)methanone | 0.039 | |
| 204 | (4-(5-(1H-indazol-5-yl)-1H-pyrrolo[2,3-b]pyridin-3-yl)-5,6-dihydropyridin-1(2H)-yl)(thiophen-2-yl)methanone | 0.057 | 0.28 |
| 205 | (4-(5-(5-((4-methylpiperazin-1-yl)methyl)thiophen-2-yl)-1H-pyrrolo[2,3-b]pyridin-3-yl)-5,6-dihydropyridin-1(2H)-yl)(thiophen-2-yl)methanone | 0.0033 | 0.023 |
| 206 | (4-(5-(5-(morpholinomethyl)thiophen-2-yl)-1H-pyrrolo[2,3-b]pyridin-3-yl)-5,6-dihydropyridin-1(2H)-yl)(thiophen-2-yl)methanone | 0.049 | |
| 207 | (4-(5-(5-(morpholinomethyl)thiophen-3-yl)-1H-pyrrolo[2,3-b]pyridin-3-yl)-5,6-dihydropyridin-1(2H)-yl)(thiophen-2-yl)methanone | 0.048 | |
| 208 | (4-(5-(3-(morpholine-4-carbonyl)phenyl)-1H-pyrrolo[2,3-b]pyridin-3-yl)-5,6-dihydropyridin-1(2H)-yl)(thiophen-2-yl)methanone | 0.19 | |
| 209 | (4-(5-(4-(morpholine-4-carbonyl)phenyl)-1H-pyrrolo[2,3-b]pyridin-3-yl)-5,6-dihydropyridin-1(2H)-yl)(thiophen-2-yl)methanone | 0.007 | 0.14 |
| 210 | (4-(5-(3,4-dimethoxyphenyl)-1H-pyrrolo[2,3-b]pyridin-3-yl)-5,6-dihydropyridin-1(2H)-yl)(5-methylthiophen-2-yl)methanone | 3.00 | |
| 211 | (4-(5-(4-(methylsulfonyl)phenyl)-1H-pyrrolo[2,3-b]pyridin-3-yl)-5,6-dihydropyridin-1(2H)-yl)(5-methylthiophen-2-yl)methanone | 3.50 | |

TABLE 1-continued

| Example | Name | TBK1 (µM) | IKKε (µM) |
|---|---|---|---|
| 212 | 4-(3-(1-(5-methylthiophene-2-carbonyl)-1,2,3,6-tetrahydropyridin-4-yl)-1H-pyrrolo[2,3-b]pyridin-5-yl)benzensulfonamide | 2.60 | |
| 213 | (4-(5-(3,4-dimethoxyphenyl)-1H-pyrrolo[2,3-b]pyridin-3-yl)-5-methyl-5,6-dihydropyridin-1(2H)-yl)(thiophen-2-yl)methanone | 0.18 | |
| 214 | (5-methyl-4-(5-(4-(methylsulfonyl)phenyl)-1H-pyrrolo[2,3-b]pyridin-3-yl)-5,6-dihydropyridin-1(2H)-yl)(thiophen-2-yl)methanone | 0.078 | |
| 215 | (4-(3-(3-methyl-1-(thiophene-2-carbonyl)-1,2,3,6-tetrahydropyridin-4-yl)-1H-pyrrolo[2,3-b]pyridin-5-yl)phenyl)(morpholino)methanone | 0.012 | |
| 216 | (5-methyl-4-(5-(5-(morpholinomethyl)thiophen-2-yl)-1H-pyrrolo[2,3-b]pyridin-3-yl)-5,6-dihydropyridin-1(2H)-yl)(thiophen-2-yl)methanone | 0.073 | |
| 217 | N-cyclopentyl-N-methyl-4-(5-(3-(methylsulfonyl)phenyl)-1H-pyrrolo[2,3-b]pyridin-3-yl)-5,6-dihydropyridine-1(2H)-carboxamide | 0.36 | |
| 218 | N-cyclopentyl-N-methyl-4-(5-(3-sulfamoylphenyl)-1H-pyrrolo[2,3-b]pyridin-3-yl)-5,6-dihydropyridine-1(2H)-carboxamide | >10 | |
| 219 | N-cyclopentyl-N-methyl-4-(5-(4-sulfamoylphenyl)-1H-pyrrolo[2,3-b]pyridin-3-yl)-5,6-dihydropyridine-1(2H)-carboxamide | >10 | |
| 220 | N-cyclopentyl-4-(5-(3,4-dimethoxyphenyl)-1H-pyrrolo[2,3-b]pyridin-3-yl)-N-methyl-5,6-dihydropyridine-1(2H)-carboxamide | 1.30 | |
| 221 | N-cyclopentyl-4-(2-methyl-5-(4-sulfamoylphenyl)-1H-pyrrolo[2,3-b]pyridin-3-yl)-5,6-dihydropyridine-1(2H)-carboxamide | 2.00 | |
| 222 | N-cyclopentyl-4-(2-methyl-5-(4-(N-methylsulfamoyl)phenyl)-1H-pyrrolo[2,3-b]pyridin-3-yl)-5,6-dihydropyridine-1(2H)-carboxamide | 6.80 | |
| 223 | N-cyclopentyl-4-(2-methyl-5-(4-(morpholine-4-carbonyl)phenyl)-1H-pyrrolo[2,3-b]pyridin-3-yl)-5,6-dihydropyridine-1(2H)-carboxamide | 1.60 | |
| 224 | tert-butyl 4-(6-amino-5-(3,4-dimethoxyphenyl)-1H-pyrrolo[2,3-b]pyridin-3-yl)-5,6-dihydropyridine-1(2H)-carboxylate | >10 | |
| 225 | tert-butyl 4-(6-amino-5-(5-(morpholinomethyl)thiophen-2-yl)-1H-pyrrolo[2,3-b]pyridin-3-yl)-5,6-dihydropyridine-1(2H)-carboxylate | >10 | |
| 226 | 4-(6-amino-5-(3,4-dimethoxyphenyl)-1H-pyrrolo[2,3-b]pyridin-3-yl)-N-cyclopentyl-5,6-dihydropyridine-1(2H)-carboxamide | >10 | |
| 227 | 4-(6-amino-5-(5-(morpholinomethyl)thiophen-2-yl)-1H-pyrrolo[2,3-b]pyridin-3-yl)-N-cyclopentyl-5,6-dihydropyridine-1(2H)-carboxamide | 1.50 | |
| 228 | N-cyclopentyl-4-(2-(3-(methylsulfonyl)phenyl)-5H-pyrrolo[2,3-b]pyrazin-7-yl)-5,6-dihydropyridine-1(2H)-carboxamide | 0.090 | 0.40 |
| 229 | N-cyclopentyl-4-(2-(5-(morpholinomethyl)thiophen-2-yl)-5H-pyrrolo[2,3-b]pyrazin-7-yl)-5,6-dihydropyridine-1(2H)-carboxamide | 0.066 | |
| 230 | tert-butyl 4-(2-(3,4-dimethoxyphenyl)-5H-pyrrolo[2,3-b]pyrazin-7-yl)-5,6-dihydropyridine-1(2H)-carboxylate | 0.32 | |
| 231 | tert-butyl 4-(2-(3-(methylsulfonyl)phenyl)-5H-pyrrolo[2,3-b]pyrazin-7-yl)-5,6-dihydropyridine-1(2H)-carboxylate | | |
| 232 | (4-(2-(3-(methylsulfonyl)phenyl)-5H-pyrrolo[2,3-b]pyrazin-7-yl)-5,6-dihydropyridin-1(2H)-yl)(thiophen-2-yl)methanone | | |
| 233 | (4-(2-(5-(morpholinomethyl)thiophen-2-yl)-5H-pyrrolo[2,3-b]pyrazin-7-yl)-5,6-dihydropyridin-1(2H)-yl)(thiophen-2-yl)methanone | 0.040 | |
| 234 | tert-butyl 4-(2-(5-(morpholinomethyl)thiophen-2-yl)-5H-pyrrolo[2,3-b]pyrazin-7-yl)-5,6-dihydropyridine-1(2H)-carboxylate | 0.47 | |
| 235 | 4-(5-(3,4-dimethoxyphenyl)-1H-pyrrolo[2,3-b]pyridin-3-yl)-N-isopropylpiperidine-1-carboxamide | >10 | >10 |
| 236 | tert-butyl 3-(5-(3,4-dimethoxyphenyl)-1H-pyrrolo[2,3-b]pyridin-3-yl)piperidine-1-carboxylate | >10 | |
| 237 | 3-(5-(3,4-dimethoxyphenyl)-1H-pyrrolo[2,3-b]pyridin-3-yl)-N-isopropyl-2,5-dihydro-1H-pyrrol-1-carboxamide | >10 | >10 |
| 238 | 3-(5-(3,4-dimethoxyphenyl)-1H-pyrrolo[2,3-b]pyridin-3-yl)-N-isopropylpyrrolidine-1-carboxamide | 6.23 | 6.05 |
| 239 | tert-butyl 4-(5-(3,4-dimethoxyphenyl)-1H-pyrrolo[2,3-b]pyridin-3-yl)-5,6-dihydropyridine-1(2H)-carboxylate | 0.3 | |
| 240 | tert-butyl 4-(5-(3-acetamidophenyl)-1H-pyrrolo[2,3-b]pyridin-3-yl)-5,6-dihydropyridine-1(2H)-carboxylate | 0.2 | |
| 241 | tert-butyl 4-(5-(4-acetamidophenyl)-1H-pyrrolo[2,3-b]pyridin-3-yl)-5,6-dihydropyridine-1(2H)-carboxylate | 0.17 | |
| 242 | tert-butyl 4-(5-(3-propoxyphenyl)-1H-pyrrolo[2,3-b]pyridin-3-yl)-5,6-dihydropyridine-1(2H)-carboxylate | 1.3 | |
| 243 | tert-butyl 4-(5-(4-propoxyphenyl)-1H-pyrrolo[2,3-b]pyridin-3-yl)-5,6-dihydropyridine-1(2H)-carboxylate | 1.7 | |

TABLE 1-continued

| Example | Name | TBK1 (µM) | IKKε (µM) |
|---|---|---|---|
| 244 | tert-butyl 4-(5-(2-methoxyphenyl)-1H-pyrrolo[2,3-b]pyridin-3-yl)-5,6-dihydropyridine-1(2H)-carboxylate | 1.8 | |
| 245 | tert-butyl 5-(5-(3,4-dimethoxyphenyl)-1H-pyrrolo[2,3-b]pyridin-3-yl)-3,4-dihydropyridine-1(2H)-carboxylate | 8.8 | |
| 246 | N-cyclopentyl-2-(4-(5-(3,4-dimethoxyphenyl)-1H-pyrrolo[2,3-b]pyridin-3-yl)phenyl)acetamide 2,2,2-trifluoroacetate | 4.10 | |
| 247 | 2-(4-(5-(5-(morpholinomethyl)thiophen-2-yl)-1H-pyrrolo[2,3-b]pyridin-3-yl)phenyl)acetic acid | 1.3 | |
| 248 | N-cyclopentyl-2-(4-(5-(5-(morpholinomethyl)thiophen-2-yl)-1H-pyrrolo[2,3-b]pyridin-3-yl)phenyl)acetamide 2,2,2-trifluoroacetate | 2.10 | |
| 249 | N-cyclopentyl-2-(4-(5-(5-(morpholine-4-carbonyl)thiophen-2-yl)-1H-pyrrolo[2,3-b]pyridin-3-yl)phenyl)acetamide | | |
| 250 | (4-(5-(4-(morpholinomethyl)phenylamino)-1H-pyrrolo[2,3-b]pyridin-3-yl)-5,6-dihydropyridin-1(2H)-yl)(thiophen-2-yl)methanone | 0.17 | 0.84 |

What is claimed is:

1. A compound selected from the group consisting of a 7-azaindole or 4,7-diazaindole compound of formula (I), a pharmaceutically acceptable salt thereof, a hydrate thereof, and a solvate thereof:

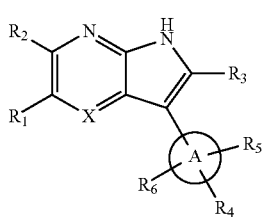

wherein,
X is C or N,
ring A is unsaturated 5-membered heterocycle containing at least one N, or saturated or unsaturated 6- or 7-membered heterocycle containing at least one N;
$R_1$ is halogen, substituted or unsubstituted $C_{5-14}$ aryl, substituted or unsubstituted 5- to 13-membered heteroaryl, or -NHY wherein Y is substituted or unsubstituted $C_{5-14}$ aryl, wherein when said $C_{5-14}$ aryl or 5- to 13-membered heteroaryl is substituted, the substituent is one or more substituents selected from the group consisting of 5- to 10-membered heterocycloalkyl-$C_{1-7}$ alkyl, $C_{1-7}$ alkoxy, halogen, $C_{1-7}$ alkyl, $C_{1-7}$ alkylamido, $C_{1-7}$ alkyl-5- to 10-membered heterocycloalkyl-$C_{1-7}$ alkyl, $C_{3-10}$ cycloalkyl-5- to 10-membered heterocycloalkyl-$C_{1-7}$ alkyl, 5- to 10-membered heterocycloalkyl-$C_{1-7}$ alkyl, $C_{1-7}$ alkyl-5- to 10-membered heterocycloalkyl-carbonyl, 5- to 10-membered heterocycloalkyl-amino, 5- to 10-membered heterocycloalkyl-oxy, $C_{1-7}$ alkyl-sulfonyl, $C_{3-10}$ cycloalkyl-sulfonyl, sulfamoyl, $C_{1-7}$ alkyl-sulfamoyl, 5- to 10-membered heterocycloalkyl-sulfonyl, amino, oxo, 5- to 13-membered heteroaryl-$C_{1-7}$ alkyl-carbamoyl, 5- to 10-membered heterocycloalkyl-$C_{1-7}$ alkoxy, 5- to 10-membered heterocycloalkyl-carbonyl, $C_{1-7}$ alkoxy-carbonyl-5- to 10-membered heterocycloalkyl-$C_{1-7}$ alkyl, 5- to 10-membered heterocycloalkyl, $C_{1-7}$ alkyl-carbonyl, $C_{1-7}$ alkoxy-carbonyl, cyano, $C_{1-7}$ alkyl-5- to 13-membered heteroaryl, di $C_{1-7}$ alkyl-sulfonyl, and $C_{1-7}$ alkyl-amino-sulfonyl;

$R_2$ is H or -$NH_2$;
$R_3$ is H or $C_{1-7}$ alkyl;
$R_4$ is $C_{1-7}$ alkyl, -C(=O)-$R_7$, -C(=O)-O-$R_8$, -C(=O)-N(-$R_9$)-$R_{10}$, -$CH_2$-C(=O)-NH-$R_{11}$ or -$CH_2$-C(=O)-$R_{12}$; $R_7$ to $R_{12}$ are each independently H, hydroxy, $C_{1-7}$ alkyl, substituted or unsubstituted $C_{3-10}$ cycloalkyl, substituted or unsubstituted 5- to 10-membered heterocycloalkyl or substituted or unsubstituted 5- to 13-membered heteroaryl; and each of said cycloalkyl, heterocycloalkyl and heteroaryl is optionally substituted with $C_{1-7}$ alkyl; and
$R_5$ and $R_6$ are each independently H, halogen, $C_{1-7}$ alkyl or substituted or unsubstituted $C_{5-14}$ aryl; when said $R_5$ and $R_6$ are $C_{1-7}$ alkyl, said $R_5$ and $R_6$ are optionally connected to each other.

2. The compound of claim 1, wherein the ring A is a heterocycle ring selected from the group consisting of:

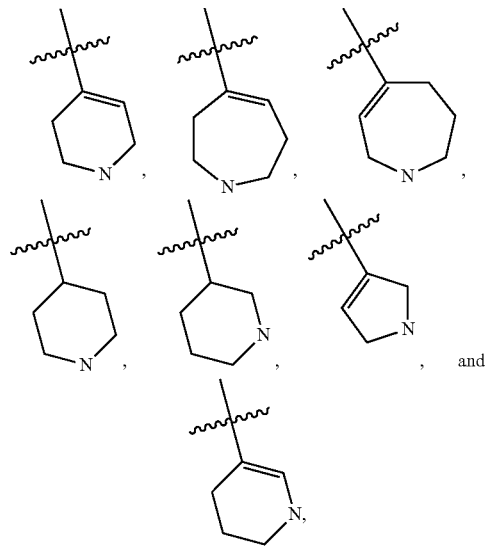

$R_4$ is substituted at N position; and
each of $R_5$ and $R_6$ is substituted at other positions.

3. The compound of claim 1, wherein $R_1$ is halogen, substituted or unsubstituted phenyl, substituted or unsubstituted thiophenyl, substituted or unsubstituted isoindolinonyl, substituted or unsubstituted pyridinyl, substituted or unsubstituted furanyl, substituted or unsubstituted benzodioxolyl, substituted or unsubstituted thiadiazolyl, substituted or unsubstituted indazolyl or substituted or unsubstituted oxoisoindolinyl.

4. The compound of claim 3, wherein the phenyl, thiophenyl, isoindolinonyl, pyridinyl, furanyl, benzodioxolyl, thiadiazolyl, indazolyl or oxoisoindolinyl is substituted with one or more substituents selected from the group consisting of fluoro, chloro, amino, tetrahydro-2H-pyran-amino, cyano, acetyl, acetamido, methylsulfonamido, methyl, morpholinomethyl, piperazinylmethyl, methylpiperazinylmethyl, ethylpiperazinylmethyl, pyrrolidinylmethyl, cyclopropylpiperazinylmethyl, tertbutyloxycarbonylpiperazinylmethyl, morpholinoethyl, methoxy, propoxy, morpholinoethoxy, morpholinopropoxy, tetrahydro-2H -pyran-oxy, methylpiperazinylcarbonyl, methoxycarbonyl, morpholinocarbonyl, methylsulfonyl, ethylsulfonyl, propylsulfonyl, cyclopropylsulfonyl, morpholinosulfonyl, sulfamoyl, methylsulfamoyl, dimethylsulfamoyl, furanylmethylcarbamoyl, morpholino, piperidine, and sulfonamido.

5. The compound of claim 1, wherein $R_4$ is methyl, ethyl, propyl, isobutyl, —C(=O)—$R_7$, —C(=O)—O—$R_8$, —C(=O)—N(—$R_9$)—$R_{10}$, —CH$_2$—C(=O)—NH—$R_{11}$ or —CH$_2$—C(=O)—$R_{12}$; said $R_7$ to $R_{12}$ are each independently H, hydroxy, methyl, ethyl, propyl, butyl, pentyl, isobutyl, isopropyl, isopentyl, isohexyl, tert-butyl, pentan-3-yl, sec-butyl, cyclopropyl, cyclopentyl, cyclohexyl, oxetan-3-yl, tetrahydrofuran-3-yl, pyrrolidin-1-yl, cyclobutyl, thiophen-2-yl or 5-methylthiophen-2-yl.

6. A compound selected from the group consisting of:
(1) 4-((5-(3-(1-methyl-1,2,3,6-tetrahydropyridin-4-yl)-1 H-pyrrolo[2,3-b]pyridin-5-yl)thiophen-2-yl)methyl) morpholine;
(2) 5-(3,4-dimethoxyphenyl)-3-(1-methyl-1,2,3,6-tetrahydropyridin-4-yl)- 1H-pyrrolo[2,3-b]pyridine;
(3) 5-(3,4-dimethoxyphenyl)-3-(1-ethyl-1,2,3,6-tetrahydropyridin-4-yl)-1 H-pyrrolo[2,3 -b]pyridine;
(4) 5-(3,4-dimethoxyphenyl)-3-(1-propyl-1,2,3,6-tetrahydropyridin-4-yl)-1H-pyrrolo[2,3-b]pyridine;
(5) 5-(3,4-dimethoxyphenyl)-3-(1-isobutyl-1,2,3,6-tetrahydropyridin-4-yl)-1H-pyrrolo[2,3-b]pyridine;
(6) 4-((5-(3-(1-ethyl-1,2,3,6-tetrahydropyridin-4-yl)-1H-pyrrolo[2,3-b]pyridin-5-yl)thiophen-2-yl)methyl)morpholine;
(7) 4-((5-(3-(1-propyl-1,2,3,6-tetrahydropyridin-4-yl)-1H-pyrrolo[2,3-b]pyridin-5-yl)thiophen-2-yl)methyl) morpholine;
(8) 1-(4-(5-(5-(morpholinomethyl)thiophen-2-yl)-1H-pyrrolo[2,3-b]pyridin-3-yl)-3,6-dihydropyridin-1(2H)-yl)ethan-1-one;
(9) 1-(4-(5-(5-(morpholinomethyl)thiophen-2-yl)-1H-pyrrolo[2,3-b]pyridin-3-yl)-3,6-dihydropyridin-1(2H)-yl)pentan-1-one;
(10) 3-methyl-1-(4-(5-(5-(morpholinomethyl)thiophen-2-yl)-1H-pyrrolo[2,3-b]pyridin-3-yl)-3,6-dihydropyridin-1(2H)-yl)butan-1-one;
(11) N-isopropyl-4-(5-phenyl-1H-pyrrolo[2,3-b]pyridin-3-yl)-5,6-dihydropyridine-1(2H)-carboxamide;
(12) N-isopropyl-4-(5-(4-methoxyphenyl)-1H-pyrrolo[2,3-b]pyridin-3-yl)-3,6-dihydropyridine-1(2H)-carboxamide;
(13) 4-(5-(4-fluorophenyl)-1H-pyrrolo[2,3-b]pyridin-3-yl)-N-isopropyl-3,6-dihydropyridine-1(2H)-carboxamide;
(14) N-isopropyl-4-(5-(3-methoxyphenyl)-1H-pyrrolo[2,3-b]pyridin-3-yl)-3,6-dihydropyridine-1(2H)-carboxamide;
(15) 4-(5-(3-fluorophenyl)-1H-pyrrolo[2,3-b]pyridin-3-yl)-N-isopropyl-3,6-dihydropyridine-1(2H)-carboxamide;
(16) N-isopropyl-4-(5-(p-tolyl)-1H-pyrrolo[2,3-b]pyridin-3-yl)-3,6-dihydropyridine-1(2H)-carboxamide;
(17) 4-(5-(4-acetamidophenyl)-1H-pyrrolo[2,3-b]pyridin-3-yl)-N-isopropyl-3,6-dihydropyridine-1(2H)-carboxamide;
(18) 4-(5-(3,4-dimethoxyphenyl)-1H-pyrrolo[2,3-b]pyridin-3-yl)-N-isopropyl-5,6-dihydropyridine-1(2H)-carboxamide;
(19) 4-(5-(3-acetamidophenyl)-1H-pyrrolo[2,3-b]pyridin-3-yl)-N-isopropyl-3,6-dihydropyridine-1(2H)-carboxamide;
(20) 4-(5-(2-fluoro-4-(morpholinomethyl)phenyl)-1H-pyrrolo[2,3-b]pyridin-3-yl)-N-isopropyl-3,6-dihydropyridine-1(2H)-carboxamide;
(21) 4-(5-(2-fluoro-5-(morpholinomethyl)phenyl)-1H-pyrrolo[2,3-b]pyridin-3-yl)-N-isopropyl-3,6-dihydropyridine-1(2H)-carboxamide;
(22) 4-(5-(4-((4-ethylpiperazin-1-yl)methyl)phenyl)-1H-pyrrolo[2,3-b]pyridin-3-yl)-N-isopropyl-3,6-dihydropyridine-1(2H)-carboxamide;
(23) 4-(5-(4-((4-cyclopropylpiperazin-1-yl)methyl)phenyl)-1H-pyrrolo[2,3-b]pyridin-3-yl)-N-isopropyl-3,6-dihydropyridine-1(2H)-carboxamide;
(24) 4-(5-(3-((4-ethylpiperazin-1-yl)methyl)phenyl)-1H-pyrrolo[2,3-b]pyridin-3-yl)-N-isopropyl-3,6-dihydropyridine-1(2H)-carboxamide;
(25) N-isopropyl-4-(5-(6-((4-methylpiperazin-1-yl)methyl)pyridin-3-yl)-1H-pyrrolo[2,3-b]pyridin-3-yl)-3,6-dihydropyridine-1(2H)-carboxamide;
(26) 4-(5-(5-((4-ethylpiperazin-1-yl)methyl)thiophen-2-yl)-1H-pyrrolo[2,3-b]pyridin-3-yl)-N-isopropyl-3,6-dihydropyridine-1(2H)-carboxamide;
(27) N-isopropyl-4-(5-(5-(pyrrolidin-1-ylmethyl)furan-2-yl)-1H-pyrrolo[2,3-b]pyridin-3-yl)-5,6-dihydropyridine-1(2H)-carboxamide;
(28) N-isopropyl-4-(5-(5-(pyrrolidin-1-ylmethyl)thiophen-2-yl)-1H-pyrrolo[2,3-b]pyridin-3-yl)-5,6-dihydropyridine-1(2H)-carboxamide;
(29) N-isopropyl-4-(5-(3-(morpholinomethyl)phenyl)-1H-pyrrolo[2,3-b]pyridin-3-yl)-5,6-dihydropyridine-1(2H)-carboxamide;
(30) N-isopropyl-4-(5-(4-(morpholinomethyl)phenyl)-1H-pyrrolo[2,3-b]pyridin-3-yl)-5,6-dihydropyridine-1(2H)-carboxamide;
(31) N-isopropyl-4-(5-(3-(4-methylpiperazine-1-carbonyl)phenyl)-1H-pyrrolo[2,3-b]pyridin-3-yl)-5,6-dihydropyridine-1(2H)-carboxamide;
(32) N-isopropyl-4-(5-(4-(4-methylpiperazine-1-carbonyl)phenyl)-1H-pyrrolo[2,3-b]pyridin-3-yl)-5,6-dihydropyridine-1(2H)-carboxamide;
(33) N-isopropyl-4-(5-(5-((4-methylpiperazin-1-yl)methyl)thiophen-2-yl)-1H-pyrrolo[2,3-b]pyridin-3-yl)-5,6-dihydropyridine-1(2H)-carboxamide;
(34) N-isopropyl-4-(5-(5-(morpholinomethyl)thiophen-2-yl)-1H-pyrrolo[2,3-b]pyridin-3-yl)-5,6-dihydropyridine-1(2H)-carboxamide;
(35) N-isopropyl-4-(5-(5-((4-methylpiperazin-1-yl)methyl)furan-2-yl)-1H-pyrrolo[2,3-b]pyridin-3-yl)-5, 6-dihydropyridine-1(2H)-carboxamide;

(36) N-isopropyl-4-(5-(5-(morpholinomethyl)furan-2-yl)-1H-pyrrolo[2,3-b]pyridin-3-yl)-5,6-dihydropyridine-1(2H)-carboxamide;
(37) N-isopropyl-4-(5-(4-((tetrahydro-2H-pyran-4-yl)amino)phenyl)-1H-pyrrolo[2,3-b]pyridin-3-yl)-3,6-dihydropyridine-1(2H)-carboxamide;
(38) N-isopropyl-4-(5-(4-((tetrahydro-2H-pyran-4-yl)oxy)phenyl)-1H-pyrrolo[2,3-b]pyridin-3-yl)-3,6-dihydropyridine-1(2H)-carboxamide;
(39) 4-(5-(7-amino-1-oxoisoindolidin-4-yl)-1H-pyrrolo[2,3-b]pyridin-3-yl)-N-isopropyl-3,6-dihydropyridine-1(2H)-carboxamide;
(40) 4-(5-(5-(morpholinomethyl)thiophen-2-yl)-1H-pyrrolo[2,3-b]pyridin-3-yl)-N-(pentan-3-yl) -3,6-dihydropyridine-1(2H)-carboxamide;
(41) 4-(5-(5-((4-methylpiperazin-1-yl)methyl)thiophen-2-yl)-1H-pyrrolo[2,3-b]pyridin-3-yl)-N-(pentan-3-yl)-3,6-dihydropyridine-1(2H)-carboxamide;
(42) N-(sec-butyl)-4-(5-(54(4-methylpiperazin-1-yl)methyl)thiophen-2-yl)-1H-pyrrolo[2,3-b]pyridin-3-yl)-5,6-dihydropyridine-1(2H)-carboxamide;
(43) N-(sec-butyl)-4-(5-(5-(morpholinomethyl)thiophen-2-yl)-1H-pyrrolo[2,3-b]pyridin-3-yl) -5,6-dihydropyridine-1(2H)-carboxamide;
(44) N-(sec-butyl)-4-(5-(3,4-dimethoxyphenyl)-1H-pyrrolo[2,3-b]pyridin-3-yl)-5,6-dihydropyridine-1(2H)-carboxamide;
(45) N-cyclopropyl-4-(5-(5-(piperazin-1-ylmethyl)thiophen-2-yl)-1H-pyrrolo[2,3-b]pyridin-3-yl)-5,6-dihydropyridine-1(2H)-carboxamide dihydrochloride;
(46) N-cyclopropyl-4-(5-(4-((4-methylpiperazin-1-yl)methyl)phenyl)-1H-pyrrolo[2,3-b]pyridin-3-yl)-5,6-dihydropyridine-1(2H)-carboxamide;
(47) N-cyclopropyl-4-(5-(5-((4-methylpiperazin-1-yl)methyl)thiophen-2-yl)-1H-pyrrolo[2,3-b]pyridin-3-yl)-5,6-dihydropyridine-1(2H)-carboxamide;
(48) N-cyclopropyl-4-(5-(5-(morpholinomethyl)thiophen-2-yl)-1H-pyrrolo[2,3-b]pyridin-3-yl) -5,6-dihydropyridine-1(2H)-carboxamide;
(49) N-cyclopentyl-4-(5-(3,4-dimethoxyphenyl)-1H-pyrrolo[2,3-b]pyridin-3-yl)-5,6-dihydropyridine-1(2H)-carboxamide;
(50) N-cyclopentyl-4-(5-(3-fluoro-4-methoxyphenyl)-1H-pyrrolo[2,3-b]pyridin-3-yl)-5,6-dihydropyridine-1(2H)-carboxamide;
(51) N-cyclopentyl-4-(5-(4-(methylsulfonyl)phenyl)-1H-pyrrolo[2,3-b]pyridin-3-yl)-5,6-dihydropyridine-1(2H)-carboxamide;
(52) N-cyclopentyl-4-(5-(3-(methylsulfonyl)phenyl)-1H-pyrrolo[2,3-b]pyridin-3-yl)-5,6-dihydropyridine-1(2H)-carboxamide;
(53) N-cyclopentyl-4-(5-(4-(ethylsulfonyl)phenyl)-1H-pyrrolo[2,3-b]pyridin-3-yl)-3,6-dihydropyridine-1(2H)-carboxamide;
(54) N-cyclopentyl-4-(5-(3-(ethylsulfonyl)phenyl)-1H-pyrrolo[2,3-b]pyridin-3-yl)-3,6-dihydropyridine-1(2H)-carboxamide;
(55) N-cyclopentyl-4-(5-(4-(propylsulfonyl)phenyl)-1H-pyrrolo[2,3-b]pyridin-3-yl)-5,6-dihydropyridine-1(2H)-carboxamide;
(56) N-cyclopentyl-4-(5-(4-(cyclopropylsulfonyl)phenyl)-1H-pyrrolo[2,3-b]pyridin-3-yl)-5,6-dihydropyridine-1(2H)-carboxamide;
(57) N-cyclopentyl-4-(5-(3-sulfamoylphenyl)-1H-pyrrolo[2,3-b]pyridin-3-yl)-5,6-dihydropyridine-1(2H)-carboxamide;
(58) N-cyclopentyl-4-(5-(4-sulfamoylphenyl)-1H-pyrrolo[2,3-b]pyridin-3-yl)-5,6-dihydropyridine-1(2H)-carboxamide;
(59) N-cyclopentyl-4-(5-(3-(N-methylsulfamoyl)phenyl)-1H-pyrrolo[2,3-b]pyridin-3-yl)-5,6-dihydropyridine-1(2H)-carboxamide;
(60) N-cyclopentyl-4-(5-(4-(N-methylsulfamoyl)phenyl)-1H-pyrrolo[2,3-b]pyridin-3-yl)-5,6-dihydropyridine-1(2H)-carboxamide;
(61) N-cyclopentyl-4-(5-(4-(morpholinosulfonyl)phenyl)-1H-pyrrolo[2,3-b]pyridin-3-yl)-5,6-dihydropyridine-1(2H)-carboxamide;
(62) N-cyclopentyl-4-(5-(3-(morpholinosulfonyl)phenyl)-1H-pyrrolo[2,3-b]pyridin-3-yl)-5,6-dihydropyridine-1(2H)-carboxamide;
(63) N-cyclopentyl-4-(5-(4-methoxy-3-(morpholinosulfonyl)phenyl)-1H-pyrrolo[2,3-b]pyridin-3-yl)-5,6-dihydropyridine-1(2H)-carboxamide;
(64) N-cyclopentyl-4-(5-(4-(2-morpholinoethyl)phenyl)-1H-pyrrolo[2,3-b]pyridin-3-yl)-5,6-dihydropyridine-1(2H)-carboxamide;
(65) 4-(5-(5-acetamido-2-aminophenyl)-1H-pyrrolo[2,3-b]pyridin-3-yl)-N-cyclopentyl-5,6-dihydropyridine-1(2H)-carboxamide;
(66) N-cyclopentyl-4-(5-(4-((furan-2-ylmethyl)carbamoyl)phenyl)-1H-pyrrolo[2,3-b]pyridin-3-yl)-5,6-dihydropyridine-1(2H)-carboxamide;
(67) N-cyclopentyl-4-(5-(3-((furan-2-ylmethyl)carbamoyl)phenyl)-1H-pyrrolo[2,3-b]pyridin-3-yl)-5,6-dihydropyridine-1(2H)-carboxamide;
(68) N-cyclopentyl-4-(5-(3-(2-morpholinoethoxy)phenyl)-1H-pyrrolo[2,3-b]pyridin-3-yl)-5,6-dihydropyridine-1(2H)-carboxamide;
(69) N-cyclopentyl-4-(5-(4-(2-morpholinoethoxy)phenyl)-1H-pyrrolo[2,3-b]pyridin-3-yl)-5,6-dihydropyridine-1(2H)-carboxamide;
(70) N-cyclopentyl-4-(5-(4-(3-morpholinopropoxy)phenyl)-1H-pyrrolo[2,3-b]pyridin-3-yl)-5,6-dihydropyridine-1(2H)-carboxamide;
(71) N-cyclopentyl-4-(5-(5-((4-methylpiperazin-1-yl)methyl)thiophen-2-yl)-1H-pyrrolo[2,3-b]pyridin-3-yl)-5,6-dihydropyridine-1(2H)-carboxamide;
(72) N-cyclopentyl-4-(5-(5-(morpholinomethyl)thiophen-2-yl)-1H-pyrrolo[2,3-b]pyridin-3-yl)-5,6-dihydropyridine-1(2H)-carbox amide;
(73) N-cyclopentyl-4-(5-(5-(morpholinomethyl)thiophen-3-yl)-1H-pyrrolo[2,3-b]pyridin-3-yl)-5,6-dihydropyridine-1(2H)-carboxamide;
(74) N-cyclopentyl-4-(5-(5-(morpholine-4-carbonyl)thiophen-2-yl)-1H-pyrrolo[2,3 -b]pyridin-3-yl)-5,6-dihydropyridine-1(2H)-carboxamide;
(75) N-cyclopentyl-4-(5-(4-(morpholine-4-carbonyl)phenyl)-1H-pyrrolo[2,3-b]pyridin-3-yl)-5,6-dihydropyridine-1(2H)-carboxamide;
(76) 4-(5-(4-chloro-3-(morpholine-4-carbonyl)phenyl)-1H-pyrrolo[2,3-b]pyridin-3-yl)-N-cyclopentyl-3,6-dihydropyridine-1(2H)-carboxamide 2,2,2-trifluoroacetate;
(77) 4-(5 -(3-chloro-5-(morpholine-4-carbonyl)phenyl)-1 H-pyrrolo[2,3-b]pyridin-3-yl)-N-cyclopentyl-3,6-dihydropyridine-1(2H)-carboxamide 2,2,2-trifluoroacetate;
(78) 4-(5 -(4-((4-methylpiperazin-1-yl)methyl)phenyl)-1H-pyrrolo[2,3-b]pyridin-3-yl)-N-(oxetan-3-yl)-5,6-dihydropyridine-1(2H)-carboxamide;
(79) 4-(5-(5-((4-methylpiperazin-1-yl)methyl)thiophen-2-yl)-1H-pyrrolo[2,3-b]pyridin-3-yl)-N-(oxetan-3-yl)-5,6-dihydropyridine-1(2H)-carboxamide;

(80) 4-(5-(5-(morpholinomethyl)thiophen-2-yl)-1H-pyrrolo[2,3-b] pyridin-3-yl)-N-(oxetan-3-yl)-5,6-dihydropyridine-1(2H)-carboxamide;
(81) 4-(5-(3,4-dimethoxyphenyl)-1H-pyrrolo[2,3-b]pyridin-3-yl)-N-(tetrahydro furan-3 -yl)-5,6-dihydropyridine-1(2H)-carbox amide;
(82) 4-(5-(4-(methylsulfonyl)phenyl)-1H-pyrrolo[2,3-b]pyridin-3-yl)-N-(tetrahydrofuran-3-yl)-5,6-dihydropyridine-1(2H)-carboxamide;
(83) 4-(5-(5-((4-methylpiperazin-1-yl)methyl)thiophen-2-yl)-1H-pyrrolo[2,3-b]pyridin-3-yl)-N-(tetrahydrofuran-3-yl)-5,6-dihydropyridine-1(2H)-carboxamide;
(84) 4-(5-(5-(morpholinomethyl)thiophen-2-yl)-1H-pyrrolo[2,3-b]pyridin-3-yl)-N-(tetrahydrofuran-3-yl)-5,6-dihydropyridine-1(2H)-carboxamide;
(85) 4-(5-(3,4-dimethoxyphenyl)-1H-pyrrolo[2,3-b]pyridin-3-yl)-N-(pyrrolidin-1-yl)-5,6-dihydropyridine-1(2H)-carboxamide 2,2,2-trifluoroacetate;
(86) N-isopropyl-2-methyl-4-(5-(4-((4-methylpiperazin-1-yl)methyl)phenyl)-1H-pyrrolo[2,3-b]pyridin-3-yl)-5,6-dihydropyridine-1(2H)-carboxamide;
(87) N-isopropyl-2-methyl-4-(5-(5-(morpholinomethyl)thiophen-2-yl)-1H-pyrrolo[2,3-b]pyridin-3-yl)-5,6-dihydropyridine-1(2H)-carboxamide;
(88) N-isopropyl-2-methyl-4-(5-(5-((4-methylpiperazin-1-yl)methyl)thiophen-2-yl)-1H-pyrrolo[2,3-b]pyridin-3-yl)-5,6-dihydropyridine-1(2H)-carboxamide;
(89) N-isopropyl-2-methyl-4-(5-(4-(4-methylpiperazine-1-carbonyl)phenyl)-1H-pyrrolo[2,3-b]pyridin-3-yl)-5,6-dihydropyridine-1(2H)-carboxamide;
(90) N-isopropyl-2-methyl-4-(5-(4-(morpholinomethyl)phenyl)-1H-pyrrolo[2,3-b]pyridin-3-yl)-5,6-dihydropyridine-1(2H)-carboxamide;
(91) 6-methyl-4-(5-(5-((4-methylpiperazin-1-yl)methyl)thiophen-2-yl)-1H-pyrrolo[2,3-b]pyridin-3-yl)-N-(pentan-3-yl)-3,6-dihydropyridine-1(2H)-carboxamide;
(92) 6-methyl-4-(5-(5-(morpholinomethyl)thiophen-2-yl)-1H-pyrrolo[2,3-b]pyridin-3-yl)-N-(pentan-3-yl)-3,6-dihydropyridine-1(2H)-carboxamide;
(93) tert-butyl 4-((5-(3-(1-(cyclopropylcarbamoyl)-6-methyl-1,2,3,6-tetrahydropyridin-4-yl)-1H-pyrrolo[2,3-b]pyridin-5-yl)thiophen-2-yl)methyl)piperazine-1-carboxylate;
(94) N-cyclopropyl-2-methyl-4-(5-(4-(4-methylpiperazine-1-carbonyl)phenyl)-1H-pyrrolo[2,3-b]pyridin-3-yl)-5,6-dihydropyridine-1(2H)-carboxamide;
(95) N-cyclopropyl-2-methyl-4-(5-(4-((4-methylpiperazin-1-yl)methyl)phenyl)-1H-pyrrolo[2,3-b]pyridin-3-yl)-5,6-dihydropyridine-1(2H)-carboxamide;
(96) N-cyclopropyl-2-methyl-4-(5-(5-((4-methylpiperazin-1-yl)methyl)thiophen-2-yl)-1H-pyrrolo[2,3-b]pyridin-3-yl)-5,6-dihydropyridine-1(2H)-carboxamide;
(97) N-cyclopropyl-2-methyl-4-(5-(5-(morpholinomethyl)thiophen-2-yl)-1H-pyrrolo[2,3-b]pyridin-3-yl)-5,6-dihydropyridine-1(2H)-carboxamide;
(98) N-cyclobutyl-2-methyl-4-(5-(4-(4-methylpiperazine-1-carbonyl)phenyl)-1H-pyrrolo[2,3-b]pyridin-3-yl)-5,6-dihydropyridine-1(2H)-carboxamide;
(99) N-cyclobutyl-2-methyl-4-(5-(4-((4-methylpiperazin-1-yl)methyl)phenyl)-1H-pyrrolo[2,3-b]pyridin-3-yl)-5,6-dihydropyridine-1(2H)-carboxamide;
(100) N-cyclobutyl-2-methyl-4-(5-(5-((4-methylpiperazin-1-yl)methyl)thiophen-2-yl)-1H-pyrrolo[2,3-b]pyridin-3-yl)-5,6-dihydropyridine-1(2H)-carboxamide;
(101) N-cyclobutyl-2-methyl-4-(5-(5-(morpholinomethyl)thiophen-2-yl)-1H-pyrrolo[2,3-b]pyridin-3-yl)-5,6-dihydropyridine-1(2H)-carboxamide;
(102) N-cyclopentyl-2-methyl-4-(5-(5-((4-methylpiperazin-1-yl)methyl)thiophen-2-yl)-1H-pyrrolo[2,3-b]pyridin-3-yl)-5,6-dihydropyridine-1(2H)-carboxamide;
(103) N-cyclopentyl-6-methyl-4-(5-(5-((4-methylpiperazin-1-yl)methyl)thiophen-2-yl)-1H-pyrrolo[2,3-b]pyridin-3-yl)-5,6-dihydropyridine-1(2H)-carboxamide;
(104) N-cyclopentyl-6-methyl-4-(5-(5-(morpholinomethyl)thiophen-2-yl)-1H-pyrrolo[2,3-b]pyridin-3-yl)-5,6-dihydropyridine-1(2H)-carboxamide;
(105) N-cyclopentyl-2-methyl-4-(5-(4-(methylsulfonyl)phenyl)-1H-pyrrolo[2,3-b]pyridin-3-yl)-5,6-dihydropyridine-1(2H)-carboxamide;
(106) N-cyclopentyl-2-methyl-4-(5-(5-(morpholinomethyl)thiophen-2-yl)-1H-pyrrolo[2,3-b]pyridin-3-yl)-5,6-dihydropyridine-1(2H)-carboxamide;
(107) N-cyclopentyl-2-methyl-4-(5-(5-((4-methylpiperazin-1-yl)methyl)thiophen-2-yl)-1H-pyrrolo[2,3-b]pyridin-3-yl)-5,6-dihydropyridine-1(2H)-carboxamide;
(108) N-cyclopentyl-4-(5-(3,4-dimethoxyphenyl)-1H-pyrrolo[2,3-b]pyridin-3-yl)-2-methyl-5,6-dihydropyridine-1(2H)-carboxamide;
(109) 2-ethyl-N-isopropyl-4-(5-(5-(morpholinomethyl)thiophen-2-yl)-1H-pyrrolo[2,3-b]pyridin-3-yl)-5,6-dihydropyridine-1(2H)-carboxamide;
(110) 6-ethyl-N-isopropyl-4-(5-(5-(morpholinomethyl)thiophen-2-yl)-1H-pyrrolo[2,3-b]pyridin-3-yl)-5,6-dihydropyridine-1(2H)-carboxamide;
(111) 2-ethyl-N-isopropyl-4-(5-(5-((4-methylpiperazin-1-yl)methyl)thiophen-2-yl)-1H-pyrrolo[2,3-b]pyridin-3-yl)-5,6-dihydropyridine-1(2H)-carboxamide;
(112) 6-ethyl-N-isopropyl-4-(5-(4-(morpholinomethyl)phenyl)-1H-pyrrolo[2,3-b]pyridin-3-yl)-3,6-dihydropyridine-1(2H)-carboxamide;
(113) 6-ethyl-N-isopropyl-4-(5-(4-(4-methylpiperazine-1-carbonyl)phenyl)-1H-pyrrolo[2,3-b]pyridin-3-yl)-3,6-dihydropyridine-1(2H)-carboxamide;
(114) N-isopropyl-2,2-dimethyl-4-(5-(5-(morpholinomethyl)thiophen-2-yl)-1H-pyrrolo[2,3-b]pyridin-3-yl)-5,6-dihydropyridine-1(2H)-carboxamide;
(115) N-isopropyl-2,6-dimethyl-4-(5-(5-(morpholinomethyl)thiophen-2-yl)-1H-pyrrolo[2,3-b]pyridin-3-yl)-3,6-dihydropyridine-1(2H)-carboxamide;
(116) N-cyclopentyl-2,6-dimethyl-4-(5-(5-(morpholinomethyl)thiophen-2-yl)-1H-pyrrolo[2,3-b]pyridin-3-yl)-3,6-dihydropyridine-1(2H)-carboxamide;
(117) N-isopropyl-3-(5-(5-(morpholinomethyl)thiophen-2-yl)-1H-pyrrolo[2,3-b]pyridin-3-yl)-8-azabicyclo[3.2.1]oct-3-ene-8-carboxamide;
(118) N-isopropyl-3-(5-(5-(morpholinomethyl)thiophen-2-yl)-1H-pyrrolo[2,3-b]pyridin-3-yl)-9-azabicyclo[3.3.1]non-3-ene-9-carboxamide;
(119) 4-(5-(3,4-dimethoxyphenyl)-1H-pyrrolo[2,3-b]pyridin-3-yl)-N-isopropyl-2-phenyl-5,6-dihydropyridine-1(2H)-carboxamide;
(120) N-cyclopentyl-4-(5-(3,4-dimethoxyphenyl)-1H-pyrrolo[2,3-b]pyridin-3-yl)-5-methyl-5,6-dihydropyridine-1(2H)-carboxamide;
(121) N-cyclopentyl-5-methyl-4-(5-(4-(methylsulfonyl)phenyl)-1H-pyrrolo[2,3-b]pyridin-3-yl)-5,6-dihydropyridine-1(2H)-carboxamide;

(122) N-cyclopentyl-5-methyl-4-(5-(3-(methylsulfonyl) phenyl)-1H-pyrrolo[2,3-b]pyridin-3-yl)-5,6-dihydropyridine-1(2H)-carboxamide;
(123) N-cyclopentyl-5-methyl-4-(5-(3-sulfamoylphenyl)-1H-pyrrolo[2,3-b]pyridin-3-yl)-5,6-dihydropyridine-1(2H)-carboxamide;
(124) N-cyclopentyl-5-methyl-4-(5-(4-sulfamoylphenyl)-1H-pyrrolo[2,3-b]pyridin-3-yl)-5,6-dihydropyridine-1(2H)-carboxamide;
(125) N-isopropyl-5-methyl-4-(5-(5-((4-methylpiperazin-1-yl)methyl)thiophen-2-yl)-1H-pyrrolo[2,3-b]pyridin-3-yl)-5,6-dihydropyridine-1(2H)-carboxamide;
(126) N-cyclopentyl-5-methyl-4-(5-(5-((4-methylpiperazin-1-yl)methyl)thiophen-2-yl)-1H-pyrrolo[2,3-b]pyridin-3-yl)-5,6-dihydropyridine-1(2H)-carboxamide;
(127) N-cyclopentyl-5-methyl-4-(5-(5-(morpholinomethyl)thiophen-2-yl)-1H-pyrrolo[2,3-b]pyridin-3-yl)-5,6-dihydropyridine-1(2H)-carboxamide;
(128) N-cyclopentyl-5-ethyl-4-(5-(5-(morpholinomethyl)thiophen-2-yl)-1H-pyrrolo[2,3-b]pyridin-3-yl)-5,6-dihydropyridine-1(2H)-carboxamide;
(129) N-cyclopentyl-4-(5-(3,4-dimethoxyphenyl)-1H-pyrrolo[2,3-b]pyridin-3-yl)-3-methyl-5,6-dihydropyridine-1(2H)-carboxamide;
(130) N-cyclopentyl-3-methyl-4-(5-(4-(methylsulfonyl) phenyl)-1H-pyrrolo[2,3-b]pyridin-3-yl)-5,6-dihydropyridine-1(2H)-carboxamide;
(131) N-cyclopentyl-3-methyl-4-(5-(5-(morpholinomethyl)thiophen-2-yl)-1H-pyrrolo[2,3-b]pyridin-3-yl)-5,6-dihydropyridine-1(2H)-carboxamide;
(132) N-cyclopentyl-3-fluoro-4-(5-(4-(methylsulfonyl) phenyl)-1H-pyrrolo[2,3-b]pyridin-3-yl)-5,6-dihydropyridine-1(2H)-carboxamide;
(133) N-cyclopentyl-4-(5-(3,4-dimethoxyphenyl)-1H-pyrrolo[2,3-b]pyridin-3-yl)-3-fluoro-5,6-dihydropyridine-1(2H)-carboxamide;
(134) N-cyclopentyl-3-fluoro-4-(5-(5-(morpholinomethyl)thiophen-2-yl)-1H-pyrrolo[2,3-b]pyridin-3-yl)-5,6-dihydropyridine-1(2H)-carboxamide;
(144) cyclopentyl 4-(5-(3,4-dimethoxyphenyl)-1H-pyrrolo[2,3-b]pyridin-3-yl)-5,6-dihydropyridine-1(2H)-carboxylate;
(145) cyclopentyl 4-(5-(3-sulfamoylphenyl)-1H-pyrrolo[2,3-b]pyridin-3-yl)-5,6-dihydropyridine-1(2H)-carboxylate;
(146) isopropyl 4-(5-(3-sulfamoylphenyl)-1H-pyrrolo[2,3-b]pyridin-3-yl)-5,6-dihydropyridine-1(2H)-carboxylate;
(147) isopropyl 4-(5-(3,4-dimethoxyphenyl)-1H-pyrrolo[2,3-b]pyridin-3-yl)-5,6-dihydropyridine-1(2H)-carboxylate;
(148) isopropyl 4-(5-(4-(methylsulfonyl)phenyl)-1H-pyrrolo[2,3-b]pyridin-3-yl)-5,6-dihydropyridine-1(2H)-carboxylate;
(149) isopropyl 4-(5-(3-(methylsulfonyl)phenyl)-1H-pyrrolo[2,3-b]pyridin-3-yl)-5,6-dihydropyridine-1(2H)-carboxylate;
(150) isopropyl 4-(5-(4-sulfamoylphenyl)-1H-pyrrolo[2,3-b]pyridin-3-yl)-5,6-dihydropyridine-1(2H)-carboxylate;
(151) tert-butyl 4-(5-(3-sulfamoylphenyl)-1H-pyrrolo[2,3-b]pyridin-3-yl)-5,6-dihydropyridine-1(2H)-carboxylate;
(152) tert-butyl 4-(5-(4-sulfamoylphenyl)-1H-pyrrolo[2,3-b]pyridin-3-yl)-5,6-dihydropyridine-1(2H)-carboxylate;
(153) tert-butyl 4-(5-(5-(morpholinomethyl)thiophen-2-yl)-1H-pyrrolo[2,3-b]pyridin-3-yl)-5,6-dihydropyridine-1(2H)-carboxylate;
(154) tert-butyl 4-(5-(4-(morpholinomethyl)phenyl)-1H-pyrrolo[2,3-b]pyridin-3-yl)-5,6-dihydropyridine-1(2H)-carboxylate;
(155) tert-butyl 4-(5-(4-(morpholine-4-carbonyl)phenyl)-1H-pyrrolo[2,3-b]pyridin-3-yl)-5,6-dihydropyridine-1(2H)-carboxylate;
(156) tert-butyl 4-(5-(3-(morpholinomethyl)phenyl)-1H-pyrrolo[2,3-b]pyridin-3-yl)-5,6-dihydropyridine-1(2H)-carboxylate;
(157) tert-butyl 4-(5-(6-morpholinopyridin-3-yl)-1H-pyrrolo[2,3-b]pyridin-3-yl)-5,6-dihydropyridine-1(2H)-carboxylate;
(158) tert-butyl 4-(5-(4-morpholinophenyl)-1H-pyrrolo[2,3-b]pyridin-3-yl)-5,6-dihydropyridine-1(2H)-carboxylate;
(159) tert-butyl 4-(5-(4-(piperidin-1-yl)phenyl)-1H-pyrrolo[2,3-b]pyridin-3-yl)-5,6-dihydropyridine-1(2H)-carboxylate;
(160) tert-butyl 4-(5-(benzo[d][1,3]dioxol-5-yl)-1H-pyrrolo[2,3-b]pyridin-3-yl)-5,6-dihydropyridine-1(2H)-carboxylate;
(161) tert-butyl 4-(5-(6-methoxypyridin-3-yl)-1H-pyrrolo[2,3-b]pyridin-3-yl)-5,6-dihydropyridine-1(2H)-carboxylate;
(162) tert-butyl 4-(5-(3-(methylsulfonyl)phenyl)-1H-pyrrolo[2,3-b]pyridin-3-yl)-5,6-dihydropyridine-1(2H)-carboxylate;
(163) tert-butyl 4-(5-(3-(N-methylsulfamoyl)phenyl)-1H-pyrrolo[2,3-b]pyridin-3-yl)-5,6-dihydropyridine-1(2H)-carboxylate;
(164) tert-butyl 4-(5-(4-(methylsulfonyl)phenyl)-1H-pyrrolo[2,3-b]pyridin-3-yl)-5,6-dihydropyridine-1(2H)-carboxylate;
(165) tert-butyl 4-(5-(4-(N-methylsulfamoyl)phenyl)-1H-pyrrolo[2,3-b]pyridin-3-yl)-5,6-dihydropyridine-1(2H)-carboxylate;
(166) tert-butyl 4-(5-(4-acetylphenyl)-1H-pyrrolo[2,3-b]pyridin-3-yl)-5,6-dihydropyridine-1(2H)-carboxylate;
(167) tert-butyl 4-(5-(4-(methoxycarbonyl)phenyl)-1H-pyrrolo[2,3-b]pyridin-3-yl)-5,6-dihydropyridine-1(2H)-carboxylate;
(168) tert-butyl 4-(5-(4-cyanophenyl)-1H-pyrrolo[2,3-b]pyridin-3-yl)-5,6-dihydropyridine-1(2H)-carboxylate;
(169) tert-butyl 4-(5-(3-cyanophenyl)-1H-pyrrolo[2,3-b]pyridin-3-yl)-5,6-dihydropyridine-1(2H)-carboxylate;
(170) tert-butyl 4-(5-(5-methyl-1,3,4-thiadiazol-2-yl)-1H-pyrrolo[2,3-b]pyridin-3-yl)-5,6-dihydropyridine-1(2H)-carboxylate;
(171) cyclopentyl 4-(5-(3-fluoro-4-methoxyphenyl)-1H-pyrrolo[2,3-b]pyridin-3-yl)-5,6-dihydropyridine-1(2H)-carboxylate;
(172) cyclopentyl 4-(5-(3-(methylsulfonyl)phenyl)-1H-pyrrolo[2,3-b]pyridin-3-yl)-5,6-dihydropyridine-1(2H)-carboxylate;
(173) cyclopentyl 4-(5-(4-(methylsulfonyl)phenyl)-1H-pyrrolo[2,3-b]pyridin-3-yl)-5,6-dihydropyridine-1(2H)-carboxylate;
(174) cyclopentyl 4-(5-(3-(ethylsulfonyl)phenyl)-1H-pyrrolo[2,3-b]pyridin-3-yl)-5,6-dihydropyridine-1(2H)-carboxylate;
(175) cyclopentyl 4-(5-(4-(cyclopropylsulfonyl)phenyl)-1H-pyrrolo[2,3-b]pyridin-3-yl)-5,6-dihydropyridine-1(2H)-carboxylate;

(176) cyclopentyl 4-(5-(4-sulfamoylphenyl)-1H-pyrrolo[2,3-b]pyridin-3-yl)-5,6-dihydropyridine-1(2H)-carboxylate;
(177) cyclopentyl 4-(5-(3-(N-methylsulfamoyl)phenyl)-1H-pyrrolo[2,3-b]pyridin-3-yl)-5,6-dihydropyridine-1(2H)-carboxylate;
(178) cyclopentyl 4-(5-(4-(N-methylsulfamoyl)phenyl)-1H-pyrrolo[2,3-b]pyridin-3-yl)-5,6-dihydropyridine-1(2H)-carboxylate;
(179) cyclopentyl 4-(5-(4-(N,N-dimethylsulfamoyl)phenyl)-1H-pyrrolo[2,3-b]pyridin-3-yl)-5,6-dihydropyridine-1(2H)-carboxylate;
(180) cyclopentyl 4-(5-(3-(morpholinosulfonyl)phenyl)-1H-pyrrolo[2,3-b]pyridin-3-yl)-5,6-dihydropyridine-1(2H)-carboxylate;
(181) cyclopentyl 4-(5-(4-(morpholinosulfonyl)phenyl)-1H-pyrrolo[2,3-b]pyridin-3-yl)-5,6-dihydropyridine-1(2H)-carboxylate;
(182) cyclopentyl 4-(5-(4-methoxy-3-(morpholinosulfonyl)phenyl)-1H-pyrrolo[2,3-b]pyridin-3-yl)-5,6-dihydropyridine-1(2H)-carboxylate;
(183) cyclopentyl 4-(5-(4-(morpholine-4-carbonyl)phenyl)-1H-pyrrolo[2,3-b]pyridin-3-yl)-5,6-dihydropyridine-1(2H)-carboxylate;
(184) cyclopentyl 4-(5-(3-(morpholine-4-carbonyl)phenyl)-1H-pyrrolo[2,3-b]pyridin-3-yl)-5,6-dihydropyridine-1(2H)-carboxylate;
(185) cyclopentyl 4-(5-(5-(morpholinomethyl)thiophen-3-yl)-1H-pyrrolo[2,3-b]pyridin-3-yl)-5,6-dihydropyridine-1(2H)-carboxylate;
(186) cyclopentyl 4-(5-(5-(morpholinomethyl)thiophen-2-yl)-1H-pyrrolo[2,3-b]pyridin-3-yl)-5,6-dihydropyridine-1(2H)-carboxylate;
(187) tert-butyl 4-(5-(3,4-dimethoxyphenyl)-1H-pyrrolo[2,3-b]pyridin-3-yl)-2,3,6,7-tetrahydro-1H-azepine-1-carboxylate;
(188) tert-butyl 5-(5-(3,4-dimethoxyphenyl)-1H-pyrrolo[2,3-b]pyridin-3-yl)-2,3,4,7-tetrahydro-1H-azepine-1-carboxylate;
(189) (4-(5-(3,4-difluorophenyl)-1H-pyrrolo[2,3-b]pyridin-3-yl)-5,6-dihydropyridin-1(2H)-yl)(thiophen-2-yl)methanone;
(190) (4-(5-(4-(morpholinosulfonyl)phenyl)-1H-pyrrolo[2,3-b]pyridin-3-yl)-5,6-dihydropyridin-1(2H)-yl)(thiophen-2-yl)methanone;
(191) (4-(5-(3,4-dimethoxyphenyl)-1H-pyrrolo[2,3-b]pyridin-3-yl)-5,6-dihydropyridin-1(2H)-yl)(thiophen-2-yl)methanone;
(192) (4-(5-(3-fluoro-4-methoxyphenyl)-1H-pyrrolo[2,3-b]pyridin-3-yl)-5,6-dihydropyridin-1(2H)-yl)(thiophen-2-yl)methanone;
(193) (4-(5-(3-(methylsulfonyl)phenyl)-1H-pyrrolo[2,3-b]pyridin-3-yl)-5,6-dihydropyridin-1(2H)-yl)(thiophen-2-yl)methanone;
(194) (4-(5-(4-(methylsulfonyl)phenyl)-1H-pyrrolo[2,3-b]pyridin-3-yl)-5,6-dihydropyridin-1(2H)-yl)(thiophen-2-yl)methanone;
(195) (4-(5-(3-(ethylsulfonyl)phenyl)-1H-pyrrolo[2,3-b]pyridin-3-yl)-5,6-dihydropyridin-1(2H)-yl)(thiophen-2-yl)methanone;
(196) (4-(5-(4-(cyclopropylsulfonyl)phenyl)-1H-pyrrolo[2,3-b]pyridin-3-yl)-5,6-dihydropyridin-1(2H)-yl)(thiophen-2-yl)methanone;
(197) 4-(3-(1-(thiophene-2-carbonyl)-1,2,3,6-tetrahydropyridin-4-yl)-1H-pyrrolo[2,3-b]pyridin-5-yl)benzensulfonamide;
(198) 3-(3-(1-(thiophene-2-carbonyl)-1,2,3,6-tetrahydropyridin-4-yl)-1H-pyrrolo[2,3-b]pyridin-5-yl)benzensulfonamide;
(199) N-methyl-3-(3-(1-(thiophene-2-carbonyl)-1,2,3,6-tetrahydropyridin-4-yl)-1H-pyrrolo[2,3-b]pyridin-5-yl)benzensulfonamide;
(200) N-methyl-4-(3-(1-(thiophene-2-carbonyl)-1,2,3,6-tetrahydropyridin-4-yl)-1H-pyrrolo[2,3-b]pyridin-5-yl)benzensulfonamide;
(201) N-(3-(3-(1-(thiophene-2-carbonyl)-1,2,3,6-tetrahydropyridin-4-yl)-1H-pyrrolo[2,3-b]pyridin-5-yl)phenyl)methansulfonamide;
(202) (44543-(morpholinosulfonyl)phenyl)-1H-pyrrolo[2,3-b]pyridin-3-yl)-5,6-dihydropyridin-1(2H)-yl)(thiophen-2-yl)methanone;
(203) (4-(5-(4-methoxy-3-(morpholinosulfonyl)phenyl)-1H-pyrrolo[2,3-yl]pyridin-3-yl)-5,6-dihydropyridin-1(2H)-yl)(thiophen-2-yl)methanone;
(204) (4-(5-(1H-indazol-5-yl)-1H-pyrrolo[2,3-Il]pyridin-3-yl)-5,6-dihydropyridin-1(2H)-yl)(thiophen-2-yl)methanone;
(205) (4-(5-(5-((4-methylpiperazin-1-yl)methyl)thiophen-2-yl)-1H-pyrrolo[2,3-yl]pyridin-3-yl)-5,6-dihydropyridin-1(2H)-yl)(thiophen-2-yl)methanone;
(206) (4-(5-(5-(morpholinomethyl)thiophen-2-yl)-1H-pyrrolo [2,3-yl]pyridin-3-yl)-5,6-dihydropyridin-1(2H)-yl)(thiophen-2-yl)methanone;
(207) (4-(5-(5-(morpholinomethyl)thiophen-3-yl)-1H-pyrrolo [2,3-yl]pyridin-3-yl)-5,6-dihydropyridin-1(2H)-yl)(thiophen-2-yl)methanone;
(208) (44543-(morpholine-4-carbonyl)phenyl)-1H-pyrrolo[2,3-b]pyridin-3-yl)-5,6-dihydropyridin-1(2H)-yl)(thiophen-2-yl)methanone;
(209) (4-(5-(4-(morpholine-4-carbonyl)phenyl)-1H-pyrrolo[2,3-b]pyridin-3-yl)-5,6-dihydropyridin-1(2H)-yl)(thiophen-2-yl)methanone;
(210) (4-(5-(3,4-dimethoxyphenyl)-1H-pyrrolo[2,3-yl]pyridin-3-yl)-5,6-dihydropyridin-1(2H)-yl)(5-methyl-thiophen-2-yl)methanone;
(211) (4-(5-(4-(methylsulfonyl)phenyl)-1H-pyrrolo[2,3-b]pyridin-3-yl)-5,6-dihydropyridin-1(2H)-yl)(5-methylthiophen-2-yl)methanone;
(212) 4-(3-(1-(5-methylthiophene-2-carbonyl)-1,2,3,6-tetrahydropyridin-4-yl)-1H-pyrrolo[2,3-yl]pyridin-5-yl)benzensulfonamide;
(213) (4-(5-(3,4-dimethoxyphenyl)-1H-pyrrolo[2,3-b]pyridin-3-yl)-5-methyl-5,6-dihydropyridin-1(2H)-yl)(thiophen-2-yl)methanone;
(214) (5-methyl-4-(5-(4-(methylsulfonyl)phenyl)-1H-pyrrolo[2,3-b]pyridin-3-yl)-5,6-dihydropyridin-1(2H)-yl)(thiophen-2-yl)methanone;
(215) (4-(3-(3-methyl-1-(thiophene-2-carbonyl)-1,2,3,6-tetrahydropyridin-4-yl)-1H-pyrrolo[2,3-b]pyridin-5-yl)phenyl)(morpholino)methanone;
(216) (5-methyl-4-(5-(5-(morpholinomethyl)thiophen-2-yl)-1H-pyrrolo[2,3-b]pyridin-3-yl)-5,6-dihydropyridin-1(2H)-yl)(thiophen-2-yl)methanone;
(217) N-cyclopentyl-N-methyl-4-(5-(3-(methylsulfonyl)phenyl)-1H-pyrrolo[2,3-b]pyridin-3-yl)-5,6-dihydropyridine-1(2H)-carboxamide;
(218) N-cyclopentyl-N-methyl-4-(5-(3-sulfamoylphenyl)-1H-pyrrolo[2,3-b]pyridin-3-yl)-5,6-dihydropyridine-1(2H)-carboxamide;
(219) N-cyclopentyl-N-methyl-4-(5-(4-sulfamoylphenyl)-1H-pyrrolo[2,3-b]pyridin-3-yl)-5,6-dihydropyridine-1(2H)-carboxamide;

(220) N-cyclopentyl-4-(5-(3,4-dimethoxyphenyl)-1H-pyrrolo[2,3-b]pyridin-3-yl)-N-methyl-5,6-dihydropyridine-1(2H)-carboxamide;
(221) N-cyclopentyl-4-(2-methyl-5-(4-sulfamoylphenyl)-1H-pyrrolo[2,3-b]pyridin-3-yl)-5,6-dihydropyridine-1(2H)-carboxamide;
(222) N-cyclopentyl-4-(2-methyl-5-(4-(N-methylsulfamoyl)phenyl)-1H-pyrrolo[2,3-b]pyridin-3-yl)-5,6-dihydropyridine-1(2H)-carboxamide;
(223) N-cyclopentyl-4-(2-methyl-5-(4-(morpholine-4-carbonyl)phenyl)-1H-pyrrolo[2,3-b]pyridin-3-yl)-5,6-dihydropyridine-1(2H)-carboxamide;
(224) tert-butyl 4-(6-amino-5-(3,4-dimethoxyphenyl)-1H-pyrrolo[2,3-b]pyridin-3-yl)-5,6-dihydropyridine-1(2H)-carboxylate;
(225) tert-butyl 4-(6-amino-5-(5-(morpholinomethyl)thiophen-2-yl)-1H-pyrrolo[2,3-b]pyridin-3-yl)-5,6-dihydropyridine-1(2H)-carboxylate;
(226) 4-(6-amino-5-(3,4-dimethoxyphenyl)-1H-pyrrolo[2,3-b]pyridin-3-yl)-N-cyclopentyl-5,6-dihydropyridine-1(2H)-carboxamide;
(227) 4-(6-amino-5-(5-(morpholinomethyl)thiophen-2-yl)-1H-pyrrolo[2,3-b]pyridin-3-yl)-N-cyclopentyl-5,6-dihydropyridine-1(2H)-carboxamide;
(228) N-cyclopentyl-4-(2-(3-(methylsulfonyl)phenyl)-5H-pyrrolo[2,3-b]pyrazin-7-yl)-5,6-dihydropyridine-1(2H)-carboxamide;
(229) N-cyclopentyl-4-(2-(5-(morpholinomethyl)thiophen-2-yl)-5H-pyrrolo[2,3-b]pyrazin-7-yl)-5,6-dihydropyridine-1(2H)-carboxamide;
(230) tert-butyl 4-(2-(3,4-dimethoxyphenyl)-5H-pyrrolo[2,3-b]pyrazin-7-yl)-5,6-dihydropyridine-1(2H)-carboxylate;
(231) tert-butyl 4-(2-(3-(methylsulfonyl)phenyl)-5H-pyrrolo[2,3-b]pyrazin-7-yl)-5,6-dihydropyridine-1(2H)-carboxylate;
(232) (4-(2-(3-(methylsulfonyl)phenyl)-5H-pyrrolo[2,3-b]pyrazin-7-yl)-5,6-dihydropyridin-1(2H)-yl)(thiophen-2-yl)methanone;
(233) (4-(2-(5-(morpholinomethyl)thiophen-2-yl)-5H-pyrrolo[2,3-b]pyrazin-7-yl)-5,6-dihydropyridin-1(2H)-yl)(thiophen-2-yl)methanone;
(234) tert-butyl 4-(2-(5-(morpholinomethyl)thiophen-2-yl)-5H-pyrrolo[2,3-b]pyrazin-7-yl)-5,6-dihydropyridine-1(2H)-carboxylate;
(235) 4-(5-(3,4-dimethoxyphenyl)-1H-pyrrolo[2,3-b]pyridin-3-yl)-N-isopropylpiperidine-1-carboxamide;
(236) tert-butyl 3-(5-(3,4-dimethoxyphenyl)-1H-pyrrolo[2,3-b]pyridin-3-yl)piperidine-1-carboxylate;
(237) 3-(5-(3,4-dimethoxyphenyl)-1H-pyrrolo[2,3-b]pyridin-3-yl)-N-isopropyl-2,5-dihydro-1H-pyrrol-1-carboxamide;
(238) 3-(5-(3,4-dimethoxyphenyl)-1H-pyrrolo[2,3-b]pyridin-3-yl)-N-isopropylpyrrolidine-1-carboxamide;
(239) tert-butyl 4-(5-(3,4-dimethoxyphenyl)-1H-pyrrolo[2,3-b]pyridin-3-yl)-5,6-dihydropyridine-1(2H)-carboxylate;
(240) tert-butyl 4-(5-(3-acetamidophenyl)-1H-pyrrolo[2,3-b]pyridin-3-yl)-5,6-dihydropyridine-1(2H)-carboxylate;
(241) tert-butyl 4-(5-(4-acetamidophenyl)-1H-pyrrolo[2,3-b]pyridin-3-yl)-5,6-dihydropyridine-1(2H)-carboxylate;
(242) tert-butyl 4-(5-(3-propoxyphenyl)-1H-pyrrolo[2,3-b]pyridin-3-yl)-5,6-dihydropyridine-1(2H)-carboxylate;
(243) tert-butyl 4-(5-(4-propoxyphenyl)-1H-pyrrolo[2,3-b]pyridin-3-yl)-5,6-dihydropyridine-1(2H)-carboxylate;
(244) tert-butyl 4-(5-(2-methoxyphenyl)-1H-pyrrolo[2,3-b]pyridin-3-yl)-5,6-dihydropyridine-1(2H)-carboxylate;
(245) tert-butyl 5-(5-(3,4-dimethoxyphenyl)-1H-pyrrolo[2,3-b]pyridin-3-yl)-3,4-dihydropyridine-1(2H)-carboxylate;
(246) N-cyclopentyl-2-(4-(5-(3,4-dimethoxyphenyl)-1H-pyrrolo[2,3-b]pyridin-3-yl)phenyl)acetamide 2,2,2-trifluoroacetate;
(247) 2-(4-(5-(5-(morpholinomethyl)thiophen-2-yl)-1H-pyrrolo[2,3-b]pyridin-3-yl)phenyl)acetic acid;
(248) N-cyclopentyl-2-(4-(5-(5-(morpholinomethyl)thiophen-2-yl)-1H-pyrrolo[2,3-b]pyridin-3-yl)phenyl)acetamide 2,2,2-trifluoroacetate;
(249) N-cyclopentyl-2-(4-(5-(5-(morpholine-4-carbonyl)thiophen-2-yl)-1H-pyrrolo[2,3-b]pyridin-3-yl)phenyl)acetamide; and
(250) (4-(5-(4-(morpholinomethyl)phenylamino)-1H-pyrrolo[2,3-b]pyridin-3-yl)-5,6-dihydropyridin-1(2H)-yl)(thiophen-2-yl)methanone,
a pharmaceutically acceptable salt thereof, a hydrate thereof, or a solvate thereof.

* * * * *